US007353152B2

(12) United States Patent
Brazhnik et al.

(10) Patent No.: US 7,353,152 B2
(45) Date of Patent: Apr. 1, 2008

(54) METHOD AND APPARATUS FOR COMPUTER MODELING DIABETES

(75) Inventors: Paul Brazhnik, Blacksburg, VA (US); Kevin Hall, Edmonton (CA); Dave Polidori, Palo Alto, CA (US); Scott Siler, Hayward, CA (US); Jeff Trimmer, Burlingame, CA (US)

(73) Assignee: Entelos, Inc., Foster City, CA (US)

( * ) Notice: Subject to any disclaimer, the term of this patent is extended or adjusted under 35 U.S.C. 154(b) by 773 days.

(21) Appl. No.: 10/040,373

(22) Filed: Jan. 9, 2002

(65) Prior Publication Data

US 2003/0058245 A1 Mar. 27, 2003

Related U.S. Application Data

(60) Provisional application No. 60/287,702, filed on May 2, 2001.

(51) Int. Cl.
*G06G 7/48* (2006.01)
*G06G 7/58* (2006.01)
*G01N 33/48* (2006.01)
*G01N 33/50* (2006.01)
*G06F 19/00* (2006.01)

(52) U.S. Cl. .............................. 703/11; 703/6; 703/12; 702/19

(58) Field of Classification Search ................ 514/866; 703/11, 13; 600/416
See application file for complete search history.

(56) References Cited

U.S. PATENT DOCUMENTS

| 5,657,255 A | * | 8/1997 | Fink et al. ..................... 703/11 |
| 5,808,918 A | * | 9/1998 | Fink et al. ..................... 703/11 |
| 5,914,891 A |   | 6/1999 | McAdams et al. |
| 5,930,154 A |   | 7/1999 | Thalhammer-Reyero |
| 5,947,899 A |   | 9/1999 | Winslow et al. |
| 5,956,501 A | * | 9/1999 | Brown ........................ 703/11 |

(Continued)

FOREIGN PATENT DOCUMENTS

WO    WO 99/27443    6/1999

(Continued)

OTHER PUBLICATIONS

AIDA online Case Selector, http://web.archive.org/web/20010126091900/http://www.2aida.org/aida/options.htm, Dec. 2000.*

(Continued)

*Primary Examiner*—Fred Ferris
*Assistant Examiner*—David Silver
(74) *Attorney, Agent, or Firm*—Karen E. Flick

(57) ABSTRACT

The present invention relates generally to a mathematical and computer model of diabetes related disorders (e.g., human type 2 diabetes) within the framework of multiple macronutrient metabolism. The model includes a representation of complex physiological control mechanisms directing, for example, fat metabolism, protein metabolism and/or carbohydrate metabolism. In one embodiment, for example, the model can account for the interconversion between macronutrients, as well as their digestion, absorption, storage, mobilization, and adaptive utilization, as well as the endocrine control of these processes. In this embodiment, the model can simulate, for example, a heterogeneous group of diabetes related disorders, from insulin resistant to severe diabetic, and can predict the likely effects of therapeutic interventions.

38 Claims, 12 Drawing Sheets

U.S. PATENT DOCUMENTS

| | | | |
|---|---|---|---|
| 5,980,096 | A | 11/1999 | Thalhammer-Reyero |
| 6,051,029 | A | 4/2000 | Paterson et al. |
| 6,069,629 | A | 5/2000 | Paterson et al. |
| 6,078,739 | A | 6/2000 | Paterson et al. |
| 6,108,635 | A | 8/2000 | Herren et al. |
| 6,167,362 | A | 12/2000 | Brown et al. |
| 6,233,539 | B1 | 5/2001 | Brown |
| 6,246,975 | B1* | 6/2001 | Rivonelli et al. ............. 703/11 |
| 6,248,527 | B1* | 6/2001 | Chen et al. .................... 435/6 |
| 6,272,480 | B1* | 8/2001 | Tresp et al. ................... 706/44 |
| 6,279,908 | B1* | 8/2001 | Hunsberger ................ 273/249 |
| 6,291,172 | B1* | 9/2001 | Davis et al. ................... 435/6 |
| 6,368,272 | B1* | 4/2002 | Porumbescu ............... 600/300 |
| 6,582,366 | B1* | 6/2003 | Porumbescu ............... 600/300 |
| 2001/0024792 | A1* | 9/2001 | Chen et al. .................... 435/6 |
| 2002/0002325 | A1* | 1/2002 | Iliff .......................... 600/300 |
| 2002/0091666 | A1 | 7/2002 | Rice et al. |
| 2002/0102573 | A1* | 8/2002 | Davis et al. ................... 435/6 |
| 2003/0009099 | A1 | 1/2003 | Lett et al. |
| 2003/0018457 | A1 | 1/2003 | Lett et al. |
| 2003/0033127 | A1 | 2/2003 | Lett |
| 2003/0087285 | A1 | 5/2003 | Chow et al. |
| 2003/0106080 | A1* | 6/2003 | Melmed et al. ............... 800/14 |
| 2005/0125158 | A1* | 6/2005 | Schlessinger et al. ......... 702/19 |

FOREIGN PATENT DOCUMENTS

| | | |
|---|---|---|
| WO | WO 00/63793 | 10/2000 |
| WO | WO 00/65523 | 11/2000 |
| WO | 01/57775 | 8/2001 |
| WO | 01/98935 | 12/2001 |
| WO | 02/44992 | 6/2002 |
| WO | WO 03/054725 | 7/2003 |

OTHER PUBLICATIONS

Jonathan Betz Brown, Allen Russell, Wiley Chan, Kathryn Pedula and Mikel Aickin, The global diabetes model: user friendly version 3.0, Diabetes Research and Clinical Practice, vol. 50, Supplement 3, , Nov. 2000, pp. S15-S46. (http://www.sciencedirect.com/science/article/B6T5Y-41N5DWT-3/2/cec92917fb9333195a8c1976db11579d).*

Kap Bum Huh et al, "Immunogenetic and nutritional profile in insulin-using youth-onset diabetics in Korea", Diabetes Research and Clinical Practice, vol. 16, Issue 1 , Apr. 1992, Abstract.*

Jonathan Betz Brown, Computer models of diabetes: almost ready for prime time, Diabetes Research and Clinical Practice, vol. 50, Supplement 3, , Nov. 2000, pp. S1-S3. (http://www.sciencedirect.com/science/article/B6T5Y-41N5DWT-1/2/c1c446d4aabc94001b65973c608d8f33).*

Richard Stevens, Amanda Adler, Alastair Gray, Andrew Briggs and Rury Holman, Life-expectancy projection by modelling and computer simulation (UKPDS 46), Diabetes Research and Clinical Practice, vol. 50, Supplement 3, , Nov. 2000, pp. S5-S13. (http://www.sciencedirect.com/science/article/B6T5Y-41N5DWT-2/2/208dcbf377cf5049c2371b8cdbec8fe7).*

Andrew J. Palmer, Arno Brandt, Valerio Gozzoli, Christian Weiss, Harald Stock and Helmut Wenzel, Outline of a diabetes disease management model: principles and applications, Diabetes Research and Clinical Practice, vol. 50, Supplement 3, , Nov. 2000, pp. S47-S56. (http://www.sciencedirect.com/science/article/B6T5Y-41N5DWT-4/2/00d049a2e835b2.*

Jonathan Betz Brown, Andrew J. Palmer, Peter Bisgaard, Wiley Chan, Kathryn Pedula and Allen Russell, The Mt. Hood challenge: cross-testing two diabetes simulation models, Diabetes Research and Clinical Practice, vol. 50, Supplement 3, , Nov. 2000, pp. S57-S64. (http://www.sciencedirect.com/science/article/B6T5Y-41N5DWT-5/2/738bb711ae8e6d722.*

Lehmann ED, Interactive educational diabetes simulators: future possibilities, Diab. Nutr. Metab. 12(6):380-7 (1999).*

Johan Hedbrant et al, Särimner: a computer model of diabetes physiology for education of physicians and patients, Diabetes Research and Clinical Practice vol. 14, Issue 2 , Nov. 1991, pp. 113-122 (Abstract Only).*

Pamela K. Fink, Modeling disease processes for drug development: bridging the gap between quantitative and heuristic models, 1996, Proceedings of the 28th conference on Winter simulation, pp. 1183-1190.*

AIDA online Explanations, http://web.archive.org/web/20010125025100/http://www.2aida.org/aida/Explain.html, Dec. 2000.*

Answers.com, http://www.answers.com/similar&r=67, Jul. 2005.*

Arizona, http://ag.arizona.edu/futures/home/glossary.html, Jan. 2006.*

Naito, A Simulation Model of Diabetes Using E-Cell System, Genome Informatics, Dec. 13, 2001 12:310-311.

Dullens et al., "A Survey of some formal models in tumor immunology", Cancer Immunology Immunotherapy (1986) 23:159-164.

Look et al., "Computer simulation of the cellular immune response to malignant lymphoid cells: logic of approach, model design and laboratory verification", Immunology (1981) 43:677-690.

Lehmann Ed, "Interactive educational diabetes simulators: future possibilities," Diab. Nutr. Metab. 12(6):380-7 (1999).

Schlessinger, L. et al., "Archimedes: a new model for simulating health care systems—the mathematical formulation," Journal of Biomedical Informatics, vol. 35, pp. 37-50, 2002; published by Elsevier Science (USA).

AIDA on-line, www.shodor.org/cgi-bin/insulin/WEB.pl, pp. 1-2, Feb. 2001.

Welcome to AIDA, www.2aida.org/aida/intro.htm, pp. 1-4, Feb. 2001.

AIDA Technical Guide, www.2aida.org/aida/technical.htm, pp. 1-21, Feb. 2001.

"Dynamics of blood glucose and its regulating hormones," D. G. Cramp et al., p. 170-201, 1979.

"An Integrated Mathematical Model of the Dynamics of Blood Glucose and Its Hormonal Control," C. Cobelli et al., Mathematical Biosciences, vol. 58, No. 1, Feb. 1982, pp. 27-60.

"A Model of Glucose-insulin Homeostasis in Man that Incororates the Heterogeneouis Fast Pool Theory of Pancreatic Insulin Release," J.R. Guyton et al., Diabetes, vol. 27, No. 10, Oct. 1978, pp. 1027-1042.

"A Mathematical Model for the Control Mechanism of Free Fatty Acid-Glucose Metabolism in Normal Humans," R. Srinivasan et al., Computers and Biomedical Research (1970), 3, pp. 146-166.

"Modeling and Control Aspects of Glucose Homeostasis," by W.P. Charette et al., Mathematical Bio-sciences, Supplement 1, Hormonal Control Systems (1969) pp. 115-149.

"A Systems Model of Blood Glucose Control," by Ewart R. Carson et al., International Journal of Bio-Medical Computing, 1976, pp. 21-34.

"What if Minkowski Had Been Ageusic? An Alternative Angle on Diabetes," by J. Denis McGarry, Science, vol. 258, Oct. 30, 1992, pp. 766-770.

* cited by examiner

Parameter Set - Muscle glucose uptake and phosphorylation

Parameter Set
Name: Muscle glucose uptake and phosphorylation

Description: This parameter set is used to modify the physiology of the muscle glucose uptake and phosphorylation. In particular, the sensitivity and responsiveness paradigm (see Notes) is used to modify baseline dose-response curves for insulin.

Value Set
Name: moderate diabetic #1

Description: This value set adjusts parameter values pertaining to muscle glucose uptake, thereby reducing the effect of insulin to stimulate glucose uptake in muscle.

| Type | Location | Parameter | Baseline Value Set | Alternate Value Set — moderate diabetic #1 | Units |
|---|---|---|---|---|---|
| | MGU insulin sensitivity | sensitivity shift | 0 | 20 | µU/ml |
| | MGU insulin respons. | basal responsiveness | 1 | 0.8 | normalized |
| | hexokinase insulin respons. | basal responsiveness | 1 | | normalized |
| | hexokinase insulin sensitivity | sensitivity shift | 0 | 20 | µU/ml |
| | insulin effect on GLUT4 Vmax | effect at low insulin | 0.6 | | normalized |
| | Diabetes v1.0 marked.elf (ED) | basal muscle glucose uptake | 28 | | mg/min |

FIG. 6

METHOD AND APPARATUS FOR COMPUTER MODELING DIABETES

CROSS-REFERENCE TO RELATED APPLICATION

The present invention is related to and claims priority to U.S. Provisional Patent Application Ser. No. 60/287,702 filed May 2, 2001, entitled "Method and Apparatus for Computer Modeling Type 2 Diabetes," which is incorporated herein by reference.

COPYRIGHT NOTICE

A portion of the disclosure of the patent document contains material that is subject to copyright protection. The copyright owner has no objection to the facsimile reproduction by anyone of the patent document of the patent disclosure, as it appears in the Patent and Trademark Office patent file or records, but otherwise reserves all copyright rights whatsoever.

BACKGROUND OF THE INVENTION

The present invention relates generally to a computer model of diabetes. More specifically, the present invention relates to a computer model of diabetes (e.g., human type 2 diabetes) within the framework of multiple macronutrient metabolism.

The process of extracting energy from the environment and using it to maintain life is called metabolism. Every cell in the human body requires a constant supply of energy in order to avoid the decay to thermodynamic equilibrium (i.e. death). The required energy comes from the ingestion of food and the carefully controlled oxidation of the carbon based macronutrients: carbohydrates, fats, and protein. The fact that humans don't eat continuously, and can survive for some period of time without food, implies that we have the ability to store nutrients for use between meals. Evolution has provided us with complex control mechanisms involving multiple organ systems that direct the storage, mobilization, and utilization of various fuels under a variety of environmental conditions including feeding of various diets, fasting, and performing physical activity.

Diabetes is a complex disease resulting from alterations in normal metabolism that are manifest in elevated fasting and post-prandial blood glucose, impaired insulin sensitivity in muscle, liver and adipose tissue, as well as impaired pancreatic function. The development of pharmaceutical treatments for this disease typically focuses on affecting these general pathways. Complex interactions between these and other pathways, however, make the selection of the appropriate intervention sites and the efficacy of drug candidates difficult to predict. Furthermore, although diabetes is typically characterized by abnormal glucose regulation, impaired fat and protein metabolism play an important role (McGarry, *Science*, 258: 766-70, 1992).

Because of the complexity of metabolic control mechanisms, mathematical and computer models of the processes directing metabolism can be used to help better understand human metabolism and make useful predictions. For example, several researchers have constructed simple mathematical models of glucose regulation and its hormonal control (Cobelli et al., *Math. Biosci.*, 58:27-60, 1982, Guyton et al., *Diabetes*, 27:1027-42, 1978. Srinivasan et al., *Comp. Biomed. Res.*, 3:146-66, 1970, Cramp et al., *Biological Systems, Modeling and Control*, D A Linkens ed. pp 171-201, 1979) Some researchers have attempted to represent diabetes related disorders, but these models were restricted to glucose regulation and did not represent the important interactions with fat or protein metabolism (Cobelli et al., *Math. Biosci.*, 58:27-60, 1982). Fat metabolism in particular is thought to play a major role in diabetes related disorders (McGarry, *Science*, 258: 766-70, 1992).

Hence, there is a need to develop a computer model of diabetes within the framework of multiple macronutrient metabolism.

SUMMARY OF THE INVENTION

The present invention relates generally to a mathematical and computer model of diabetes related disorders (e.g., human type 2 diabetes) within the framework of multiple macronutrient metabolism. The model includes a representation of complex physiological control mechanisms related to, for example, fat metabolism, protein metabolism and/or carbohydrate metabolism. In one embodiment, for example, the model can account for the interconversion between macronutrients, as well as their digestion, absorption, storage, mobilization, and adaptive utilization, as well as the endocrine control of these processes. In this embodiment, the model can simulate, for example, a heterogeneous group of diabetes related disorders, from insulin resistant to severe diabetic, and can predict the likely effects of therapeutic interventions. In another embodiment, the model includes modeling of fat and/or protein metabolism without explicitly modeling carbohydrate metabolism.

BRIEF DESCRIPTION OF THE DRAWINGS

FIG. 6 illustrates an example of a user-interface screen for the parameter set of a type 2 diabetes lesion.

DETAILED DESCRIPTION

Overview

Figure 1:
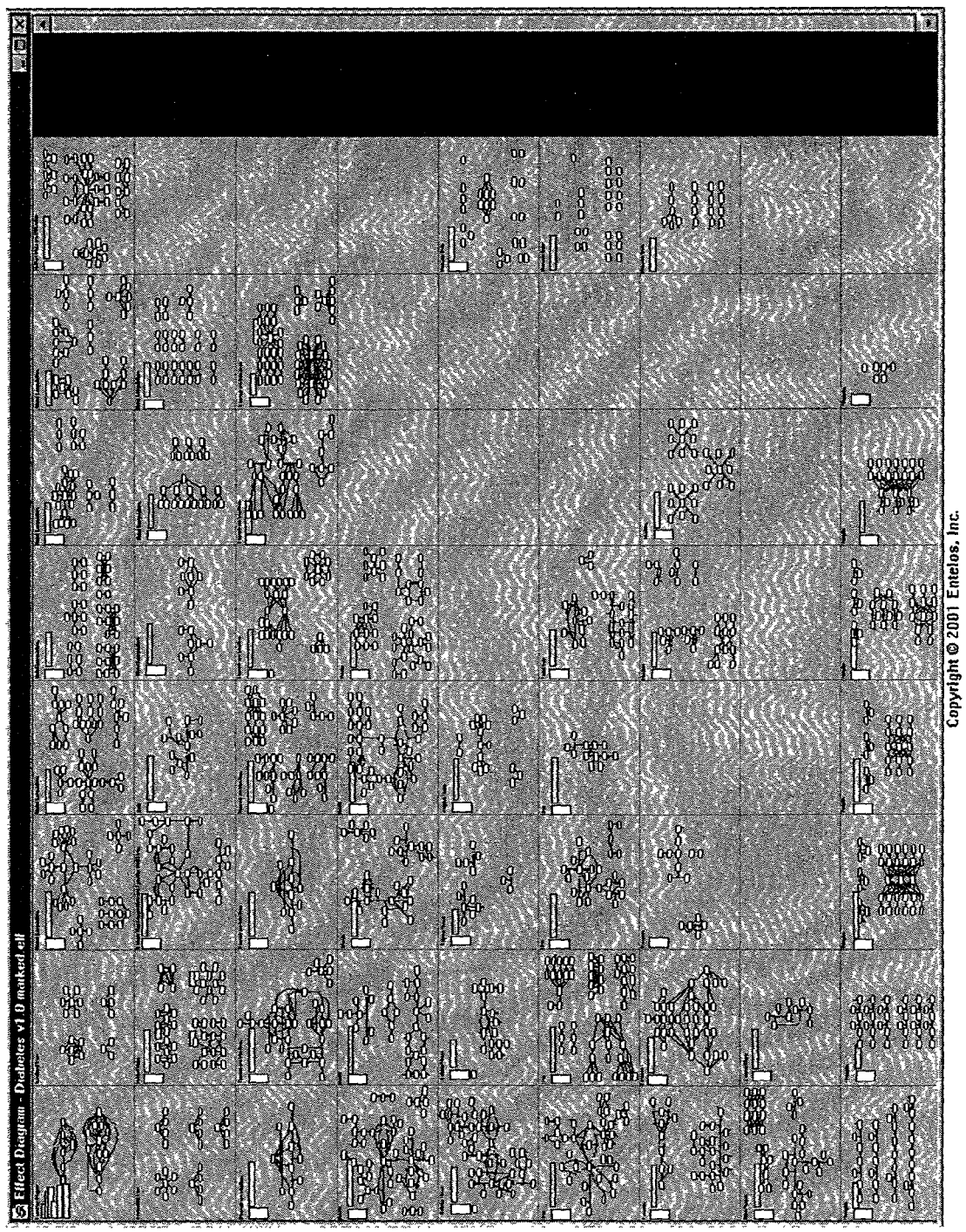
FIG. 1 illustrates an example of an Effect Diagram, which shows the dynamic relationships that exist among these elements of the physiologic system.

Embodiments of the present invention relate to a computer model of diabetes (e.g., human type 2 diabetes) within the framework of multiple macronutrient metabolism. The computer model of diabetes-related disorders includes modeling the metabolism of fat and/or protein metabolism in addition to, or in place of, carbohydrate metabolism. Furthermore, the present invention relates to a computer model of diabetes-related disorders that includes modeling fat and/or protein metabolism without explicitly modeling carbohydrate metabolism.

In one embodiment, the computer executable software code numerically solves the mathematical equations of the model under various simulated experimental conditions. Furthermore, the computer executable software code can facilitate visualization and manipulation of the model equations and their associated parameters to simulate different patients subject to a variety of stimuli. See, e.g., U.S. Pat. No. 6,078,739, entitled "Managing objects and parameter values associated with the objects within a simulation model," the disclosure of which is incorporated herein by reference. Thus, the computer model can be used to rapidly test hypotheses and investigate potential drug targets or therapeutic strategies.

Mathematical Model

The mathematical model of the computer-executable software code represents the dynamic biological processes controlling multiple macronutrient metabolism. The form of the mathematical equations employed may include, for example partial differential equations, stochastic differential equations, differential algebraic equations, difference equations, cellular automata, coupled maps, equations of networks of Boolean or fuzzy logical networks, etc. In one embodiment, the form of the mathematical equations used in the model are ordinary differential equations:

$$dx/dt = f(x, p, t),$$

where x is an N dimensional vector whose elements represent the biological variables of the system (for example plasma glucose, insulin, free fatty acids, etc.), t is time, dx/dt is the rate of change of x, p is an M dimensional set of system parameters (for example basal muscle glucose uptake rate, level of physical activity, nutrient composition of diet, etc.), and f is a function that represents the complex interactions among biological variables.

The term "multiple macronutrient metabolism" refers to the biological processes related to the metabolism of at least one of the macronutrients, i.e., carbohydrates, fats, and/or proteins. In particular, in the present invention, this term could refer to processes related to metabolism of at least two of the macronutrients, i.e. carbohydrates and fats, or carbohydrates and proteins, or fats and proteins. In one embodiment, the diabetes model only includes the biological processes related to fat metabolism. In another embodiment, the diabetes model only includes the biological processes related to protein metabolism.

The term "biological variables" refers to the extra-cellular and/or intra-cellular constituents that make up a biological process. For example, the biological variables can include metabolites, DNA, RNA, proteins, enzymes, hormones, cells, organs, tissues, portions of cells, tissues, or organs, subcellular organelles, chemically reactive molecules like $H^+$, superoxides, ATP, citric acid, protein albumin, as well as combinations or aggregate representations of these types of biological variables.

The term "biological process" is defined herein to mean an interaction or series of interactions between biological variables. Thus, the above function f mathematically represents the biological processes in the model. Biological processes can include, for example, digestion, absorption, storage, and oxidation of carbohydrate, fat, and protein, as well as the endocrine control of these processes. Each biological variable of the biological process can be influenced, for example, by at least one other biological variable in the biological process by some biological mechanism, which need not be specified or even understood.

The term "biological state" is used herein to mean the result of the occurrence of a series of biological processes. As the biological processes change relative to each other, the biological state also undergoes changes. One measurement of a biological state, is the level of activity of biologic variables, parameters, and/or processes at a specified time and under specified experimental or environmental conditions.

In one embodiment the biological state can be mathematically defined by the values of x and p at a given time. Once a biological state of the model is mathematically specified, numerical integration of the above equation using a computer determines, for example, the time evolution of the biological variables x(t) and hence the evolution of the biological state over time.

The term "simulation" is used herein to mean the numerical or analytical integration of a mathematical model. For example, simulation can mean the numerical integration of the mathematical model of the biological state defined by the above equation, i.e. $dx/dt = f(x, p, t)$.

A biological state can include, for example, the state of an individual cell, an organ, a tissue, and/or a multi-cellular organism. A biological state can also include the state of a nutrient or hormone concentration in the plasma, interstitial fluid, intracellular fluid, and/or cerebrospinal fluid; e.g. the states of hypoglycemia or hypoinsulinemia are low blood sugar or low blood insulin. These conditions can be imposed experimentally, or may be conditions present in a patient type. For example, a biological state of a neuron can include the state in which the neuron is at rest, the state in which the neuron is firing an action potential, and the state in which the neuron is releasing neurotransmitter. In another example, the biological states of the collection of plasma nutrients can include the state in which the person awakens from an overnight fast, the state just after a meal, and the state between meals.

The term "biological attribute" is used herein to mean clinical signs and diagnostic criteria associated with a disease state. The biological attributes of a disease state can be quantified with measurements of biological variables, parameters, and/or processes. For example, for the disease state of diabetes, the biological attributes can include fasting plasma glucose, casual plasma glucose, or oral glucose tolerance test (OGTT) value.

The term "disease state" is used herein to mean a biological state where one or more biological processes are related to the cause or the clinical signs of the disease. A disease state can be, for example, of a diseased cell, a diseased organ, a diseased tissue, and/or a diseased multi-cellular organism. Such diseases can include, for example, diabetes, asthma, obesity, and rheumatoid arthritis. A diseased multi-cellular organism can be, for example, an individual human patient, a specific group of human patients, or the general human population as a whole. A diseased state could also include, for example, a diseased protein (such as a defective glucose transporter) or a diseased process, such as defects in clearance, degradation or synthesis or a system constituent, which may occur in several different organs.

The term "reference pattern of the disease state" is used herein to mean a set of biological attributes that are measured in a diseased biological system under specified experimental conditions. For example, the measurements may be performed on blood samples at some specified time following a particular glucose or insulin stimulus. Alternatively, measurements may be performed on biopsy samples, or cell cultures derived from a diseased human or animal. Examples of diseased biological systems include cellular or animal models of diabetes, including a human diabetic patient.

The computer model of diabetes includes the biological processes related to multiple macronutrient metabolism. In one embodiment, the model includes the processes related to the metabolism of all three macronutrients, i.e., carbohydrates, fats, and proteins. In another embodiment, the model includes the processes related to fat metabolism. In yet another embodiment, the model includes the processes related to protein metabolism. In other embodiments of the invention, the model includes processes related to the metabolism of two macronutrients, i.e., carbohydrates and fats, carbohydrates and proteins, or fats and proteins. These different embodiments enable a researcher to understand the pathophysiology of diabetes in the presence of one, two, or all three macronutrients.

To represent metabolism of macronutrients, the biological processes can include the processes of digestion and absorption of carbohydrates, fat, and/or proteins. In addition, the appropriate hormonal responses to carbohydrates, fat, and/or proteins can be included.

To represent carbohydrate metabolism, the model can include, for example, muscle glucose uptake regulation; muscle glycogen regulation; lactate metabolism; hepatic carbohydrate regulation including gluconeogenesis (i.e. creation of glucose 6-phosphate) from lactate, glycerol, and amino acids, glycogenolysis and glycogen synthesis, and glucose uptake and output; brain glucose uptake and utilization; adipose tissue glucose uptake for triglyceride esterification (i.e. fat storage); carbohydrate oxidation in tissues other than the brain and skeletal muscle; and renal glucose excretion.

To represent fat metabolism, the model can include, for example, the regulation of adipose tissue uptake of free fatty acids (FFA) from circulating FFA and lipoproteins (chylomicra and VLDL (very low density lipoprotein)); the regulation of adipose tissue lipolysis (i.e. the release of FFA and glycerol from fat cells); regulation of adipose tissue triglyceride esterification; hepatic lipoprotein regulation; and muscle FFA uptake and utilization.

To represent amino acid metabolism, the model can include, for example, the regulation of skeletal muscle protein turnover in response to activity, exercise, fat mass, dietary composition, and insulin; production of amino acids from carbohydrate in the muscle; hepatic gluconeogenesis from amino acid substrate; and oxidation of amino acids in muscle and other tissues (primarily the liver).

Computer System

Figure 10:
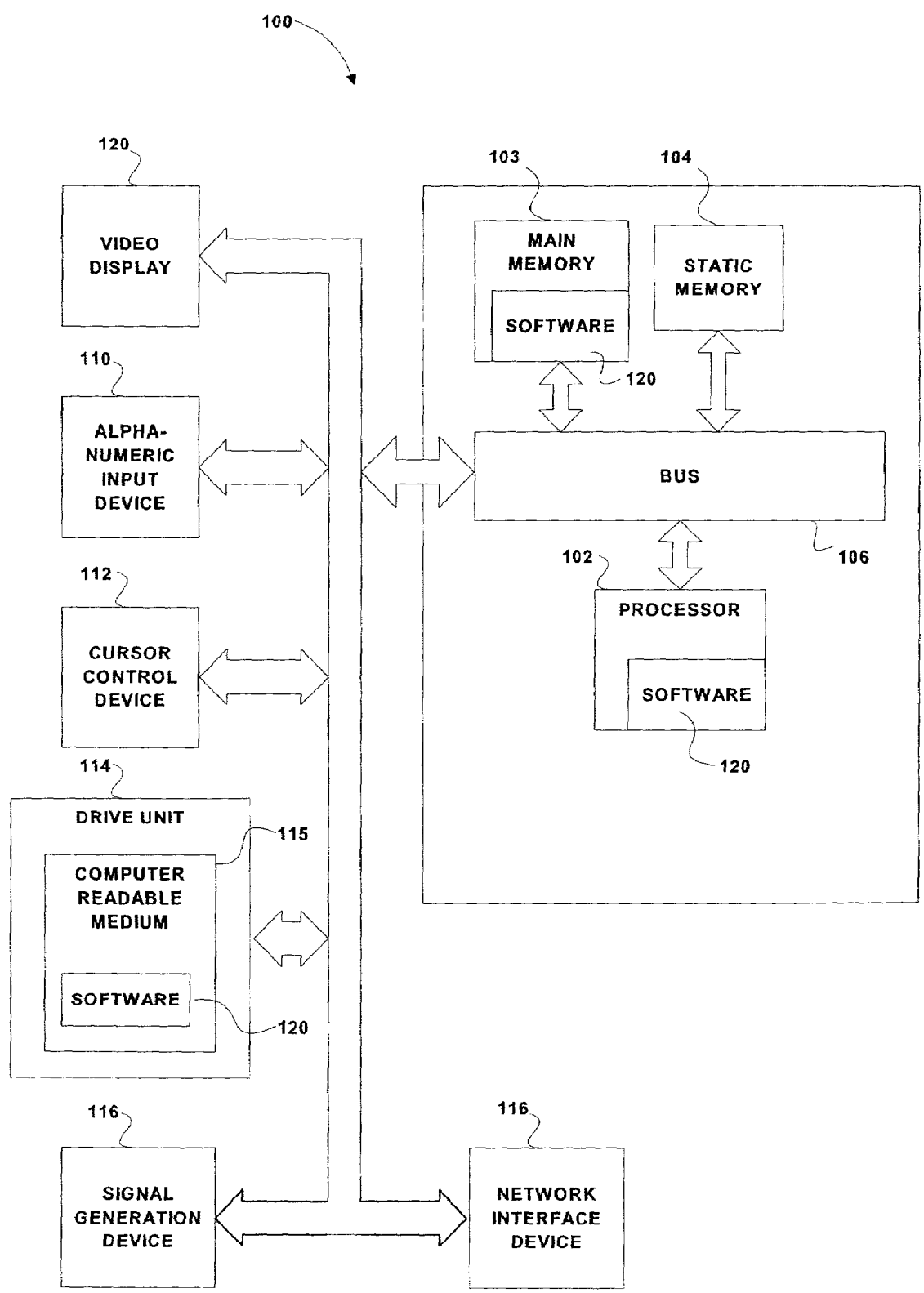
FIG. 10 shows a system block diagram of a computer system within which the methods described above can operate via software code, according to an embodiment of the present invention.

FIG. 10 shows a system block diagram of a computer system within which the methods described above can operate via software code, according to an embodiment of the present invention. The computer system 100 includes a processor 102, a main memory 103 and a static memory 104, which are coupled by bus 106. The computer system 100 can further include a video display unit 108 (e.g., a liquid crystal display (LCD) or cathode ray tube (CRT)) on which a user interface can be displayed. The computer system 100 can also include an alpha-numeric input device 110 (e.g., a keyboard), a cursor control device 112 (e.g., a mouse), a disk drive unit 114, a signal generation device 116 (e.g., a speaker) and a network interface device medium 115. The disk drive unit 114 includes a computer-readable medium 115 on which software 120 can be stored. The software can also reside, completely or partially, within the main memory 103 and/or within the processor 102. The software 120 can also be transmitted or received vai the network interface device 118.

The term "computer-readable medium" is used herein to include any medium which is capable of storing or encoding a sequence of instructions for performing the methods described herein and can include, but not limited to, optical and/or magnetic storage devices and/or disks, and carrier wave signals.

Computer Model

Suitably, a computer model can be used to implement at least some embodiments of the present invention. The computer model can be used for a variety of purposes. For example, the computer model can enable a researcher to: (1) simulate the dynamics of the biological state associated with type 2 diabetes, (2) visualize key metabolic pathways and the feedback within and between these pathways, (3) gain a better understanding of the metabolism and physiology of type 2 diabetes, (4) explore and test hypotheses about type 2 diabetes and normal metabolisms, (5) identify and prioritize potential therapeutic targets, (6) identify patient types and their responses to various interventions, (7) identify surrogate markers of disease progression, and (8) organize knowledge and data that relate to type 2 diabetes.

In addition to simulation capabilities, the computer model can include a built-in database of references to the scientific literature on which the model is based. Users can augment this database with additional references or other commentary and can link the information to the relevant disease component. The computer model can be a multi-user system in which the information can be shared throughput an organization. Thus, the computer model can be a specialized knowledge management system focused on diabetes.

Effect Diagram and Summary Diagram

In one embodiment, the computer model contains software code allowing visual representation of the mathematical model equations as well as the interrelationships between the biological variables, parameters, and processes. This visual representation can be referred to as an "Effect Diagram", illustrated in FIG. 1. The Effect Diagram comprises multiple modules or functional areas that, when grouped together, represent the large complex physiology model. These modules represent and encode sets of ordinary differential equations for numerical integration, as discussed more fully below in the section entitled "Mathematical Equations Encoded in the Effect Diagram."

Figure 2:
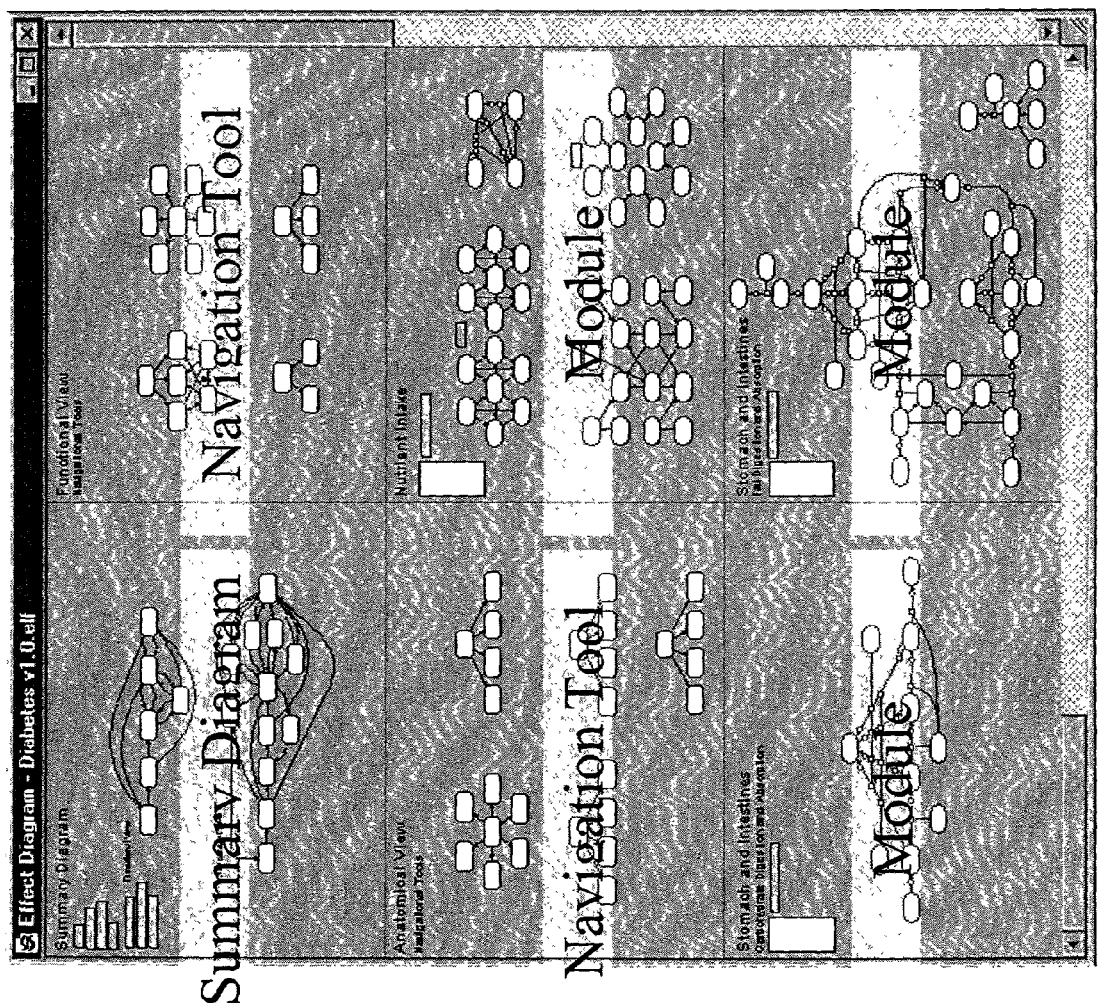
FIG. 2 illustrates an enlargement of the upper left portion of the Effect Diagram shown in FIG. 1.

The Effect Diagram depicted in FIG. 1 includes a Summary Diagram in the upper left corner 1. FIG. 2 is an enlargement of the upper left portion of the Effect Diagram showing that the Summary Diagram can provide navigational links to modules of the model. The navigational tools can relate to a functional view or the anatomical view since the Effect Diagram can include the modules for the various anatomical elements of the human physiologic system, and a given function may involve multiple anatomical structures. From the Summary Diagram, a user can select any of these related user-interface screens by selecting such a screen from the Summary Diagram (e.g., by clicking a hyperlink to a related user-interface screen).

Figure 3:
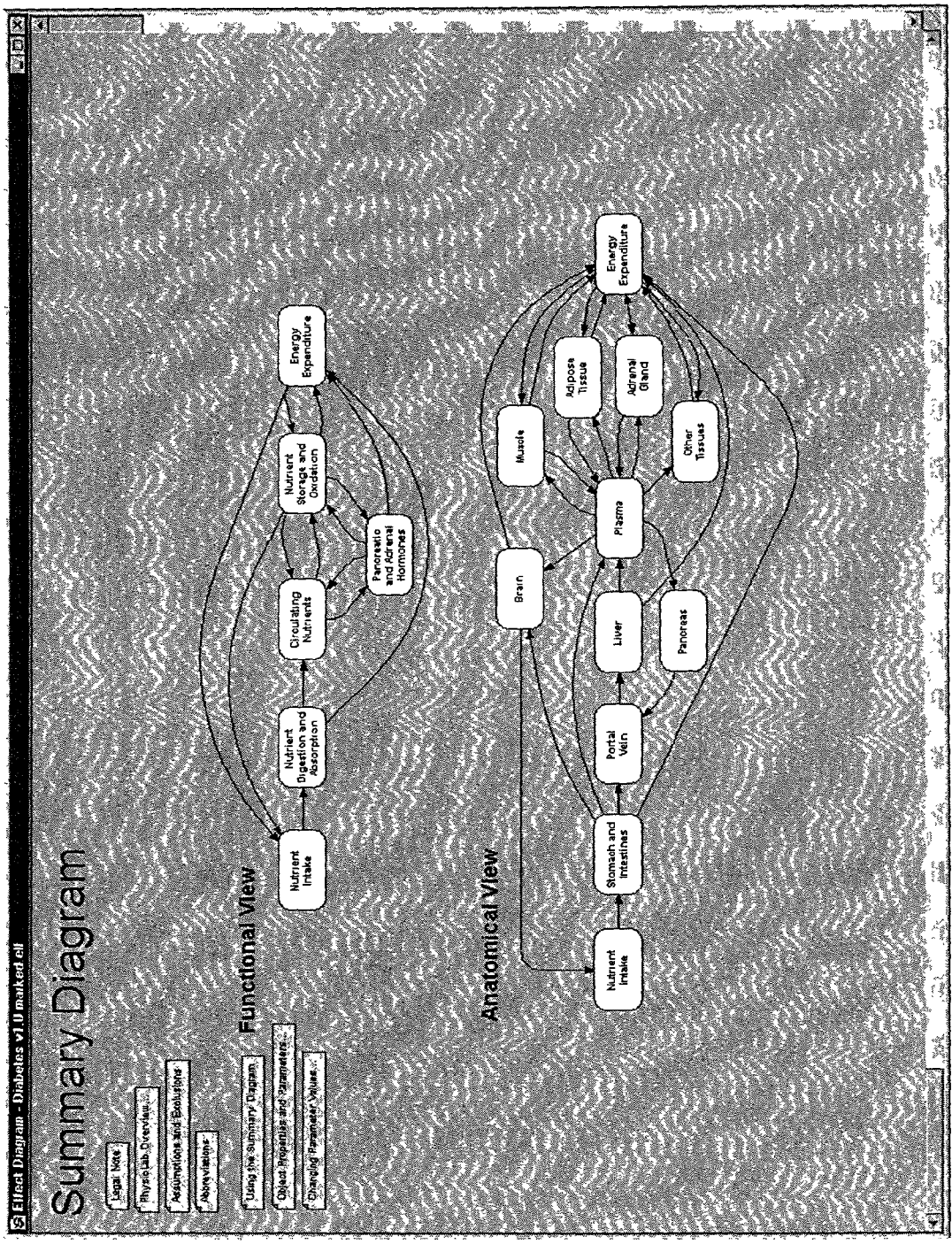
FIG. 3 illustrates an example of a Summary Diagram from the Effect Diagram of FIG. 1.

FIG. 3 illustrates an example of a Summary Diagram from the Effect Diagram of FIG. 1. As shown in FIG. 3, the Summary Diagram can provide an overview of the contents of the Effect Diagram and can contain nodes that link to modules in the Effect Diagram. These modules can be based on, for example, the anatomical elements of the human physiology such as stomach and intestines, portal vein, liver, pancreas, etc. (as shown in the Anatomical View of the Summary Diagram).

Figure 4:
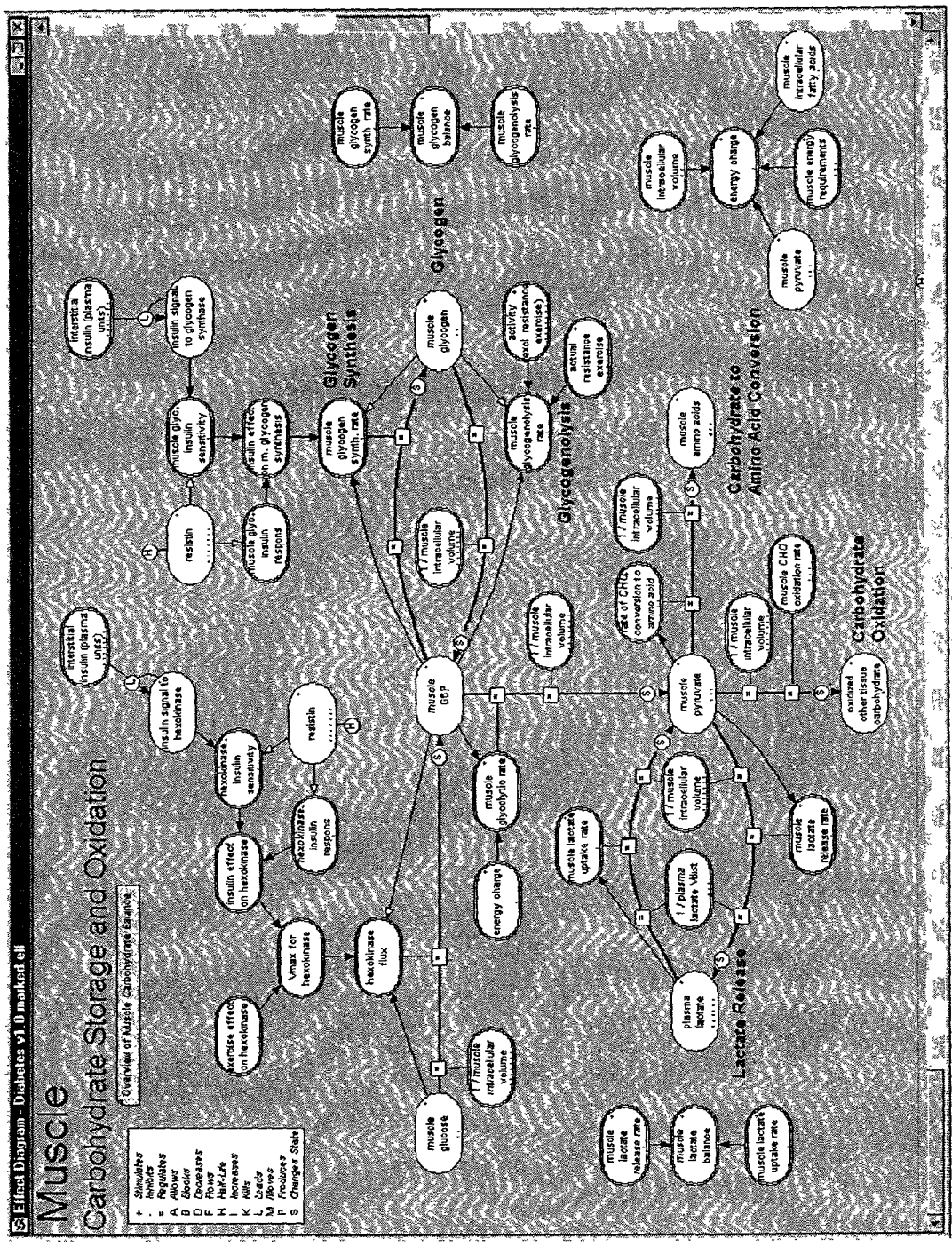
FIG. 4 illustrates an example of a module diagram for one of the anatomical elements shown in the Summary Diagram of FIG. 3.

FIG. 4 illustrates an example of a module diagram for one of the anatomical elements shown in the Summary Diagram of FIG. 3. More specifically, FIG. 4 illustrates a module diagram for the carbohydrate storage and oxidation functions of the muscle. Both the biological relationships as well as the mathematical equations are represented through the use of diagrammatic symbols. Through the use of these symbols, the complex and dynamic mathematical relationships for the various elements of the physiologic system are represented in a user-friendly manner.

Pages A-1 through A-39 of Appendix A lists additional examples of user-interface screens for other modules for anatomical elements and physiologic functions shown in the Summary Diagram. For purposes of clarity, pages A-40A through A-78B of Appendix A lists enlarged versions of pages A-1 through A-39, respectively; each user-interface screen from pages A-1 through A-39 are vertically divided over two enlarged pages (e.g., page A-1 is enlarged over two pages A-40A and A-40B).

Mathematical Equations Encoded in the Effect Diagram

As mentioned above, the Effect Diagram is a visual representation of the model equations. This section describes how the diagram encodes a set of ordinary differential equations. Note that although the discussion below regarding state and function nodes refers to biological variables for consistency, the discussion also relates to variables of any appropriate type and need not be limited to just biological variables.

State and Function Nodes

State and function nodes display the names of the biological variables they represent and their location in the model. Their arrows and modifiers indicate their relation to other nodes within the model. State and function nodes also contain the parameters and equations that are used to compute the values or their biological variables in simulated experiments. In one embodiment of the computer model, the state and function nodes are generated according to the method described in U.S. Pat. No. 6,051,029 and co-pending application Ser. No. 09/588,855, both of which are entitled "Method of generating a display for a dynamic simulation model utilizing node and link representations," and both of which are incorporated herein by reference. Further examples of state and function nodes are further discussed below.

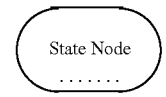

State nodes, the single-border ovals in the Effect Diagram, represent biological variables in the system the values of which are determined by the cumulative effects of its inputs over time.

State node values are defined by differential equations. The predefined parameters for a state node include its initial value ($S_O$) and its status. State nodes that have a half-life have the additional parameter of a half-life (h) and are labeled with a half-life 🔑 symbol.

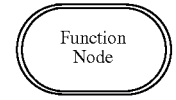

Function nodes, the double-border ovals in the Effect Diagram, represent biological variables in the system the values of which, at any point in time, are determined by inputs at that same point in time.

Function nodes are defined by algebraic functions of their inputs. The predefined parameters for a function node include its initial value ($F_O$) and its status.

Setting the status of a node effects how the value of the node is determined. The status of a state or function node can be:

Computed—the value is calculated as a result of its inputs
Specified-Locked—the value is held constant over time
Specified Data—the value varies with time according to predefined data points.

State and function nodes can appear more than once in the Effect Diagram as alias nodes. Alias nodes are indicated by one or more dots, as in the state node illustration above. All nodes are also defined by their position, with respect to arrows and other nodes, as being either source nodes (S) or target nodes (T). Source nodes are located at the tails of arrows, and target nodes are located at the heads of arrows. Nodes can be active or inactive. Active nodes are white. Inactive nodes match the background color of the Effect Diagram.

State Node Equations

The computational status of a state node can be Computed, Specified-Locked, or Specified Data.

State Node Computed $$\frac{dS}{dt} = \begin{cases} \text{sum of } arrowterms & \text{when } h = 0 \\ \frac{\ln\frac{1}{2}}{h}S(t) + \text{sum of } arrowterms & \text{when } h > 0 \end{cases}$$

Where S is the node value, t is time, S(t) is the node value at time, t, and h is the half-life. The three dots at the end of the equation indicate there are additional terms in the equation resulting from any effect arrows leading into it and by any conversion arrows that lead out of it. If h is equal to 0, then the half-life calculation is not performed and dS/dt is determined solely by the arrows attached to the node.

State Node Specified-Locked $$S(t) = S_0 \text{ for all } t$$

State Node Specified Data S(t) is defined by specified data entered for the state node.

State node values can be limited to a minimum value of zero and a maximum value of one. If limited at zero, S can never be less than zero and the value for S is reset to zero if it goes negative. If limited at one, S cannot be greater than one and is reset to one if it exceeds one.

Function Node Equations

Function node equations are computed by evaluating the specified function of the values of the nodes with arrows pointing into the function node (arguments), plus any object and Effect Diagram parameters used in the function expression. To view the specified function, click the Evaluation tab in the function node Object window.

The Effect Diagram—Arrows

Arrows link source nodes to target nodes and represent the mathematical relationship between the nodes. Arrows can be labeled with circles that indicate the activity of the arrow. A key to the annotations in the circles is located in the upper left corner of each module in the Effect Diagram. If an arrowhead is solid, the effect is positive. If the arrowhead is hollow, the effect is negative.

Arrow Types

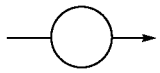

Effect arrows, the thin arrows on the Effect Diagram, link source state or function nodes to target state nodes. Effect arrows cause changes to target nodes but have no effect on source nodes. They are labeled with circles that indicate the activity of the arrow.

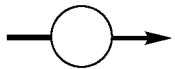

Conversion arrows, the thick arrows on the Effect Diagram, represent the way the contents of state nodes are converted into the contents of the attached state nodes. They are labeled with circles that indicate the activity of the arrow. The activity may effect the source node or the target node or both nodes. The conversion can go either way.

Argument arrows specify which nodes are input arguments for function nodes. They do not contain parameters or equations and are not labeled with activity circles.

Arrow Characteristics

Effect or conversion arrows can be constant, proportional, or interactive.

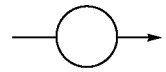

Arrows that are constant have a break in the arrow shaft. They are used when the rate of change of the target is independent of the values of the source and target nodes.

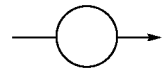

Arrows that are proportional have solid, unbroken shafts and are used when the rate of change is dependent on, or is a function of, the values of the source node.

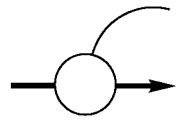

Arrows that are interactive have a loop from the activity circle to the target ode. They indicate that the rate of change of the target is dependent on, or a function of, the value of both the source node and the target node.

Arrow Properties can be displayed in an Object window (not shown). The window may also include tabs for displaying Notes and Arguments associated with the arrow. If Notes are available in the Object window, the arrow is labeled with a red dot (•).

Arrow Equations: Effect Arrows

Proportional Effect Arrow: The rate of change of target tracks source node value.

$$\frac{dT}{dt} = C \cdot S(t)^a + \ldots$$

Where T is the target node, C is a coefficient, S is the source node, and a is an exponent.

Constant Effect Arrow: The rate of change of the target is constant.

$$\frac{dT}{dt} = K + \ldots$$

Where T is the target node and K is a constant.

Interaction Effect Arrow: The rate of change of the target depends on both the souce node and target node values.

$$\frac{dT}{dt} = C(S(t)^a - T(t)^b) + \ldots$$

Where T is the target node, S is the source node, and a and b are exponents. This equation can vary depending on the operation selected in the Object window. The operations available are S+T, S−T, S*T, T/S, and S/T.

Arrow Equations: Conversion Arrows

Proportional Conversion Arrow: The rate of change of the target tracks the value of source node.

$$\frac{dT}{dt} = C \cdot R \cdot S(t)^a + \ldots$$

$$\frac{dS}{dt} = -C \cdot S(t)^a + \ldots$$

Where T is the target node, S is the source node, C is a coefficient, R is a conversion ratio, and a is an exponent.

Constant Conversion Arrow: The rates of change of target and source are constant such that an increase in target corresponds to a decrease in source.

$$\frac{dT}{dt} = K \cdot R + \ldots$$

$$\frac{dS}{dt} = -K + \ldots$$

Where T is the target node, S is the source node, K is a constant, and R is a conversion ratio.

Interaction Conversion Arrow: The rates of change of the target and source depend on both source and target node values such that an increase in target corresponds to a decrease in source.

$$\frac{dT}{dt} = R \cdot C(S(t)^a - T(t)^b) + \ldots$$

$$\frac{dS}{dt} = -C(S(t)^a - T(t)^b) + \ldots$$

Where T is the target node, S is the source node, a and b are exponents, and R is a conversion ratio. This equation can vary depending on the operation selected in the Object window. The operations available are S+T, S−T, S*T, T/S, and S/T.

Modifiers

Modifiers indicate the effects nodes have on the arrows to which they are connected. The type of modification is qualitatively indicated by a symbol in the box. For example, a node can allow Ⓐblock Ⓑregulate ⊟inhibit ⊡or stimulate ⊞an arrow rate.

A key to the modifier annotations is located in the upper left corner of each module.

Modifier Properties can be displayed in the Object Window. The window may also include tabs for displaying the notes, arguments, and specified data associated with the modifier. If notes are available in the Object window, the modifier is labeled with a red dot (•).

Effect Arrow, Modifier Equation:

$$\frac{dT}{dt} = M \cdot f\left(\frac{u}{N}\right) \cdot arrowterm + \ldots$$

Where T is the target node, M is a multiplier constant, N is a normalization constant, f( ) is a function (either linear or specified by a transform curve), and arrowterm is an equation fragment from the attached arrow.

Modifier Effect

By default, conversion arrow modifiers affect both the source and target arrow terms. However, in some cases, a unilateral, modifier is used. Such modifier will affect either a source arrow term or on target arrow term; it does not affect both arrow terms.

Conversion arrow, Source Only Modifier Equation:

$$\frac{dS}{dt} = M \cdot f\left(\frac{u}{N}\right) \cdot arrowterm + \text{other attached } arrowterms$$

Conversion arrow, Target Only Modifier Equation:

$$\frac{dT}{dt} = M \cdot f\left(\frac{u}{N}\right) \cdot arrowterm + \text{other attached } arrowterms$$

The equation for a source and target modifier uses both the Source Only equation and the Target Only equation.

When multiplicative and additive modifers are combined, effect is given precedence. For example, if the following modifiers are on an arrow, a1,a2: Additive, Source and Target
m1,m2: Multiplicative, Source and Target
A1,A2: Additive, Target Only
M1,M2: Multiplicative, Target Only then the rates are modified by
Target node: (a1+a2+A1+A2)*(m1*m2)*(M1*M2)
Source node: (a1+a2)*(m1*m2)

Example of a Model Component: Skeletal Muscle Glucose Uptake

The following discussion provides an example of a process by which the modules of the above-described computer model can be developed. As discussed above, the various elements of the physiologic system are represented by the components shown in the Effect Diagram. These components are denoted by state and function nodes, which represent mathematical relationships that define the elements of the physiologic system. In general, these mathematical relationships are developed with the aid of appropriate publicly available information on the relevant physiological components. The development of the mathematical relationships underlying the module diagram for glucose uptake functions of the muscle will be discussed here as an example.

Figure 11:
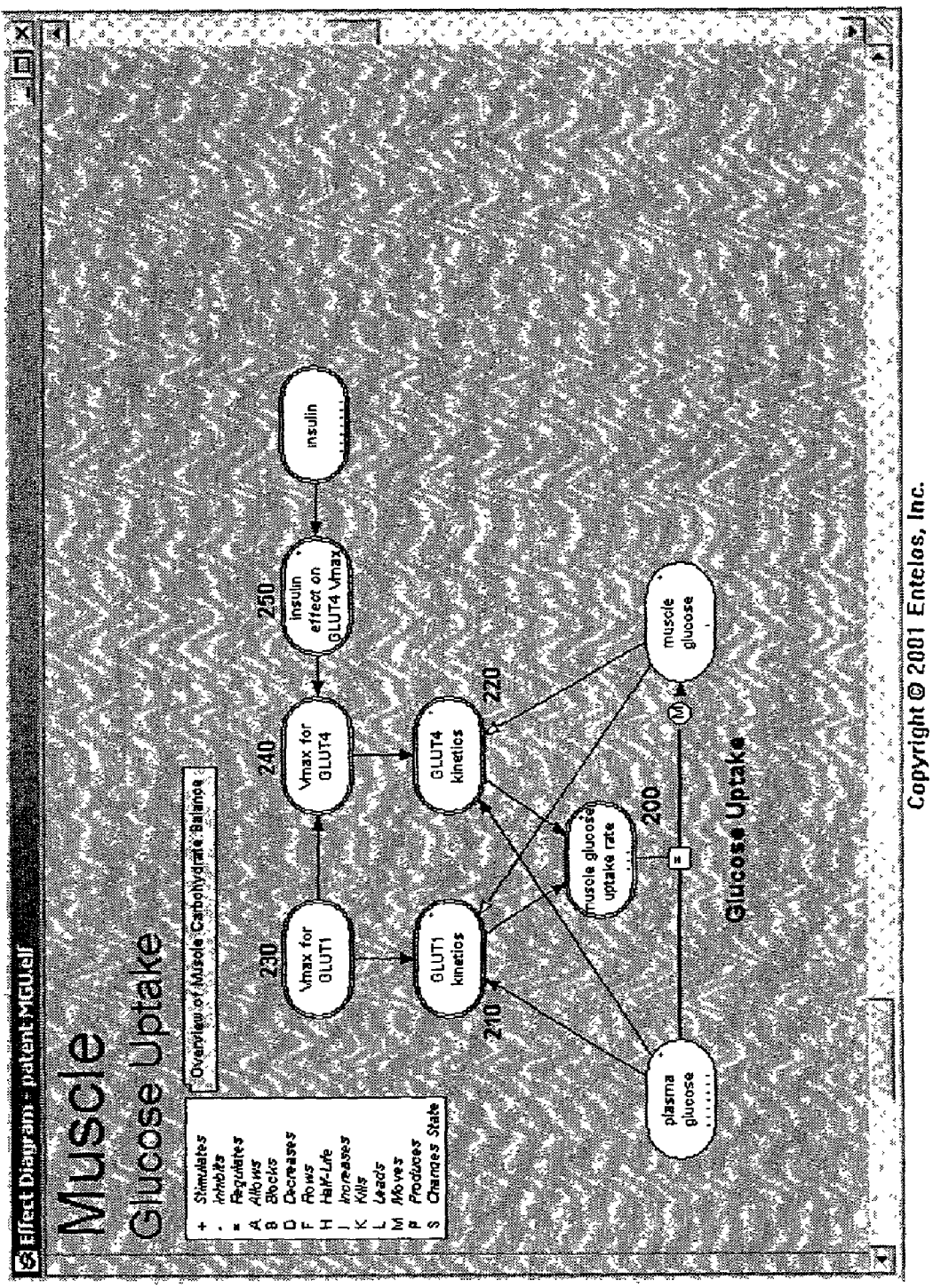
FIG. 11 shows an example of the module diagram for the glucose uptake functions of the muscle, according to an embodiment of the present invention.

FIG. 11 shows an example of a module diagram for the glucose uptake functions of the muscle. Note that for illustration purposes, this module diagram is a rearranged version of the module diagram depicted on pages A9 and A48 in Appendix A. FIG. 11 illustrates the primary factors involved in the muscle glucose uptake, whereas the module depicted on pages A9 and A48 in Appendix A also includes the secondary effects of free fatty acids, activity and exercise.

As FIG. 11 illustrates, the relevant physiological components for the glucose uptake functions of the muscle include: node 200, muscle glucose uptake rate (MGU); node 210, GLUT1 kinetics; node 220, GLUT4 kinetics; node 230, Vmax for GLUT1; node 240, Vmax for GLUT4; and node 250, insulin effect on GLUT4 Vmax. The following discussion relates to deriving the underlying mathematical relationships for these physiological components based on the appropriate publicly available information. Although not discussed herein, the remaining physiological components for the glucose uptake functions can be similarly derived from publicly available information.

Skeletal muscle glucose uptake is a facilitated diffusion process mediated primarily by transmembrane GLUT1 and GLUT4 proteins. Both GLUT1 and GLUT4 obey Michaelis Menten kinetics and the rate of glucose uptake is distributed through GLUT1 and GLUT4 according to their relative membrane content and their kinetic parameters. Following meals, glucose levels in the circulation rise causing increased pancreatic insulin secretion and concomitant elevations in muscle interstitial insulin. Increased insulin leads to a complex signaling cascade finally causing an increased number of transmembrane GLUT4 thereby increasing glucose uptake. These biological processes are well known and are reviewed in (PR Shepherd et al. New Eng. J. Med. 341:248-57, 1999).

Since GLUT1 and GLUT4 obey Michaelis Menton kinetics, the equation for muscle glucose uptake (MGU) has two terms: bi-directional glucose mediated flux by GLUT1 and bidirectional glucose meditated flux by GLUT4:

$$MGU = \frac{V_{max1}K_{m1}(g_e - g_i)}{(K_{m1} + g_e)(K_{m1} + g_i)} + \frac{V_{max4}(i)K_{m4}(g_e - g_i)}{(K_{m4} + g_e)(K_{m4} + g_i)}$$

where, $g_e$ is extracellular glucose concentration; $g_i$ is intracellular glucose concentration; i is interstitial insulin concentration; $K_{m1}$ and $K_{m4}$ are the Michaelis Menten constants for GLUT1 and GLUT4, respectively; $V_{max1}$ is the maximal unidirectional flux for GLUT1 mediated transportation; $V_{max4}(i)$ is the maximal unidirectional flux for GLUT4 mediated transportation as a function of insulin.

Insulin's action on MGU is via an increase in effective GLUT4 number. Consequently, interstitial insulin concentration only enters the computation for MGU through $V_{max4}$. Under basal concentrations of glucose and insulin ($\sim g_e$, $\sim g_i$), the basal MGU, denoted by B, and the ratio of the membrane GLUT4 and the GLUT1 denoted by r; the values for $V_{max1}$ and $V_{max4}$ can be obtained from the following equations $$V_{max1} = \frac{B}{\tilde{g}_e - \tilde{g}_i}\left[\frac{K_{m1}}{(K_{m1} + \tilde{g}_e)(K_{m1} + \tilde{g}_i)} + \frac{rK_{m4}}{(K_{m4} + \tilde{g}_e)(K_{m4} + \tilde{g}_i)}\right]$$

$$V_{max4}(i) = rV_{max1}f(i)$$

The function, f(i), represents the effect of insulin on GLUT4 membrane content. The function f(i) is a sigmoidal function having a value under basal concentrations of f( ) equal to 1. The function f(i) is selected to match steady state MGU during hyperinsulinemic clamps. Some studies, for example, use leg A-V balance technique to measure leg glucose uptake. See, e.g., Dela, F. et al., Am. J. Physiol. 263:E1134-43 (1992). Thus, for each steady state, the MGU can be computed as the LGU divided by the leg fraction of body muscle, f. The leg fraction of body muscle, f, is for example, about ¼ for normal people.

The values for the parameters within equations for $V_{max1}$ and $V_{max4}$ can be obtained, for example, from publicly available information. For example, the normal basal MGU, B, can be assigned a value of 30 mg/min and the normal basal extracellular concentration, $\sim g_e$, can be assigned a value of 90 mg/dl; see, e.g., Dela, F., et al., Am. J. Physiol. 263:E1134-43 (1992). The normal basal intracellular concentration, $\sim g_i$, can be assigned a value of 2 mg/dl; see, e.g., Cline, G. W., et al., NEJM 341:240-6 (1999). The normal basal interstitial insulin concentration, can be assigned a value of 5 iU/ml; see, e.g., Sjostrand, M., et al., Am. J. Physiol. 276:E151-4 (1999). The normal basal ratio of membrane GLUT4 and GLUT1, r, can be assigned a value 4; see, e.g., Marette, A., et al., Am. J. Physiol. 263:C443-52 (1992). The normal Michaelis constant for GLUT1, $K_{m1}$, can be assigned a value of 2 mM or 36 mg/dl; see, e.g., Shepherd, P. R., et al., NEJM 341:248-57 (1999). The normal Michaelis constant for GLUT4, $K_{m4}$, can be assigned a value of 16 mM or 290 mg/dl; see, e.g., Ploug, T., et al., Am. J. Physiol., 264:E270-8 (1993).

Returning to FIG. 11, the above-described equations can be related to nodes 200 through 250 of FIG. 11. More specifically, the mathematical relationships associated with node 200 corresponds to the equation for MGU above, where nodes 210 and 220 correspond to each of the respective GLUT1 and GLUT4 transport terms in the MGU equation. The above-derived equations for $V_{max1}$ and $V_{max4}(i)$ are defined in nodes 230 and 240 respectively. Similarly, the mathematical relationship associated with node 250 (for the insulin effect on GLUT4$_{Vmax}$) corresponds to the above-derived function f(i).

As this example of glucose uptake model component generally illustrates, the components of the Effects Diagram, denoted by state and function nodes, represent mathematical relationships that define the elements of the physiologic system. These mathematical relationships can be developed with the aid of appropriate publicly available information on the relevant physiological components. In other words, the Effect Diagrams indicate that type of mathematical relationships that are modeled within a given model component. The publicly available information can then put into a form that matches the structure of the Effect Diagram. In this way, the structure of the model and can be developed.

Simulation of Biological Attributes of Diabetes

Once a normal physiology has been defined, a user can then select specific defects in the normal physiology by which the physiology for diabetes (e.g., type 2 diabetes) can be modeled and simulated. The term "defect" as used herein means an imperfection, failure, or absence of a biological variable or a biological process associated with a disease state. Diabetes, including type 2 diabetes, is a disease resulting from a heterogenous combination of defects. The computer model can be designed so that a user can simulate defects of varying severity, in isolation or combination, in order to create various diabetic and prediabetic patient types. The model thus can provide several simulated patient types of varying degrees of diabetes.

For example, it is known that skeletal muscle glucose uptake is defective in patients with type 2 diabetes. In spite of having abnormally high basal glucose and insulin levels, people with type 2 diabetes generally have basal rates of MGU comparable to that of normal people without type 2 diabetes. Consequently, type 2 diabetic skeletal muscle is likely insulin resistant. Such a defect can be introduced within the computer model by altering the shape of the function f(i) (representing the effect of insulin on GLUT4 membrane content), as shown in FIG. 12.

Figure 12:
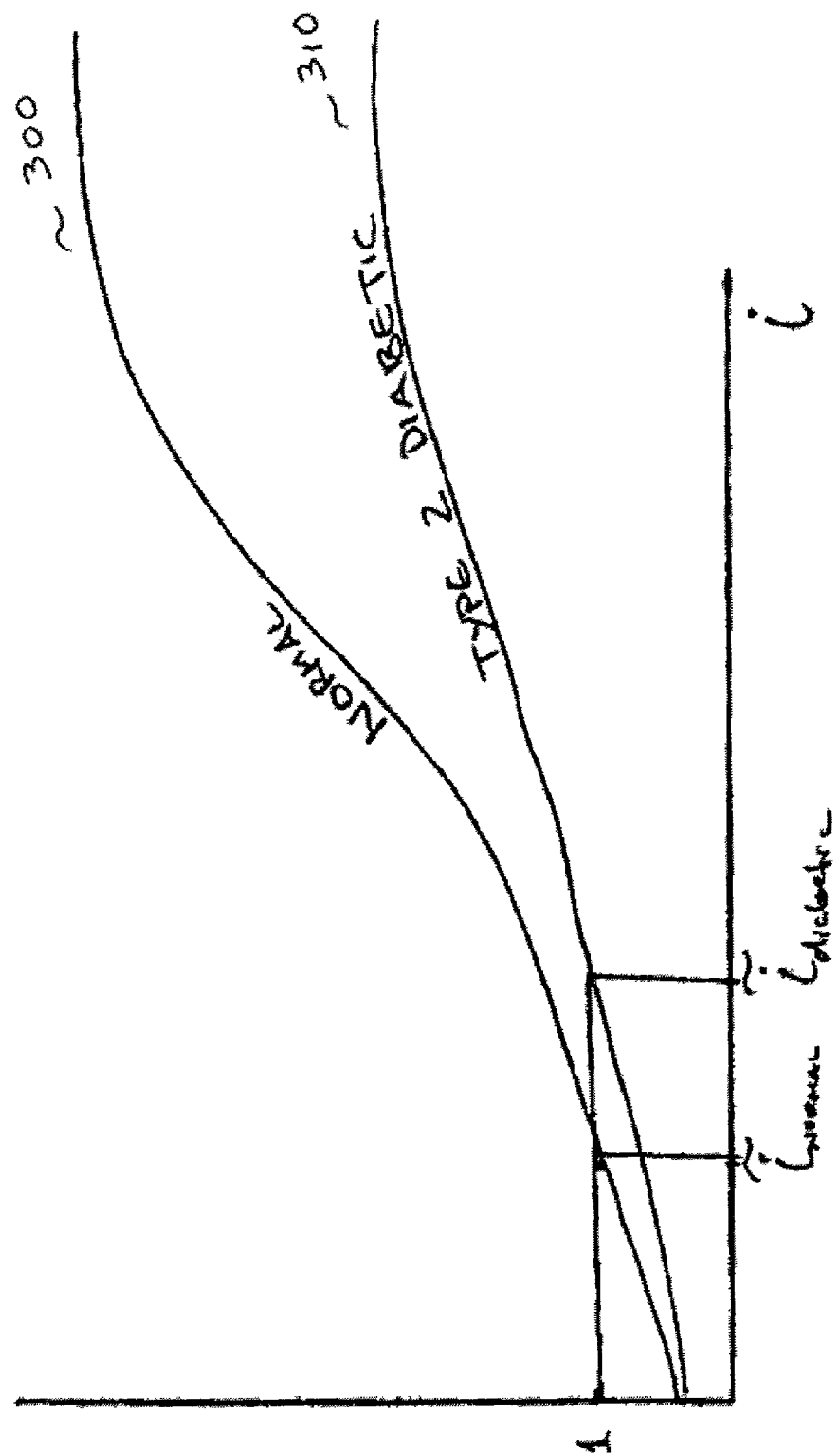
FIG. 12 shows a graph of the function f(i) (representing the effect of insulin on GLUT4 membrane content) versus the interstitial insulin concentration, i.

FIG. 12 shows a graph of the function f(i) (representing the effect of insulin on GLUT4 membrane content) versus the interstitial insulin concentration, i. FIG. 12 shows curve 300 for a normal person and curve 310 for a person with type 2 diabetes. The curves differ in that insulin has less effect in the case of curve 310 compared to curve 300 thereby representing insulin resistance known to occur in the type 2 diabetic skeletal muscle. Mathematically, the curves 300 and 310 differ by parameter values that define the shape of the curve.

Figure 5:
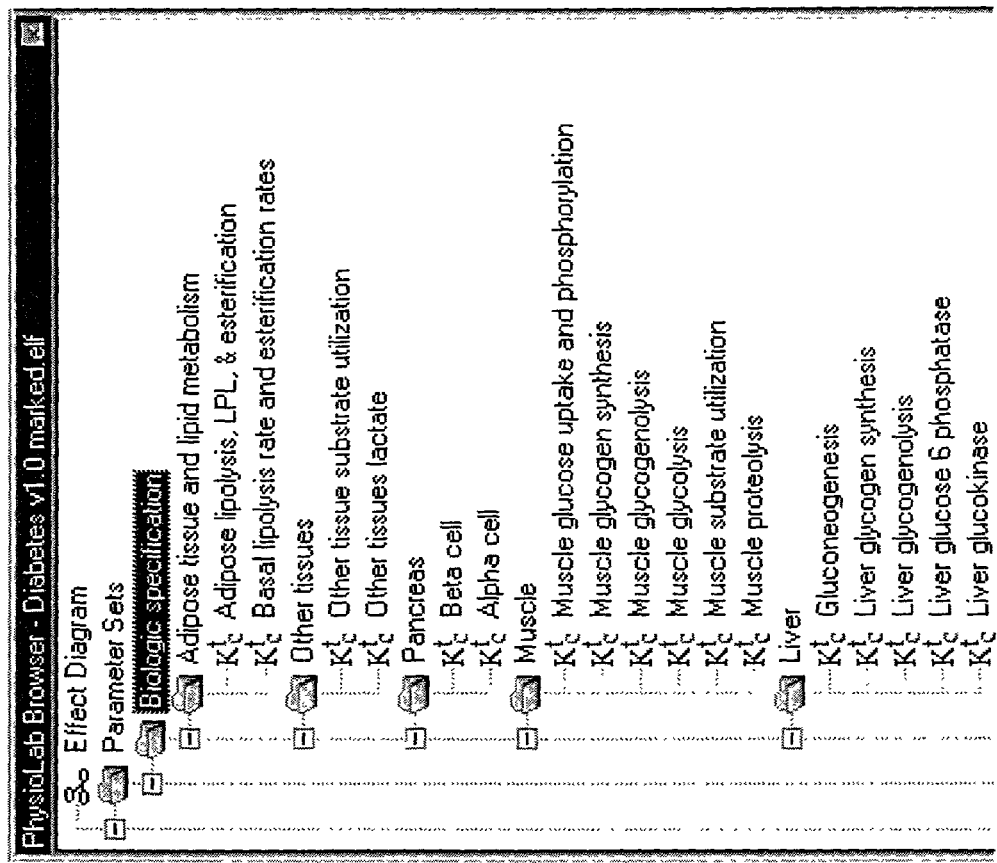
FIG. 5 illustrates an example of a browser screen that lists, by biological areas, lesions (or defects) for type 2 diabetes that can be modeled.

In one embodiment, a user can select the specific defects (relevant for diabetes) from a browser screen. FIG. 5 illustrates an example of a browser screen that lists, by biological areas, defect indicators associated with defects for diabetes that can be modeled. The term "defect indicators" relates to the display, for example, via the browser screen of defects relevant for diabetes. The user can select a particular defect indicator, for example, by a mouse click or keyboard selection.

For example, FIG. 5 illustrates various biologic areas such as adipose issue and lipid metabolism, other tissues, pancreas, muscle and liver. For each of the biologic areas, the browser illustrated in FIG. 5 lists various defect indicators associated with defects that can be specified for that biologic area. To define a specific diabetes physiology, a user can select specific defect indicators to indicate defects for modeling and then can customize the parameters for that defect.

For each selected defect, the user can then specify the values for parameters associated with physiology of the various elements of the physiology system. FIG. 6 illustrates an example of a user-interface screen for the parameter set of a type 2 diabetes defect. More specifically, FIG. 6 illustrates the user-interface screen for the parameter set to modify the physiology of muscle glucose uptake and phosphorylation. In one embodiment of the computer model, a parameter set is based on the method described in U.S. Pat. No. 6,069,629, entitled "Method of providing access to object parameters within a simulation model," the disclosure of which is incorporated herein by reference.

As FIG. 6 illustrates, the user-interface screen allows a user to specify alternative value sets to the baseline value sets associated with a normal physiology. The baseline value sets and the alternative value sets associated with the various type 2 diabetes defects can be based on, for example, real physiological values relied upon from the related literature. In one embodiment of the computer model, the user can specify alternative value sets according to the method described in U.S. Pat. No. 6,078,739, entitled "Managing objects and parameter values associated with the objects within a simulation model," the disclosure of which is incorporated herein by reference. Although FIG. 6 only shows a single example of a user-interface screen for a parameter set of a type 2 diabetes defect, many other parameters sets are possible relating to other various physiological elements.

Thus, a user can select the defect relating to insulin resistance of the type 2 diabetic skeletal muscle through a browser screen described above in reference to FIG. 5. In other words, the browser screen that lists defects for diabetes can include an entry for insulin resistance of the type 2 diabetic skeletal muscle. When a user selects such an entry, curve 300 (for a normal person without type 2 diabetes) is substituted within the computer model with curve 310 (for a person with type 2 diabetes). Of course, when a user deselects such an entry curve 310 is substituted with curve 300.

In addition to the defects listed above, parameter sets and value sets can be created for processes not listed above. Many systems not involved in creating the pathophysiology of diabetes are nevertheless affected by those changes (e.g. gastric emptying). Some of these systems can use alternate parameterization to that representing a normal individual.

As described above, simulation of the biological attributes of diabetes is done in a cross-sectional manner, where defects are introduced statically via parameter changes. Alternatively, the computer model can represent the progression of diabetes. For example, one means of including diabetes progression in the computer model can involve replacing defect parameters, formerly fixed at a particular value, with biological variables (defect variables) that evolve over time. The time-evolution of the new defect variables can be specified either as a direct function of time, an algebraic function of other biological or defect variables, or via a dynamical systems equation such as an ordinary differential equation. As the defect variables change over time, the progression of the disease can be modeled. For example, the parameters that specify the insulin sensitivity of skeletal muscle GLUT4 translocation to can be made to decrease over time. The depiction of progression of diabetes in the computer model can be used to study, for example, the progress of a normal human to an obese patient to an obese-insulin-resistant patient to ultimately a diabetic patient. Also, pharmaceutical treatments can be explored to prevent or reverse the progression of diabetes.

Numerical solution of the Mathematical Equations and Outputs of the Computer Model Since the Effect Diagram defines a set of ordinary differential equations as described above, once the initial values of the biological variables are specified, along with the values for the model parameters, the equations can be solved numerically by a computer using standard algorithms. See, for example, William H. Press et al. Numerical Recipes in C: The Art of Scientific Computing, 2nd edition (January 1993) Cambridge Univ. Press. As illustrated above in the muscle glucose uptake example, one can derive equations, obtain initial conditions, and estimate parameter values from the public literature. Likewise, other initial conditions and parameter values can be estimated under different conditions and can be used to simulate the time evolution of the biological state.

Note that parameters can also be used to specify stimuli and environmental factors as well as intrinsic biological properties. For example, model parameters can be chosen to simulate in vivo experimental protocols including: pancreatic clamps; infusions of glucose, insulin, glucagon, somatostatin, and FFA; intravenous glucose tolerance test (IVGTT); oral glucose tolerance test (OGTT); and insulin secretion experiments demonstrating acute and steady state insulin response to plasma glucose steps. Furthermore, model parameters can be chosen to represent various environmental changes such as diets with different nutrient compositions, as well as various levels of physical activity and exercise.

The time evolution of all biological variables in the model can be obtained, for example, as a result of the numerical simulation. Thus, the computer model can provide, for example, outputs including any biological variable or function of one or more biological variables. The outputs are useful for interpreting the results of simulations performed using the computer model. Since the computer model can be used to simulate various experimental tests (e.g. glucose-insulin clamps, glucose tolerance tests, etc.), and clinical measurements (e.g. % HbA1c, fructosamine), the model outputs can be compared directly with the results of such experimental and clinical tests.

The model can be configured so as to compute many outputs including: biological variables like plasma glucose, insulin, C-peptide, FFA, triglycerides, lactate, glycerol, amino acids, glucagon, epinephrine, muscle glycogen, liver glycogen; body weight and body mass index; respiratory quotient and other measures of substrate utilization; clinical indices of long-term hyperglycemia including glycosylated hemoglobin (% HbA1c) and fructosamine; substrate and energy balances; as well as metabolic fluxes including muscle glucose uptake, hepatic glucose output, glucose disposal rate, lipolysis rate, glycogen synthesis, and glycogenolysis rates. The outputs can also be presented in several commonly used units.

Figure 7:
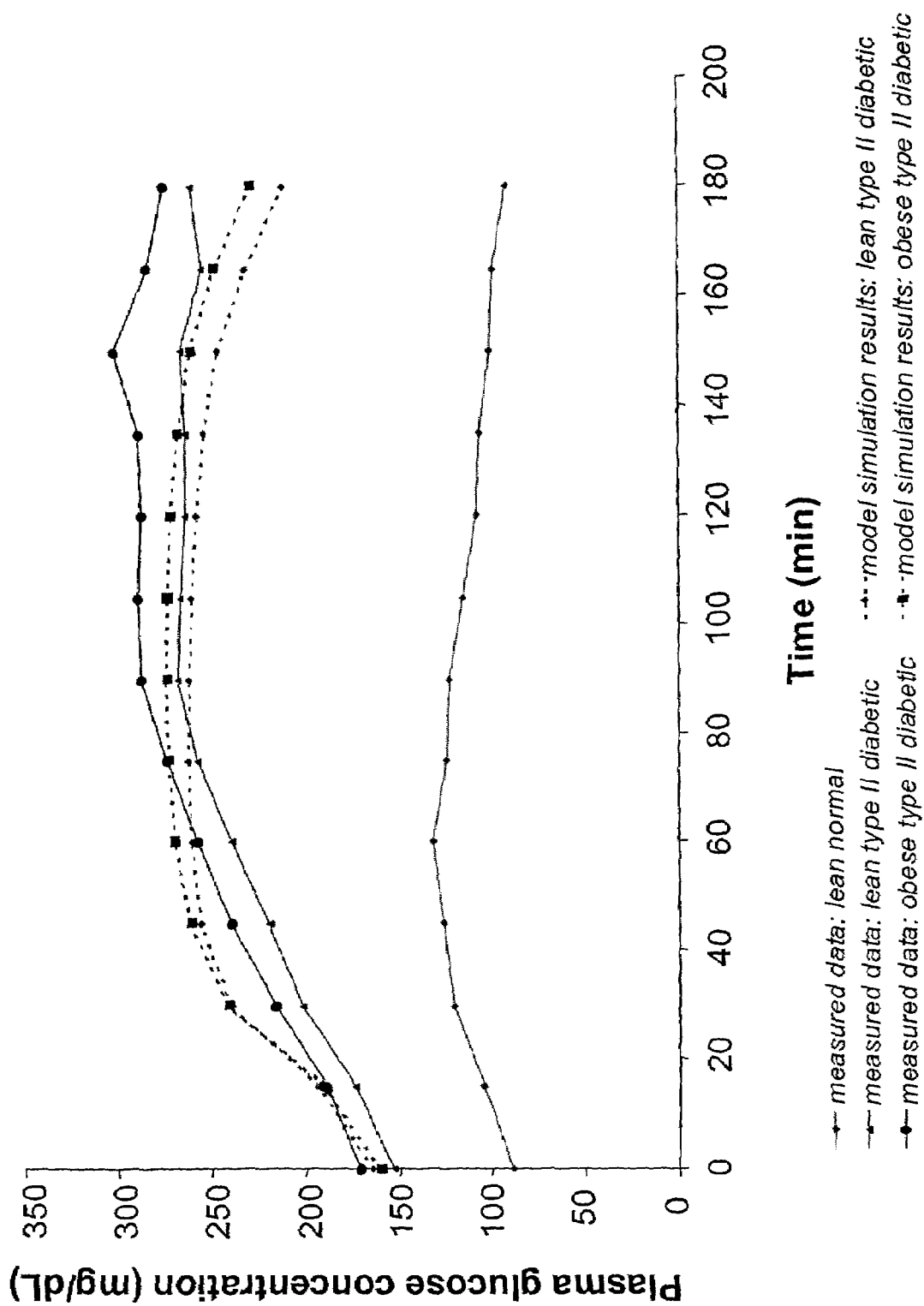
FIG. 7 illustrates a graph comparing the model results against measured data for an oral glucose tolerance test.
Figure 8A:
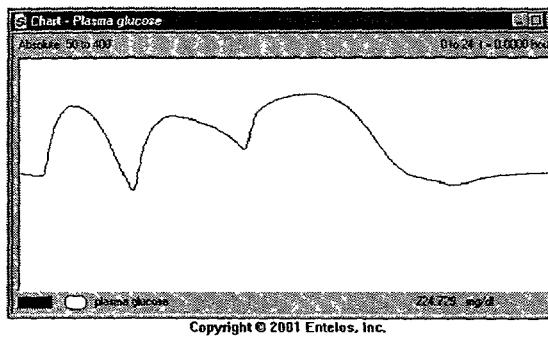
FIGS. 8A-H graphically illustrate an example of the model results for a 24-hour simulation of an obese diabetic patient eating 3 typical meals.
Figure 8B:
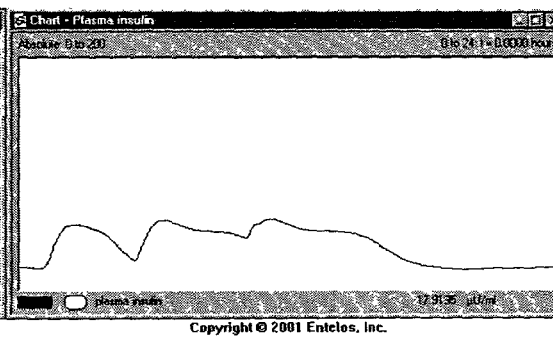
Figure 8C:
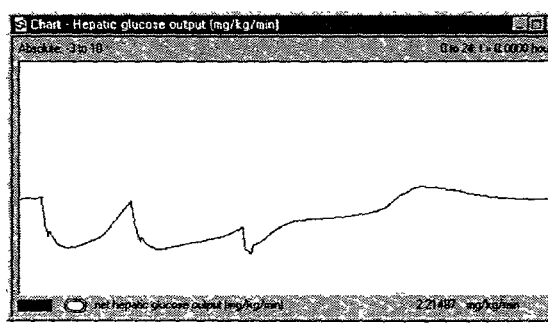
Figure 8D:
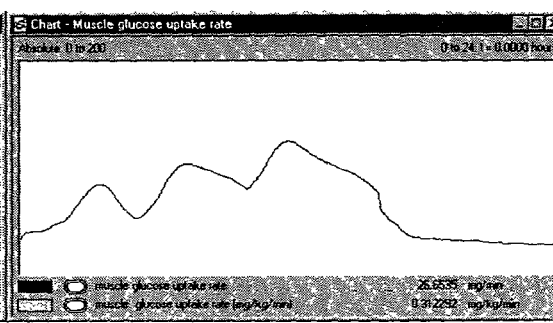
Figure 8E:
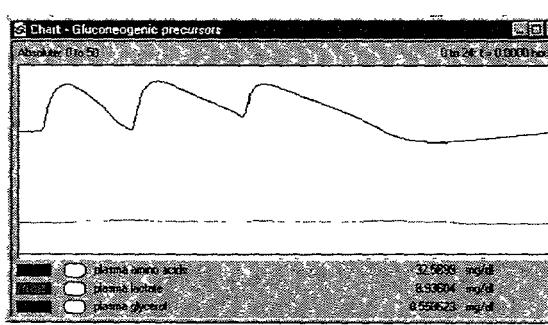
Figure 8F:
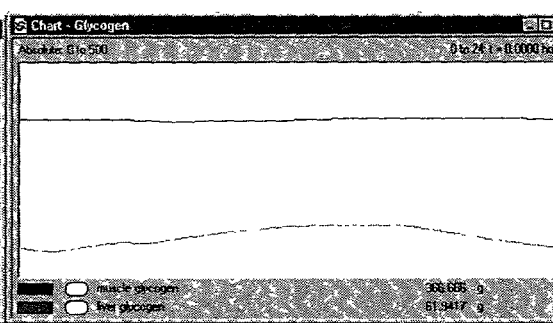
Figure 8G:
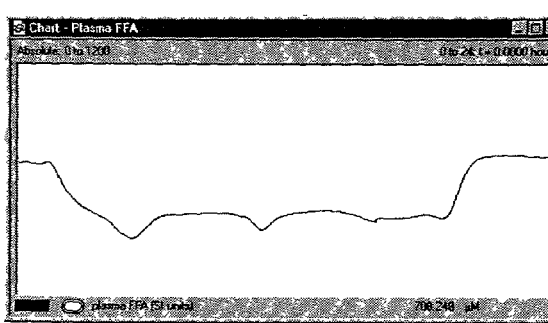
Figure 8H:
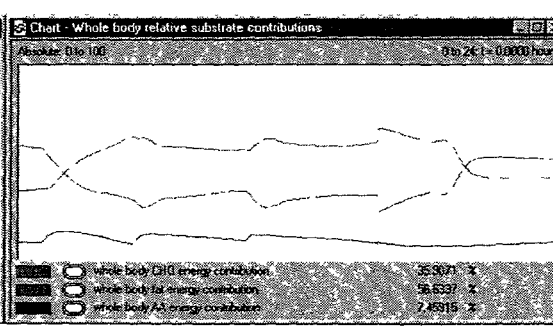
Figure 9:
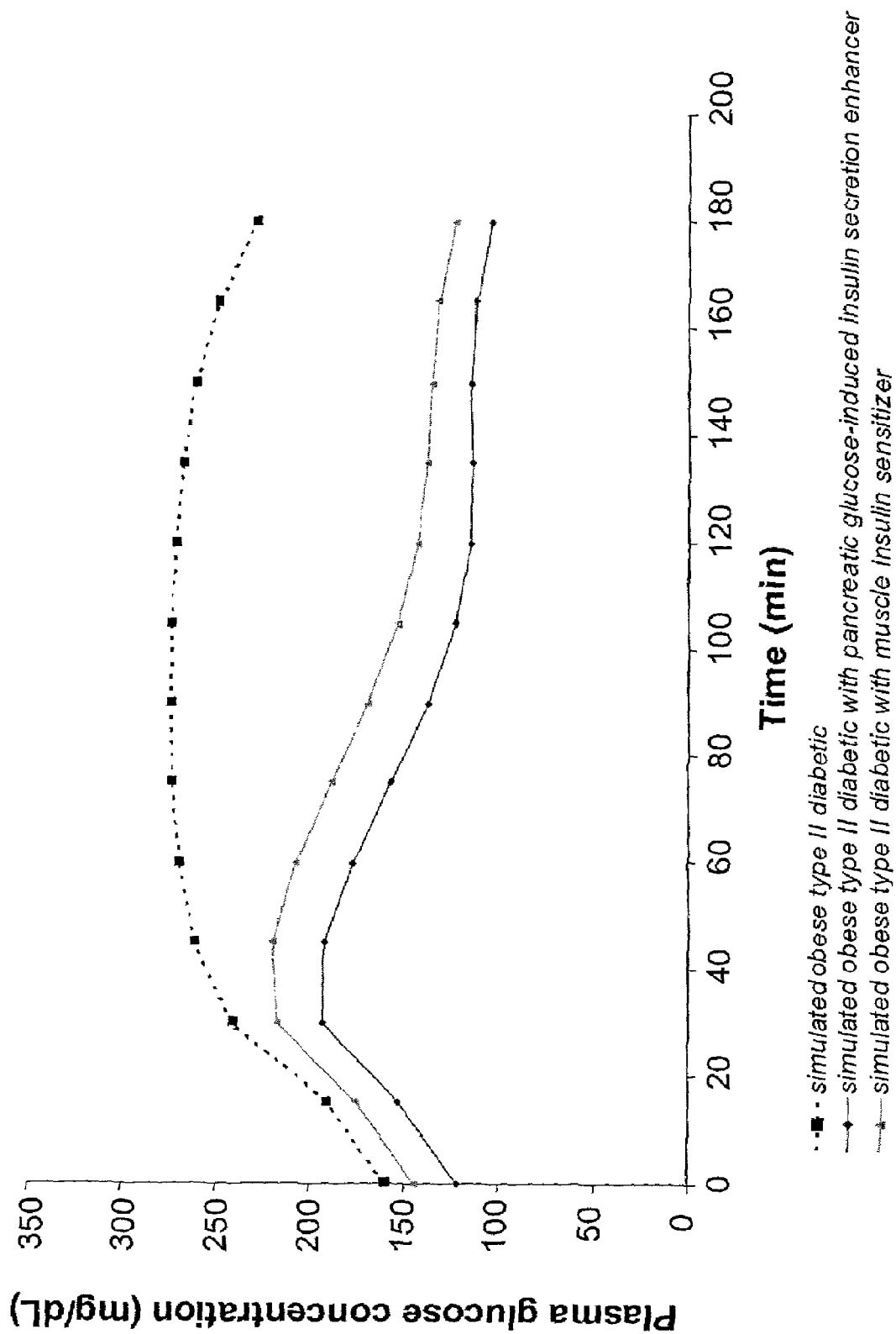
FIG. 9 illustrates a graph showing an example of the model results for an oral glucose tolerance test.

FIGS. 7 through 9 provide examples of outputs of the computer model under various conditions. FIG. 7 illustrates a graph comparing the model results against measured data for an oral glucose tolerance test. An oral glucose tolerance test was simulated based on the metabolic characteristics of a simulated lean control, simulated lean type 2 diabetic and a simulated obese type 2 diabetic. The simulation time for the patients considered was two years. The measurements were made at a time that corresponds to an overnight-fasted individual shortly after waking. The model results were compared to measured data from Group et al., *J. Clin. Endocrin. Metab.*, 72:96-107 (1991). The results shown in FIG. 7 demonstrate the ability of the model to simulate accurately oral glucose tolerance tests in lean and obese type 2 diabetic patients as well as controls.

FIGS. 8A-H illustrate an example of model outputs for a 24-hour simulation of an obese diabetic patient consuming three meals (55% carbohydrates, 30% fat, 15% protein). While all model biological variables are simulated, the results are shown for circulating levels of glucose (FIG. 8A), insulin (FIG. 8B), free fatty acids (FFA) (FIG. 8G), gluconeogenic precursors (FIG. 8E): lactate, amino acids, and glycerol, as well as the dynamics of processes like hepatic glucose output (FIG. 8C), muscle glucose uptake (FIG. 8D), relative contributions of whole-body carbohydrate, fat and amino acid oxidation (FIG. 8H). The expansion and depletion of the muscle and liver glycogen storage pools are also shown (FIG. 8F). The simulated responses of these and other biological variables are in agreement with data measured in obese type 2 diabetic patients. For example, the glucose and insulin results can be compared with data presented in Palonsky et al., *N. Engl. J Med.*, 318(19): 1231-1239 (1988).

Note that the computer model can simulate therapeutic treatments. For example, a therapy can be modeled in a static manner by modifying the parameter set of the appropriate tissue(s) to represent the affect of the treatment on that tissue(s). Alternatively, therapeutic treatments can be modeled in a dynamic manner by allowing the user to specify the delivery of a treatment(s), for example, in a time-varying (and/or periodic) manner. To do this, the computer model includes pharmacokinetic representations of various therapeutic classes (e.g., injectable insulins, insulin secretion enhancers, and/or insulin sensitizers) and how these therapeutic treatments can interact with the various tissues in a dynamic manner.

FIG. 9 illustrates a graph showing an example of the model results for an oral glucose tolerance test. The graph shown in FIG. 9 is based on a simulated obese type 2 diabetic patient following treatment with muscle insulin sensitizer or pancreatic glucose-induced insulin secretion enhancer. An oral glucose tolerance test was simulated in obese diabetic patients with or without two theoretical interventions. One simulated patient received a muscle insulin sensitizer, while the other received a pancreatic glucose-induced insulin secretion enhancer. Note that the simulated post-prandial glucose excursions were considerably lower in treated patients as compare to simulated diabetic controls, indicating the potential effectiveness of these theoretical agents.

The computer model allows a user to simulate a variety of diabetic and pre-diabetic patients by combining defects in various combinations where those defects have various degrees of severity. This can allow a more effective modeling of the type 2 diabetes population, which is heterogeneous. In other words, diabetes can have a wide range of impairment, some of which can be distinguished clinically. Furthermore, clinically similar diabetics can have differences in their physiology that can be modeled by using different defect combinations. Consequently, the computer model can be used to better understand and classify the real patient population for type 2 diabetes and to anticipate what drug target may work best on certain classes of patients, thereby improving the design of clinical trials and target prioritization.

In sum, the computer model can enable a researcher, for example, to: (1) simulate the dynamics of hyperglycemia in type 2 diabetes, (2) visualize key metabolic pathways and the feedback within and between these pathways, (3) gain a better understanding of the metabolism and physiology of type 2 diabetes, (4) explore and test hypotheses about type 2 diabetes and normal metabolisms, (5) identify and prioritize potential therapeutic targets, (6) identify patient types and their responses to various interventions, and (7) organize knowledge and data that relate to type 2 diabetes.

Validation of the Computer Model

Typically, the computer model should behave similar to the biological state they represent as closely as possible. Thus, the responses of the computer model can be validated against biological responses. The computer model can be validated, for example, with in vitro and in vivo data obtained using reference patterns of the biological state being modeled. Methods for validation of computer models are described in co-pending application entitled "Developing, analyzing and validating a computer-based model," filed on May 17, 2001, Application No. 60/292,175.

The diabetic patients produced with the diabetes computer model can be validated by running the following tests on the computer model: overnight-fasted concentrations of glucose, post-prandial concentrations of glucose, metabolic response to 24 hour fast, oral glucose tolerance test (OGTT), intravenous glucose tolerance test (IVGTT), euglycemic-hyperinsulinemic clamp, hyperglycemic clamp, normal everyday behaviour. The computer model of diabetes can be considered a valid model if the simulated biological attribute obtained is substantially consistent with a corresponding biological attribute obtained from a cellular or whole animal model of diabetes or human diabetic patient. The term "substantially consistent" as used herein does not mean that the biological attributes have to be identical. The term "substantially consistent" can be, for example, relative changes that are similar but with different absolute values. FIG. 7 shows examples of model simulation results that are "substantially consistent" with the corresponding biological attributes obtained from glucose following a glucose tolerance test. Table 1 lists the values for the responses that can be evaluated in a non-diabetic and diabetic following over night fasting. One means of validation of a diabetes computer model would be to verify that the model produces results substantially consistent with those present in Table 1 for a non-diabetic and a diabetic. As the understanding of diabetes evolves in the art, the responses against which the computer model is validated can be modified.

TABLE 1

| Response [Overnight fasted] | Value for Non-diabetic | Value for Diabetic |
| --- | --- | --- |
| Plasma glucose | 90 mg/dl | 126-300 mg/dll |
| Plasma insulin | 10 µU/ml | 5-30 µU/ml |
| Plasma FFA | 500 µM | 500-900 µM |
| Plasma lactate | 8 mg/dl | 8-10 mg/dl |
| Plasma glycerol | 0.5 mg/dl | 0.65 mg/dll |
| Plasma amino acids | 32 mg/dl | 32 mg/dl |
| Plasma triglycerides | 100 mg/dl | 150-1000 mg/dl |
| Plasma glucagon | 75 mg/dl | 80 mg/dl |
| Muscle glycogen | 400 g | 200 g |
| Liver glycogen | 72 g | 40 g |
| Muscle glucose uptake rate | 28 mg/min | 28-35 mg/min |
| Hepatic glucose output | 140 mg/min | 155-275 mg/min |

Table 2 lists the values for post-prandial responses that can be evaluated in a non-diabetic and a diabetic. Another means of validation of a diabetes computer model would be to verify that the model produces results substantially consistent with those present in Table 2 for a non-diabetic and a diabetic. As the understanding of diabetes evolves in the art, the responses against which the computer model is validated can be modified.

TABLE 2

| Response [Post-prandial] | Value for Non-diabetic | Value for Diabetic |
| --- | --- | --- |
| Plasma glucose | Increase 40% | Increase 50% |
| Plasma insulin | Increase 490% | Increase 240% |
| Plasma FFA | Decrease 38% | Decrease 50% |
| Plasma lactate | Increase 10% | Increase 20% |

Table 3 lists other tests that can be used to obtain responses in a non-diabetic and a diabetic. Yet another means of validation of a diabetes computer model would be to verify that the model produces results substantially consistent with those present in Table 3 for a non-diabetic and a diabetic. As the understanding of diabetes evolves in the art, the responses against which the computer model is validated can be modified.

TABLE 3

| Response [Other tests] | Value for Non-diabetic | Value for Diabetic |
| --- | --- | --- |
| 2 hr OGTT glucose value | 98-120 mg/dl | 230-350 mg/dl |
| Euglycemic, hyperinsulinemic clamp glucose disposal rate | 7.2 mg/kg LBM/min | 3,42 mg/kg LBM/min |
| Hyperglycemic clamp insulin response | $1^{st}$ phase, $2^{nd}$ phase | $2^{nd}$ phase only |

While various embodiments of the invention have been described above, it should be understood that they have been presented by way of example only, and not limitation. Thus, the breadth and scope of the present invention should not be limited by any of the above-described embodiments, but should be defined only in accordance with the following claims and their equivalents.

The previous description of the embodiments is provided to enable any person skilled in the art to make or use the invention. While the invention has been particularly shown and described with reference to embodiments thereof, it will be understood by those skilled in the art that various changes in form and details may be made therein without departing from the spirit and scope of the invention.

For example, although a certain embodiment of a computer system is described above, other embodiments are possible. Such computer system embodiments can be, for example, a networked or distributed computer system.

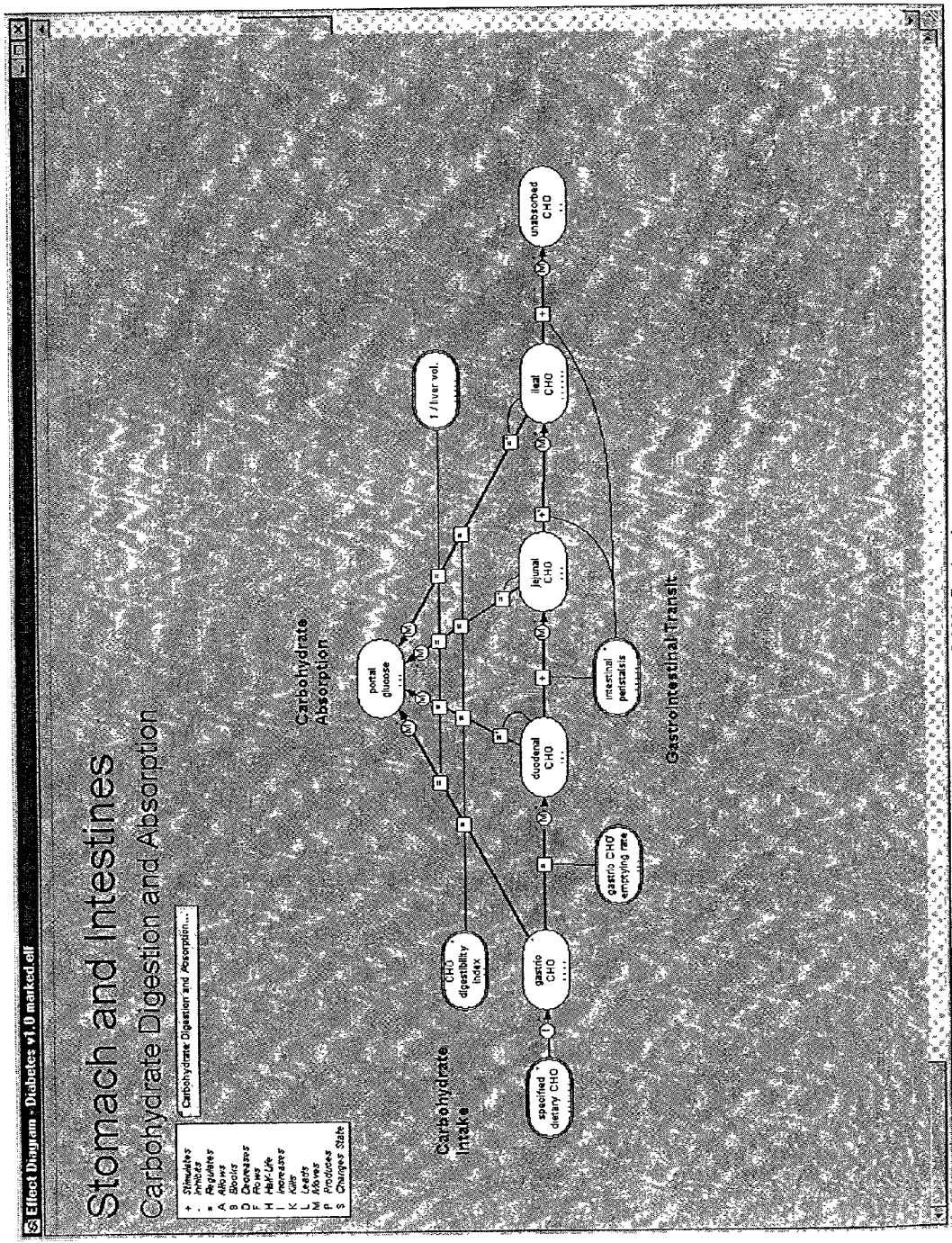

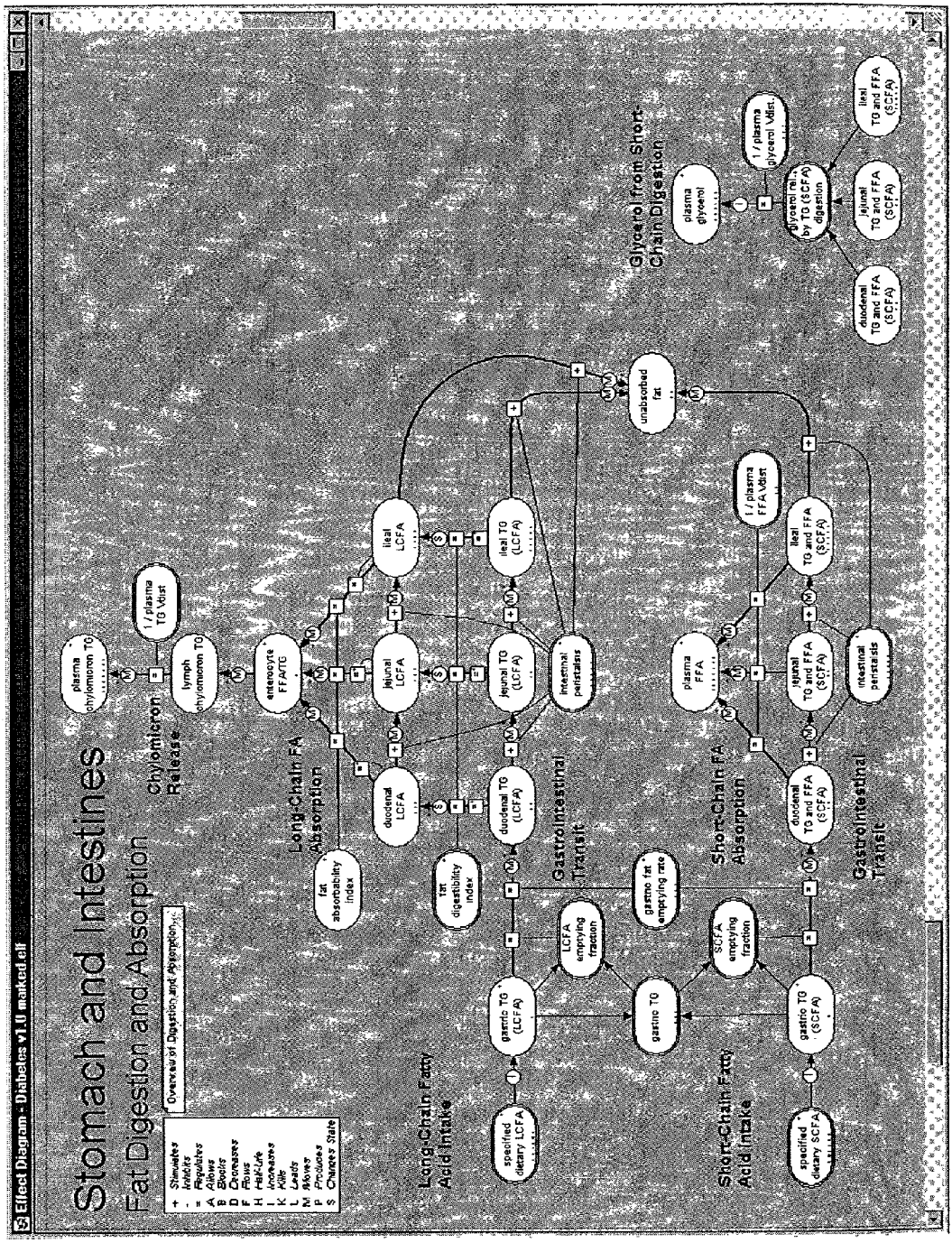

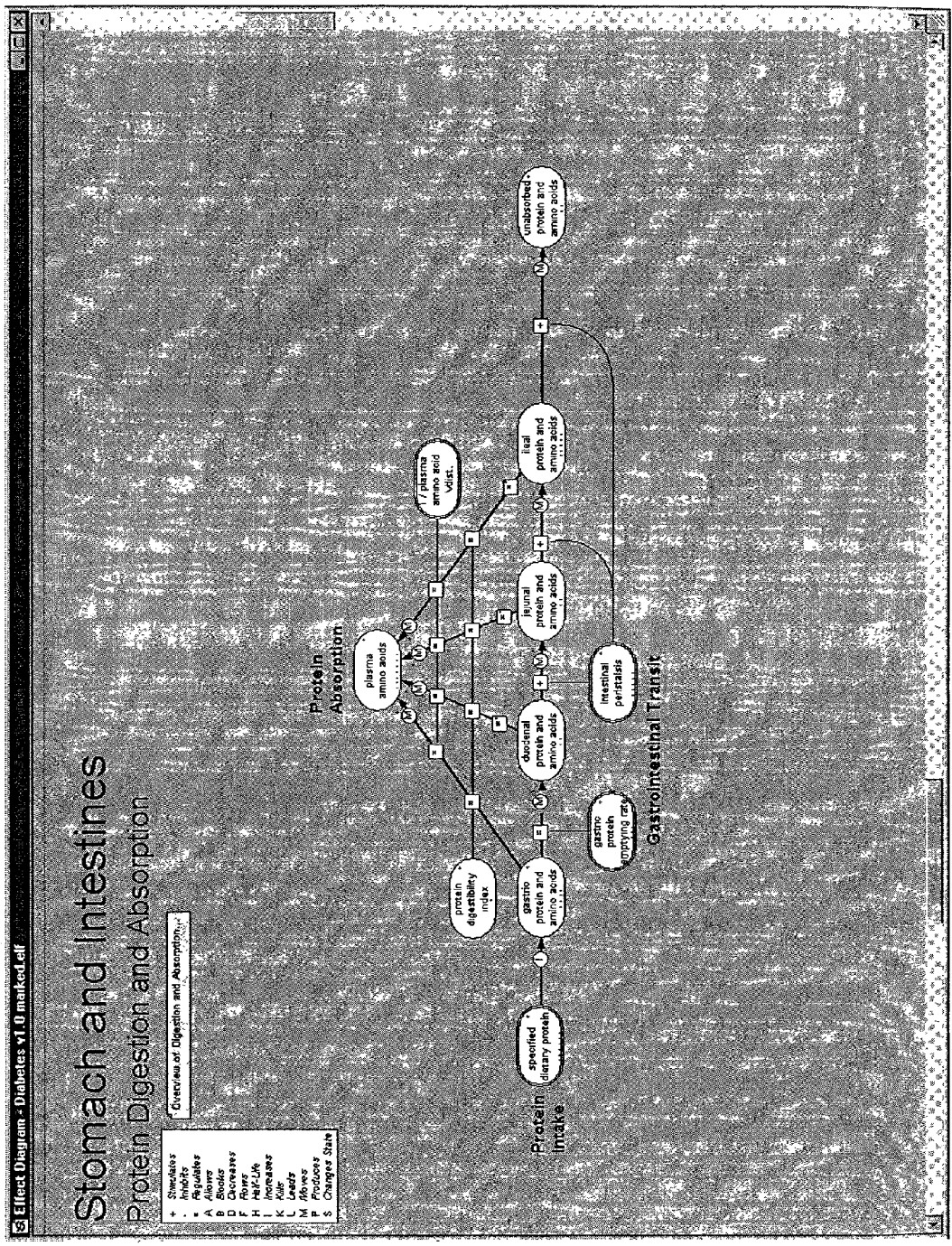

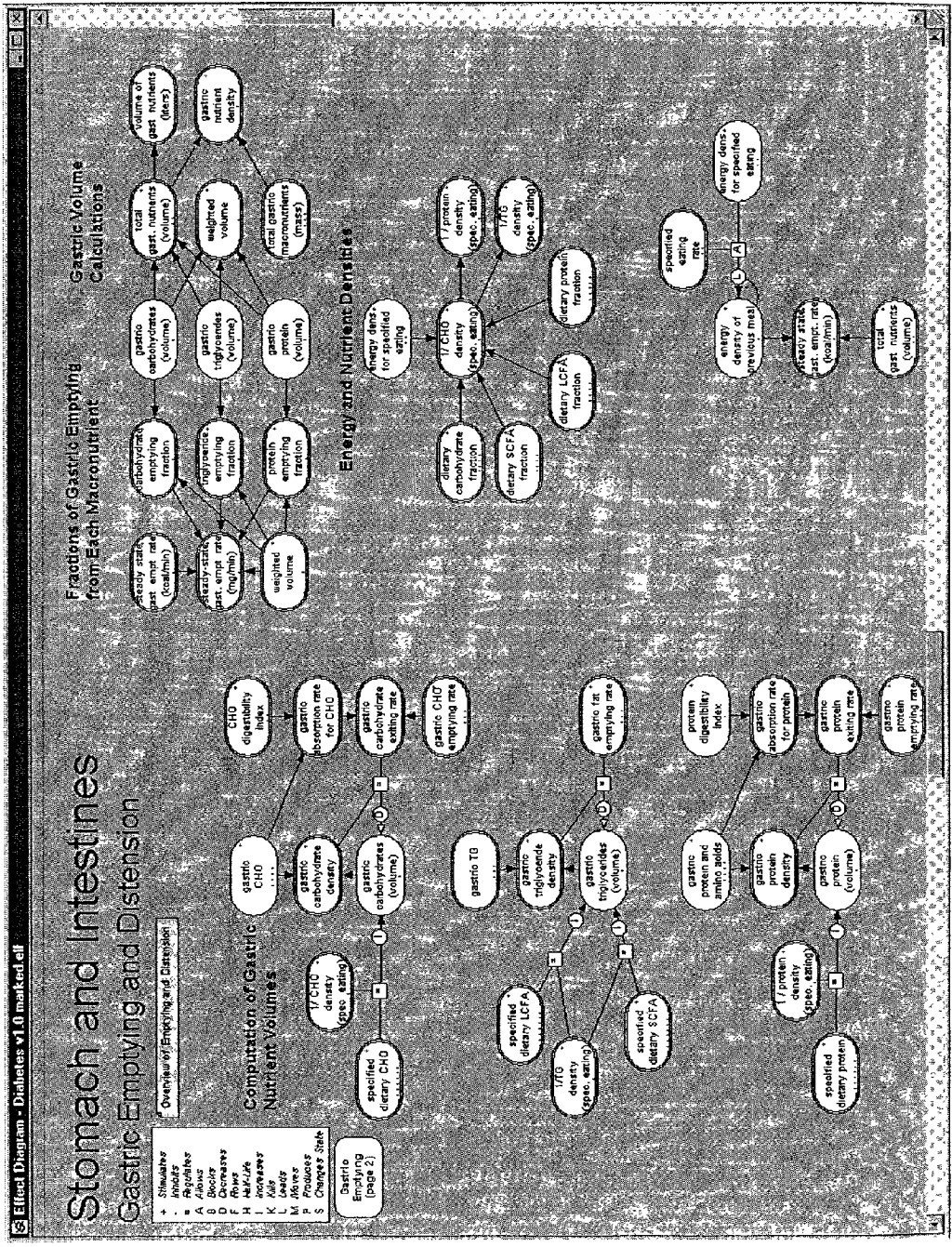

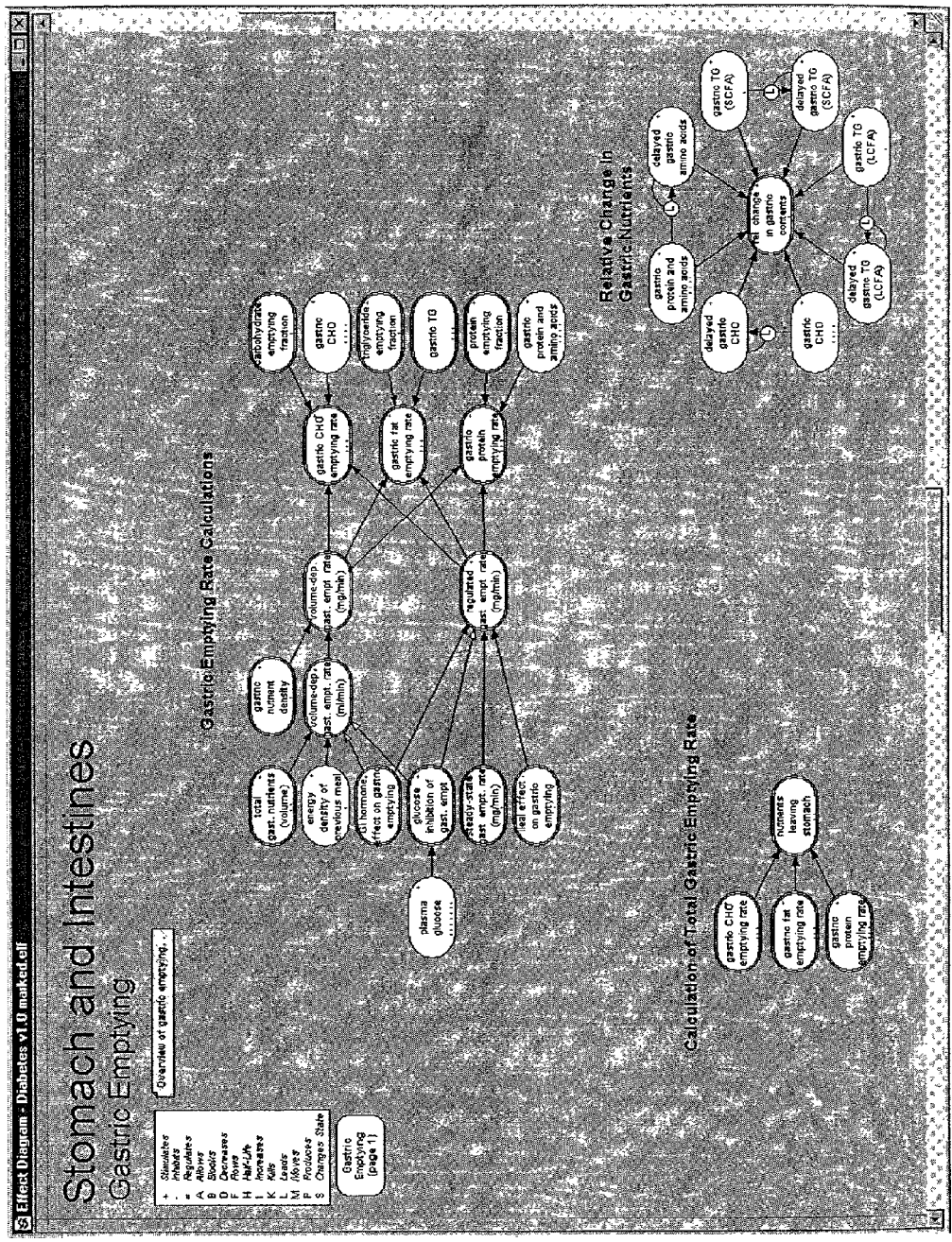

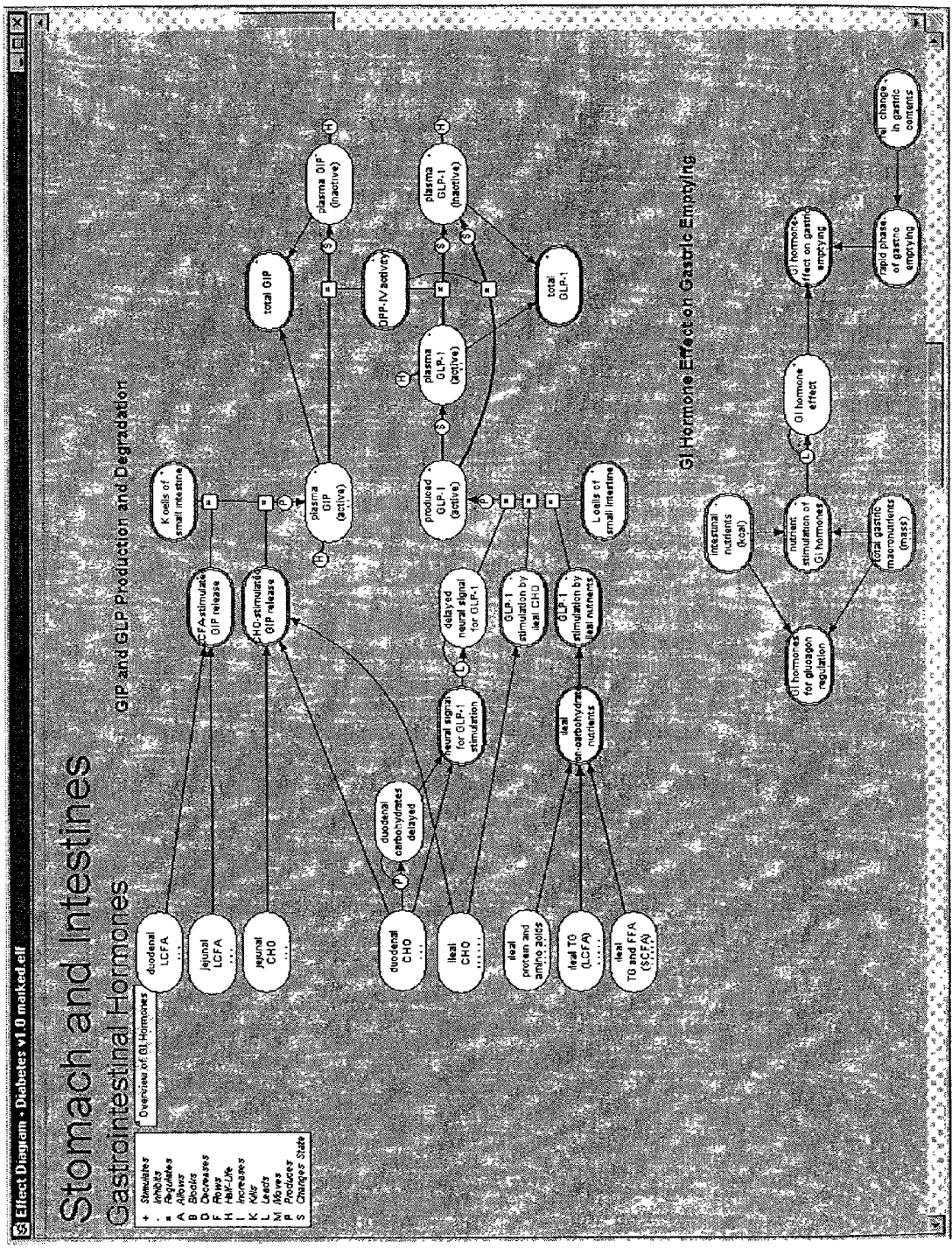

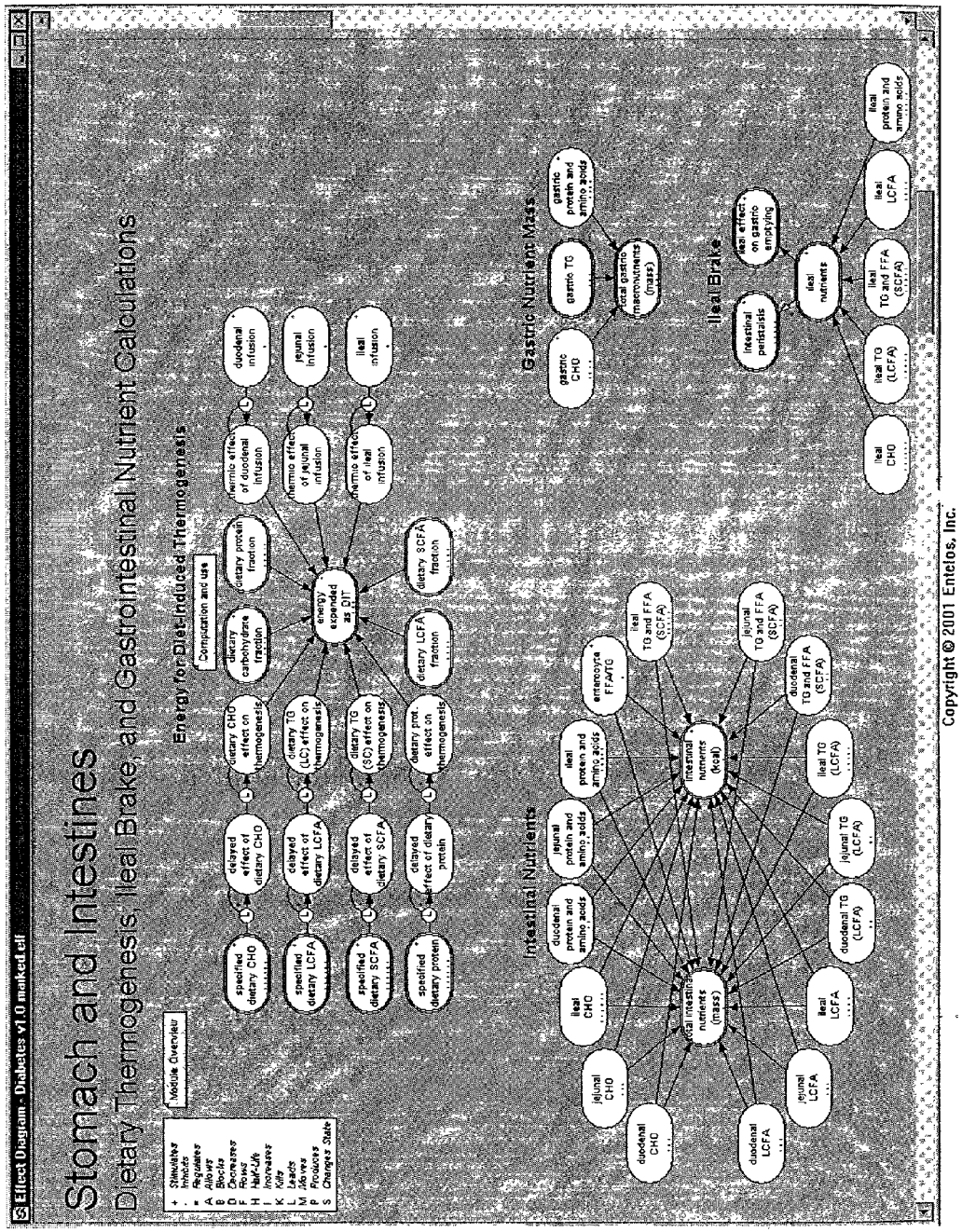

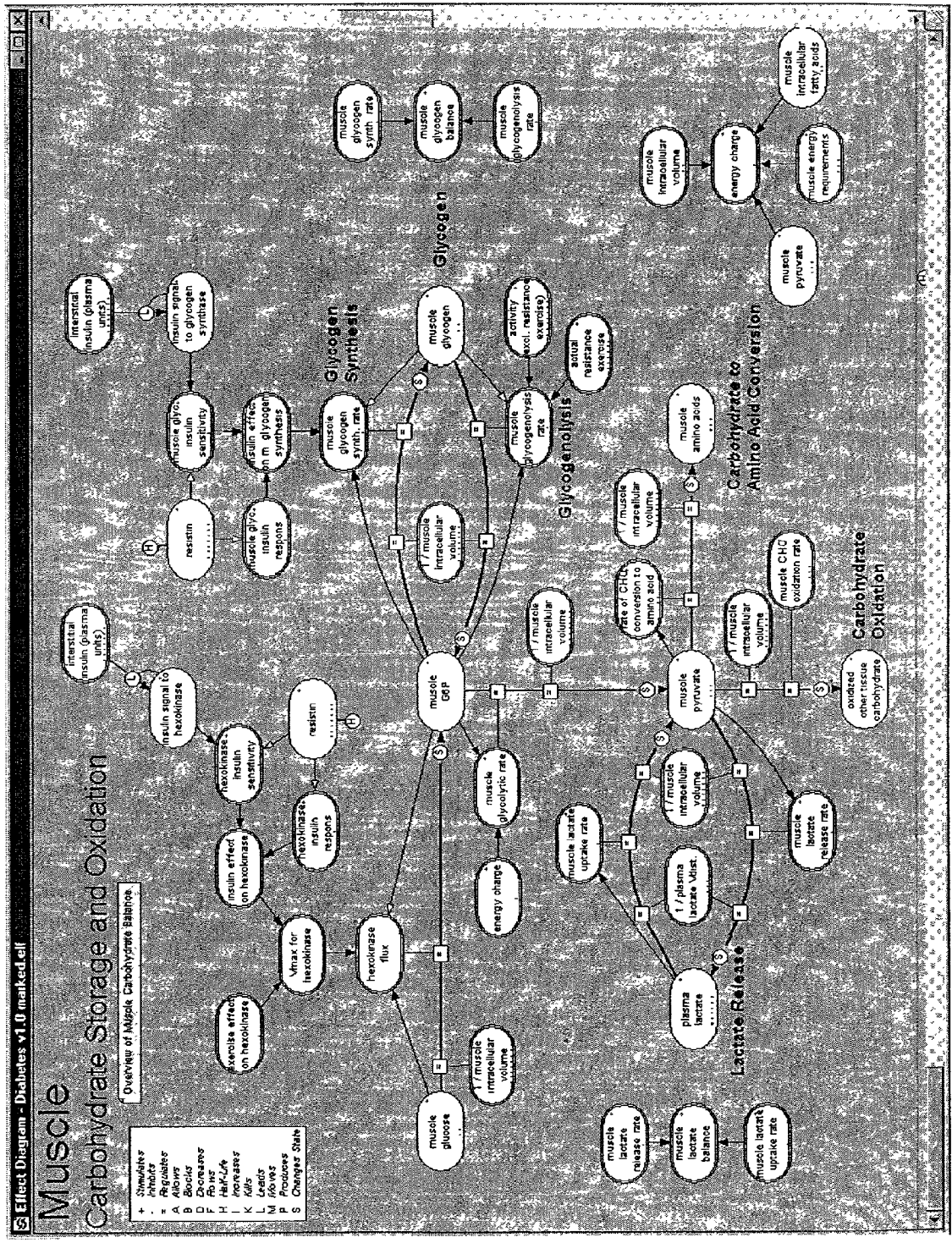

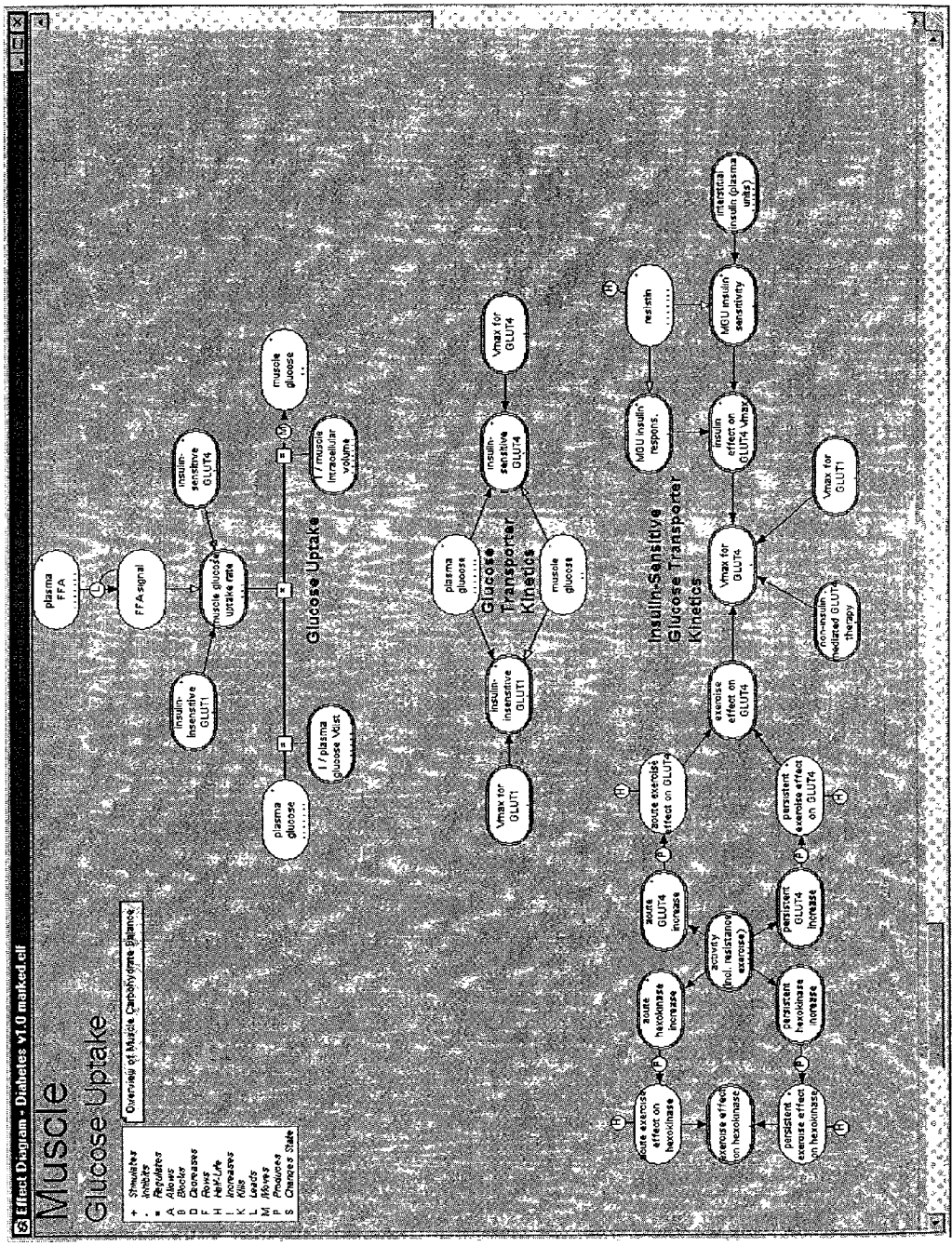

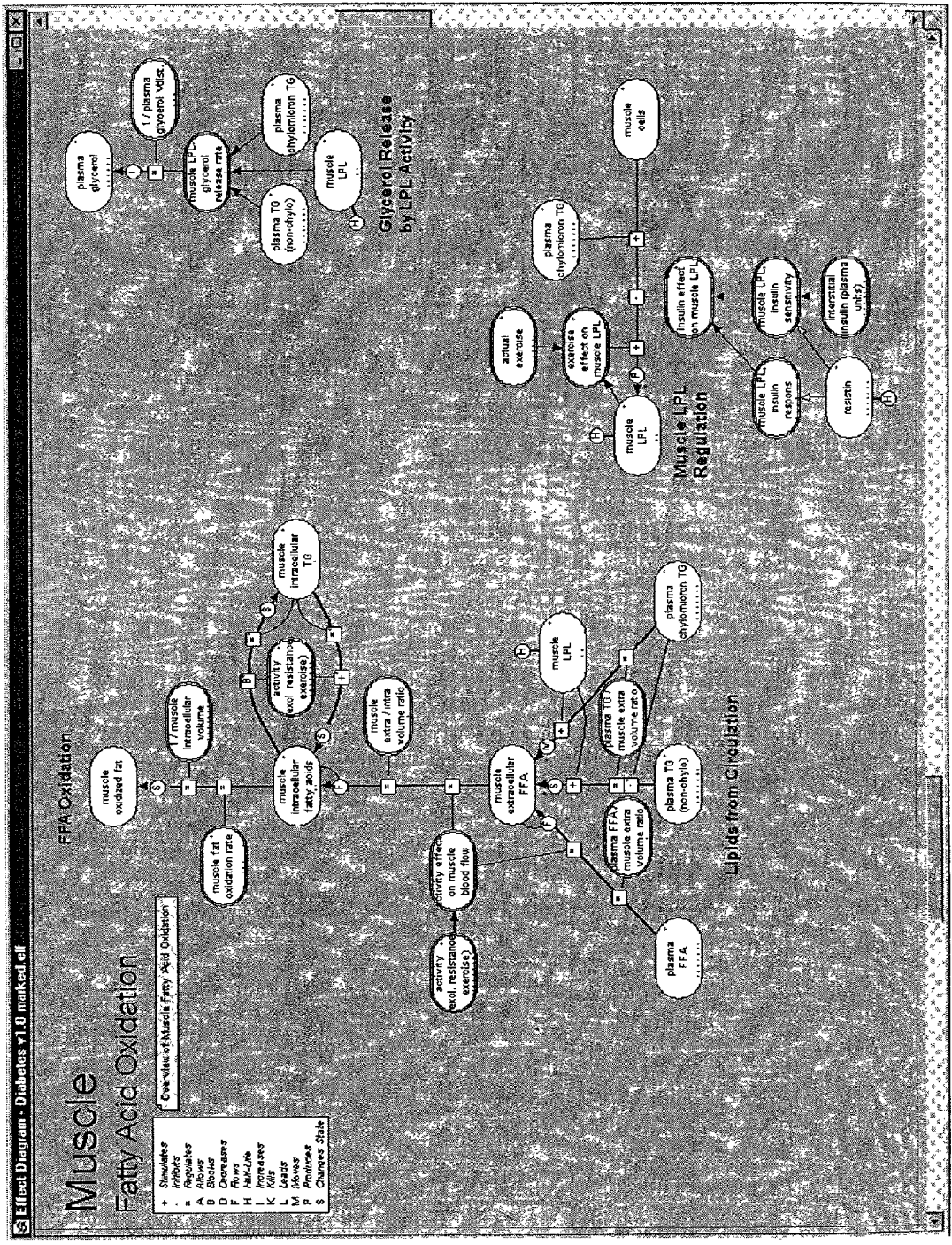

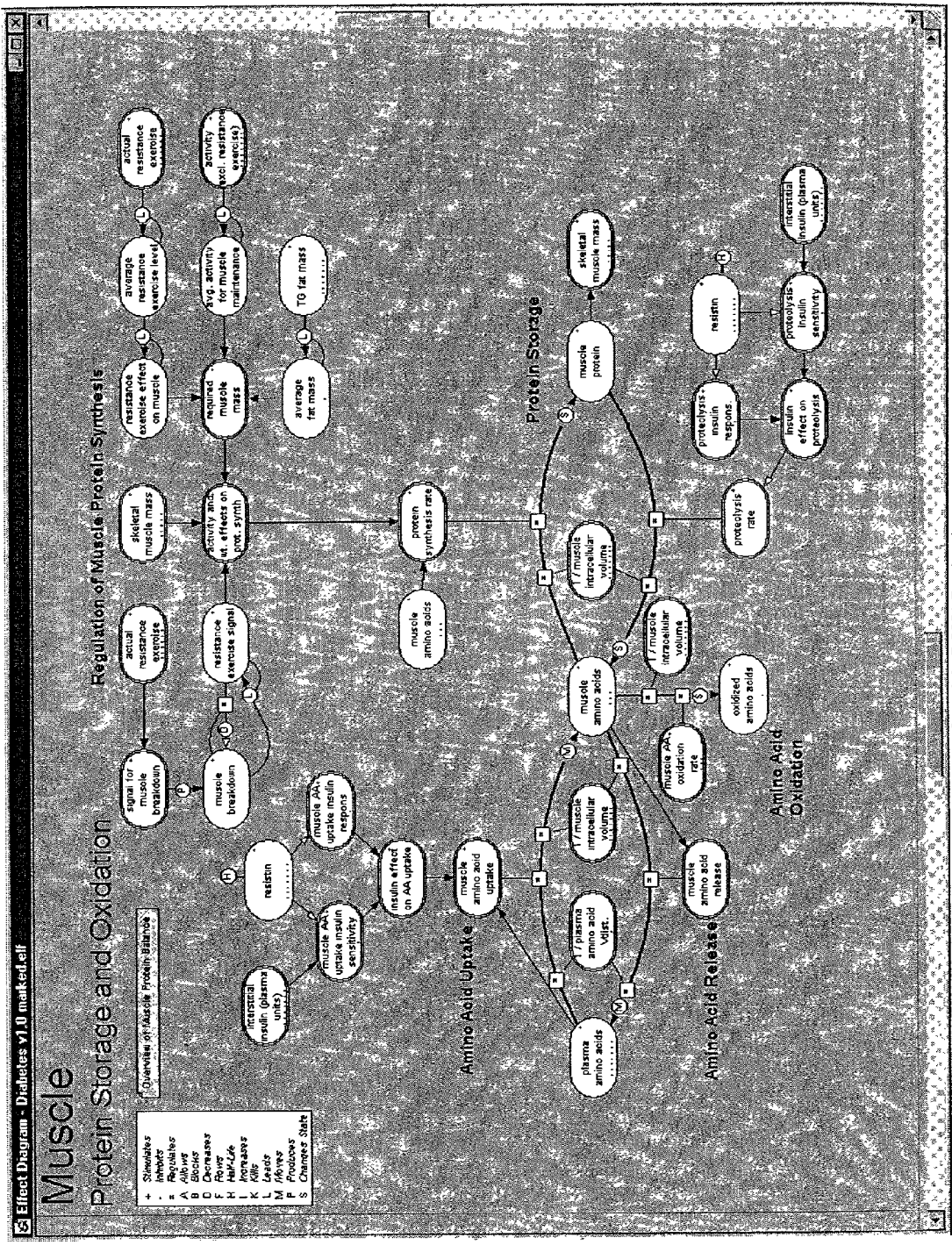

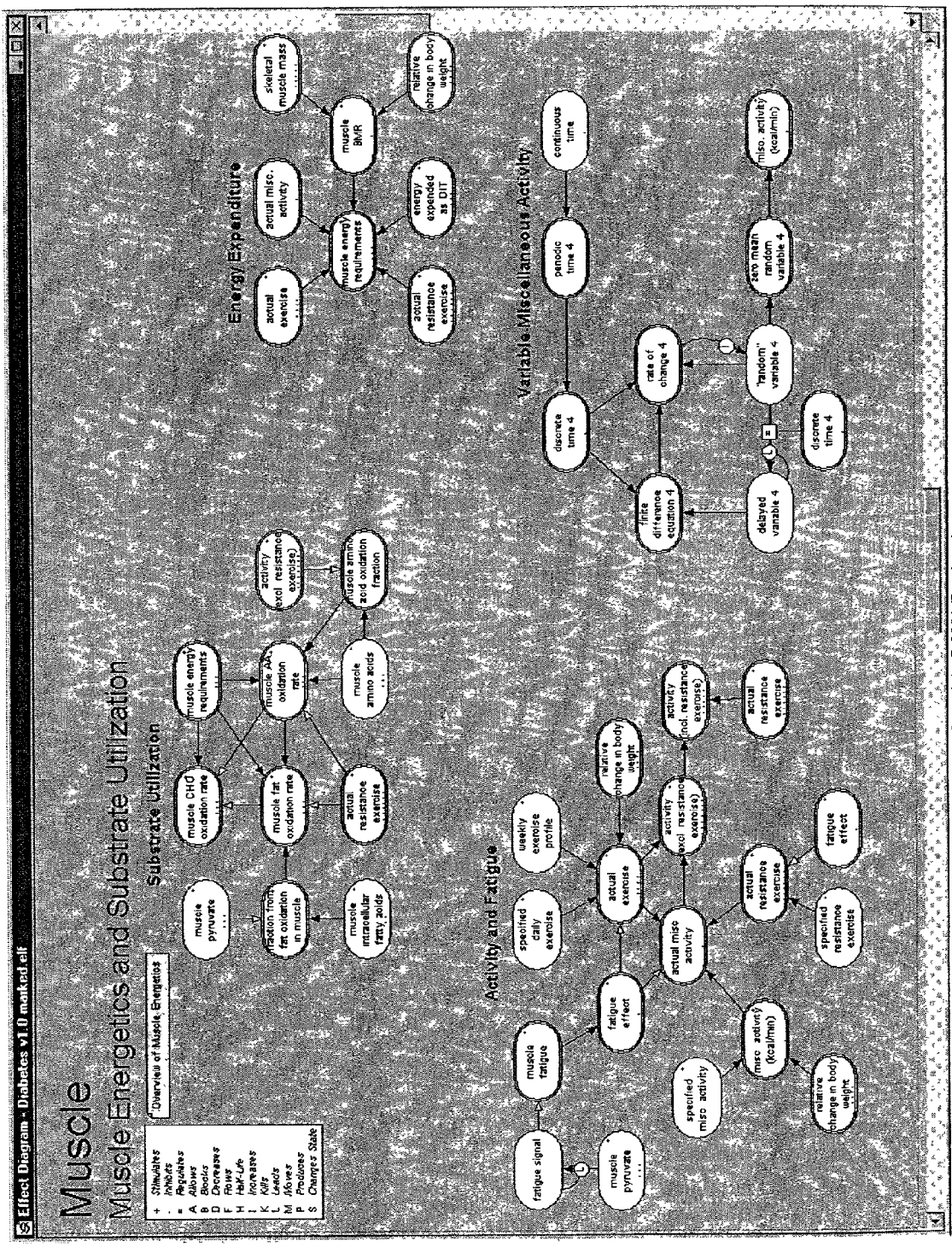

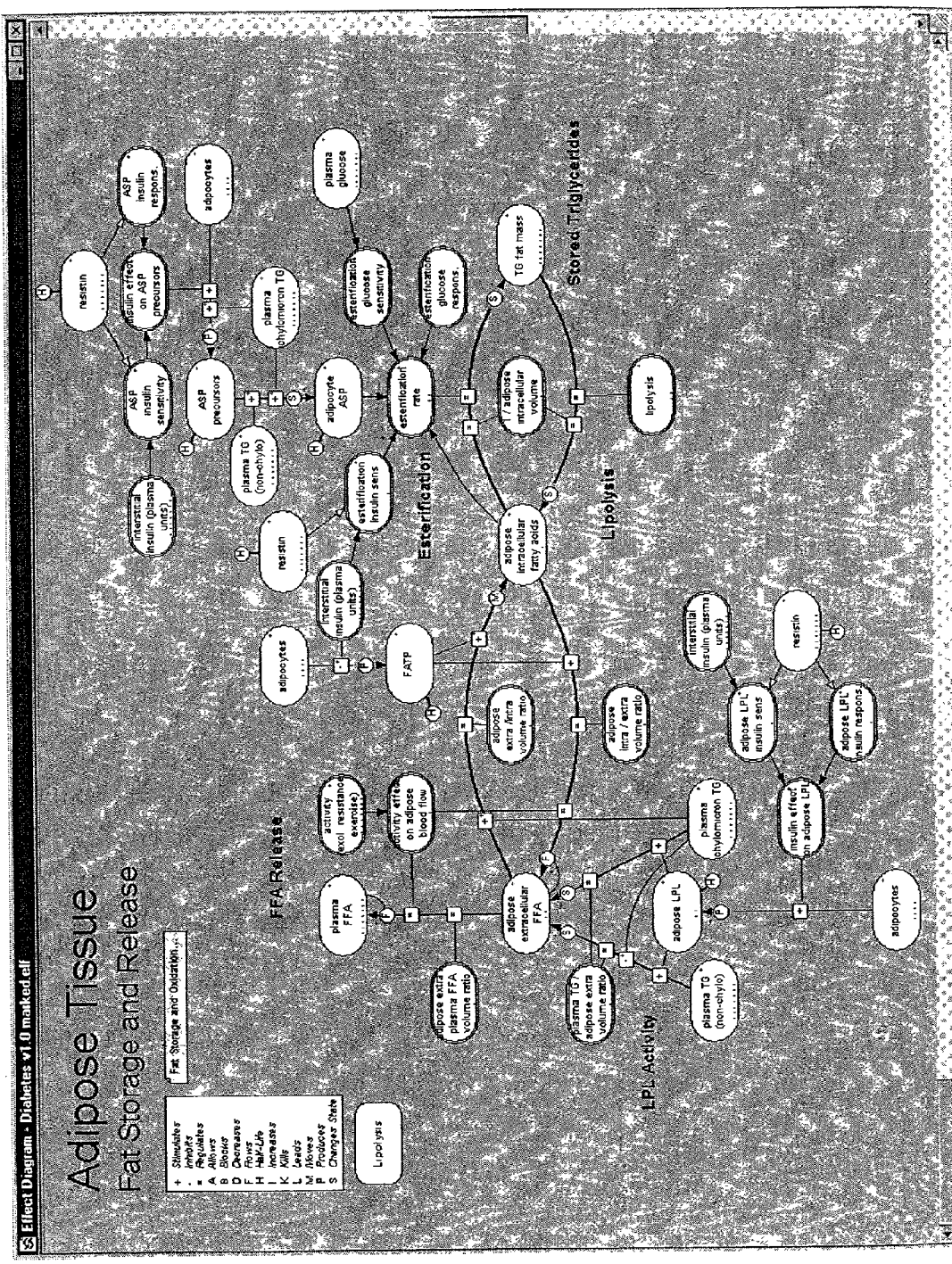

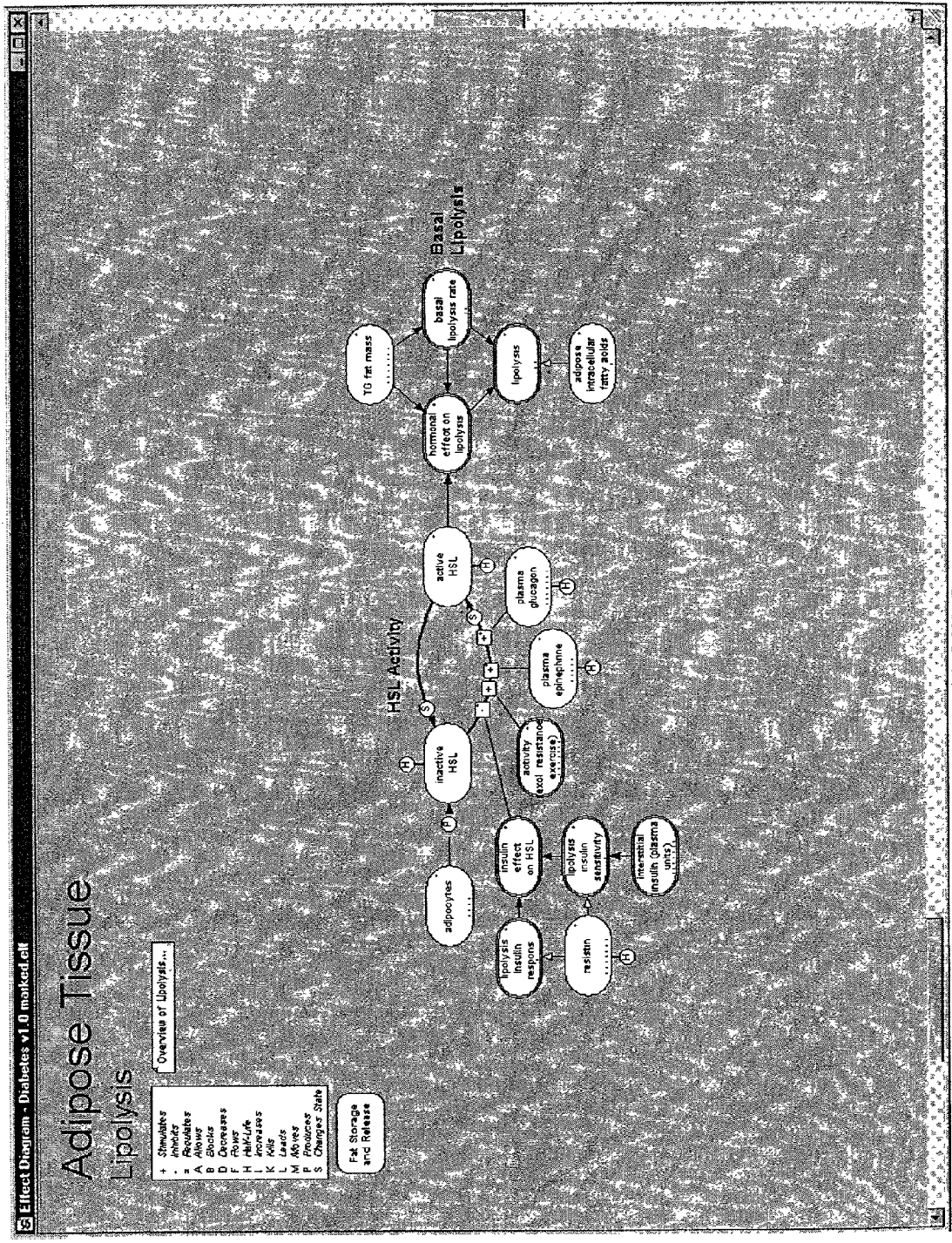

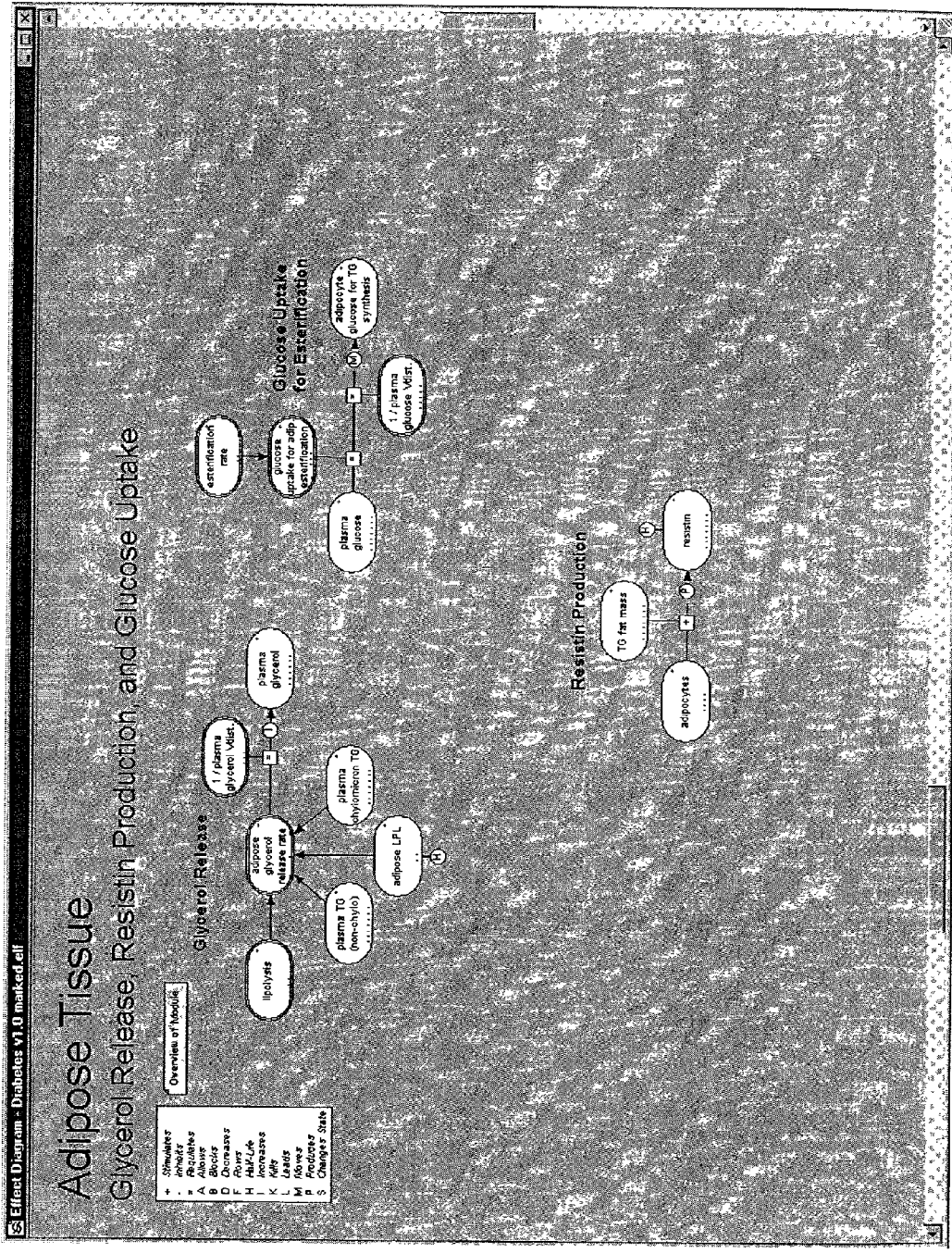

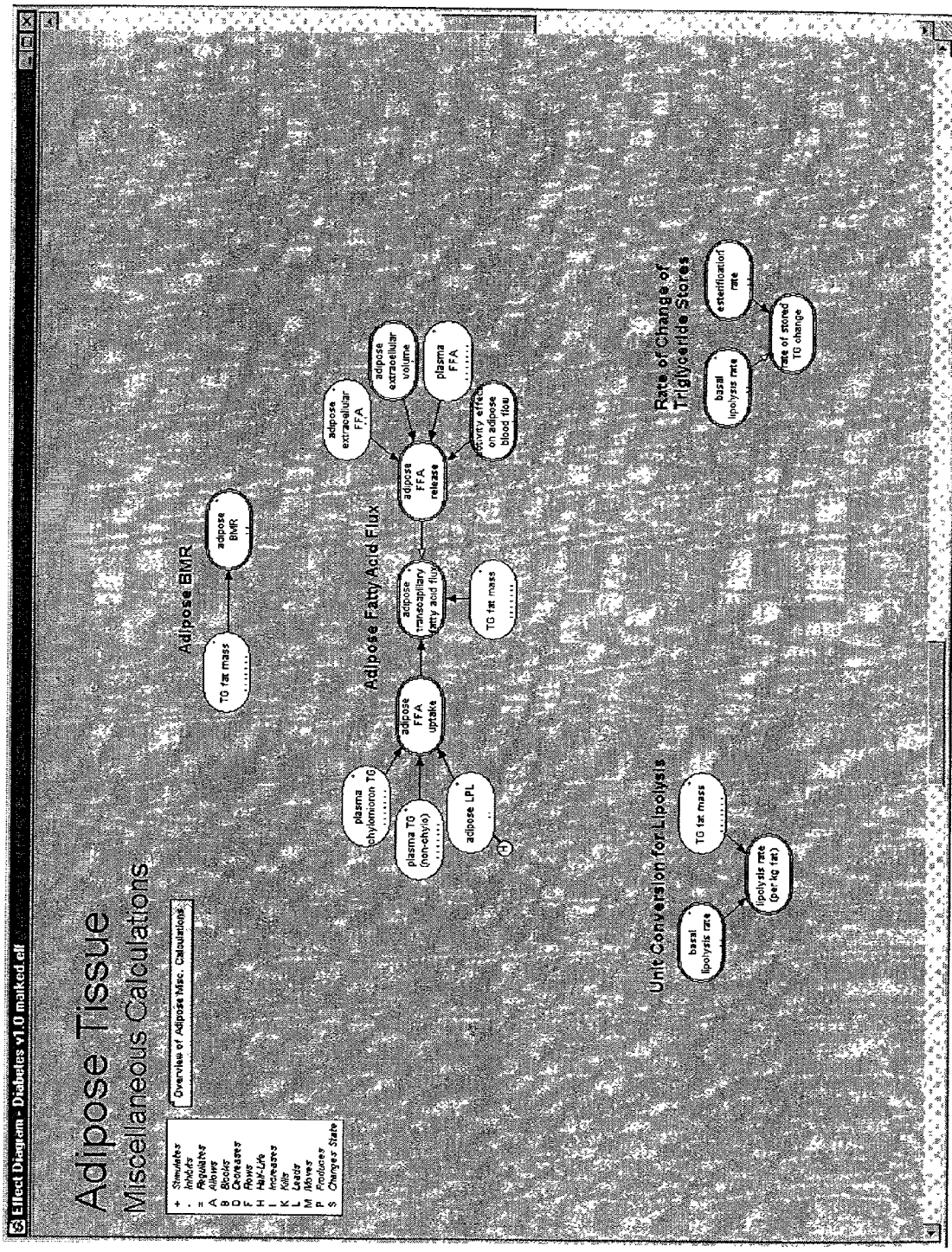

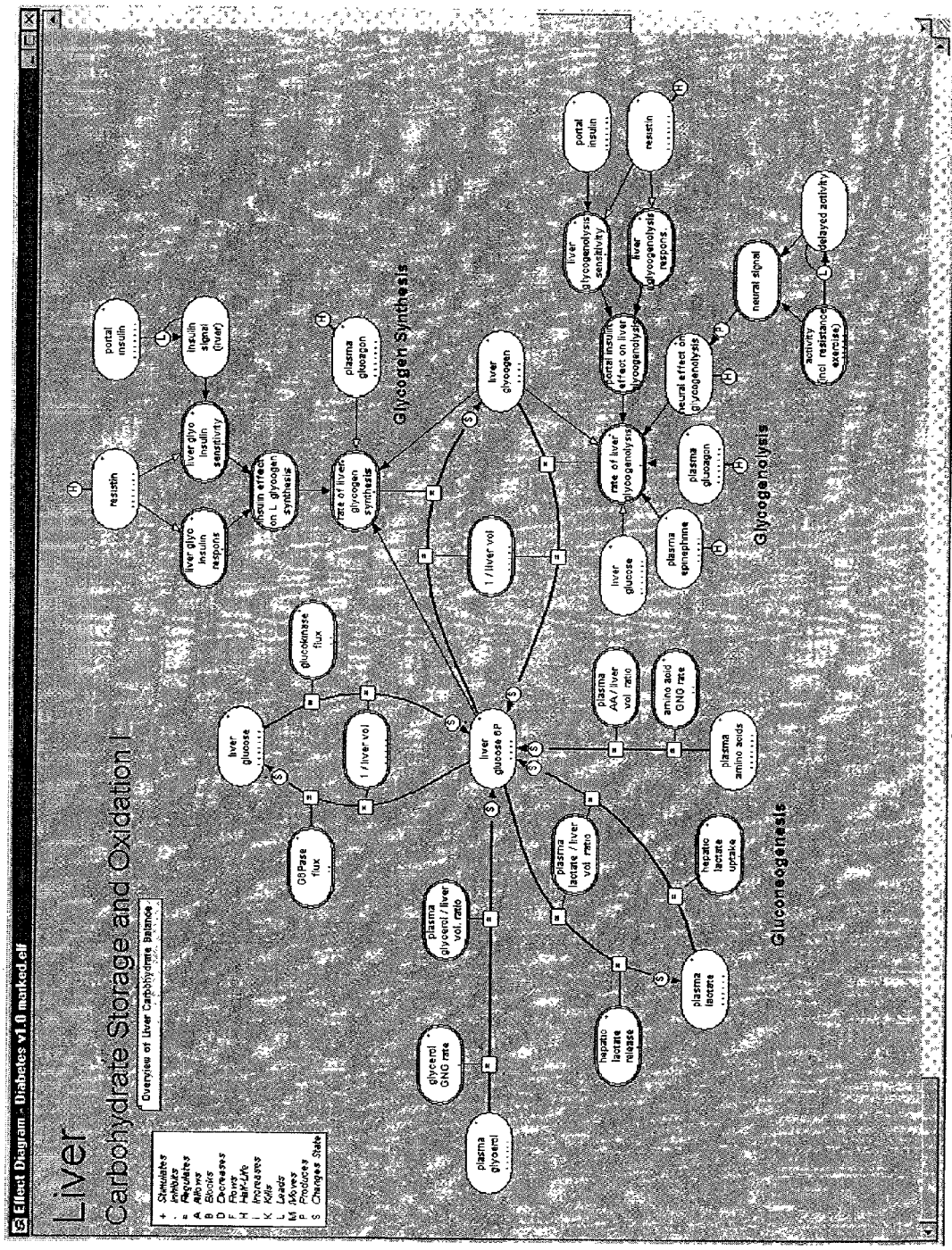

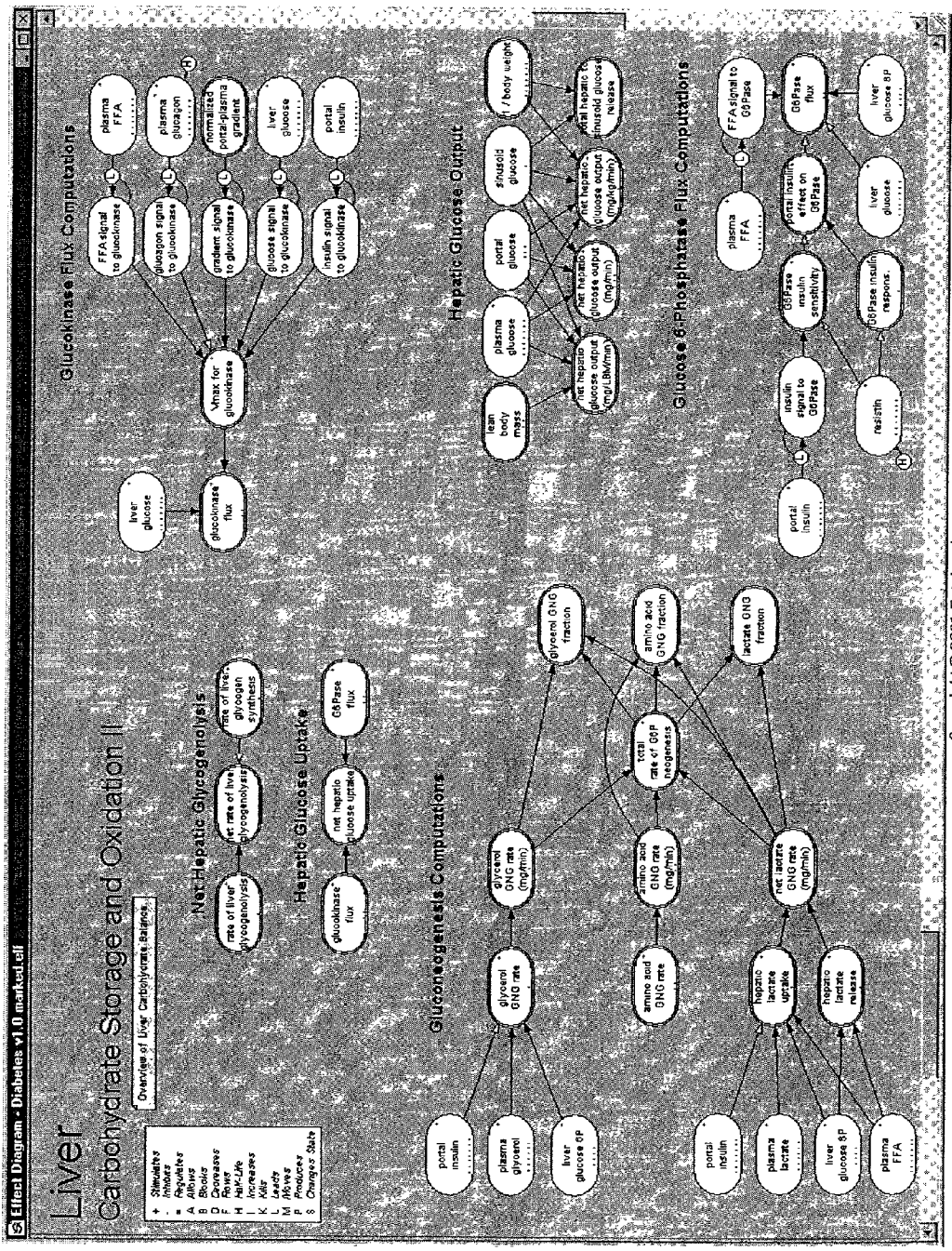

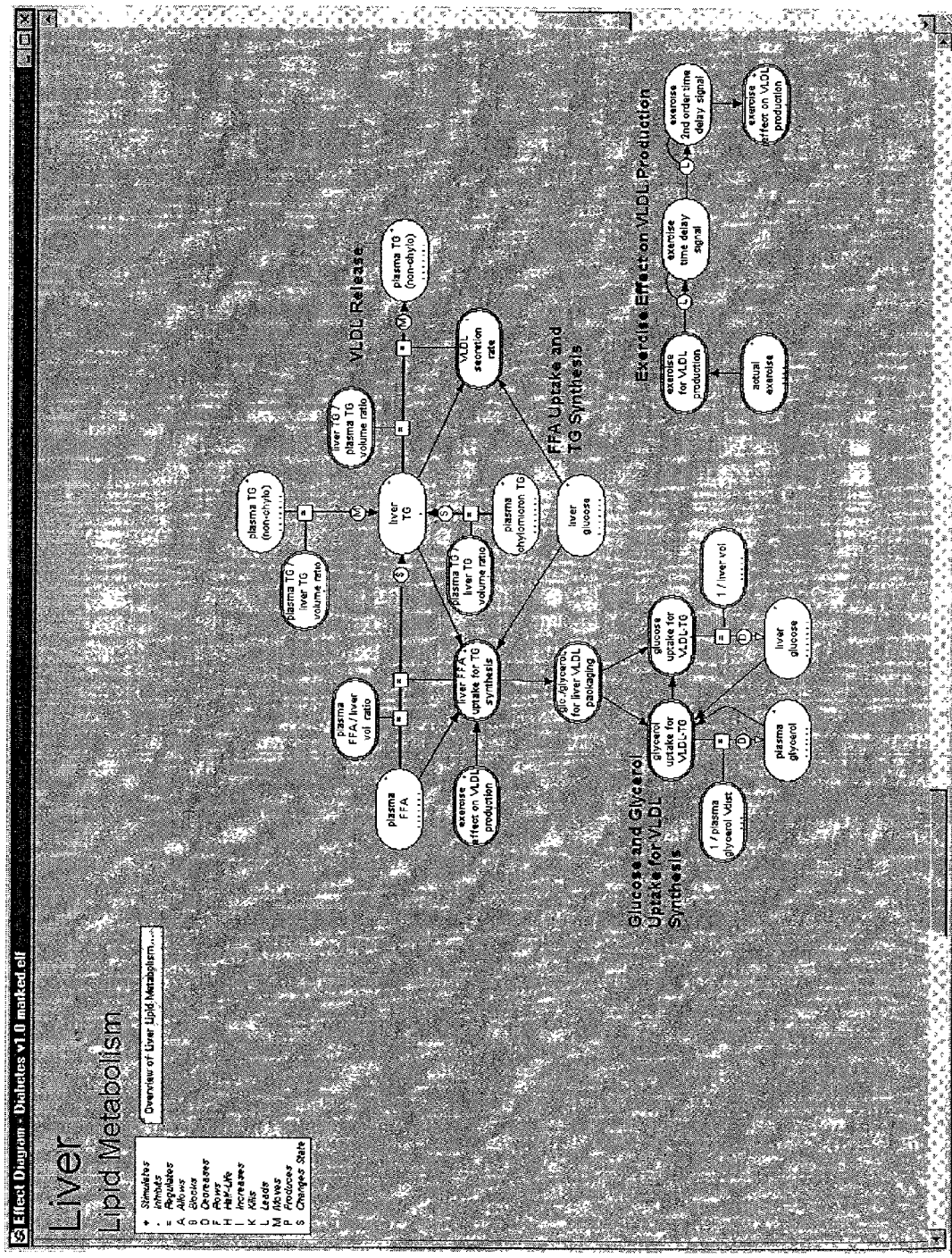

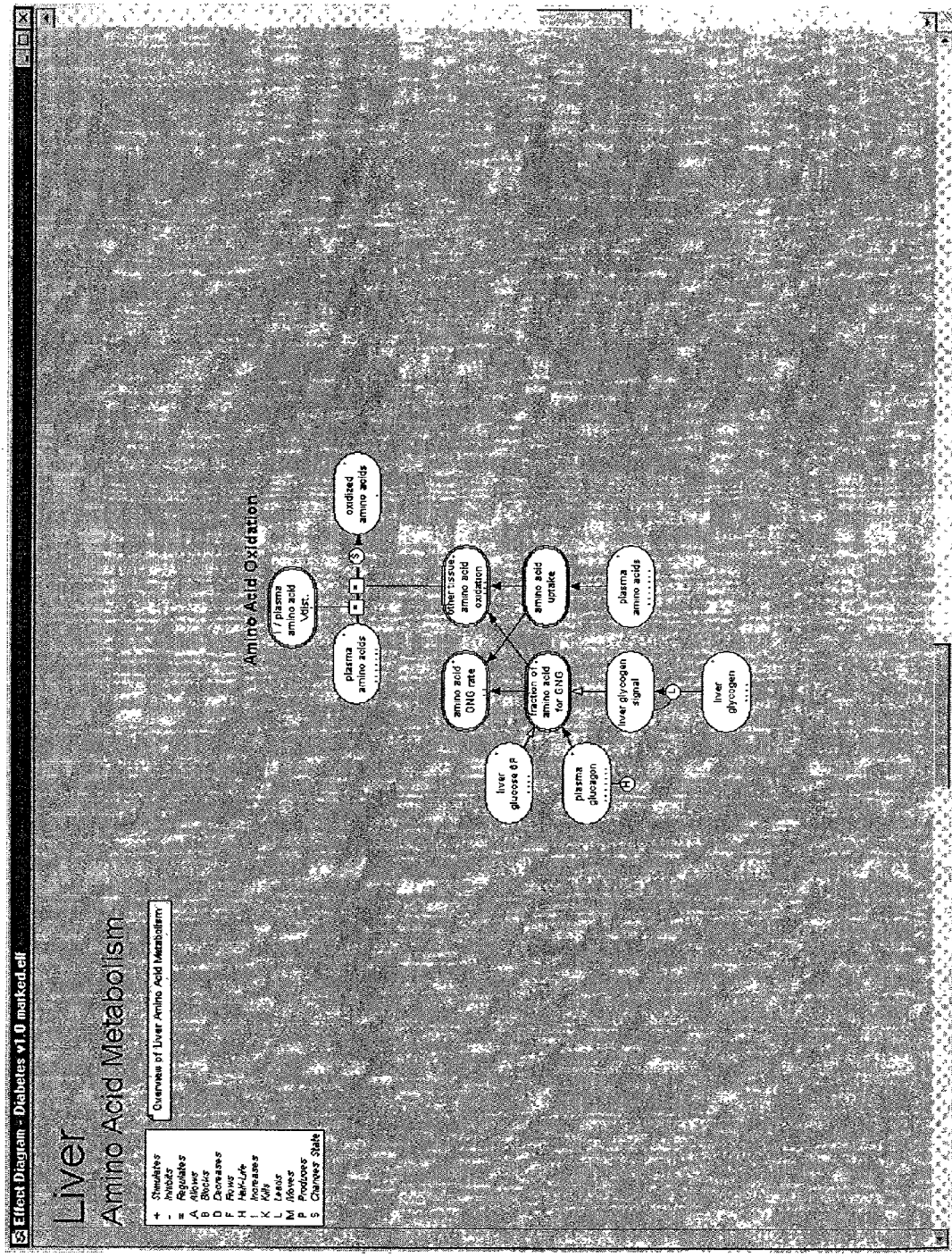

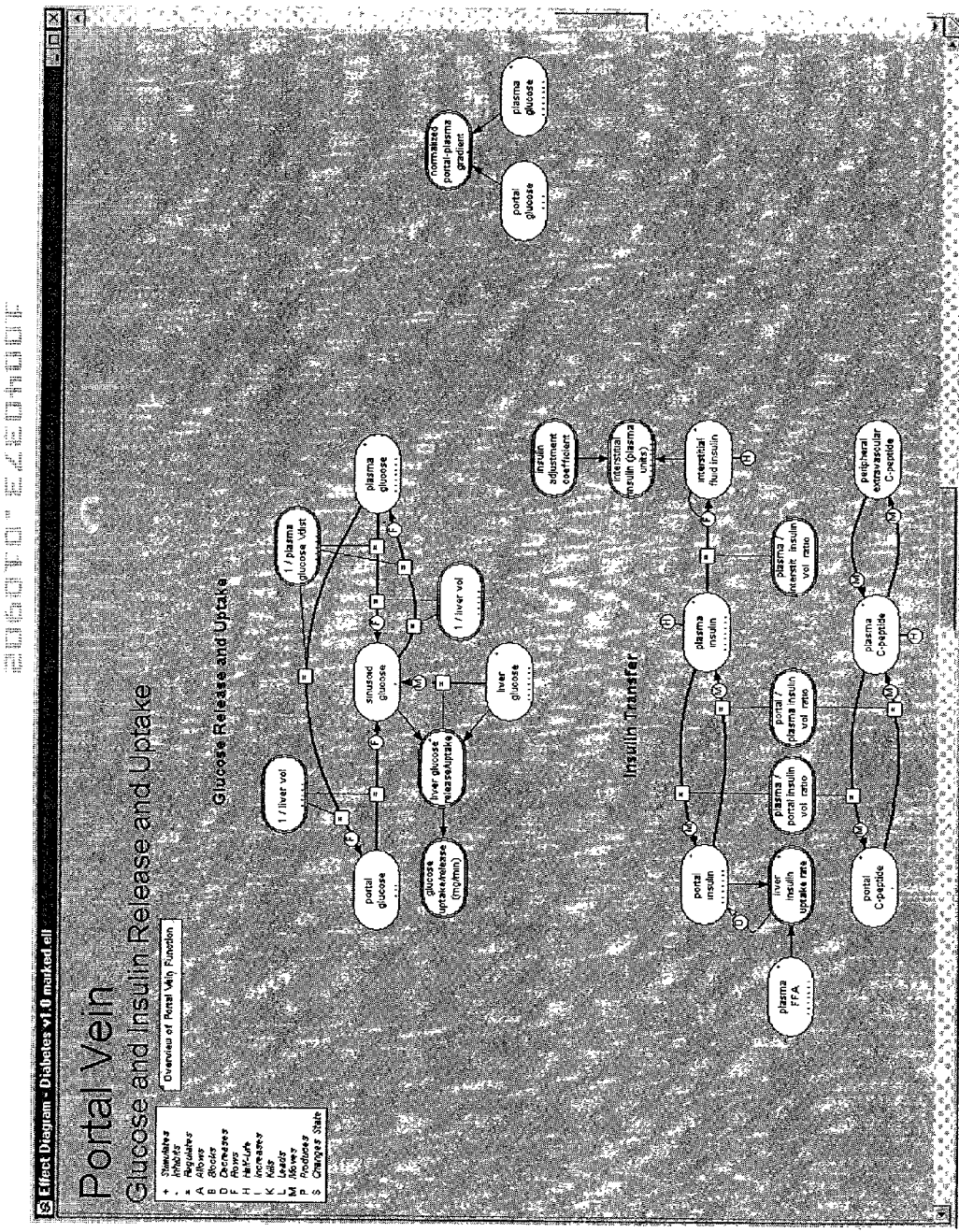

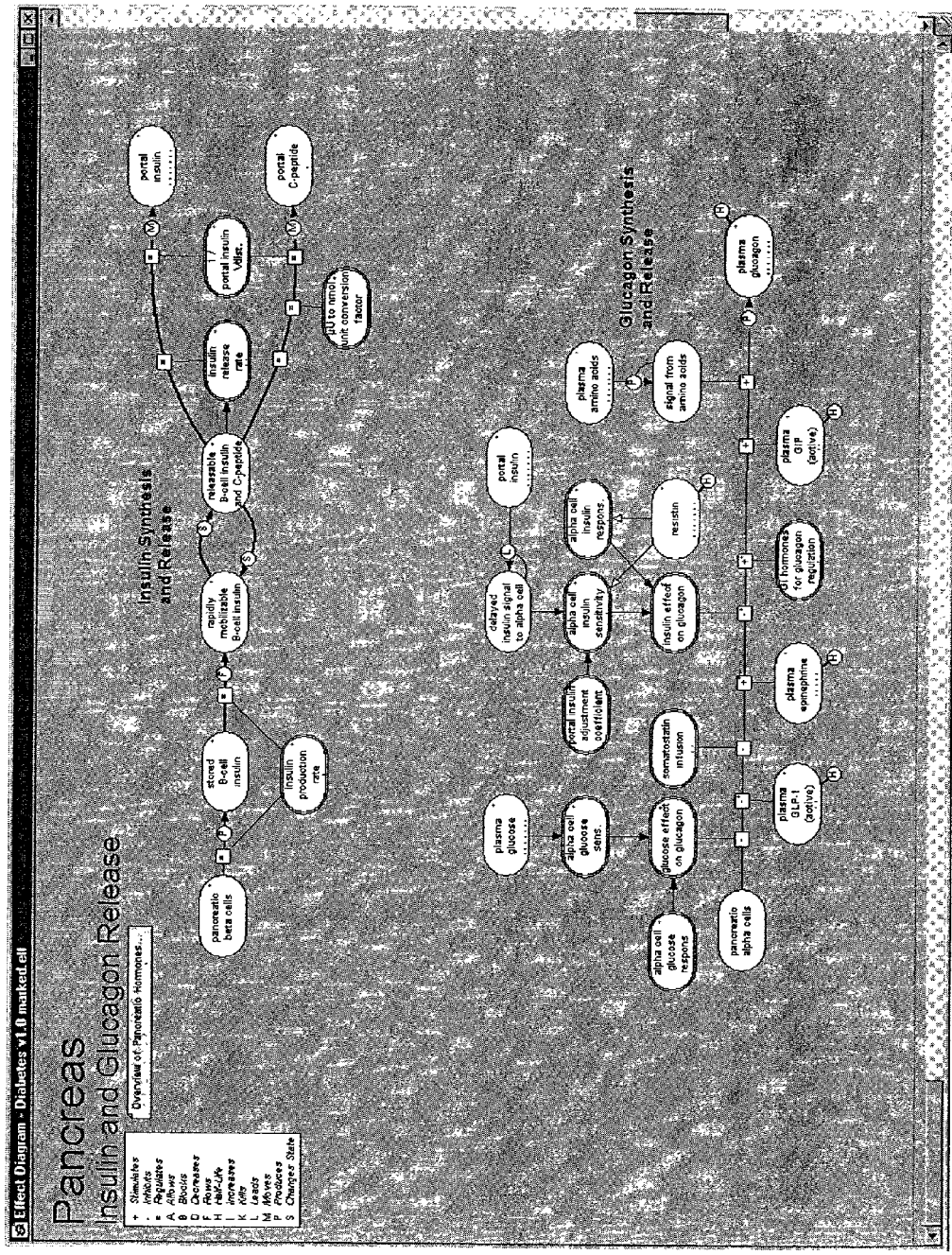

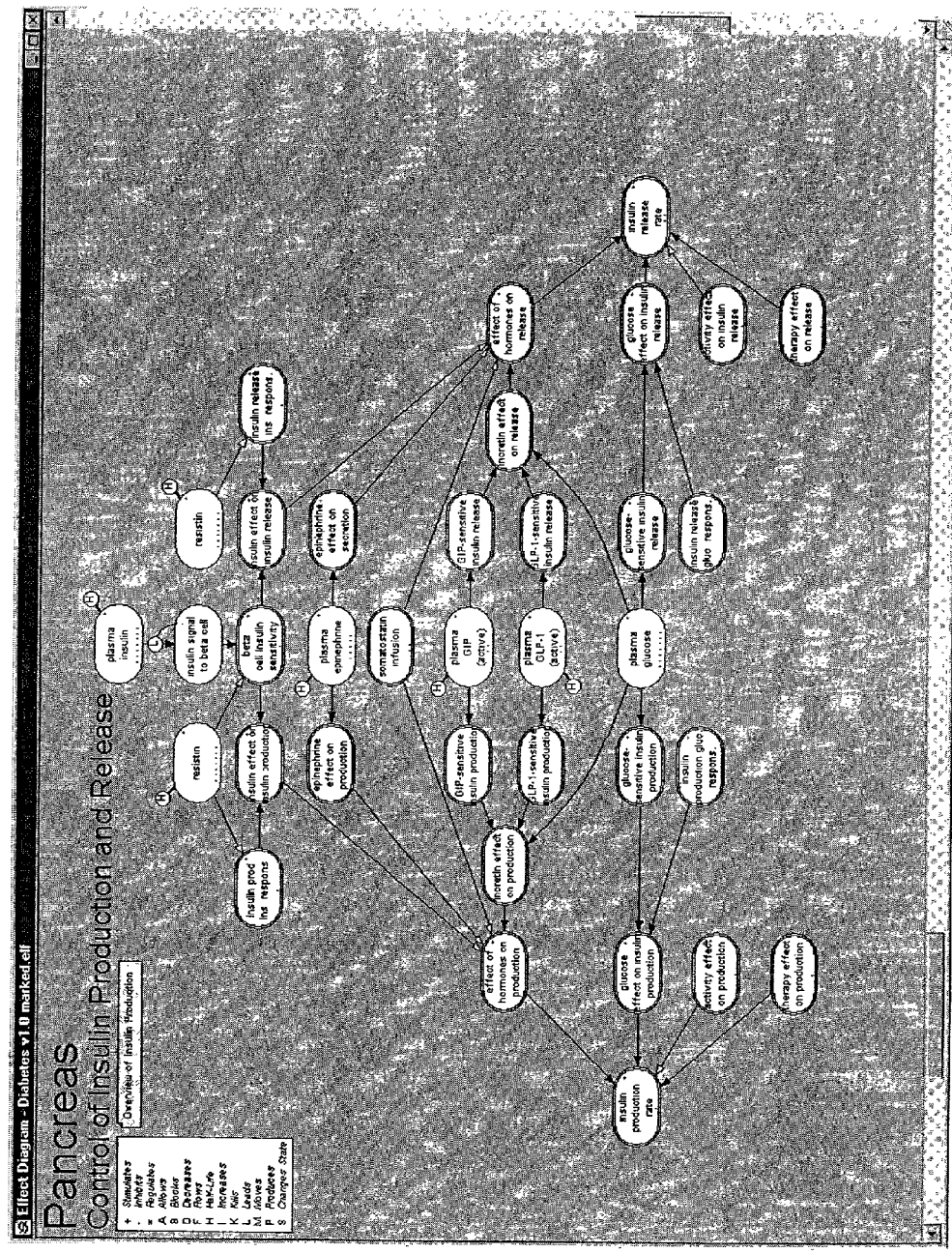

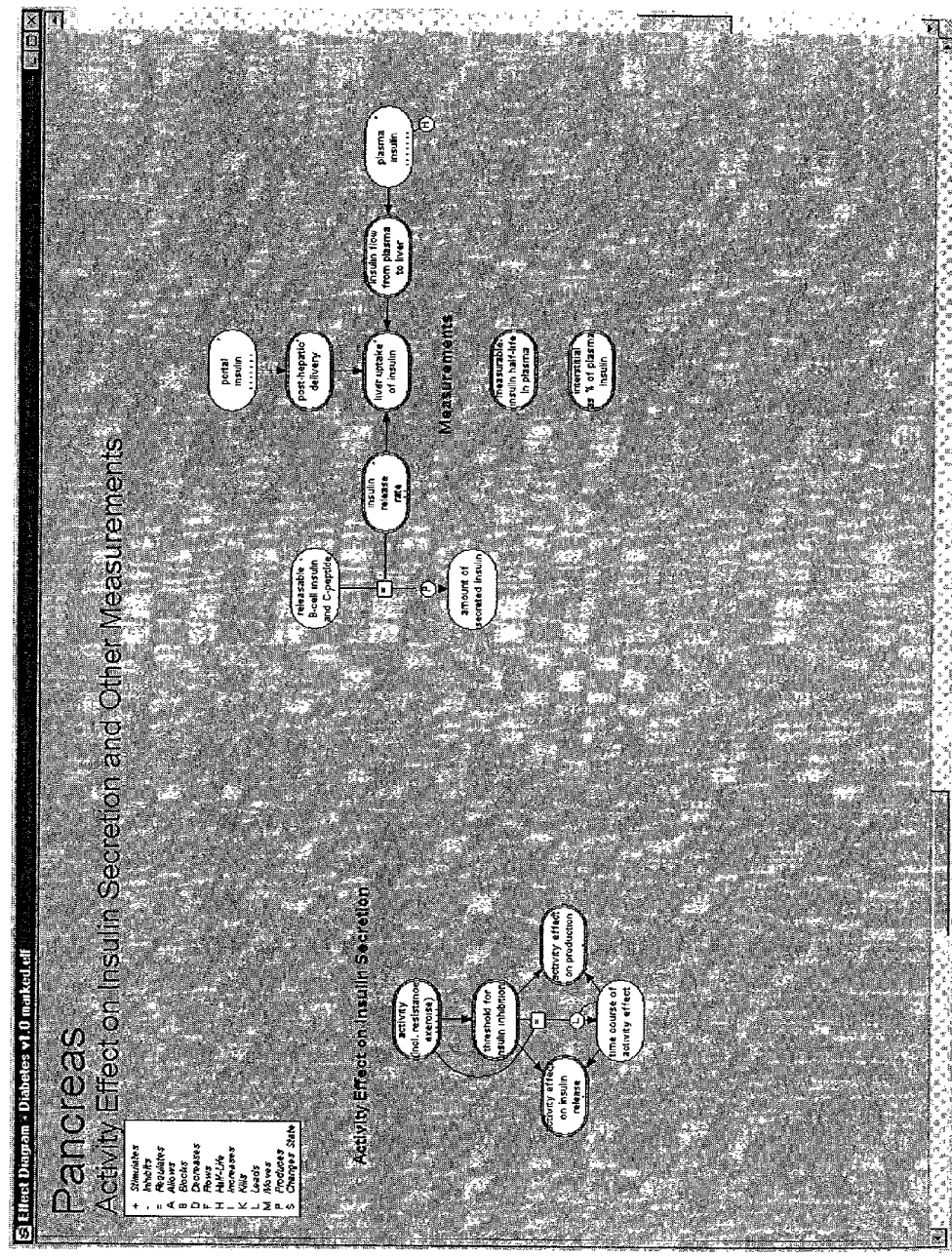

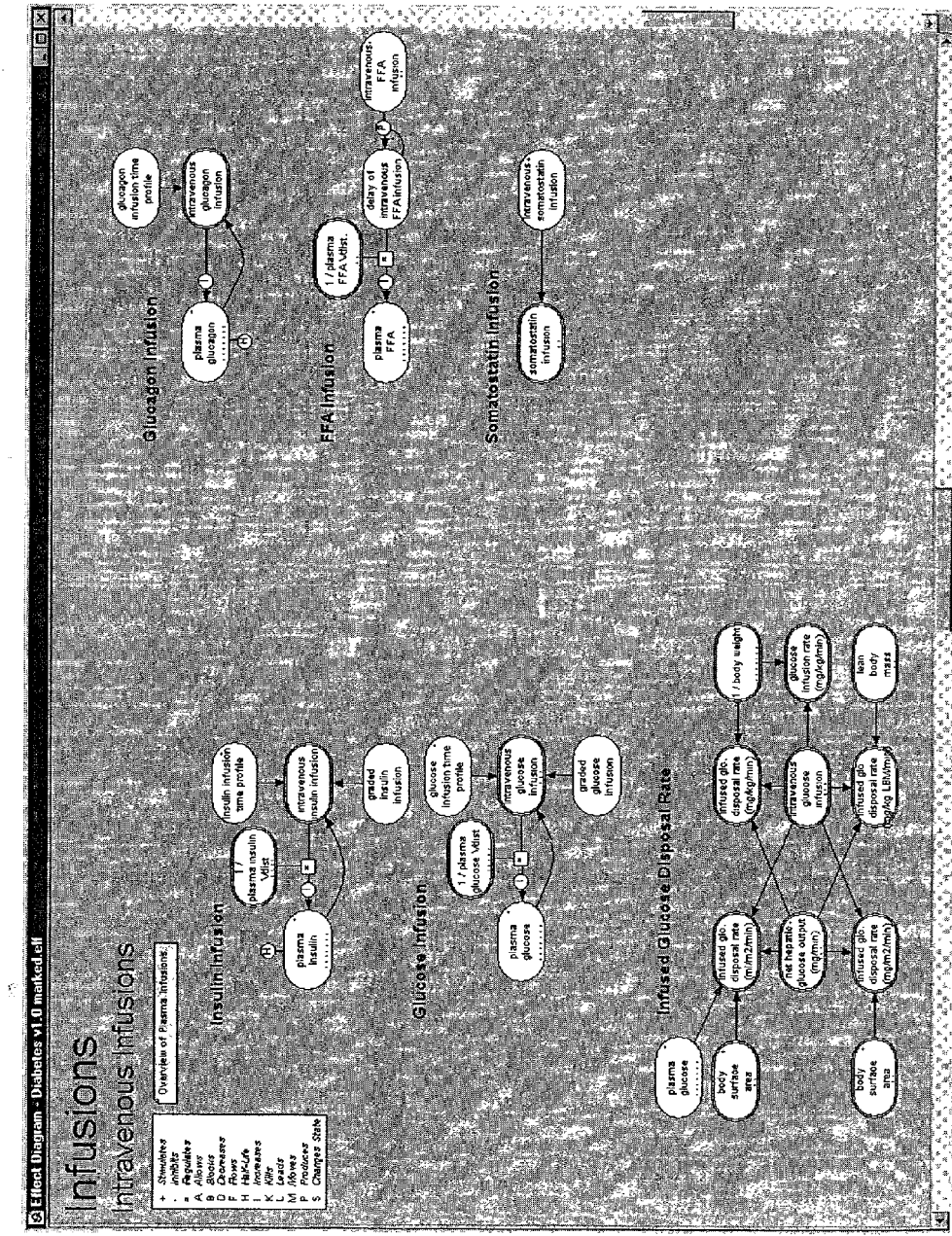

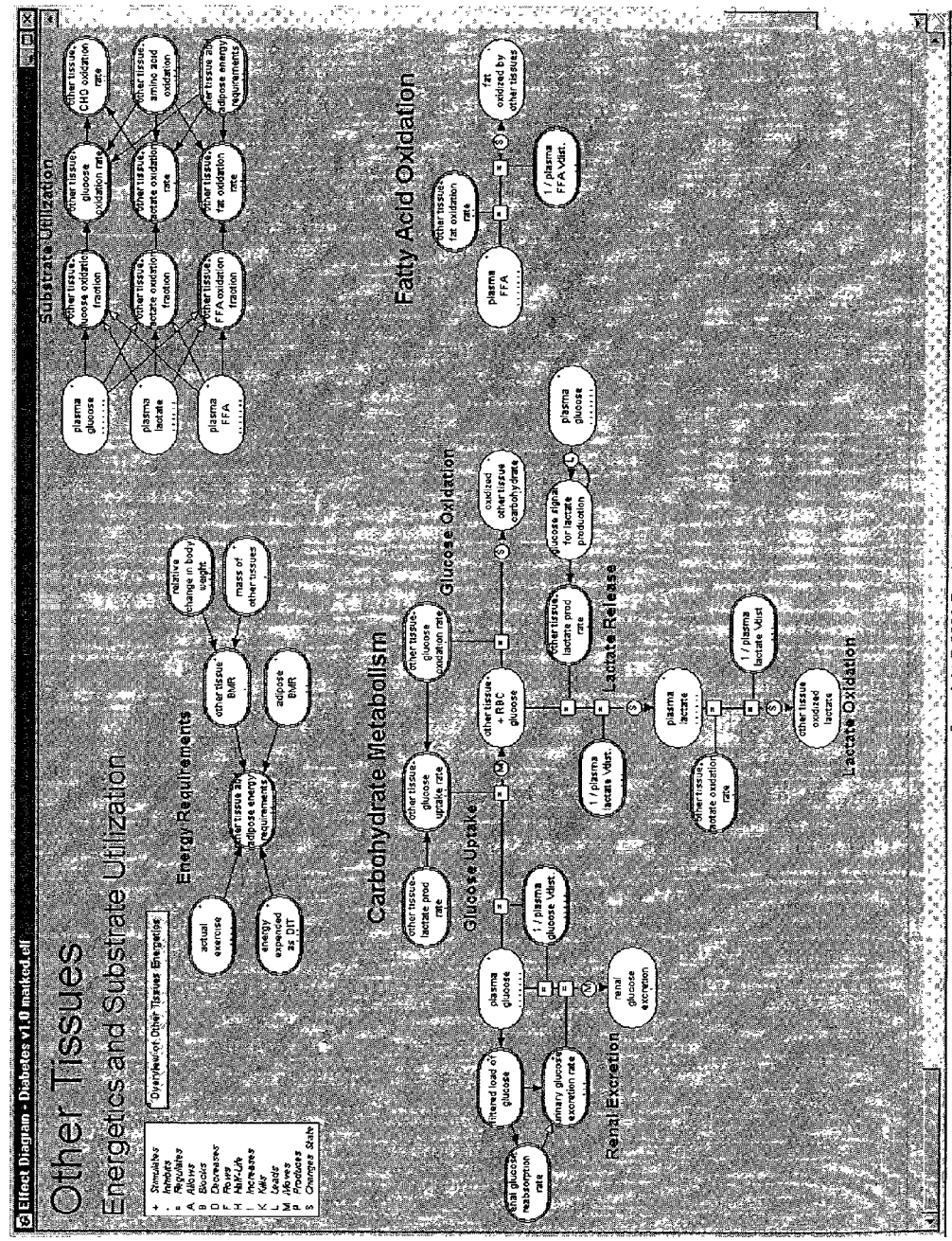
A - 26

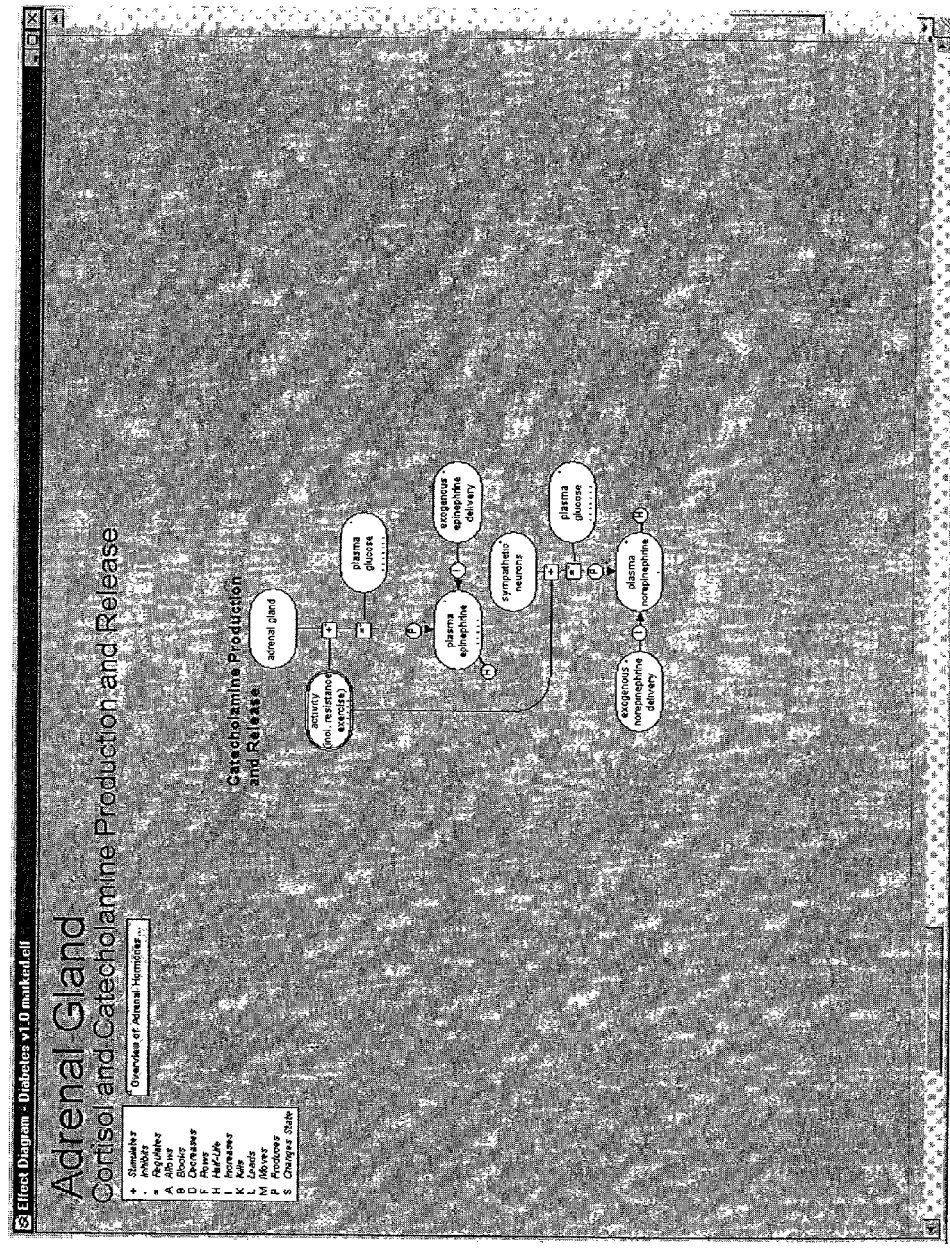

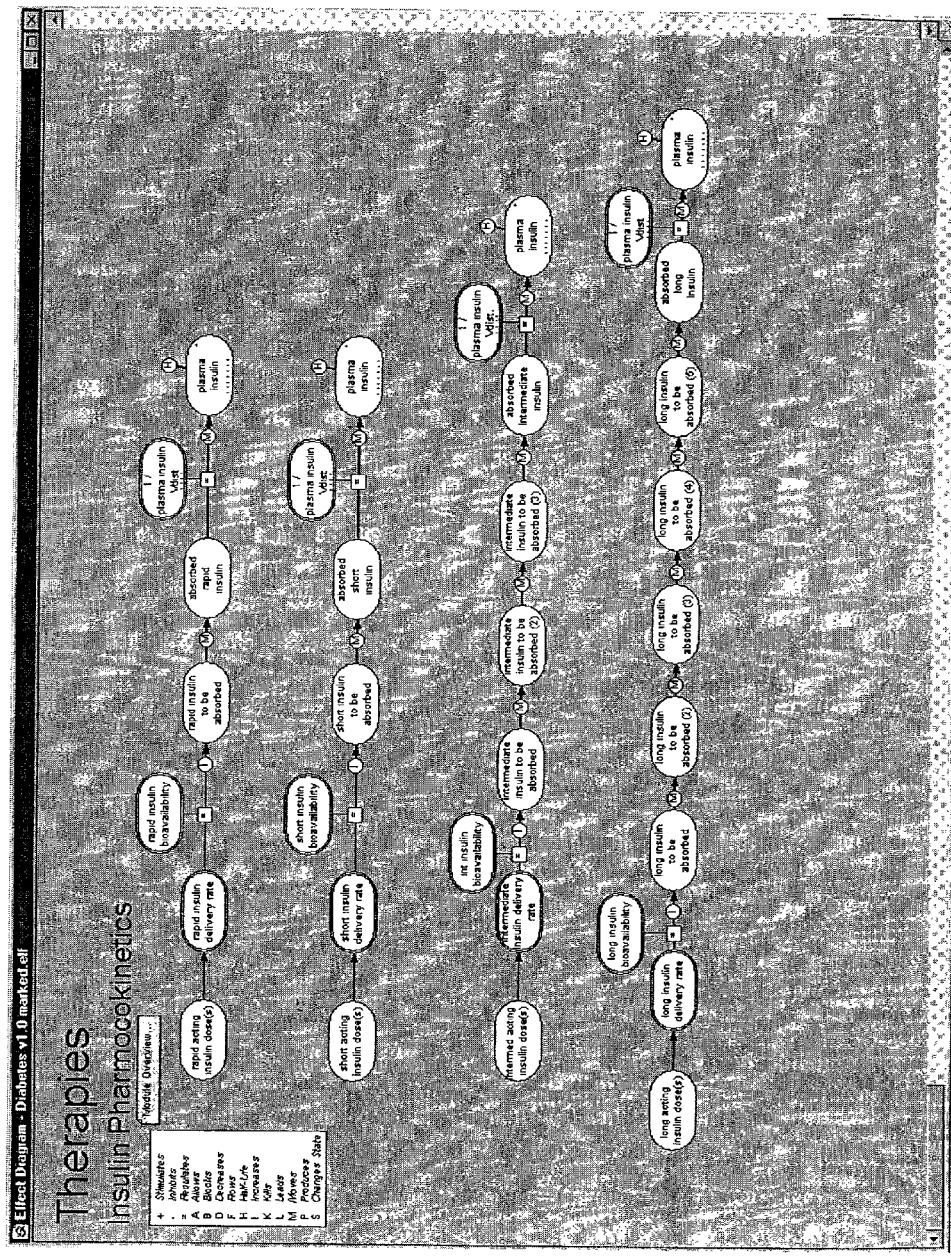

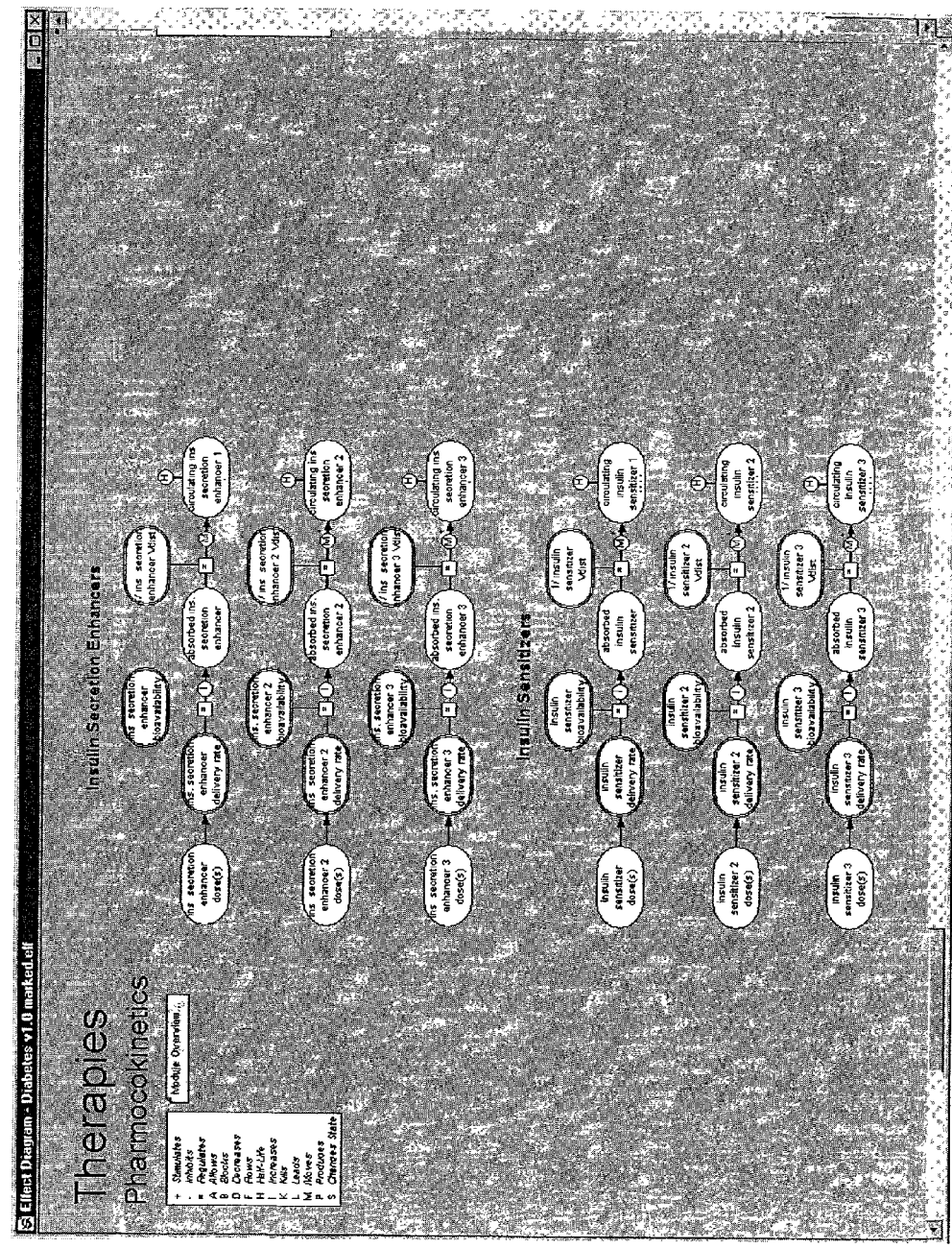

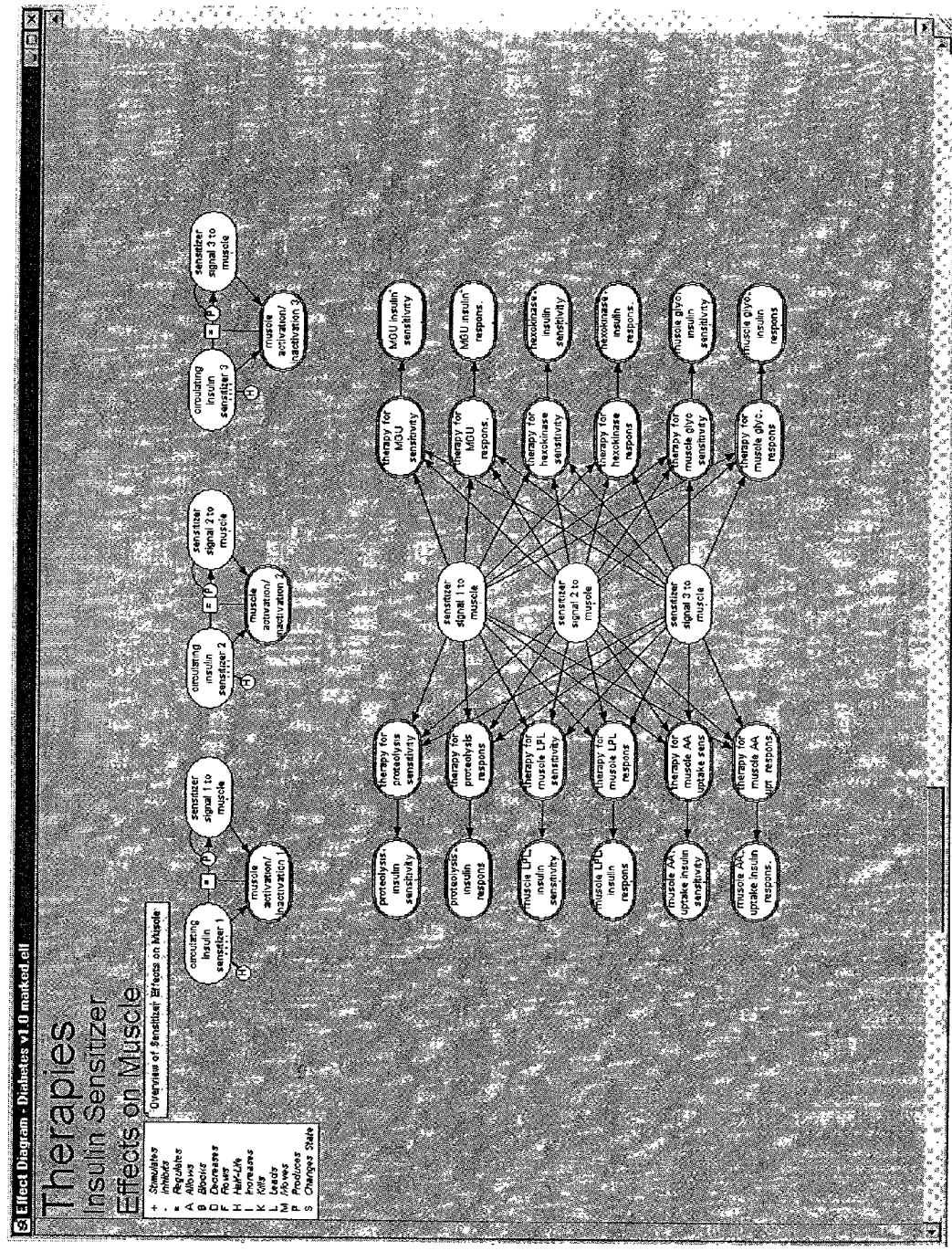

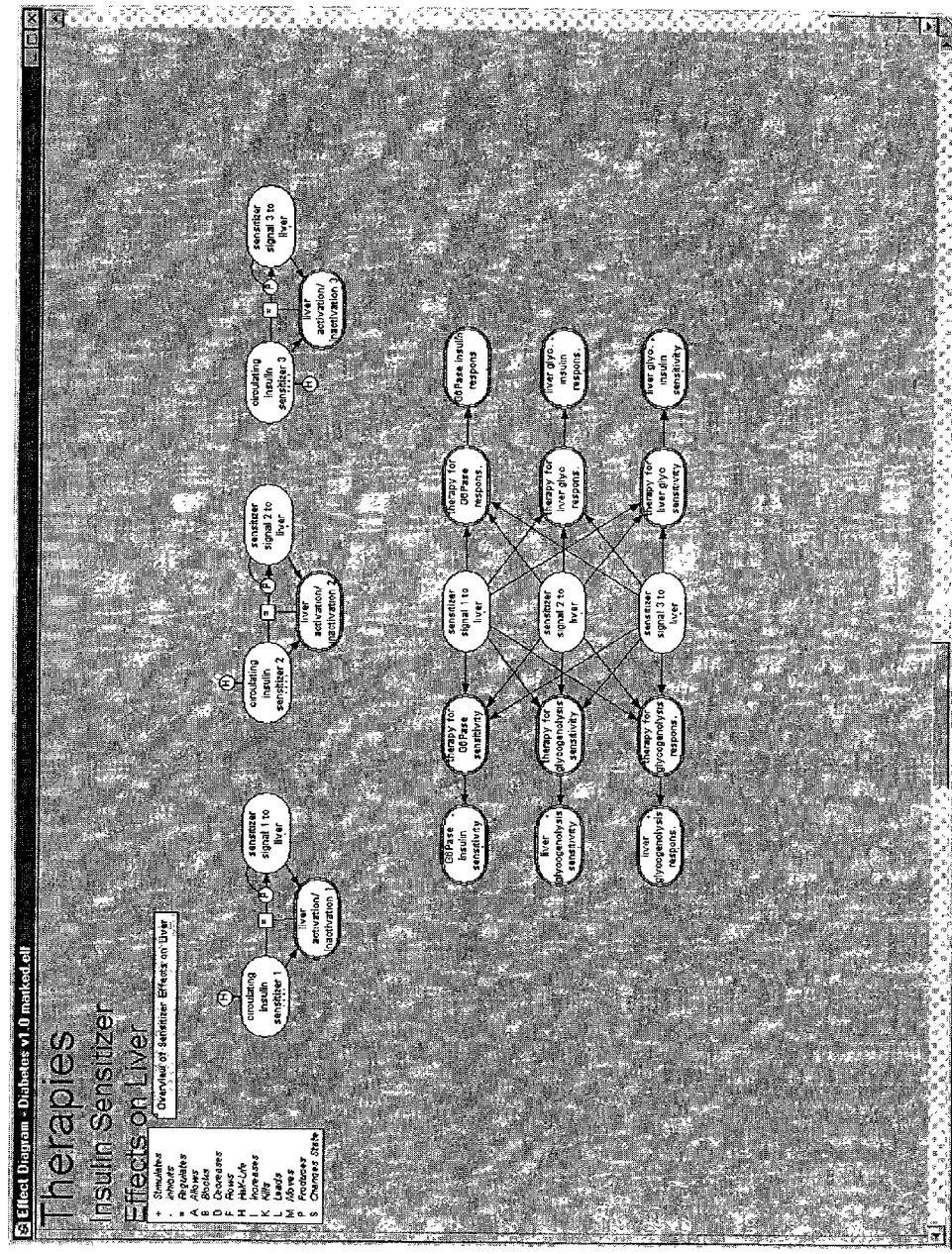

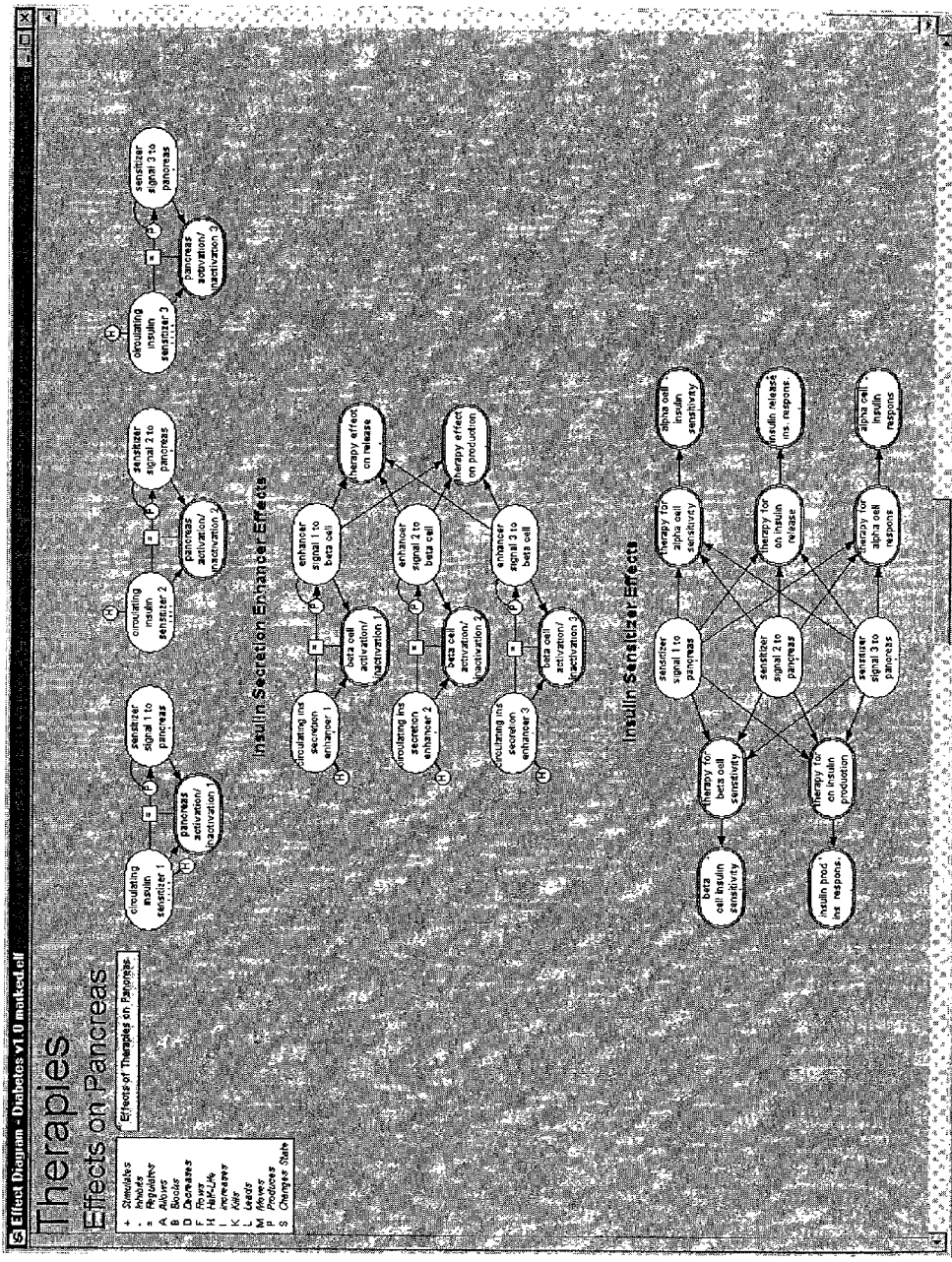

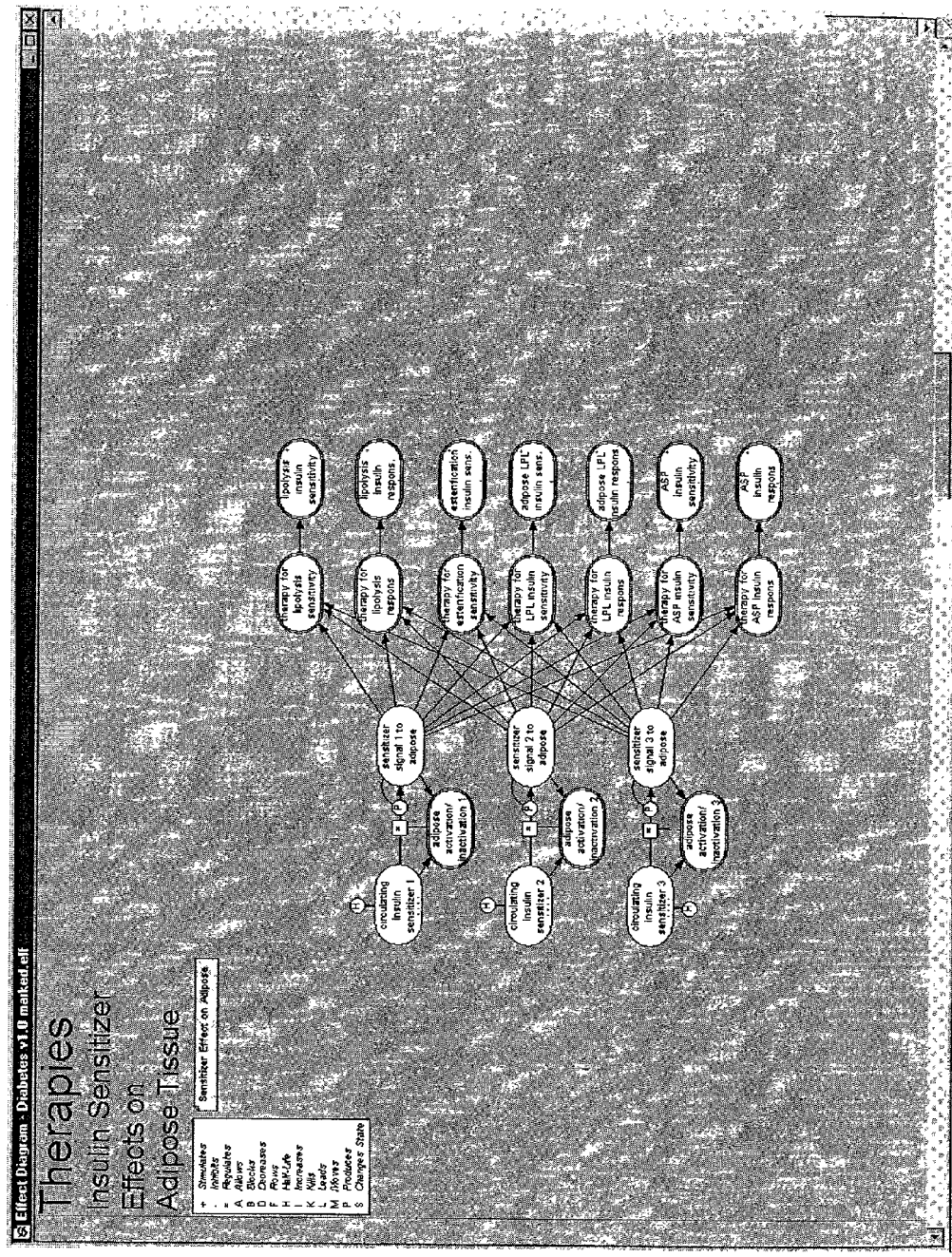

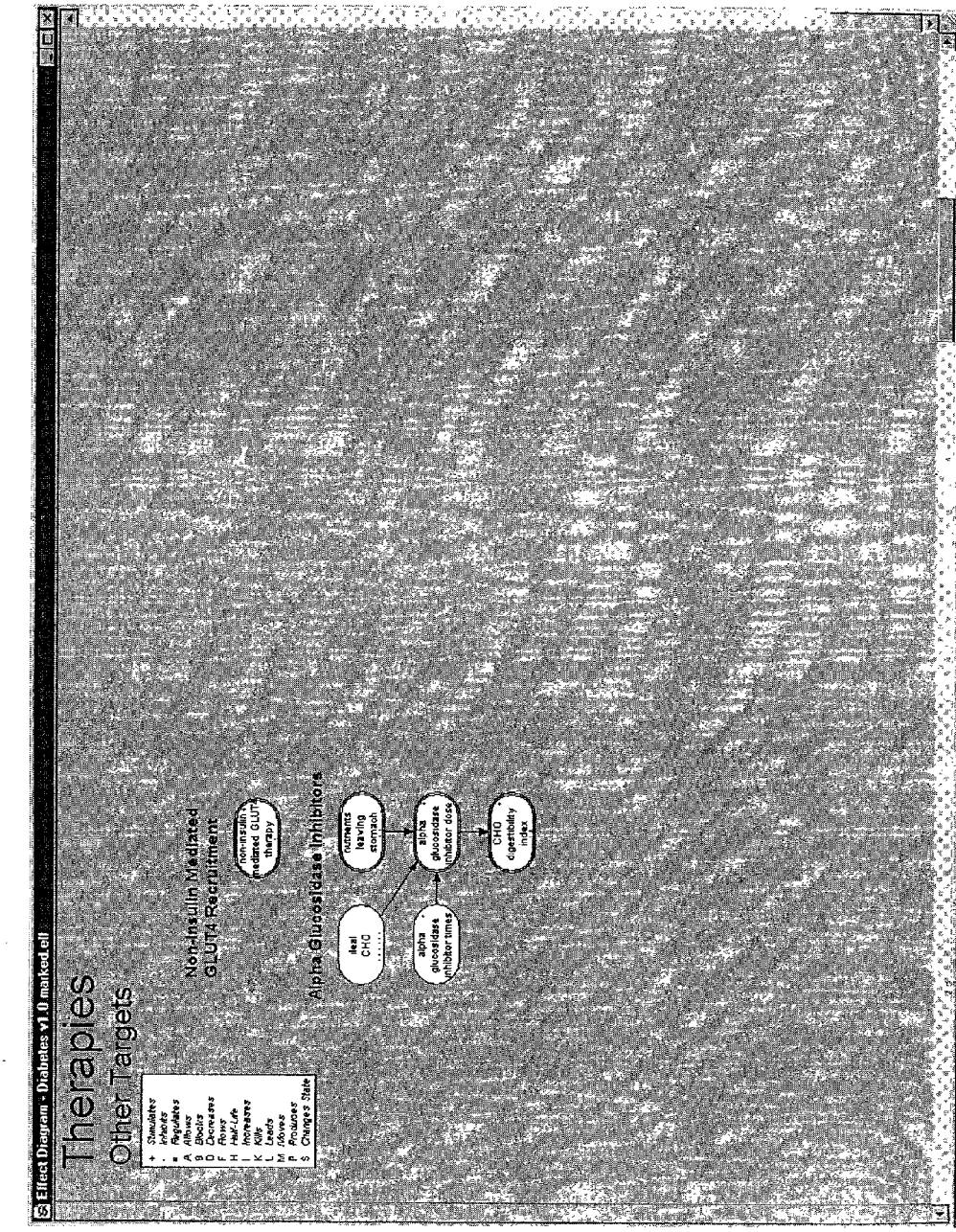

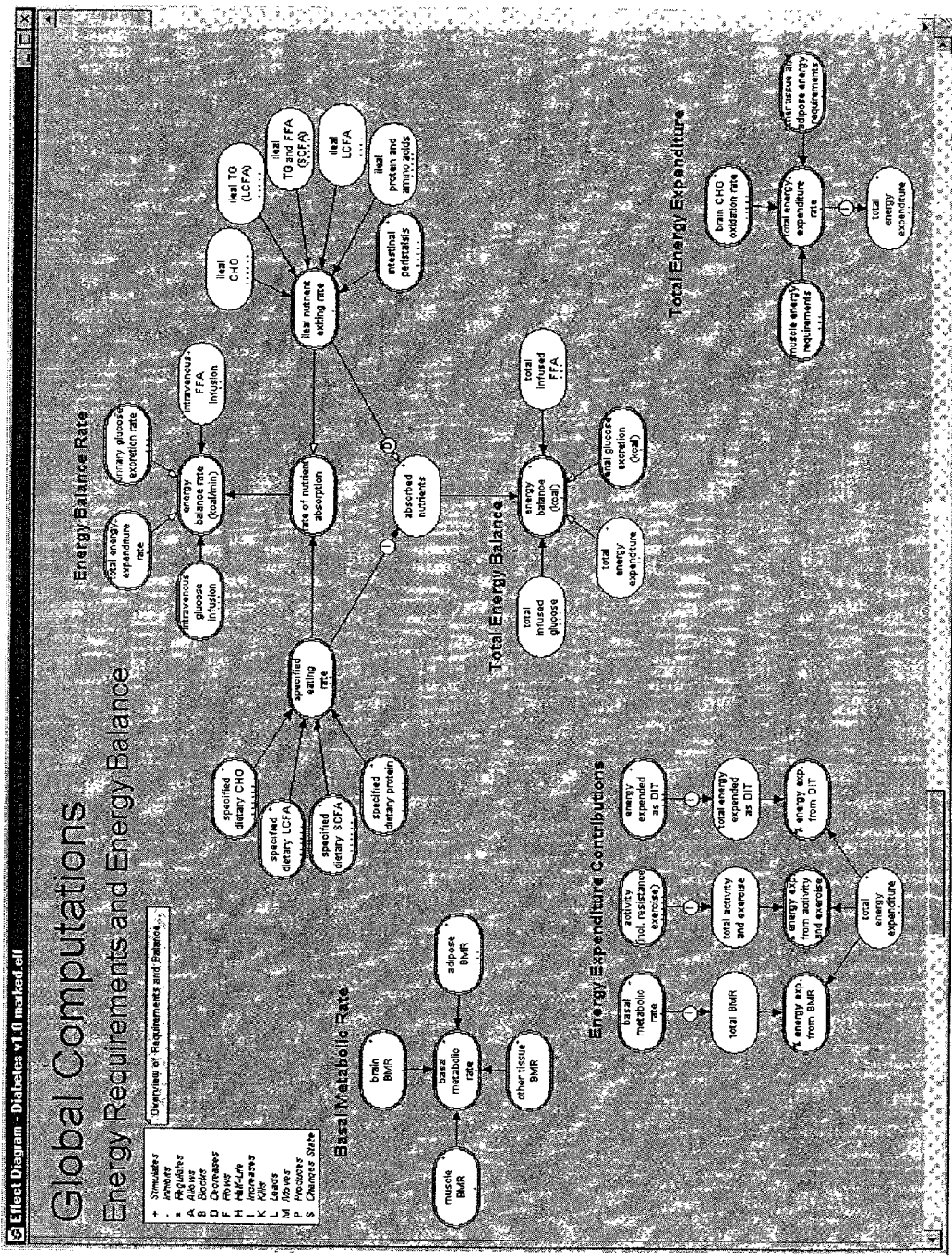

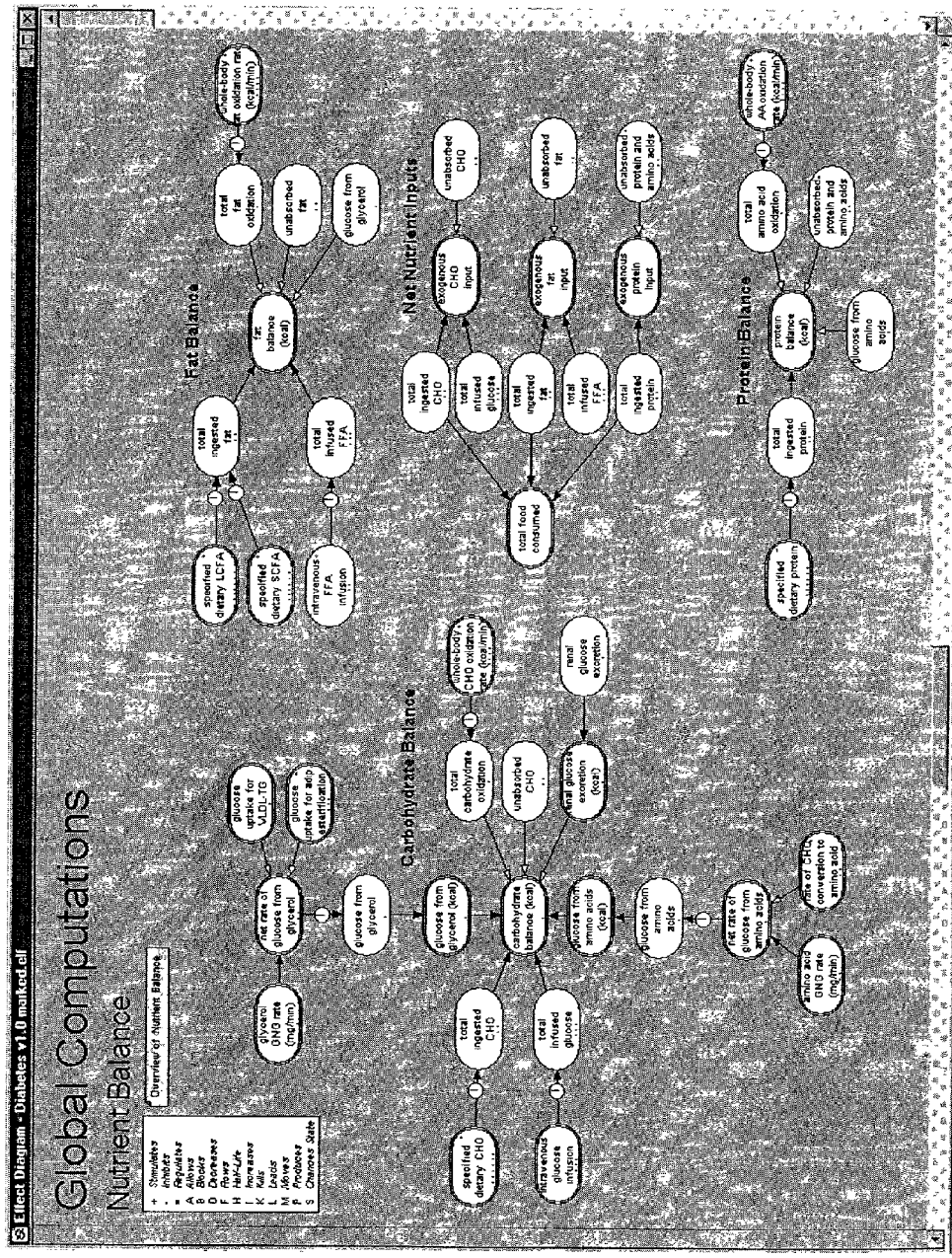

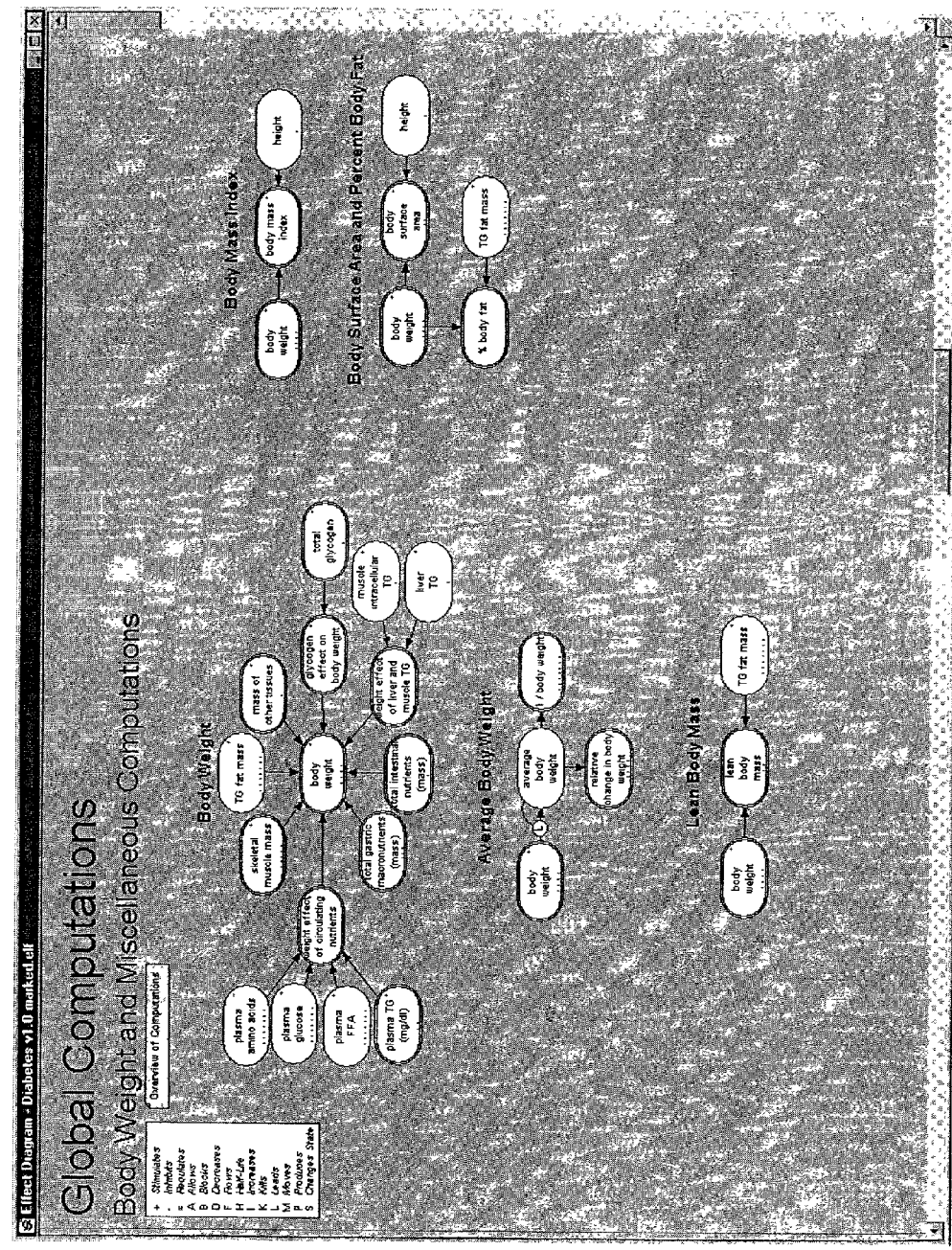

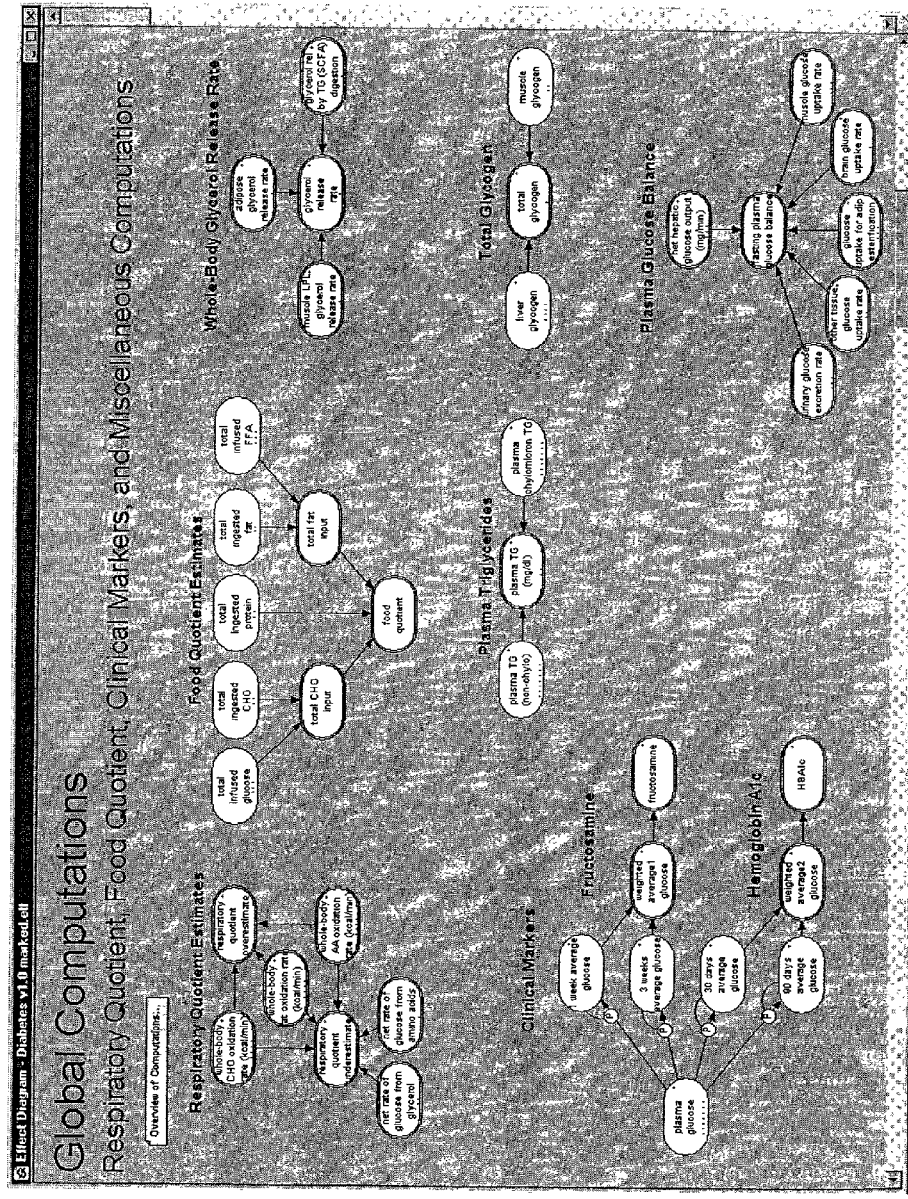

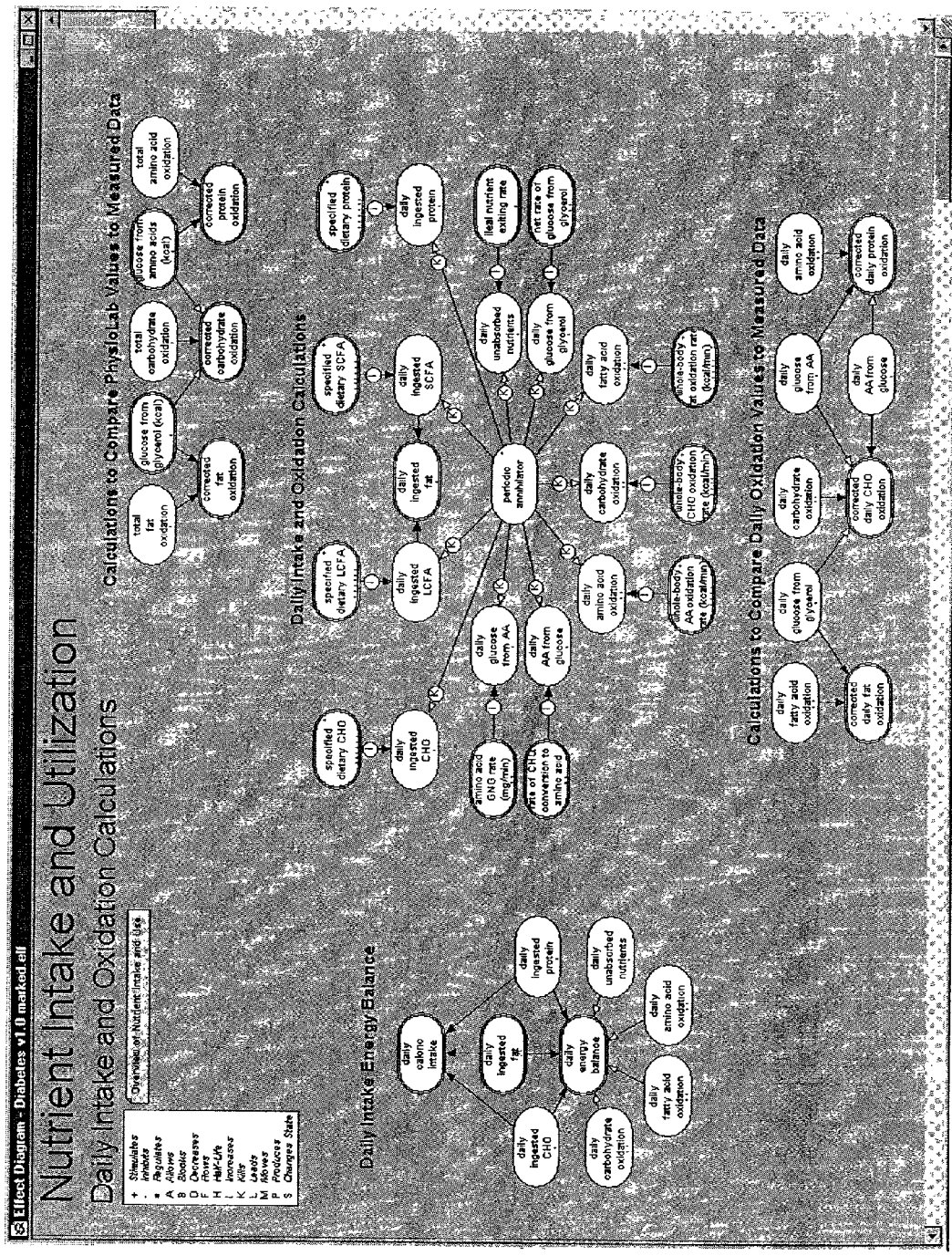

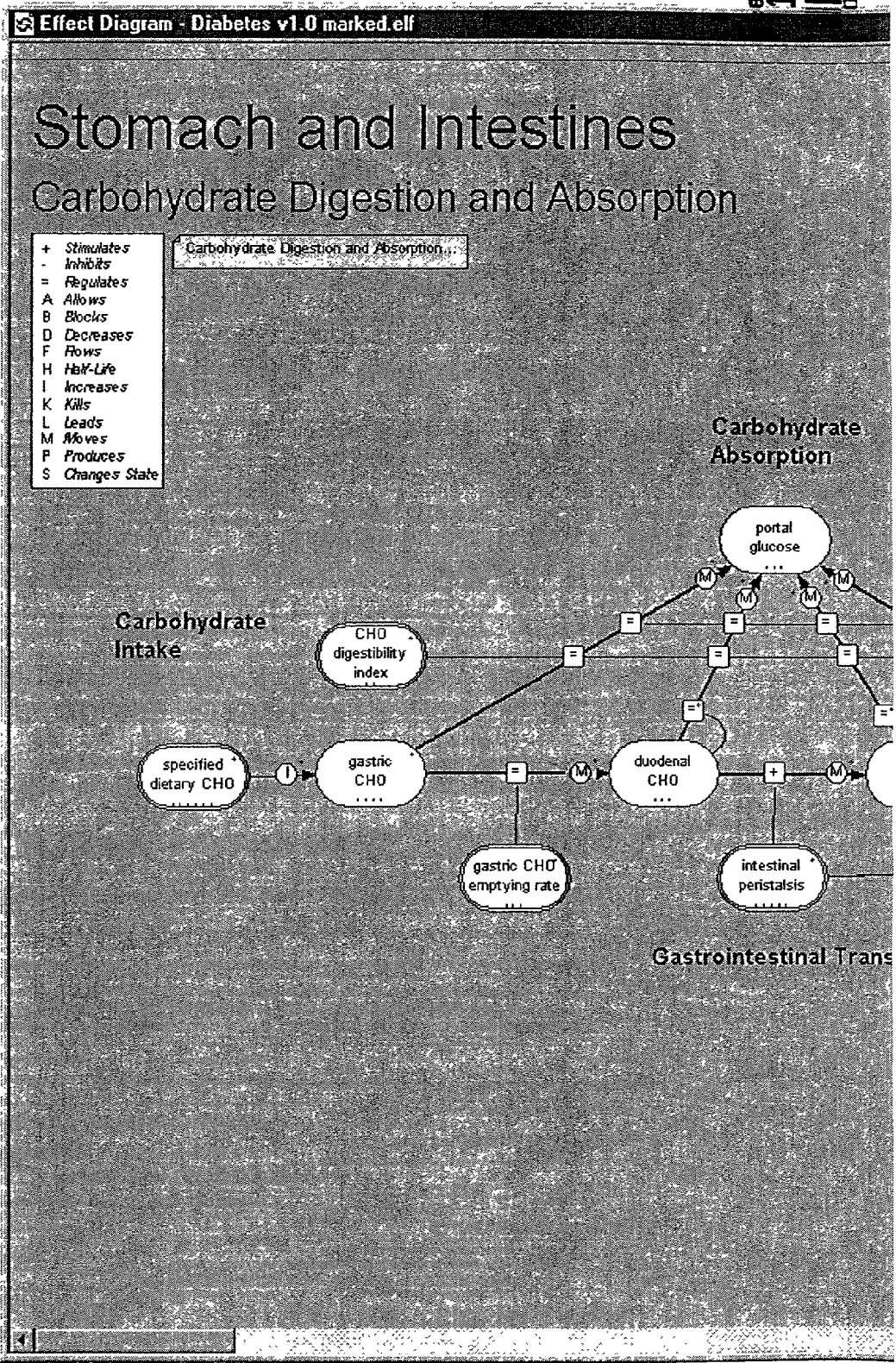

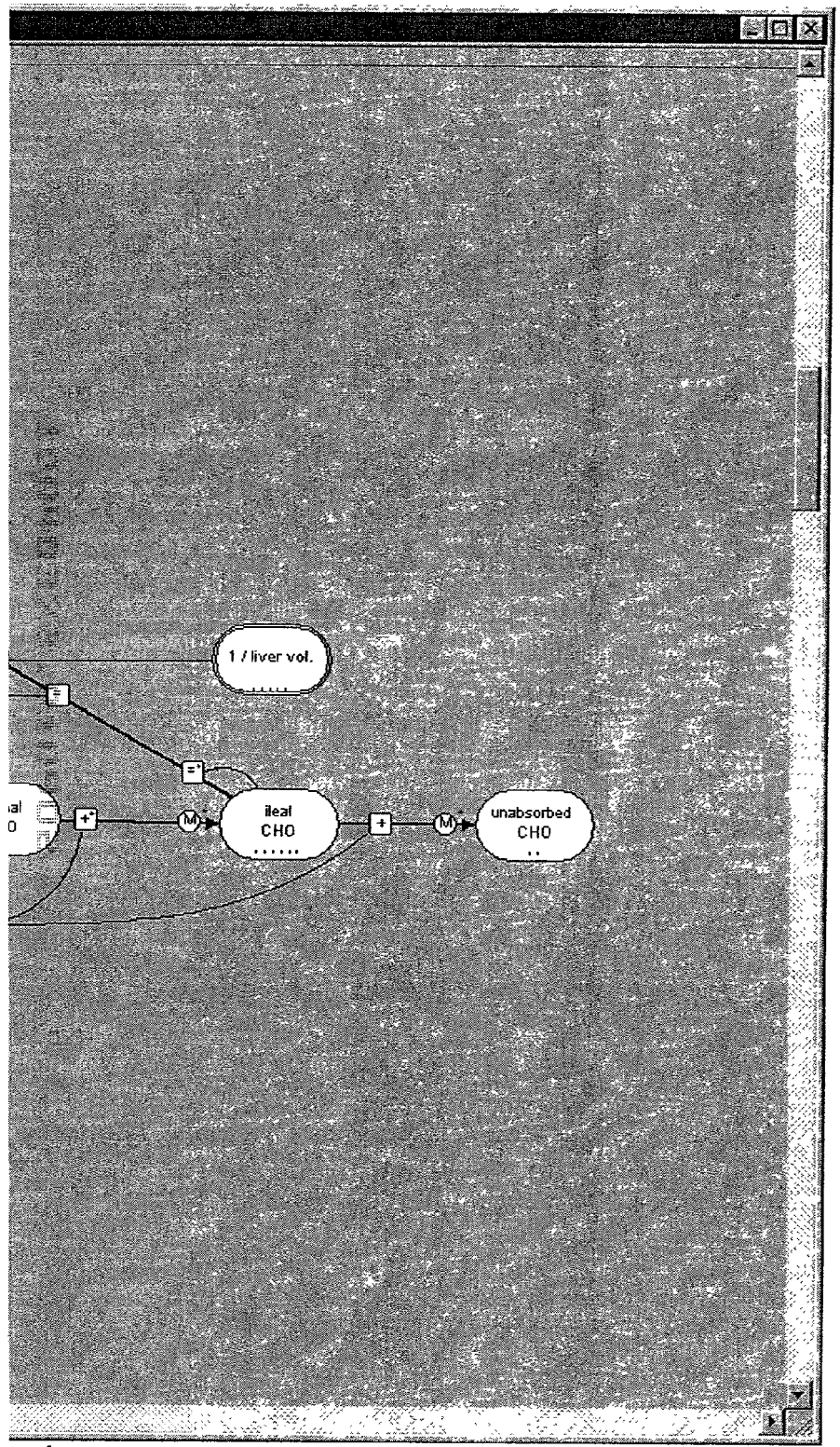

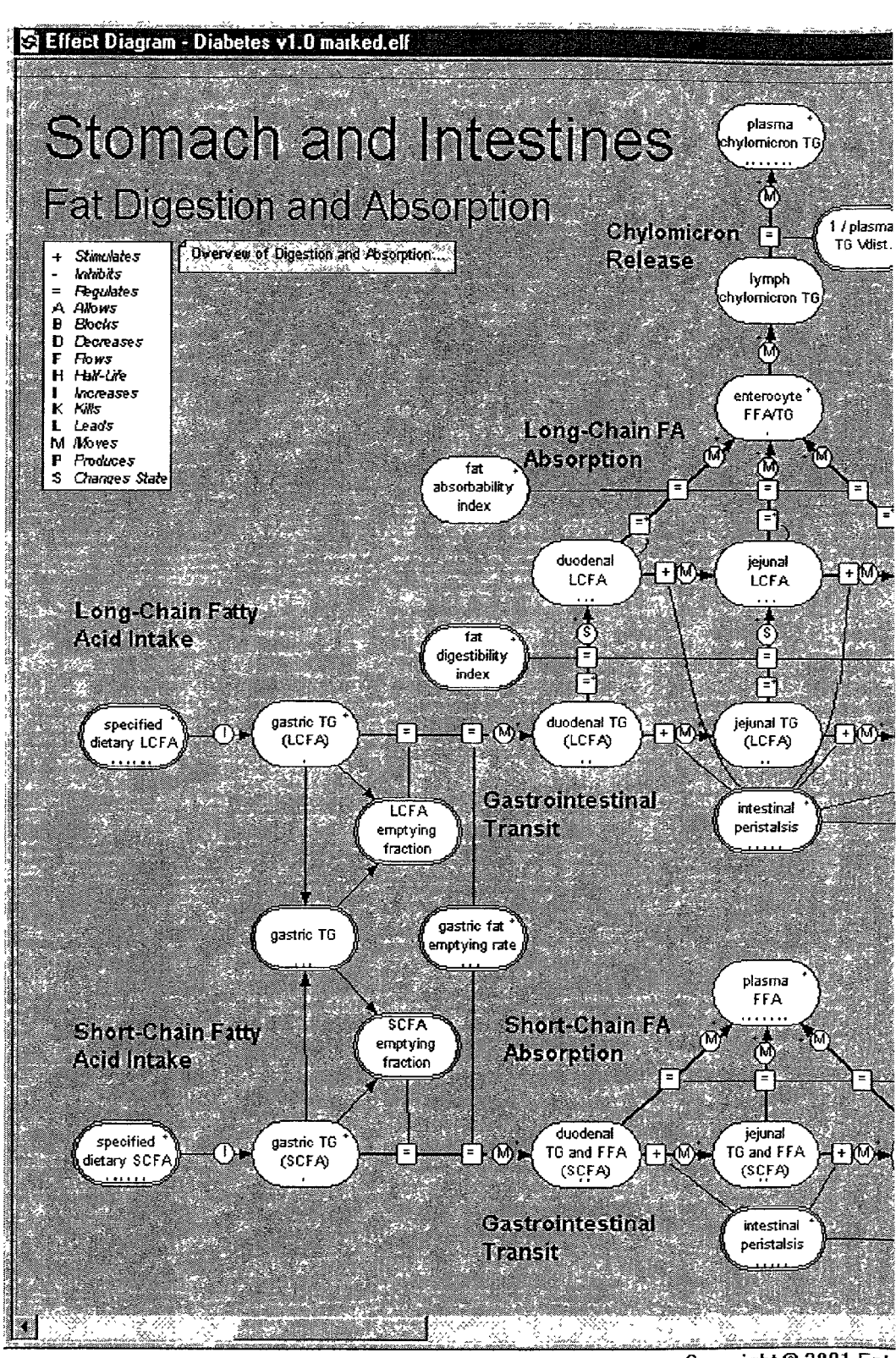

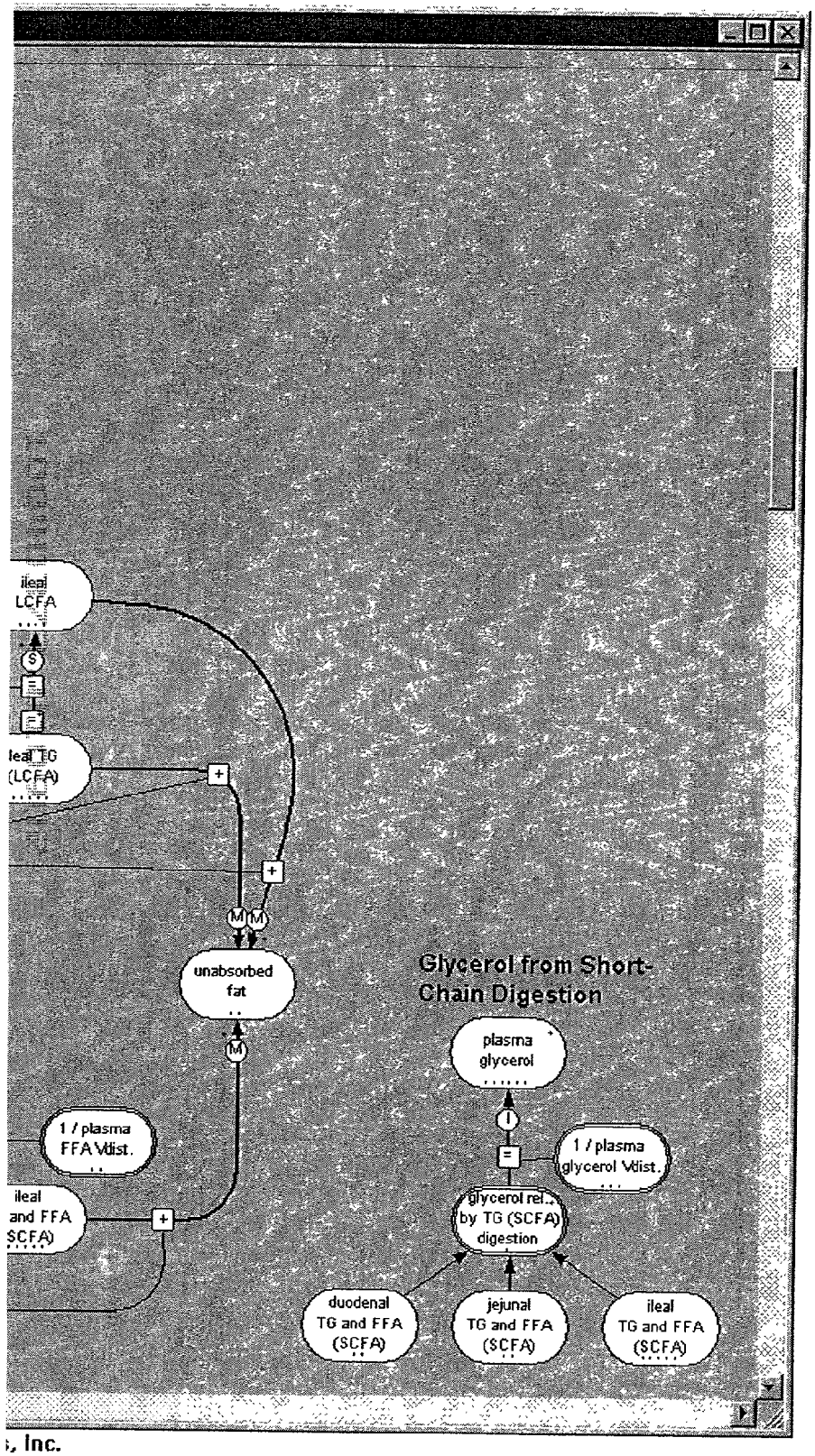

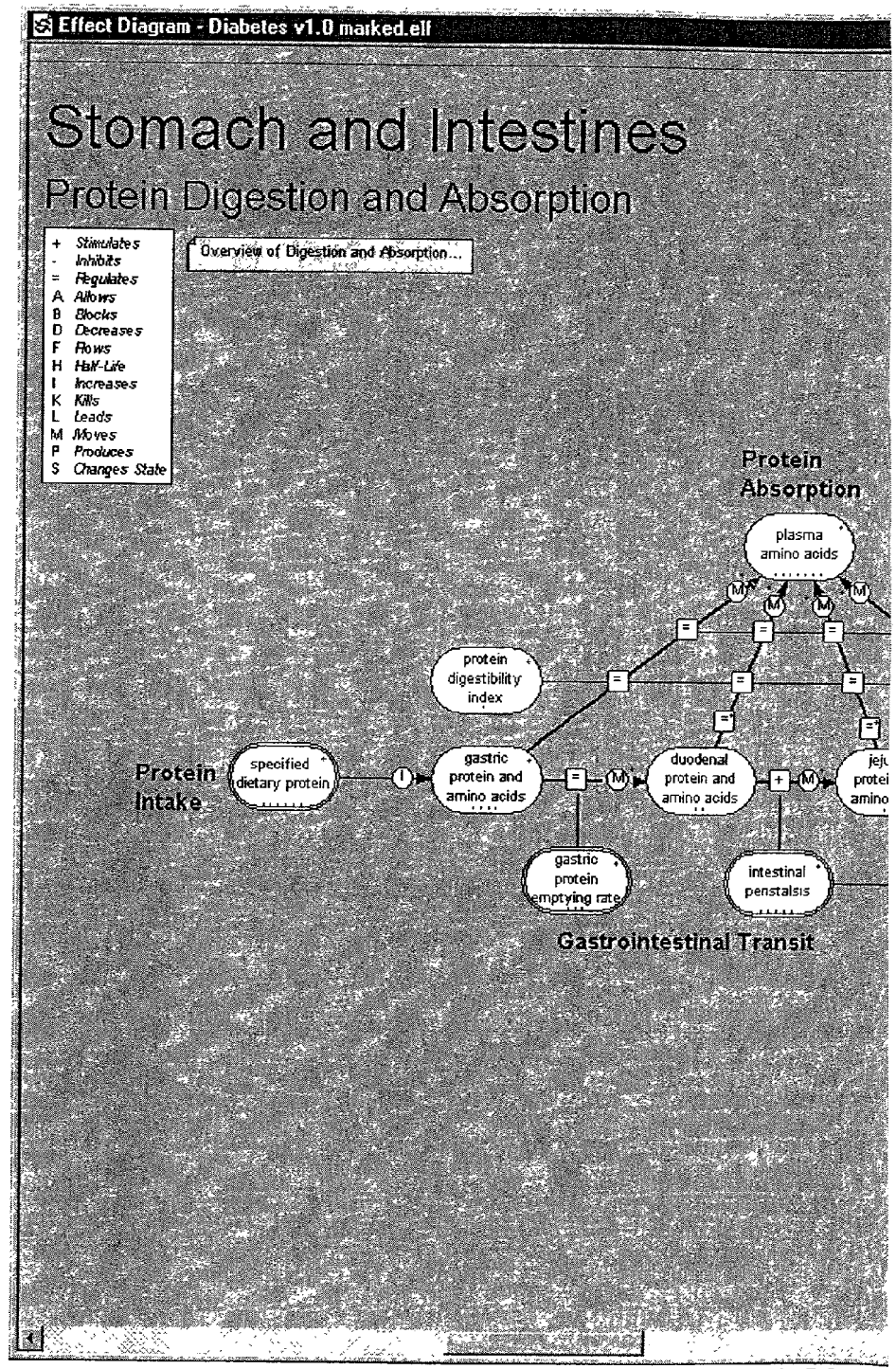

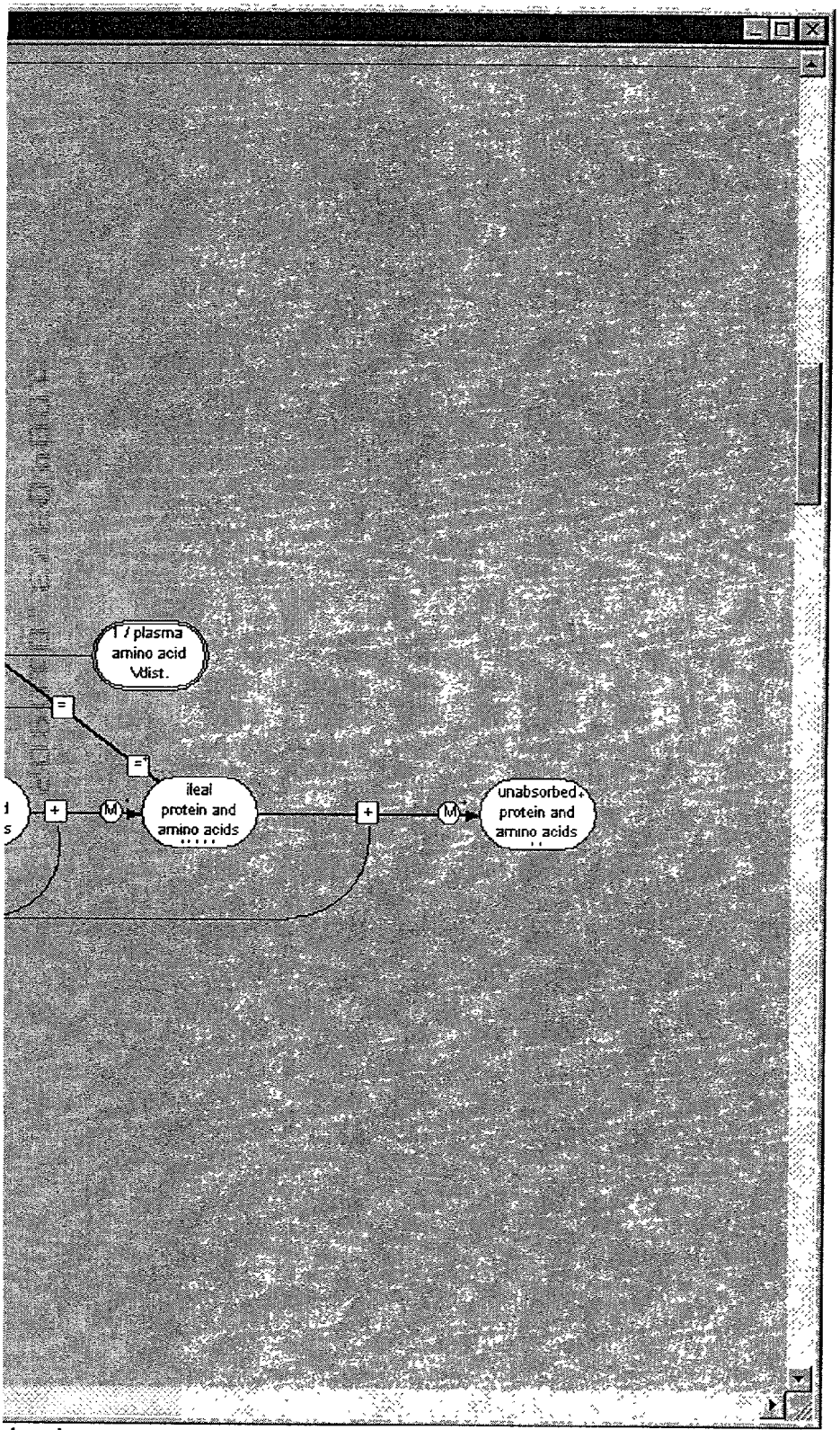

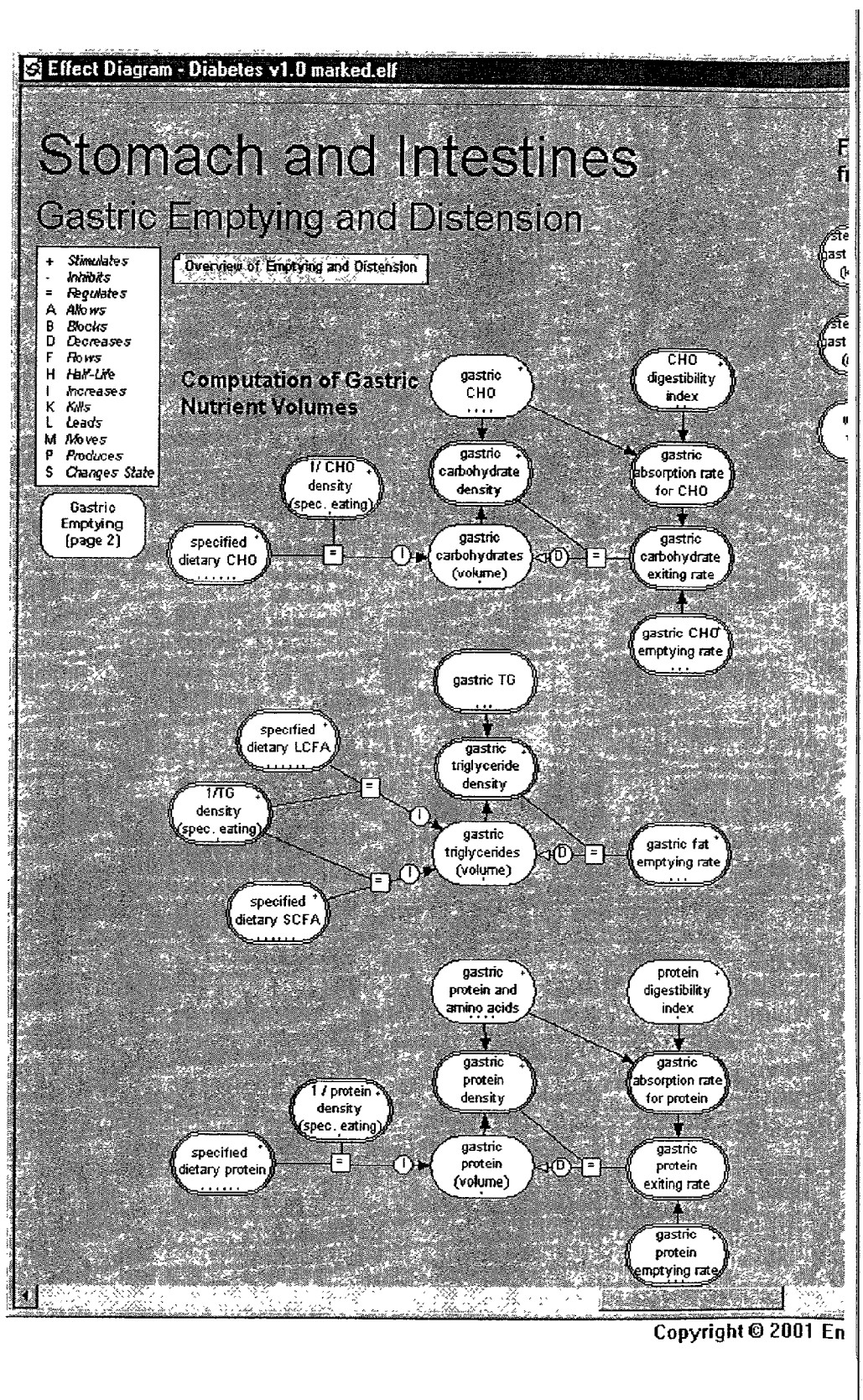

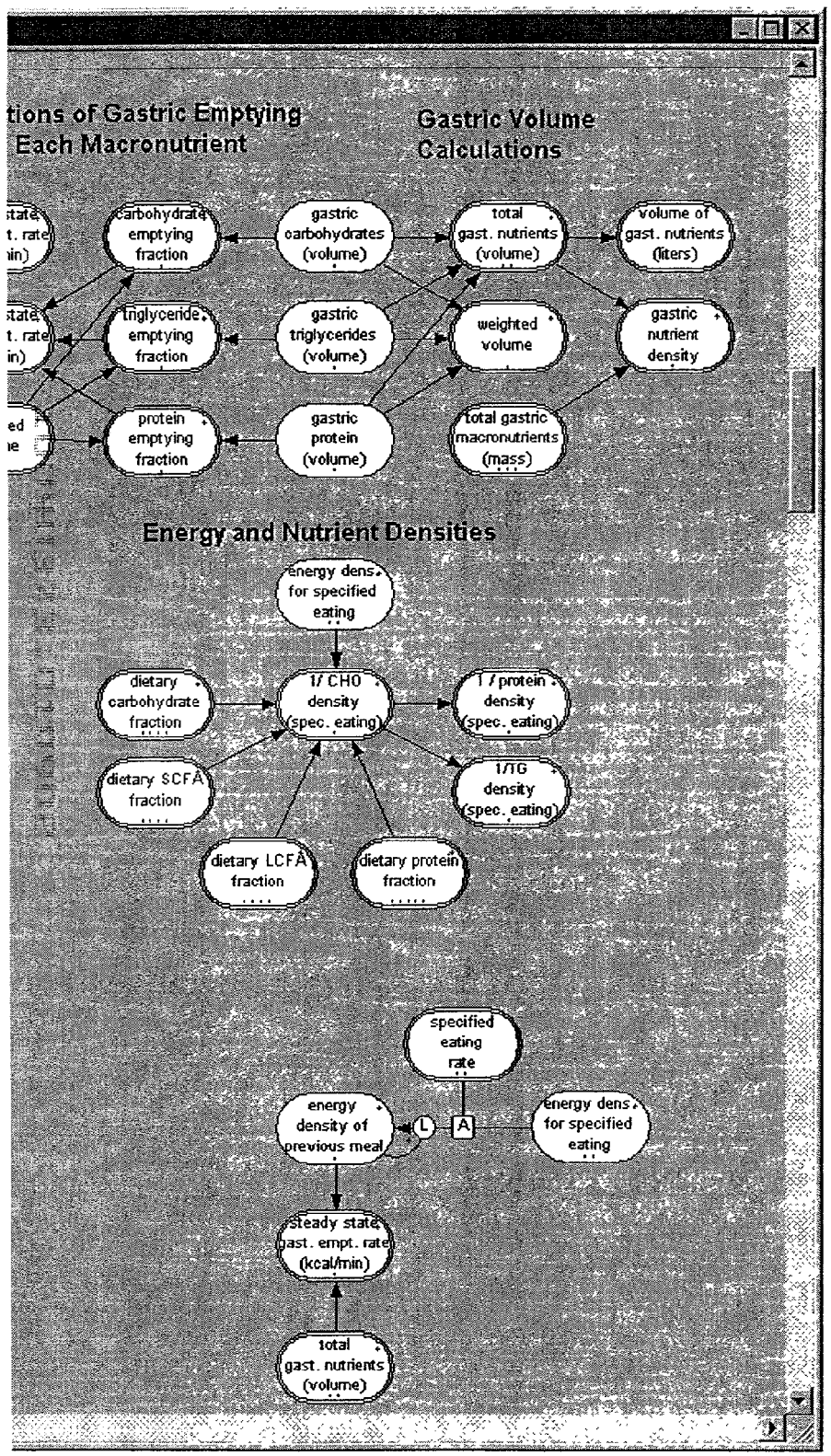

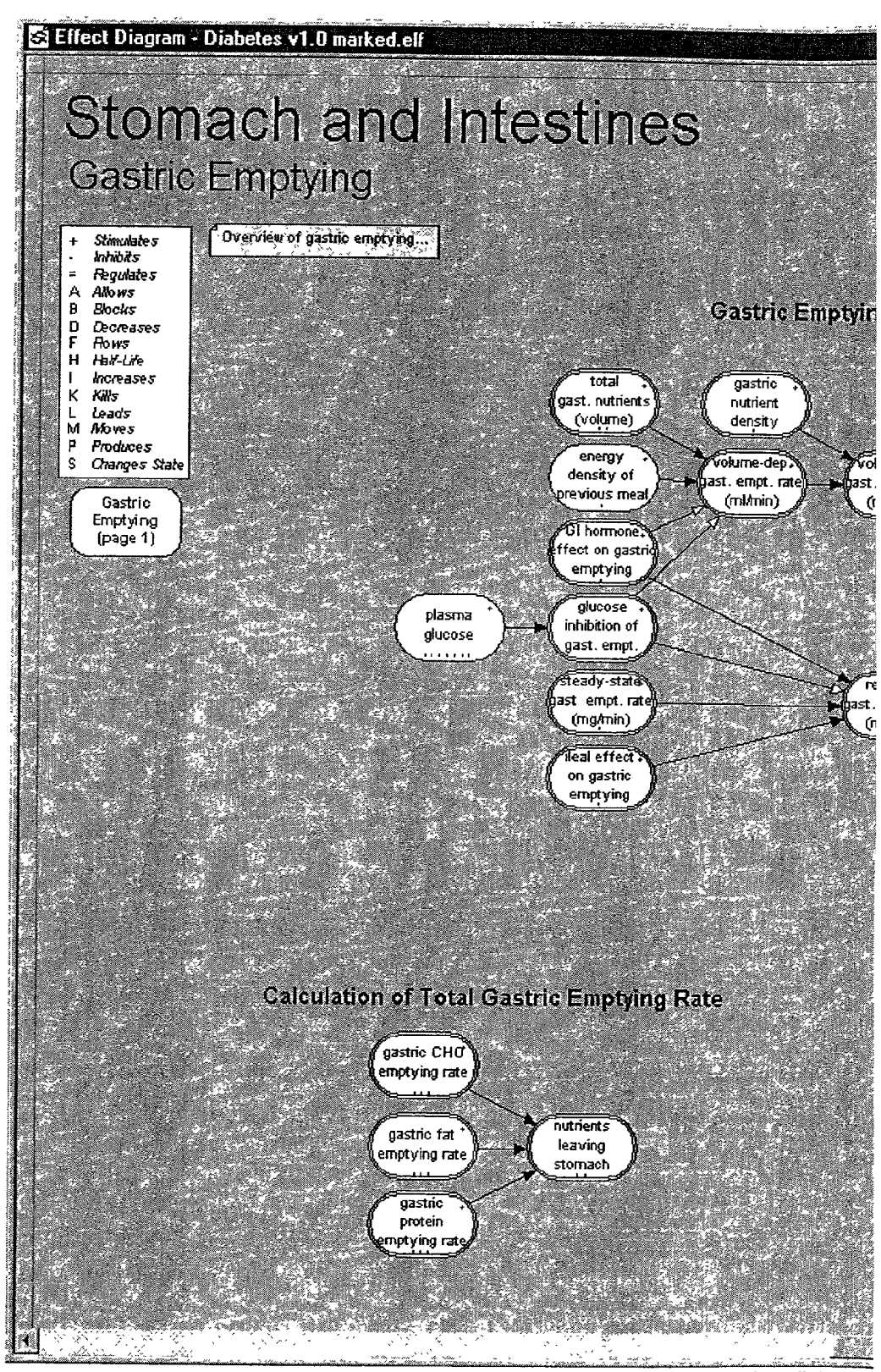

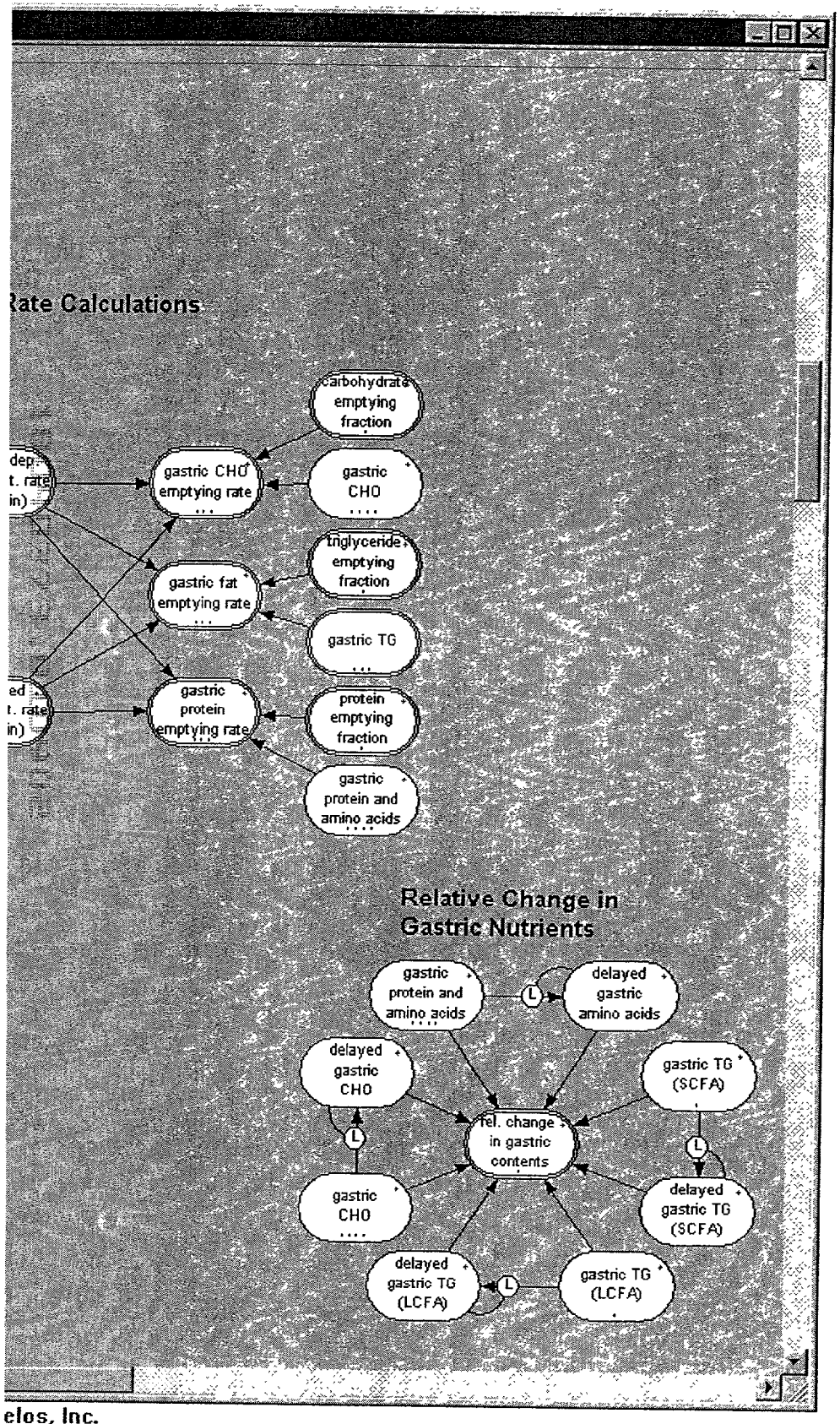

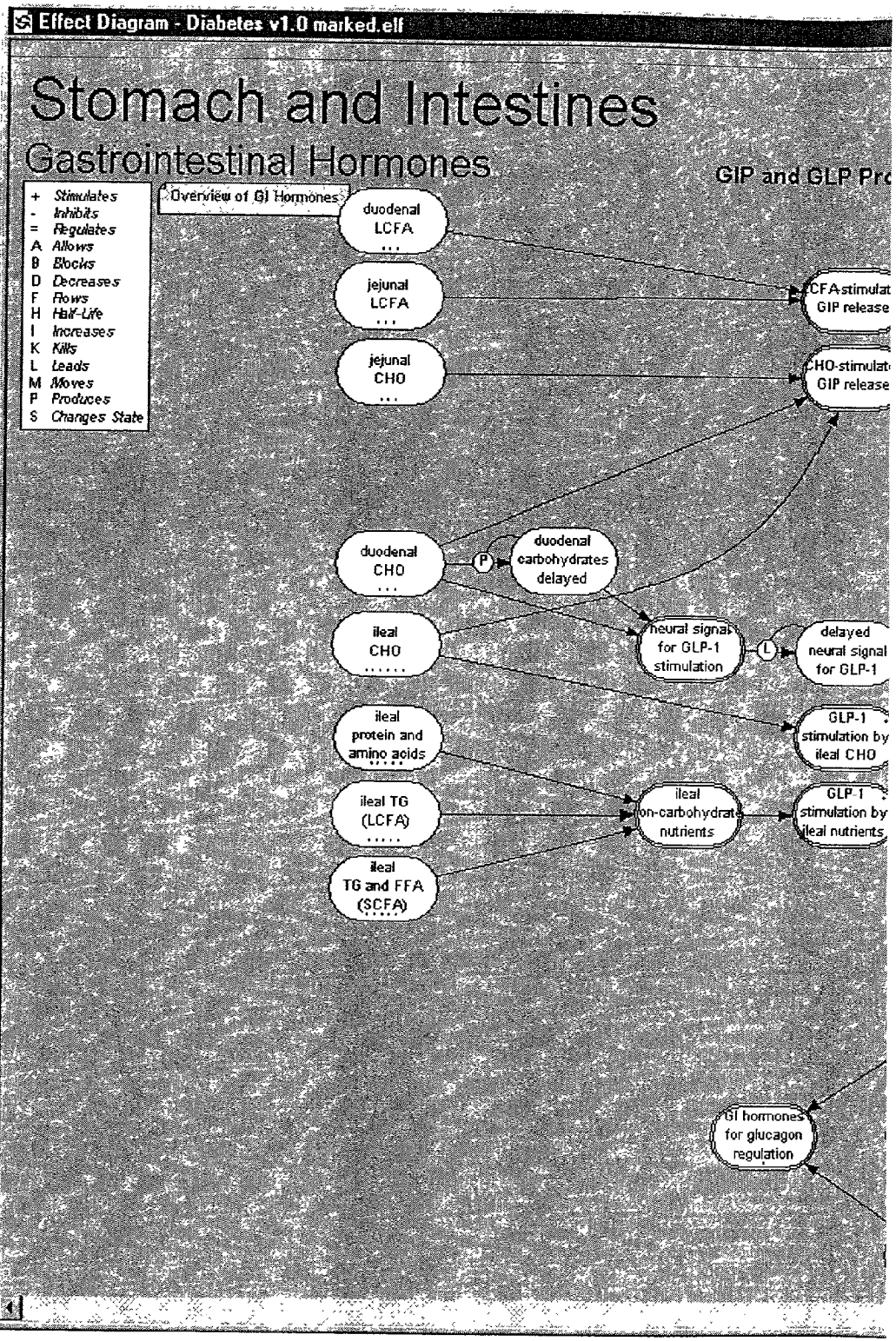

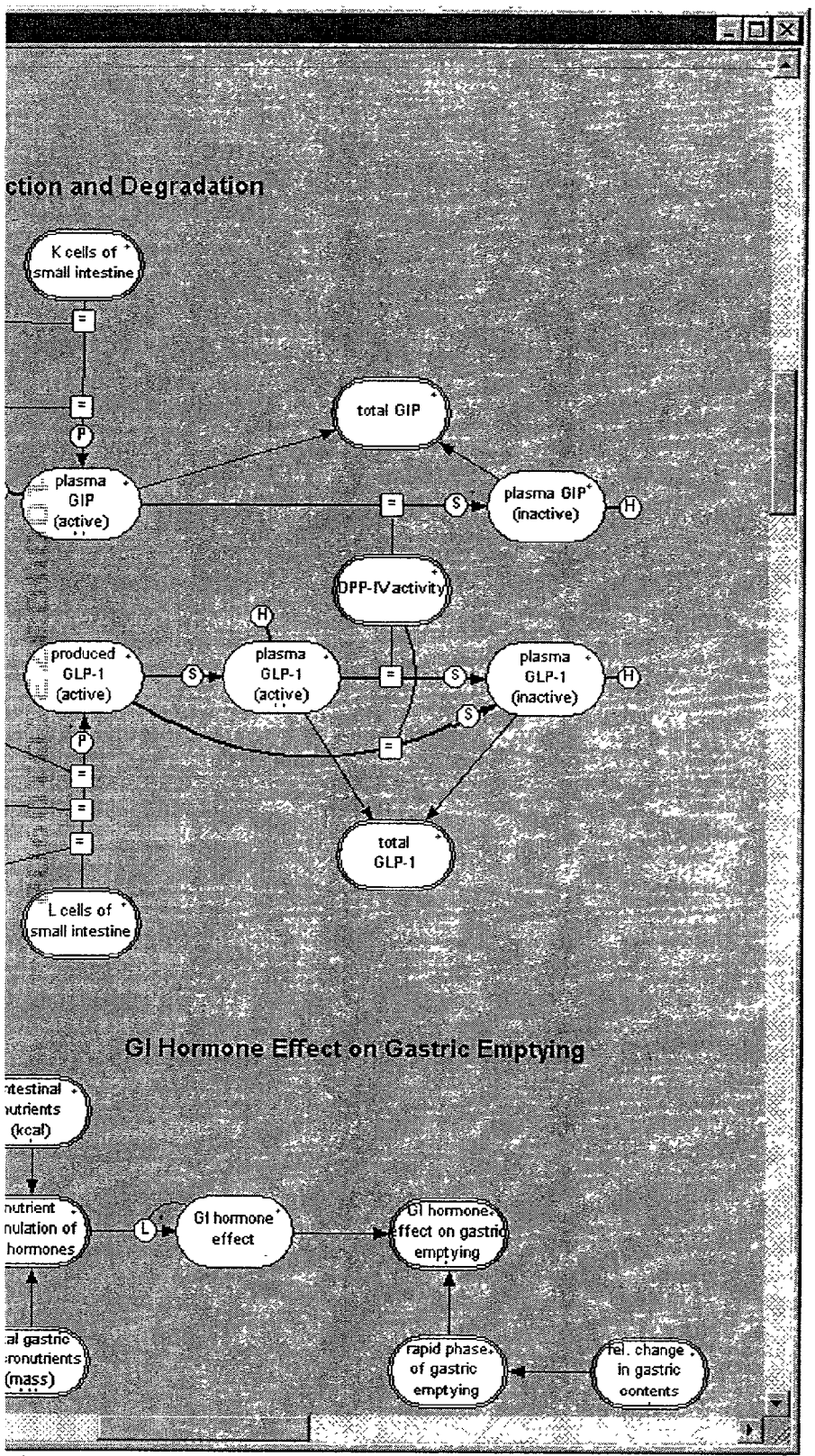

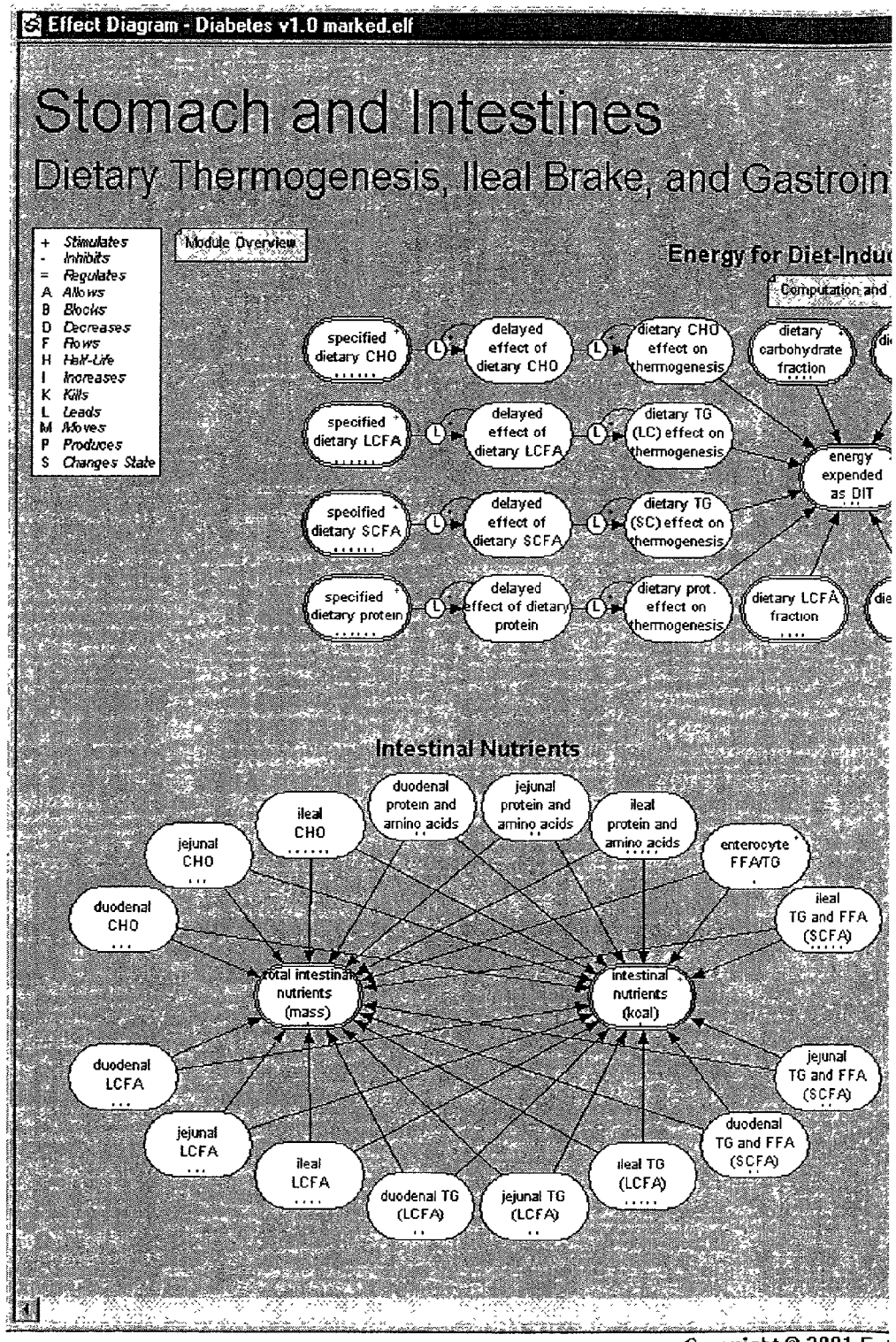

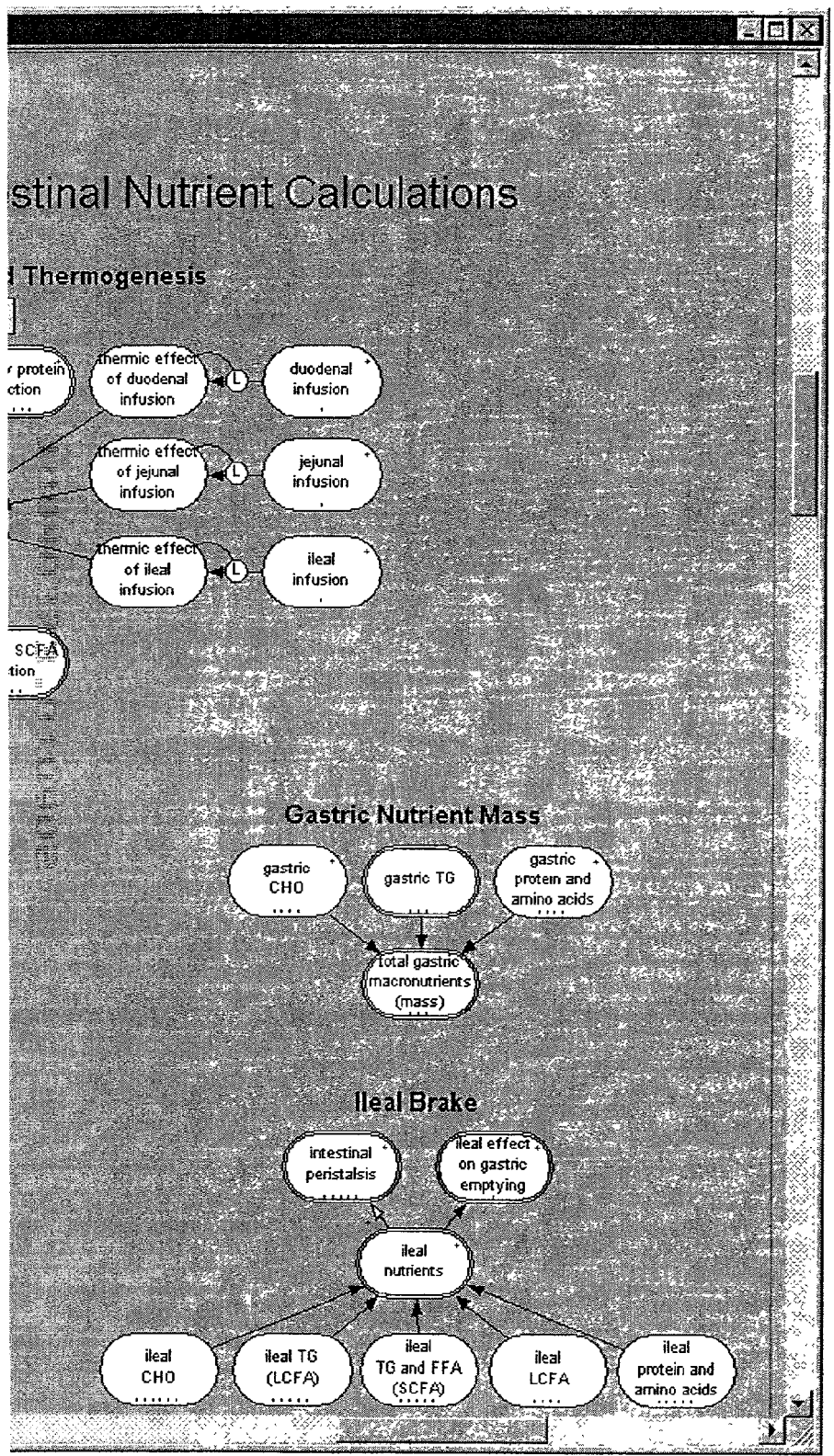

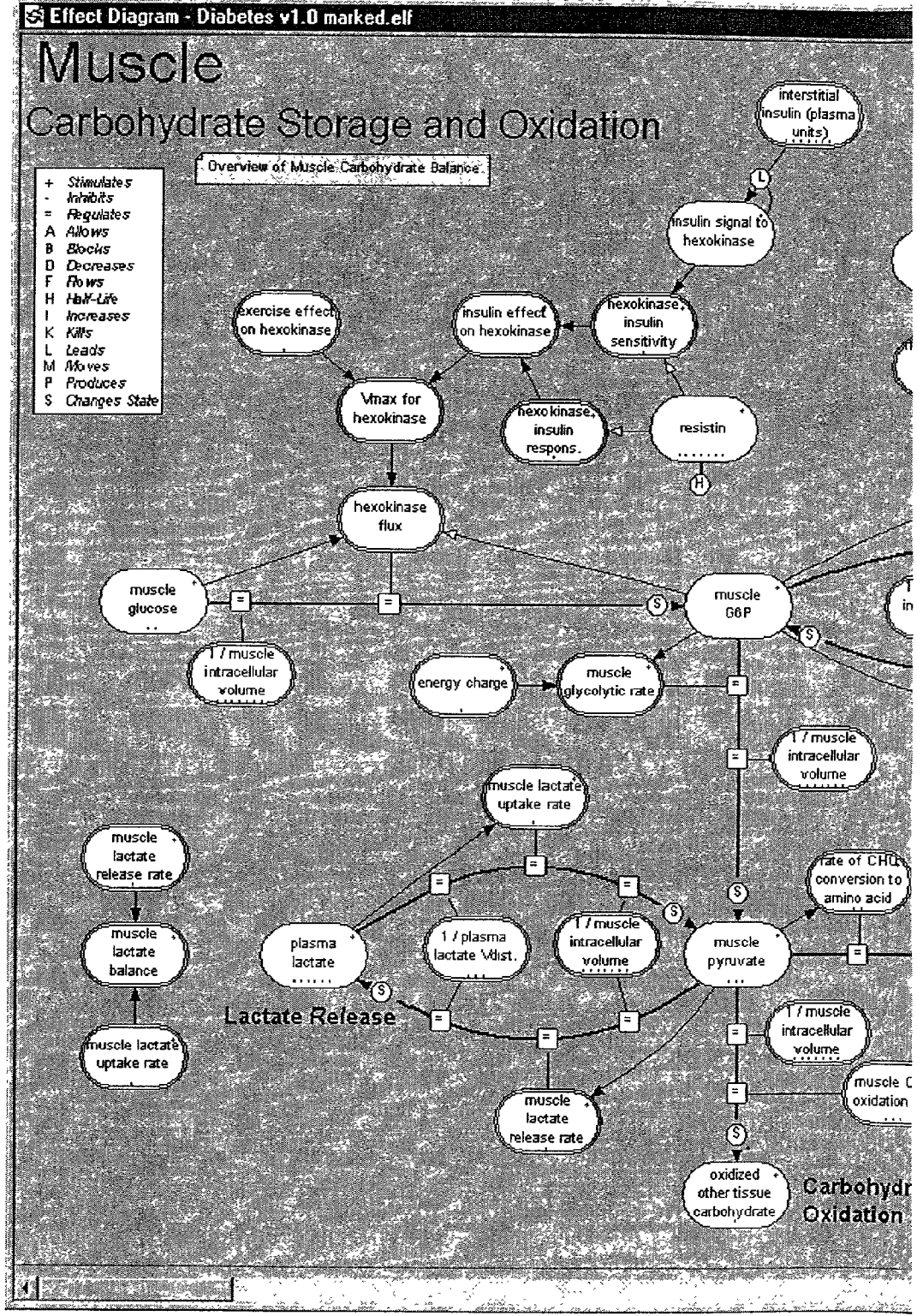

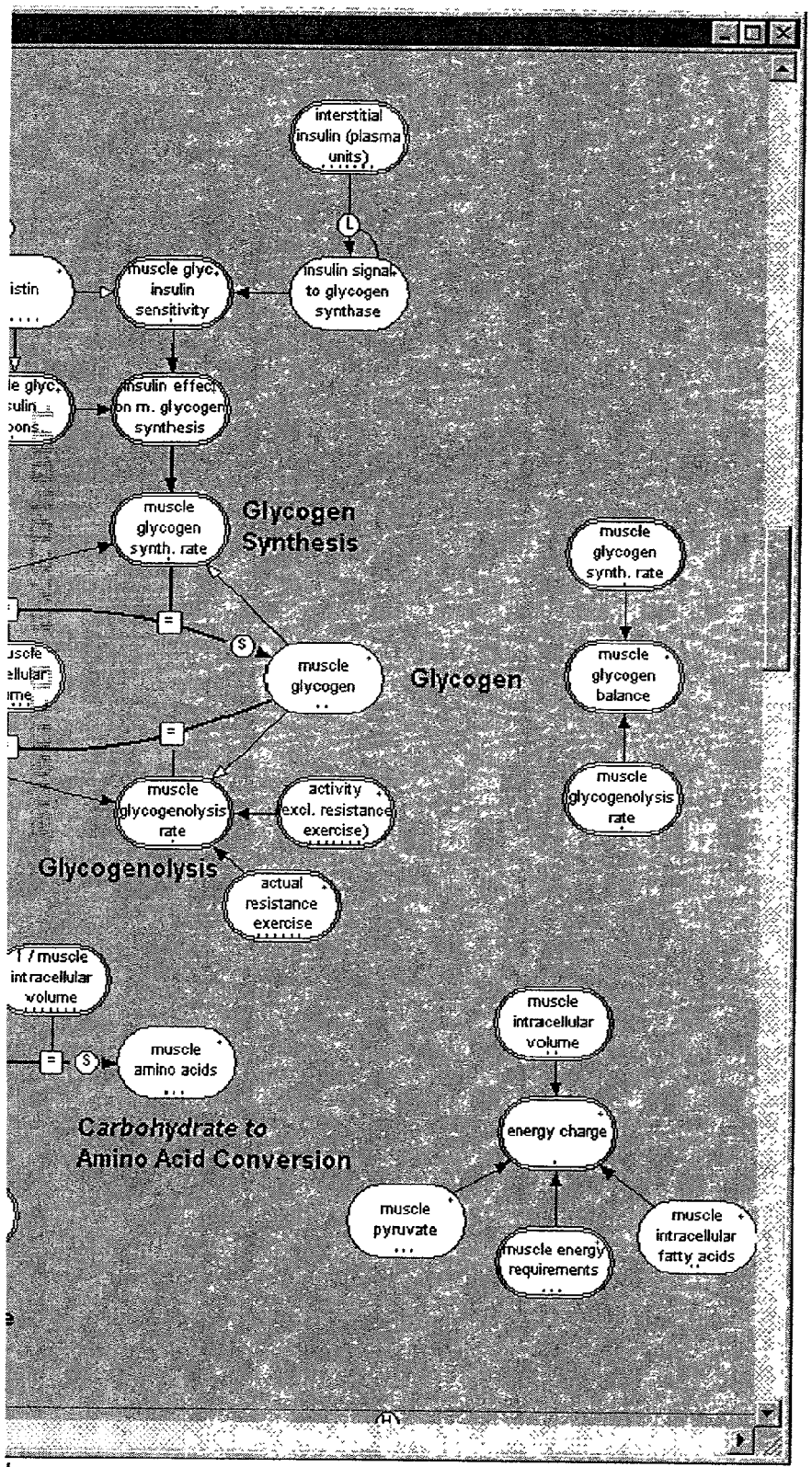

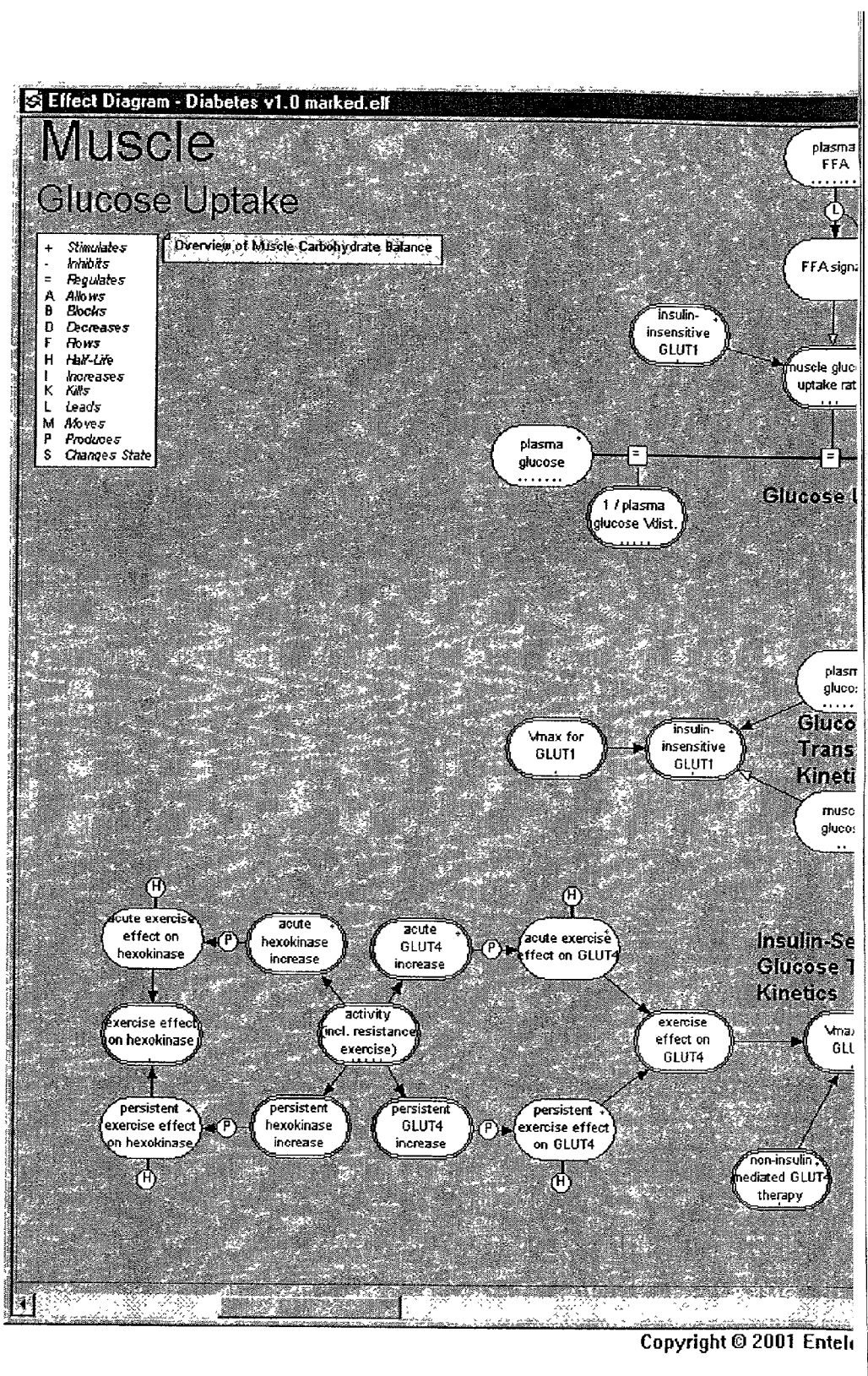

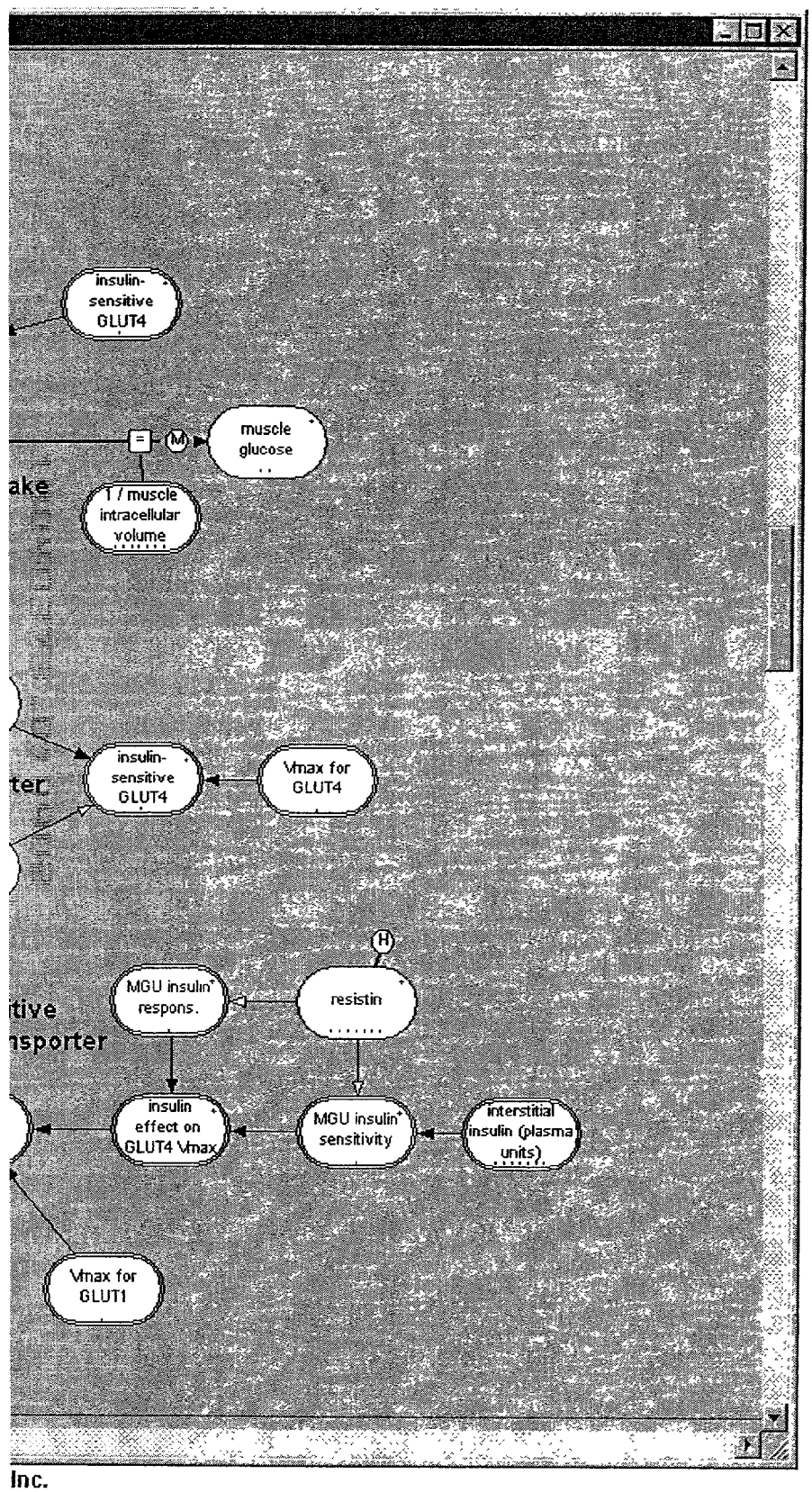

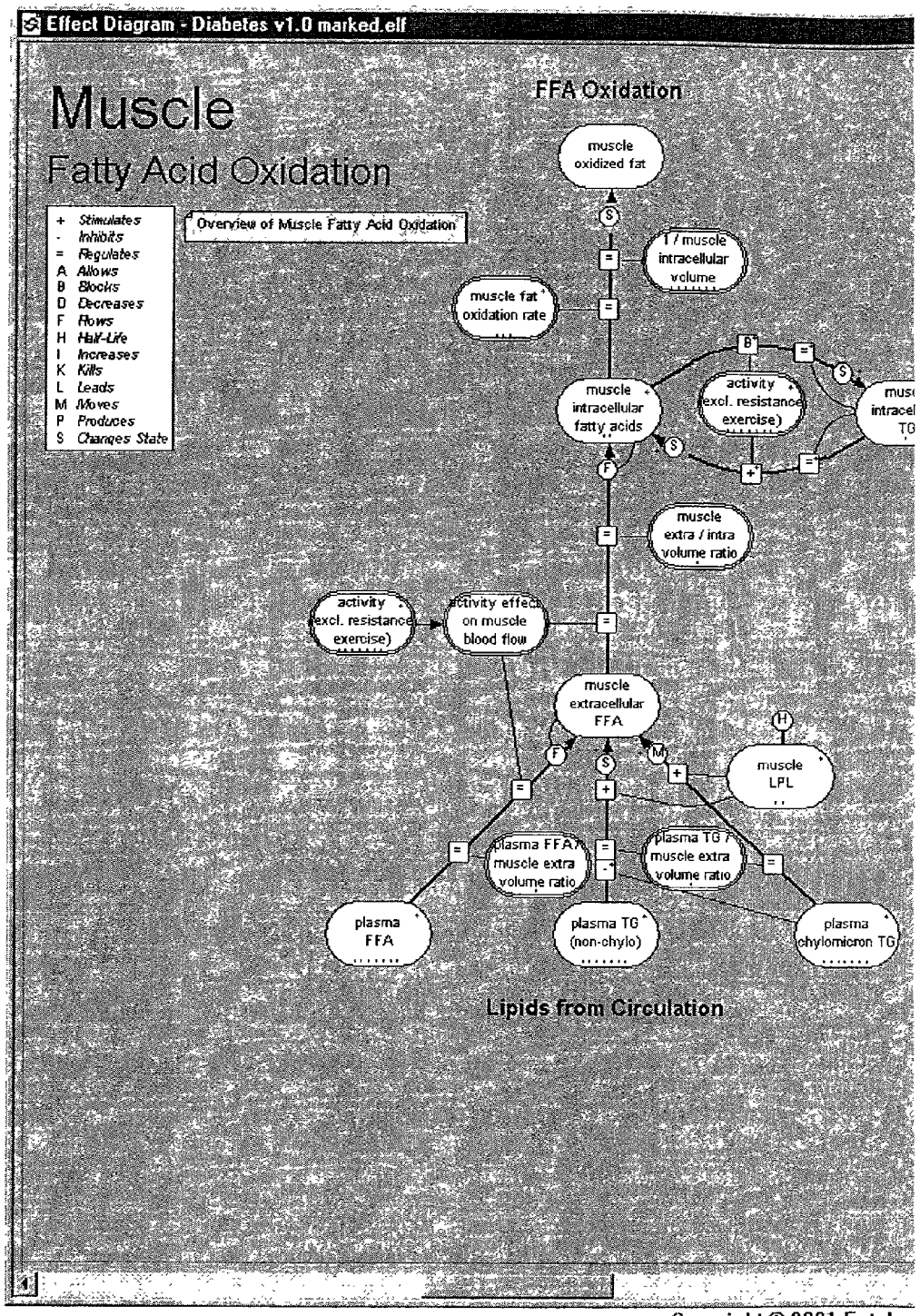

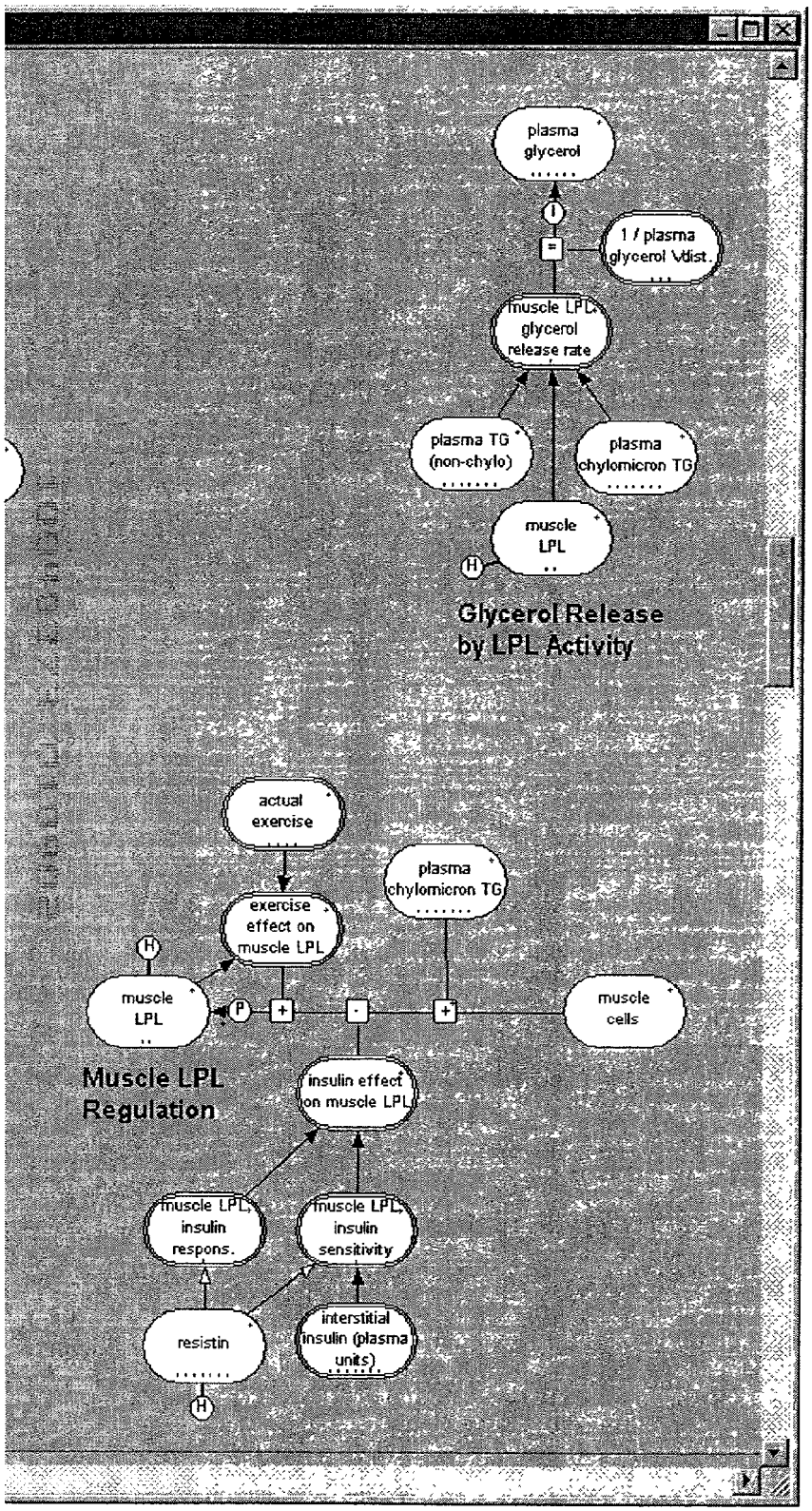

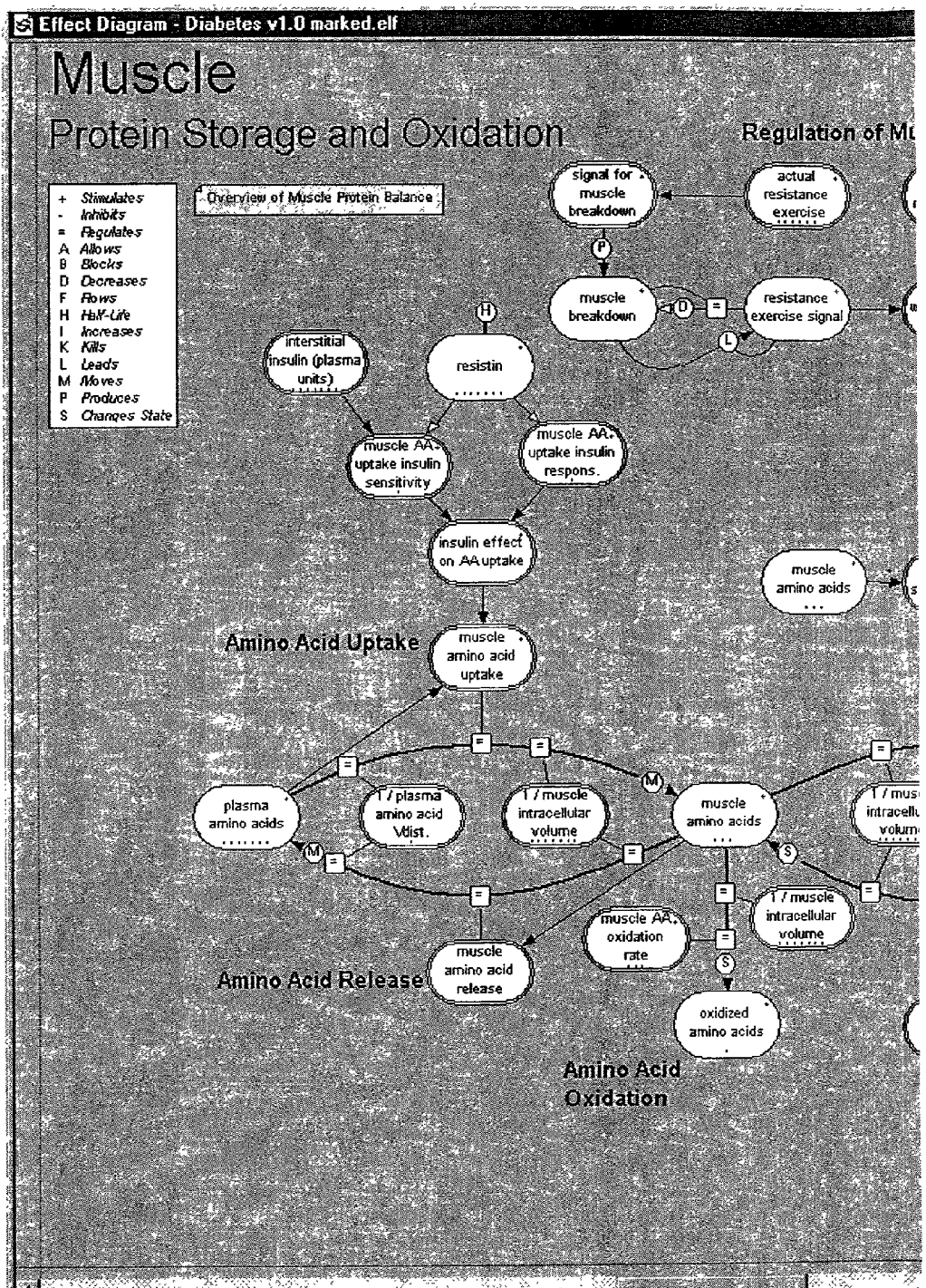

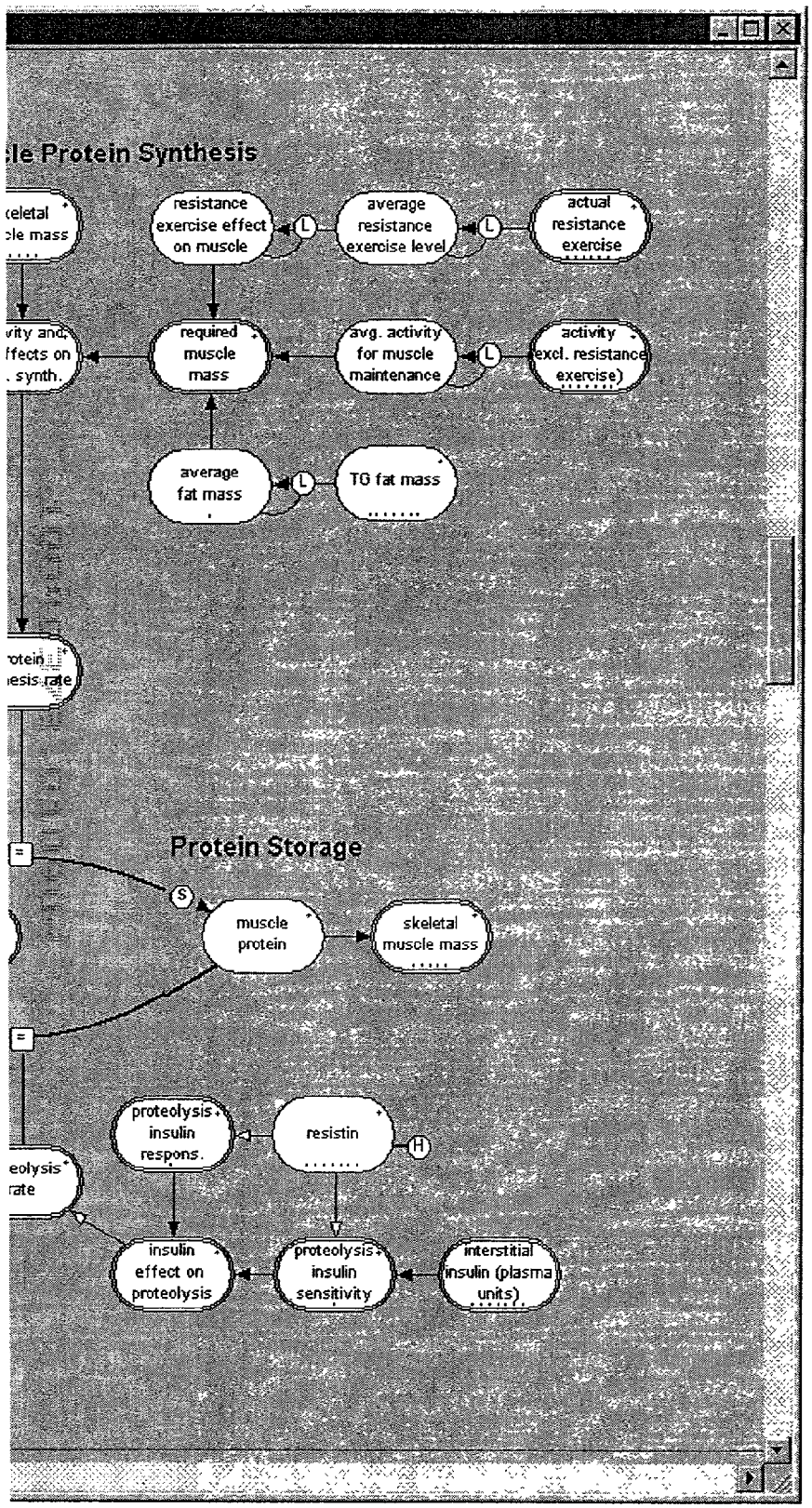

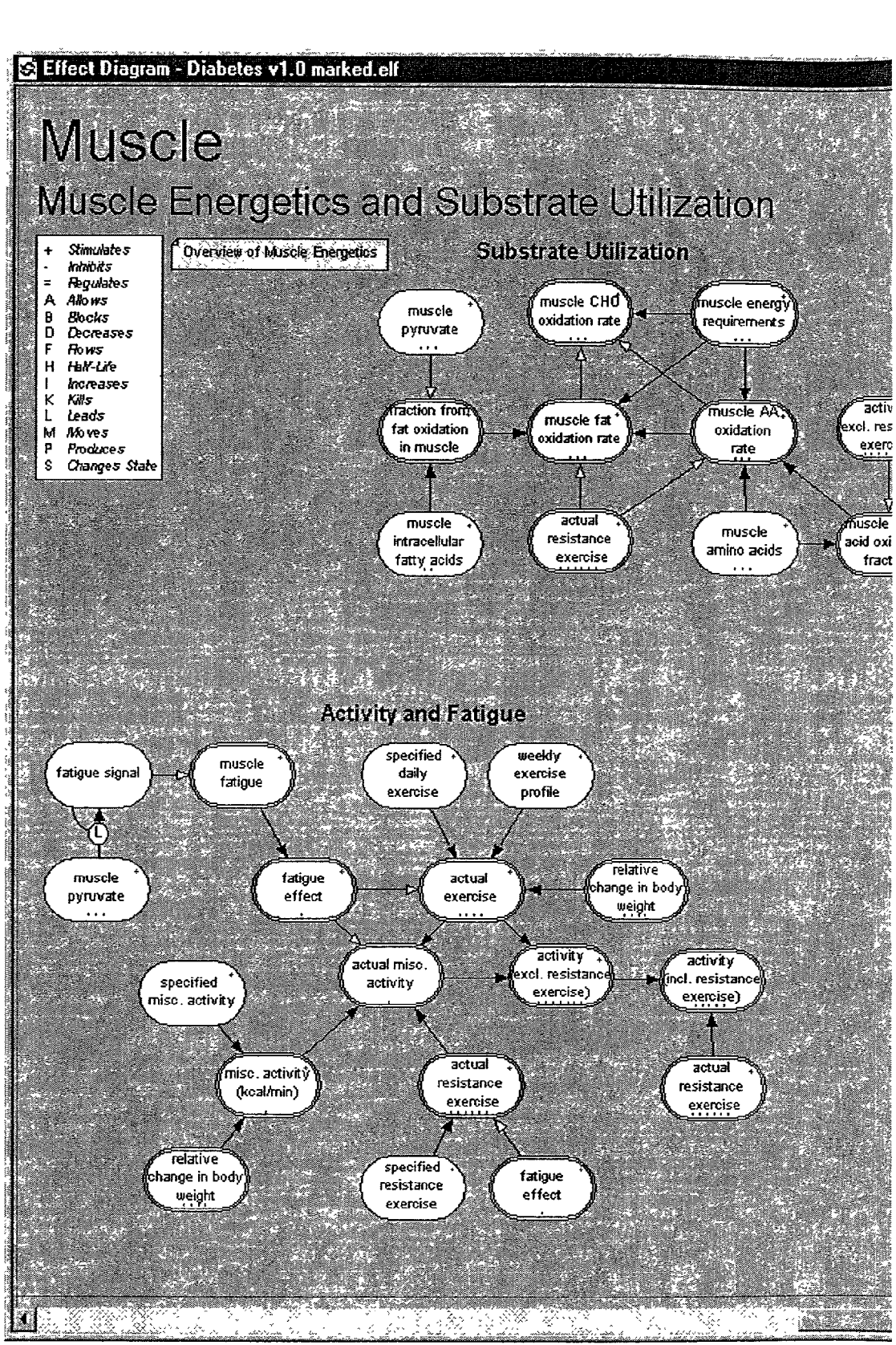

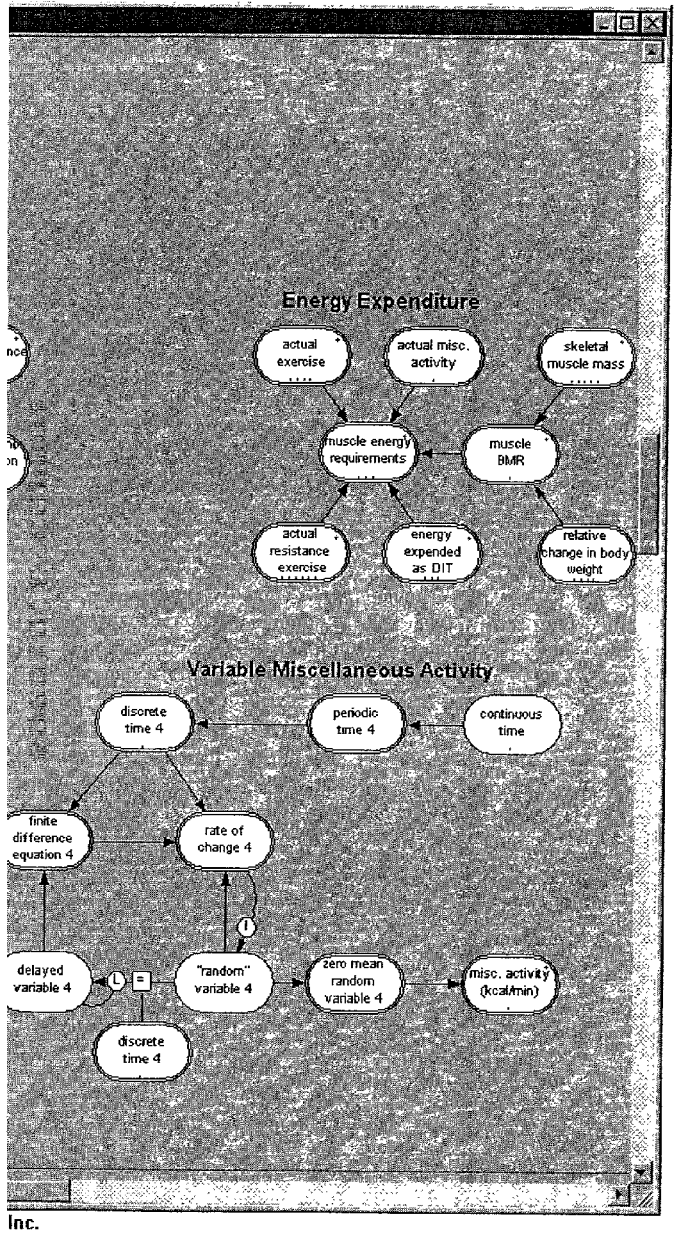

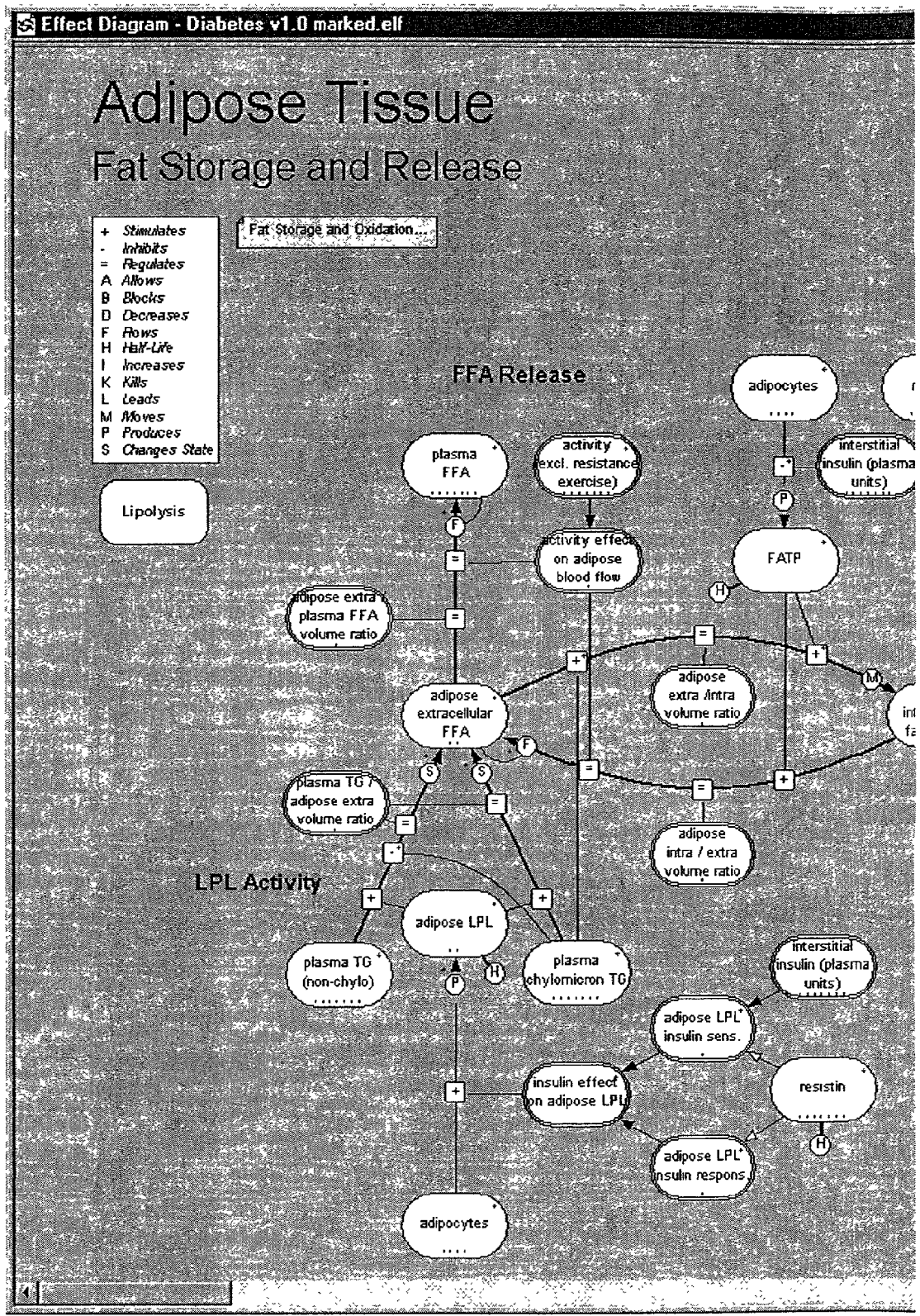

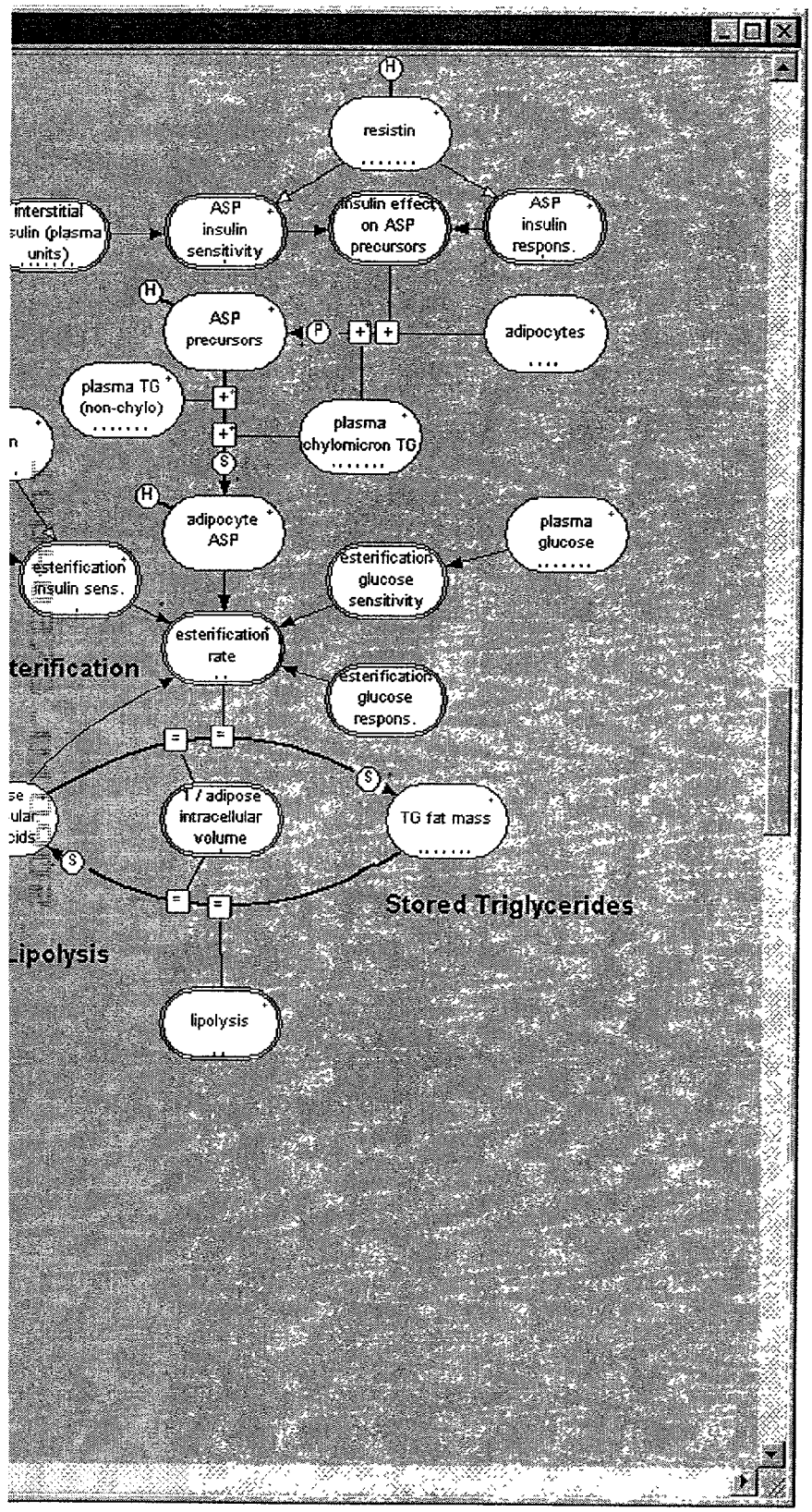

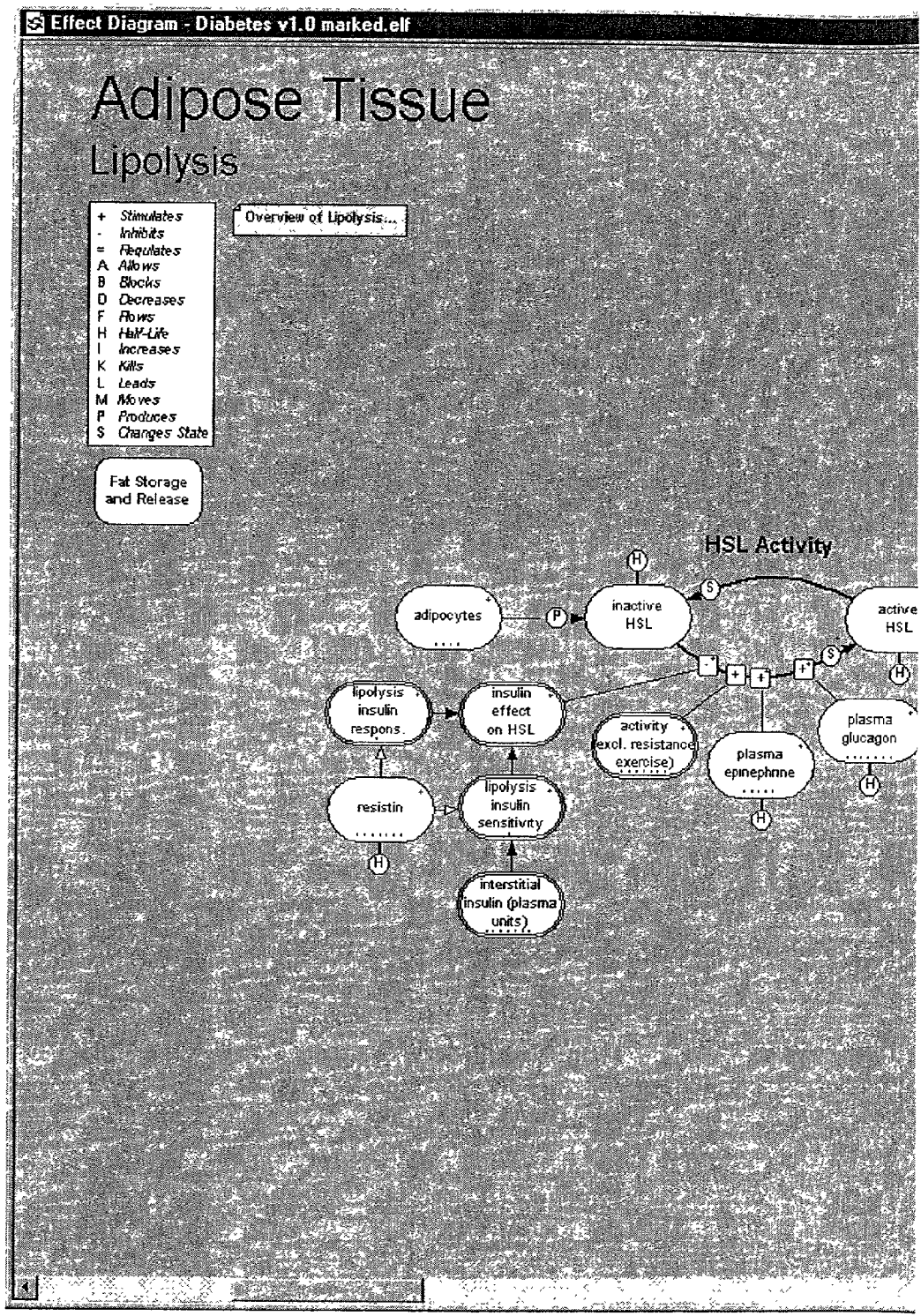

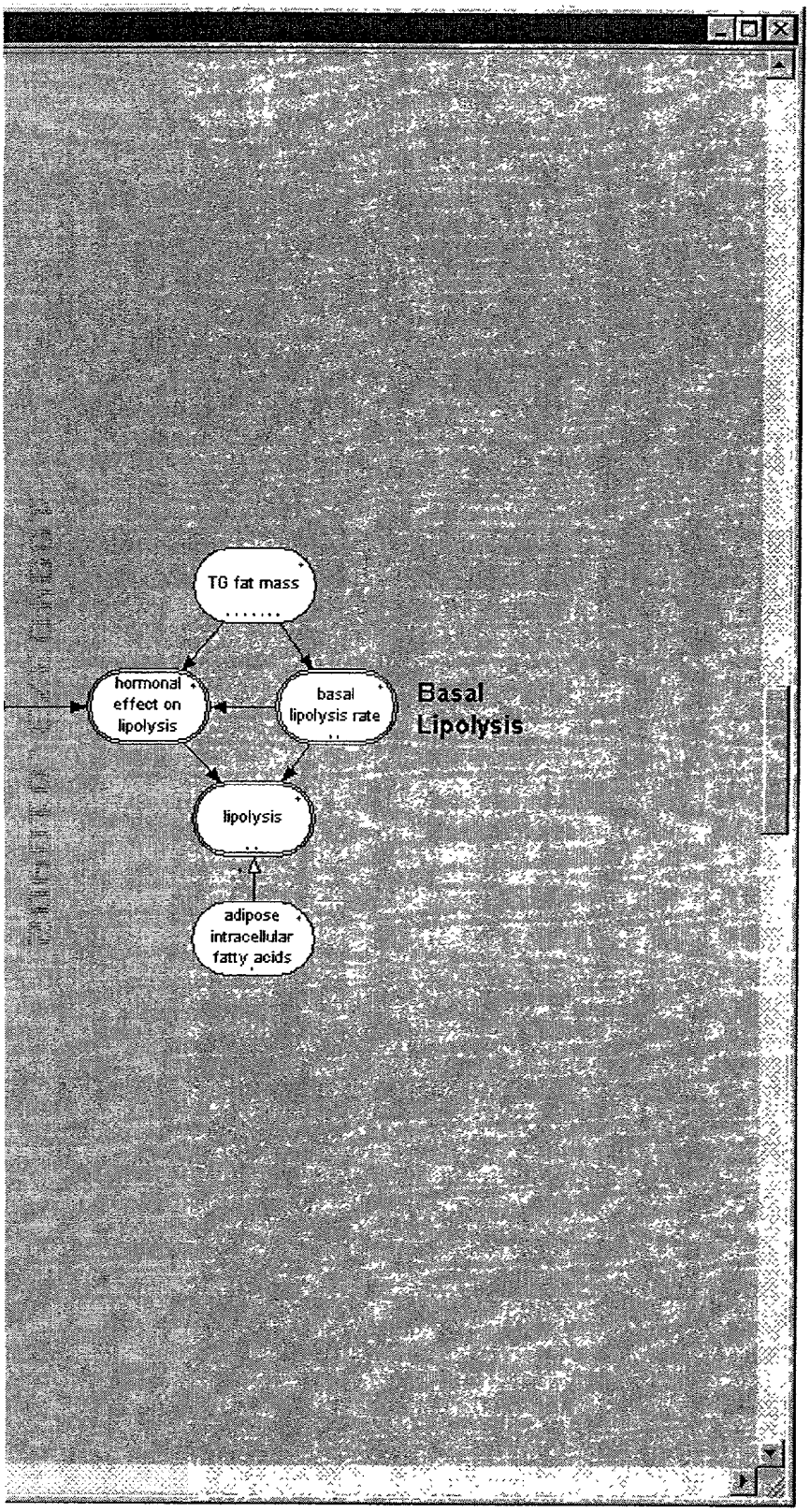
c.

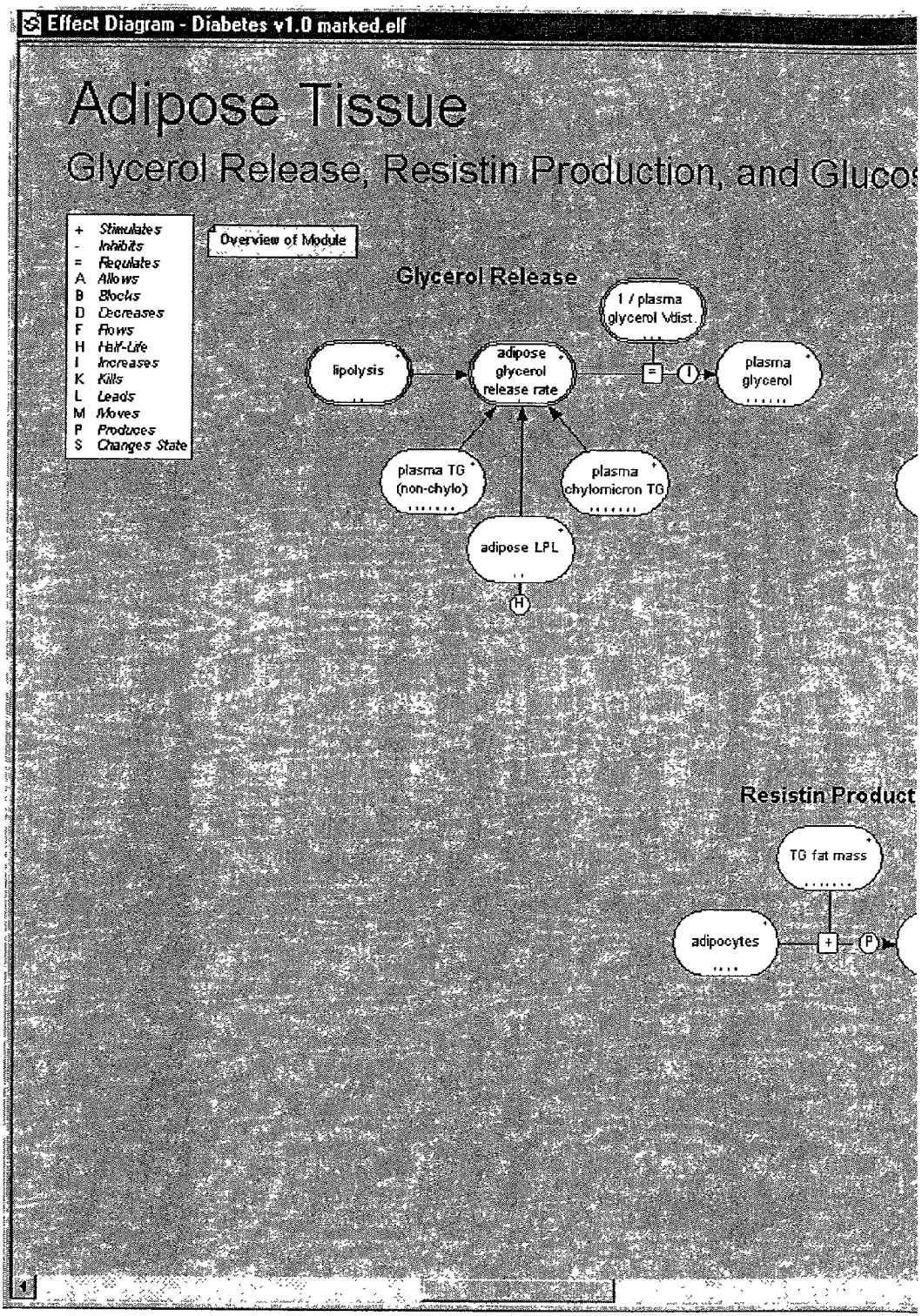

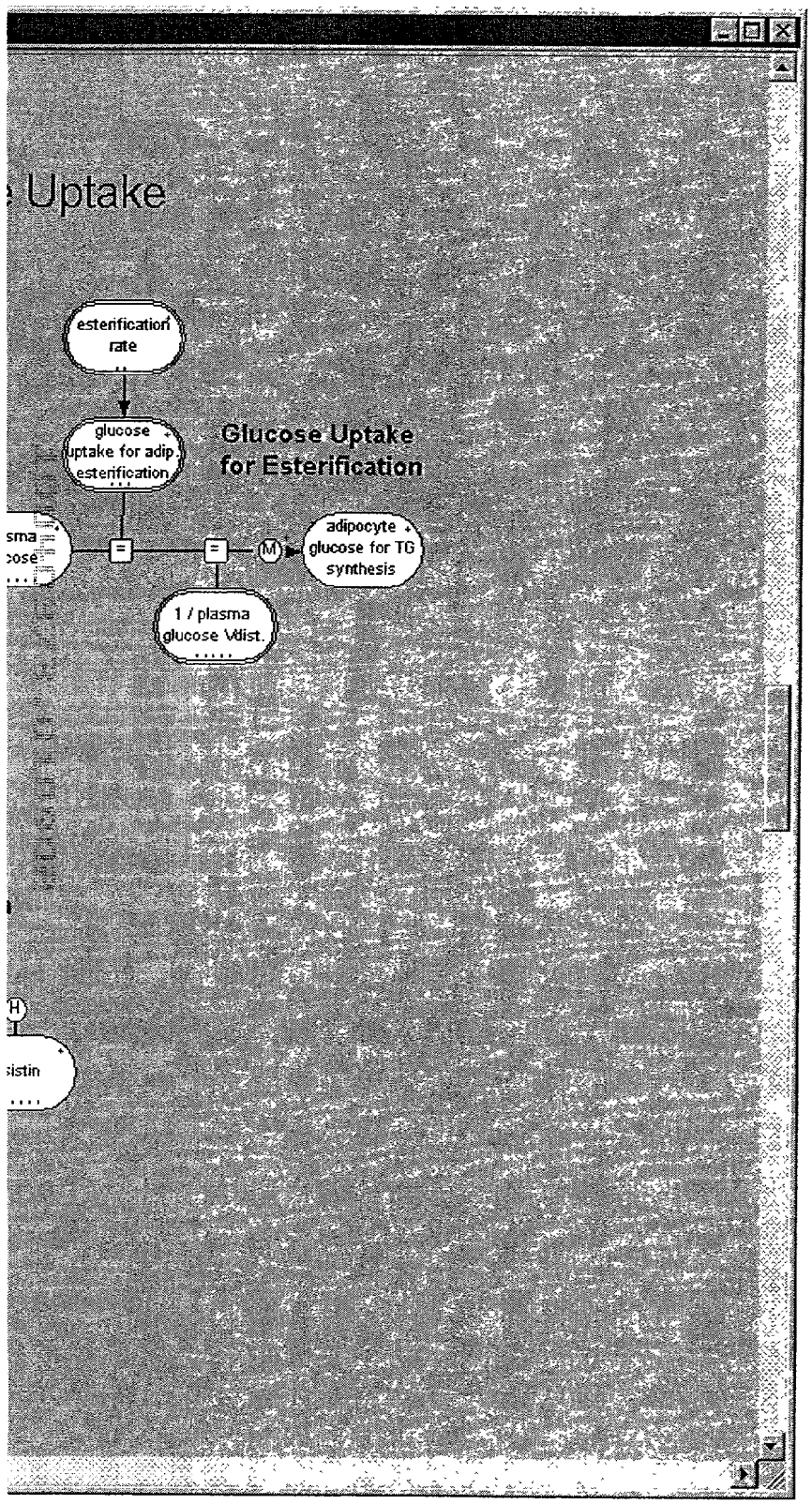

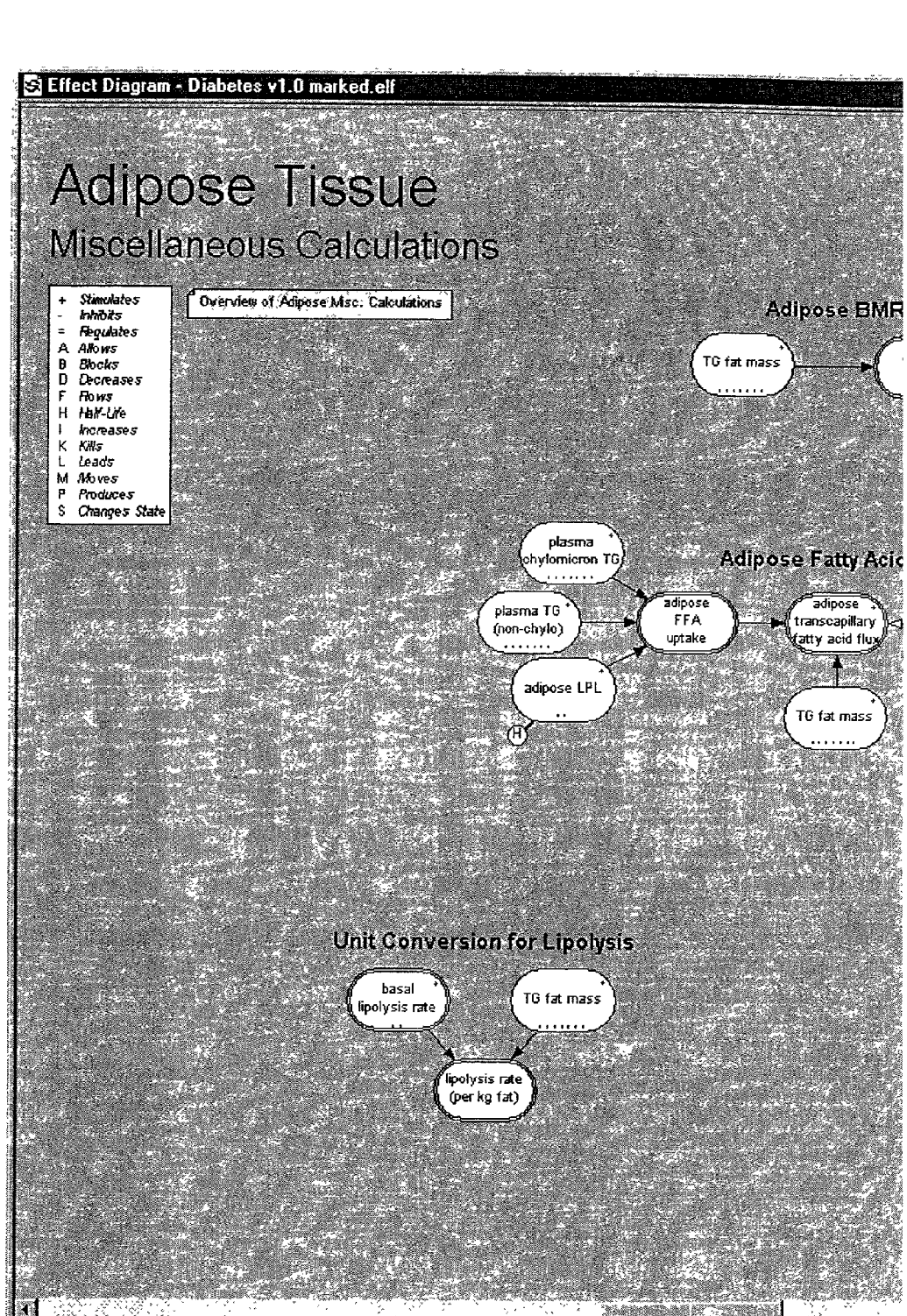

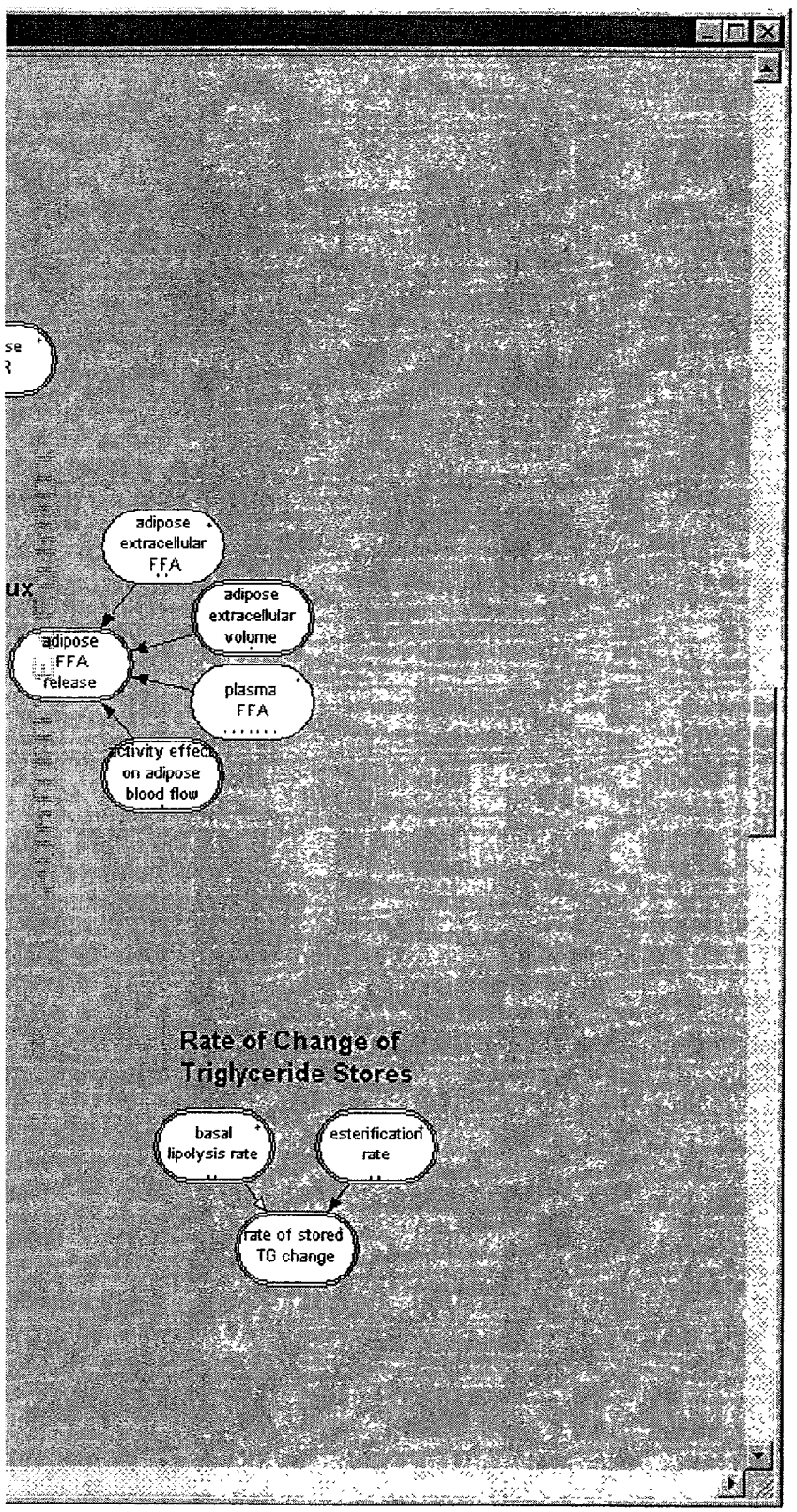

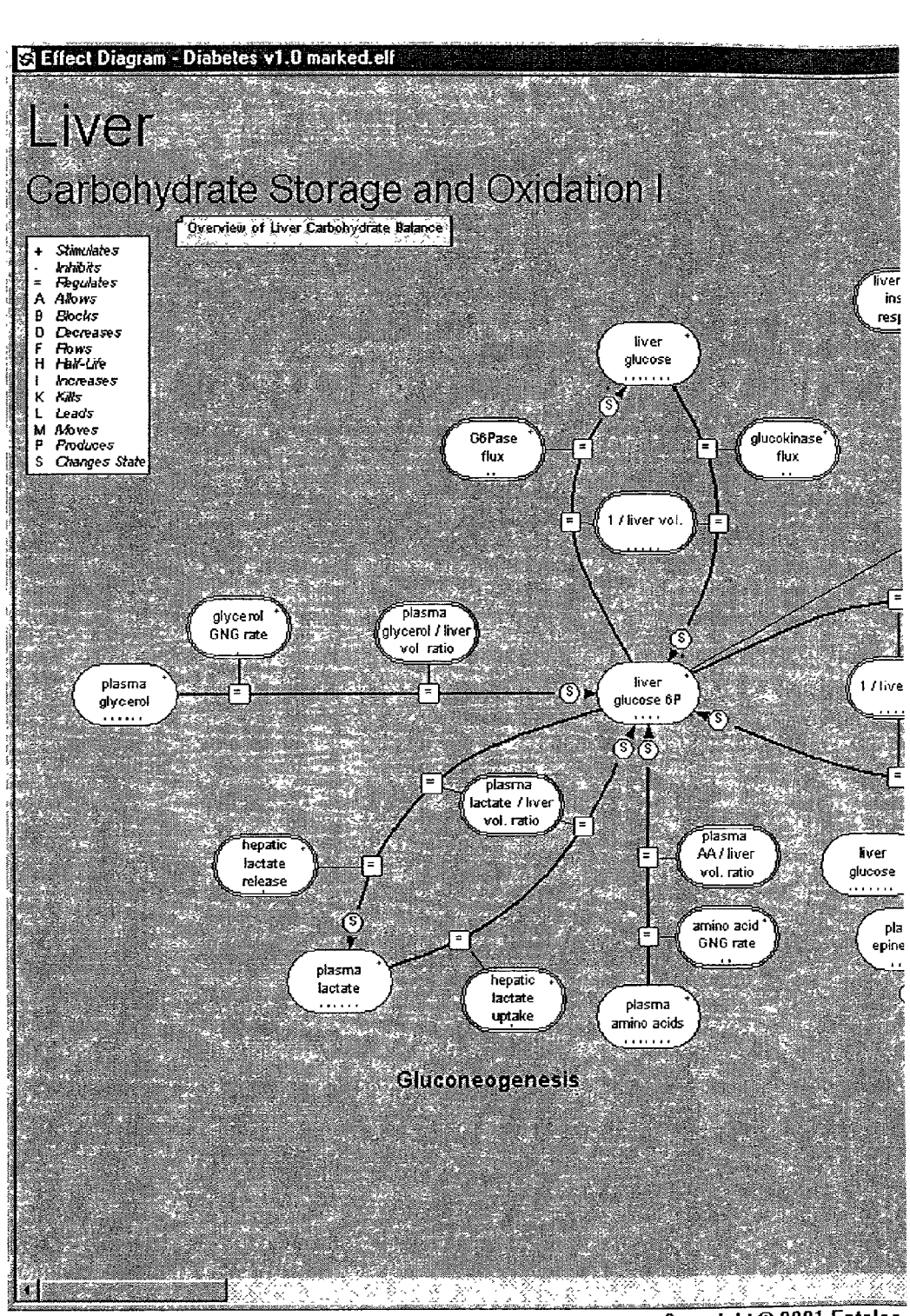

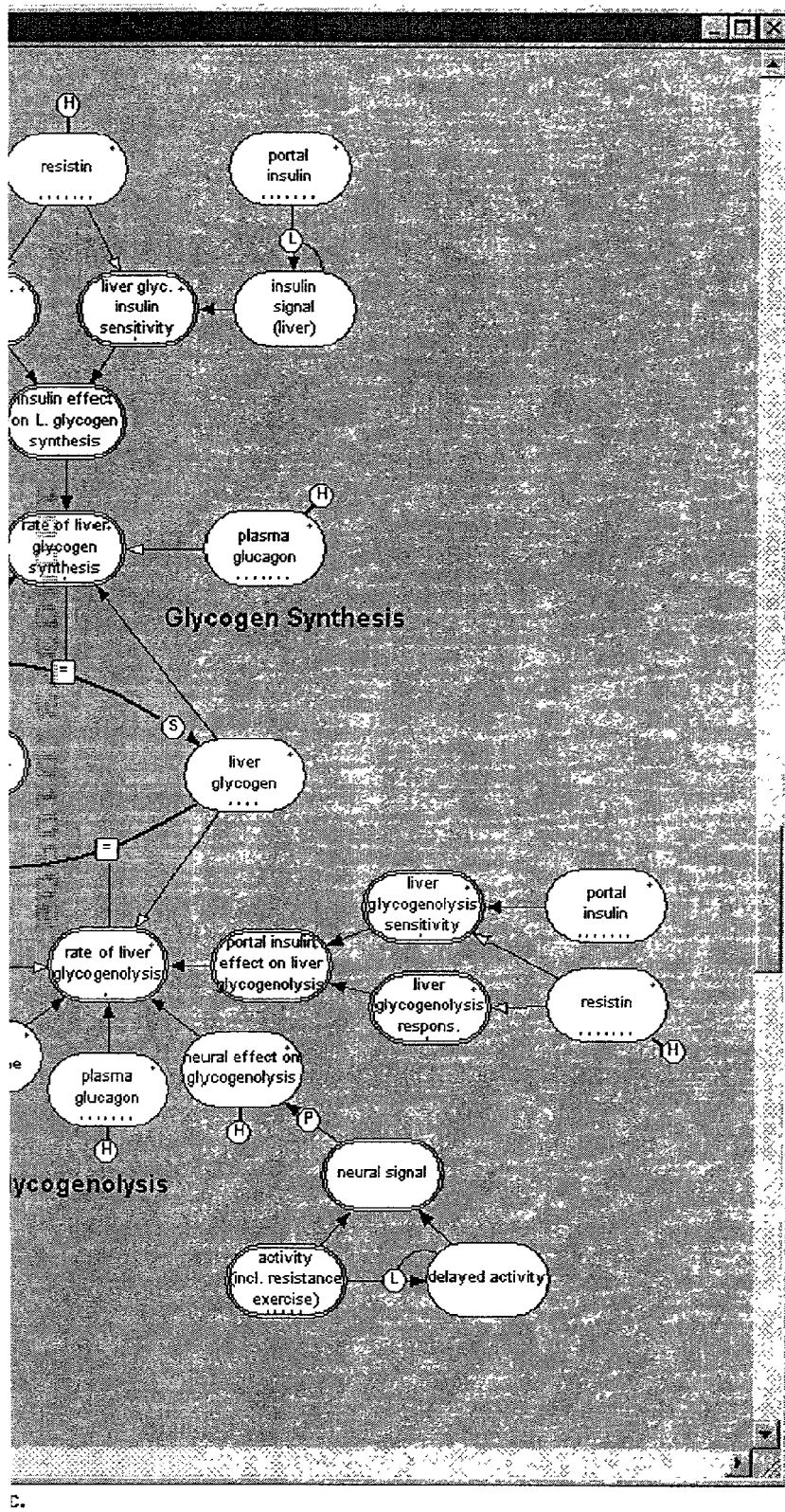

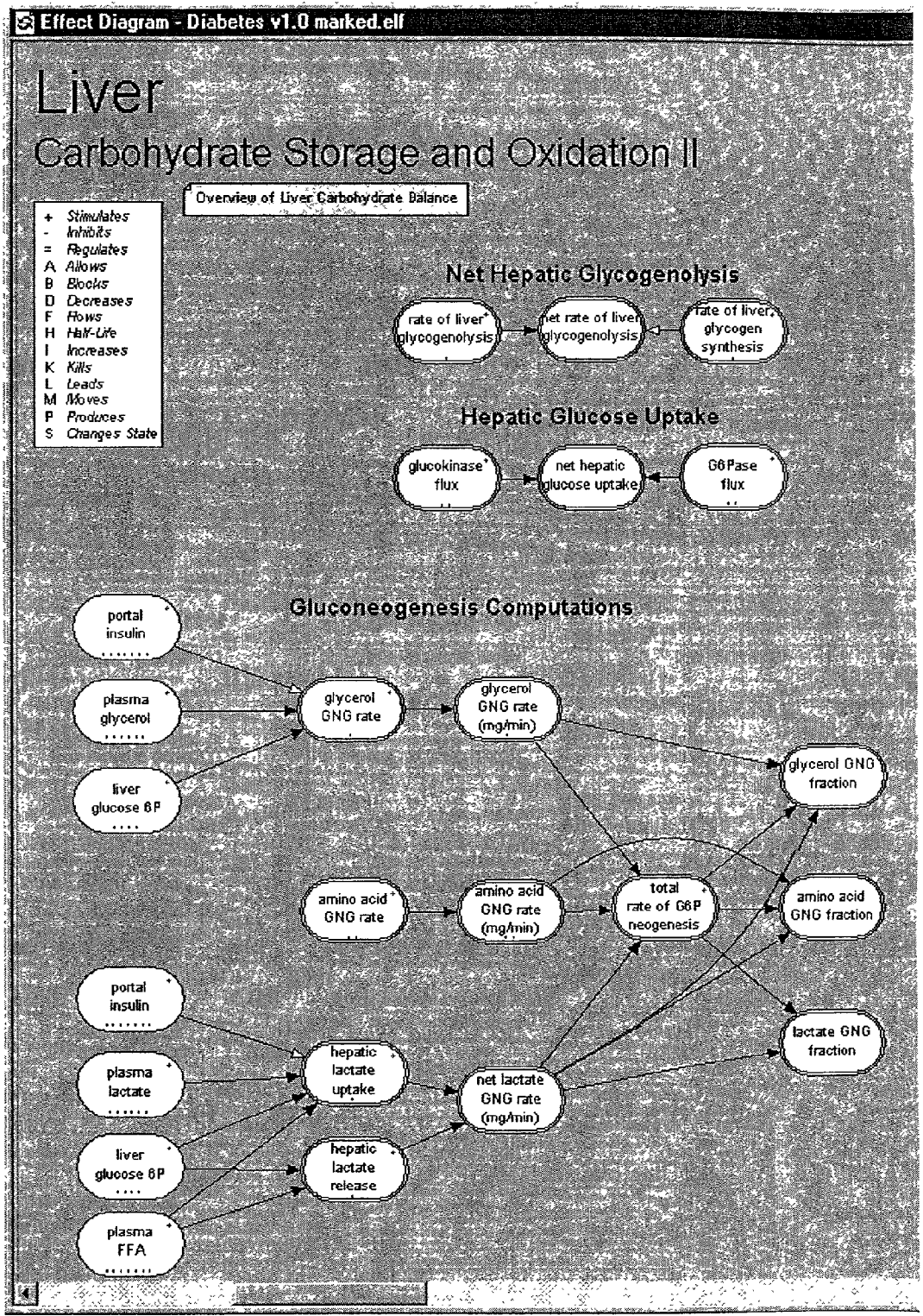

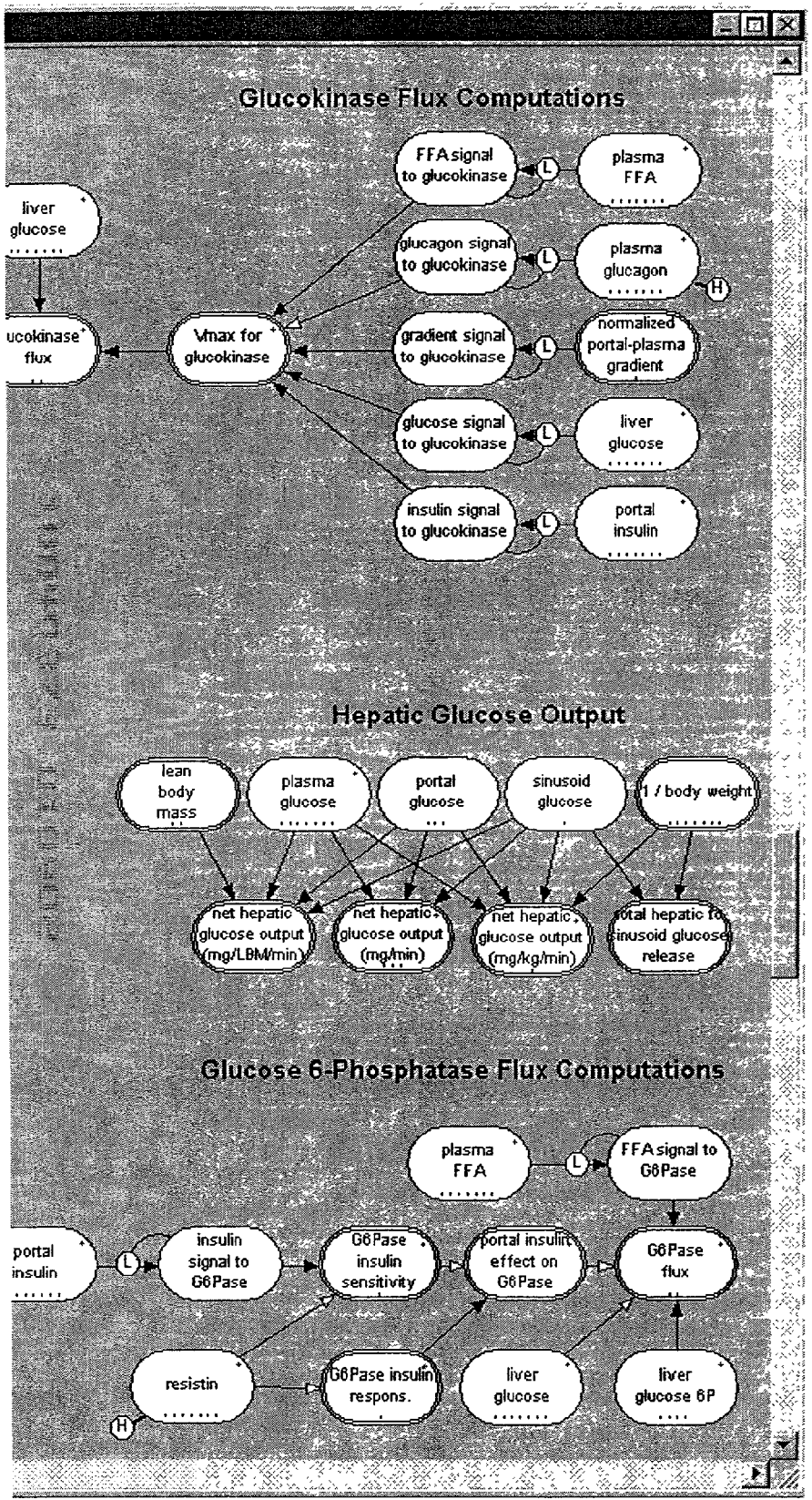

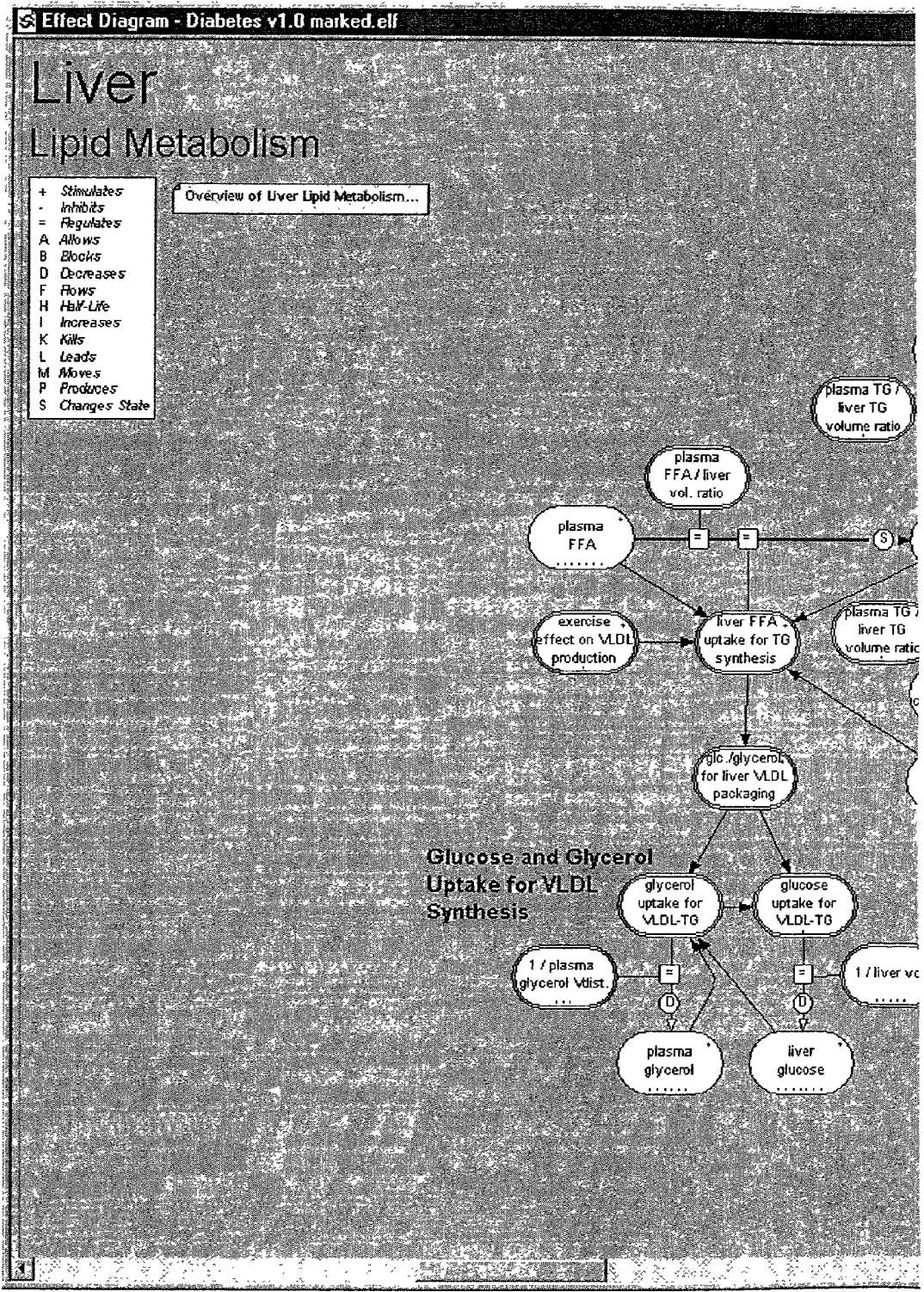

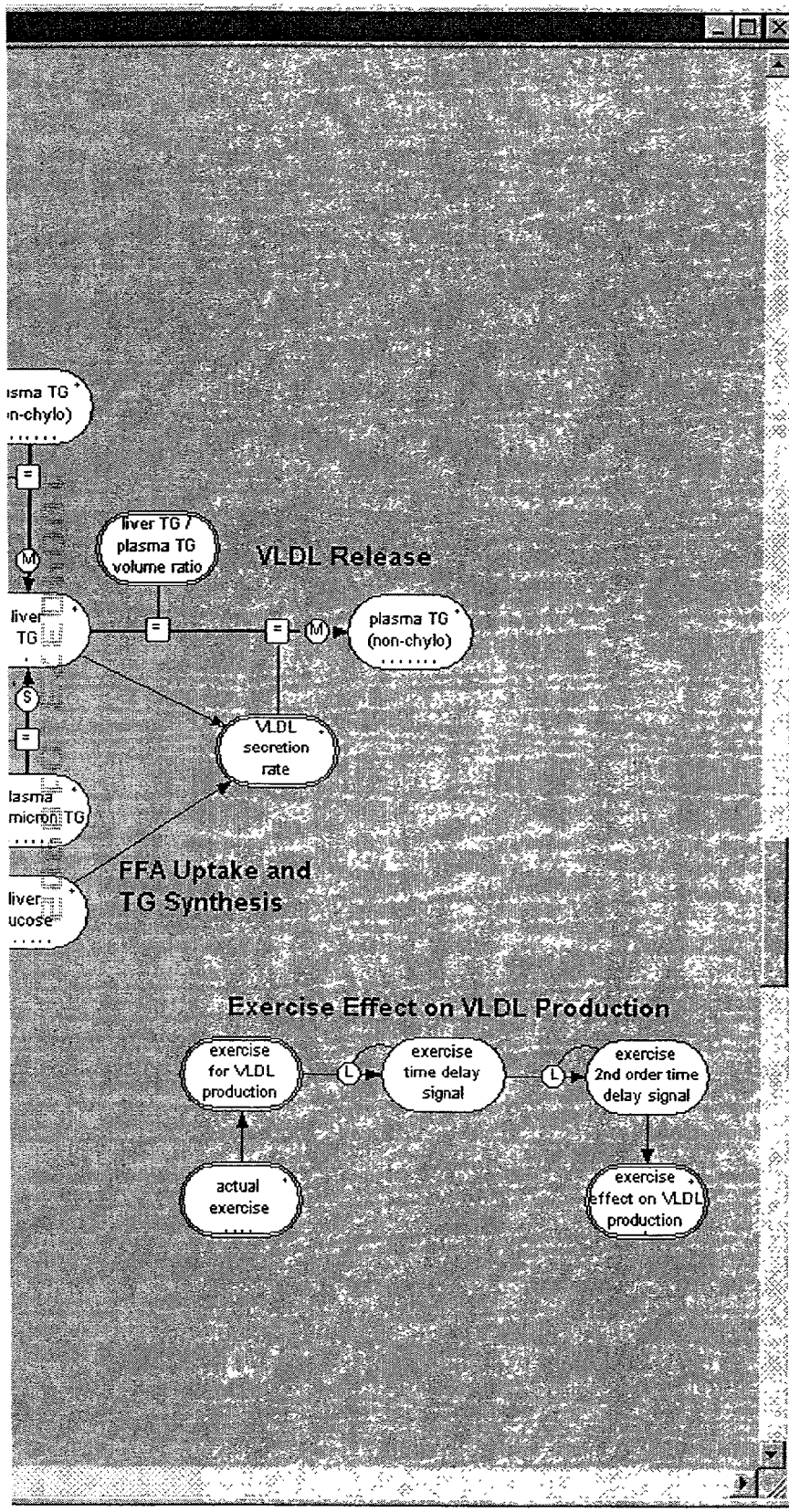

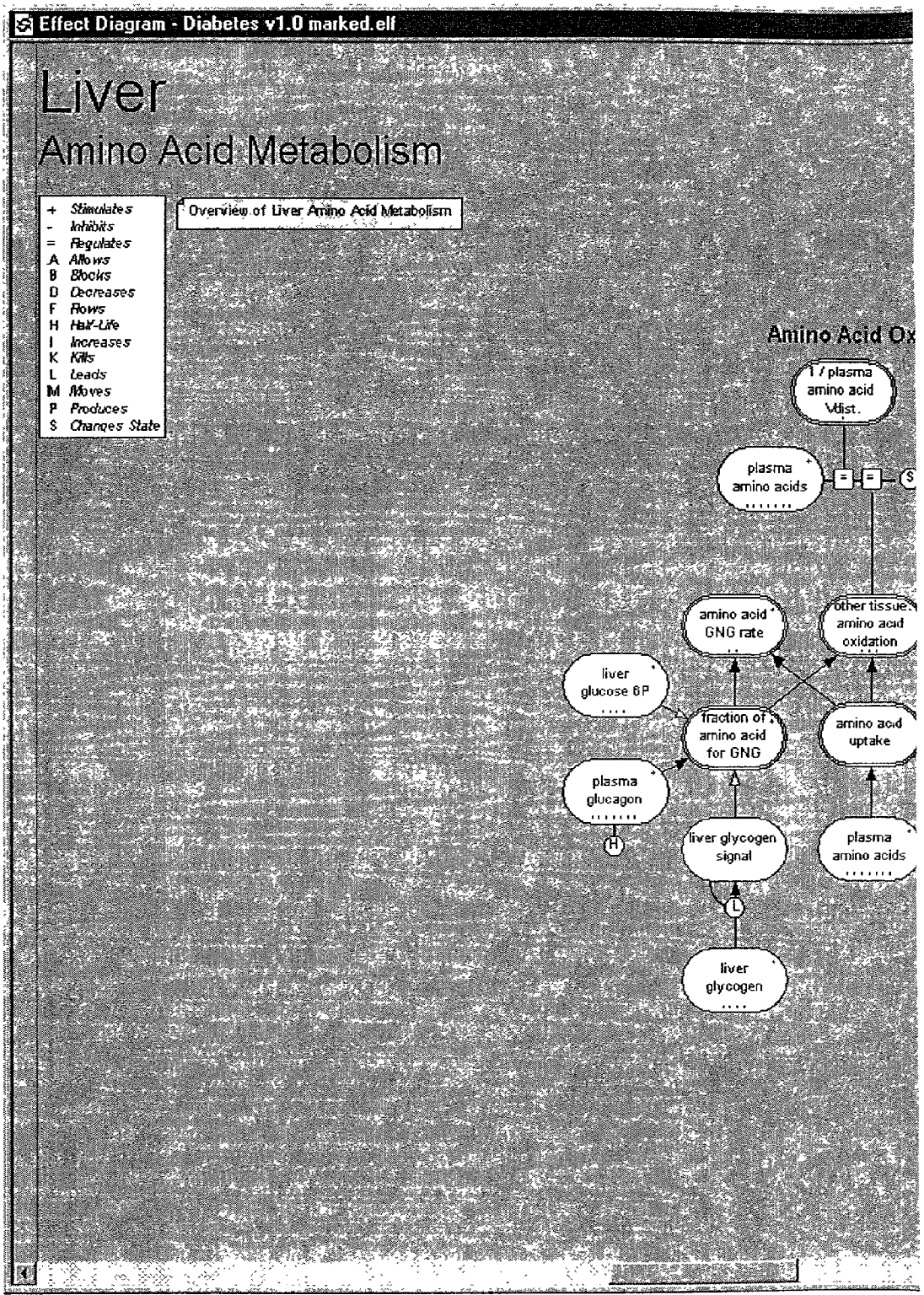

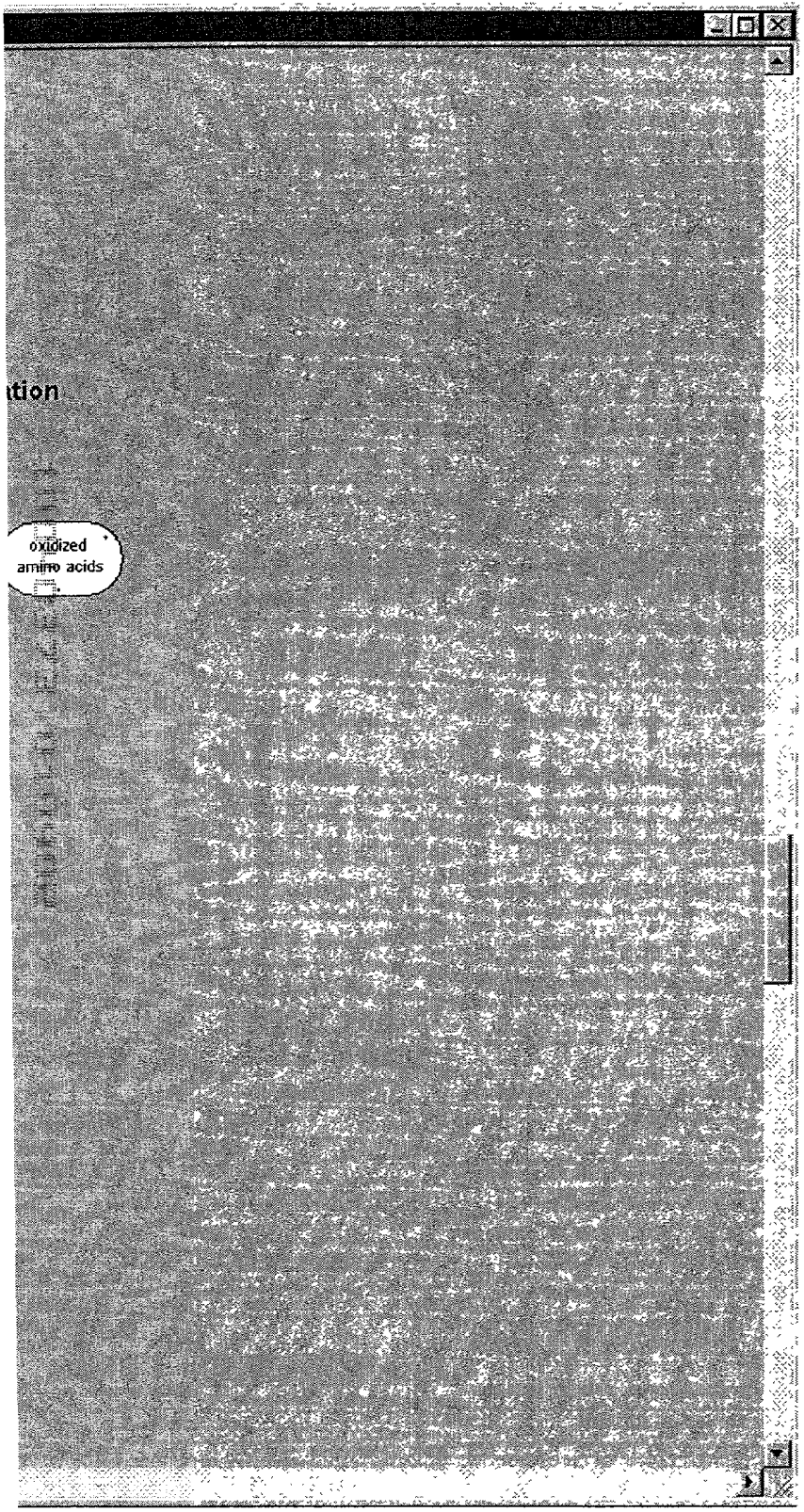

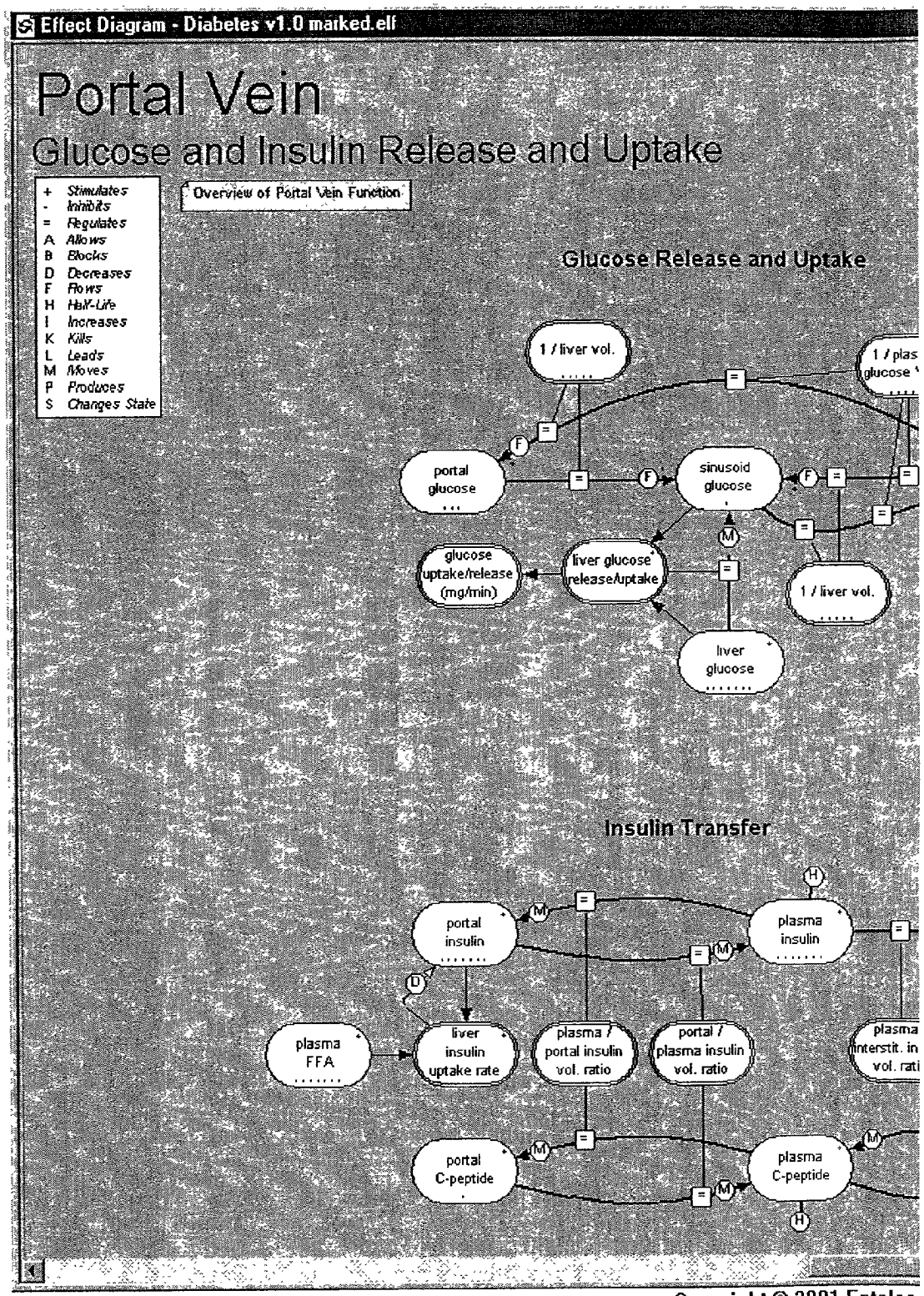

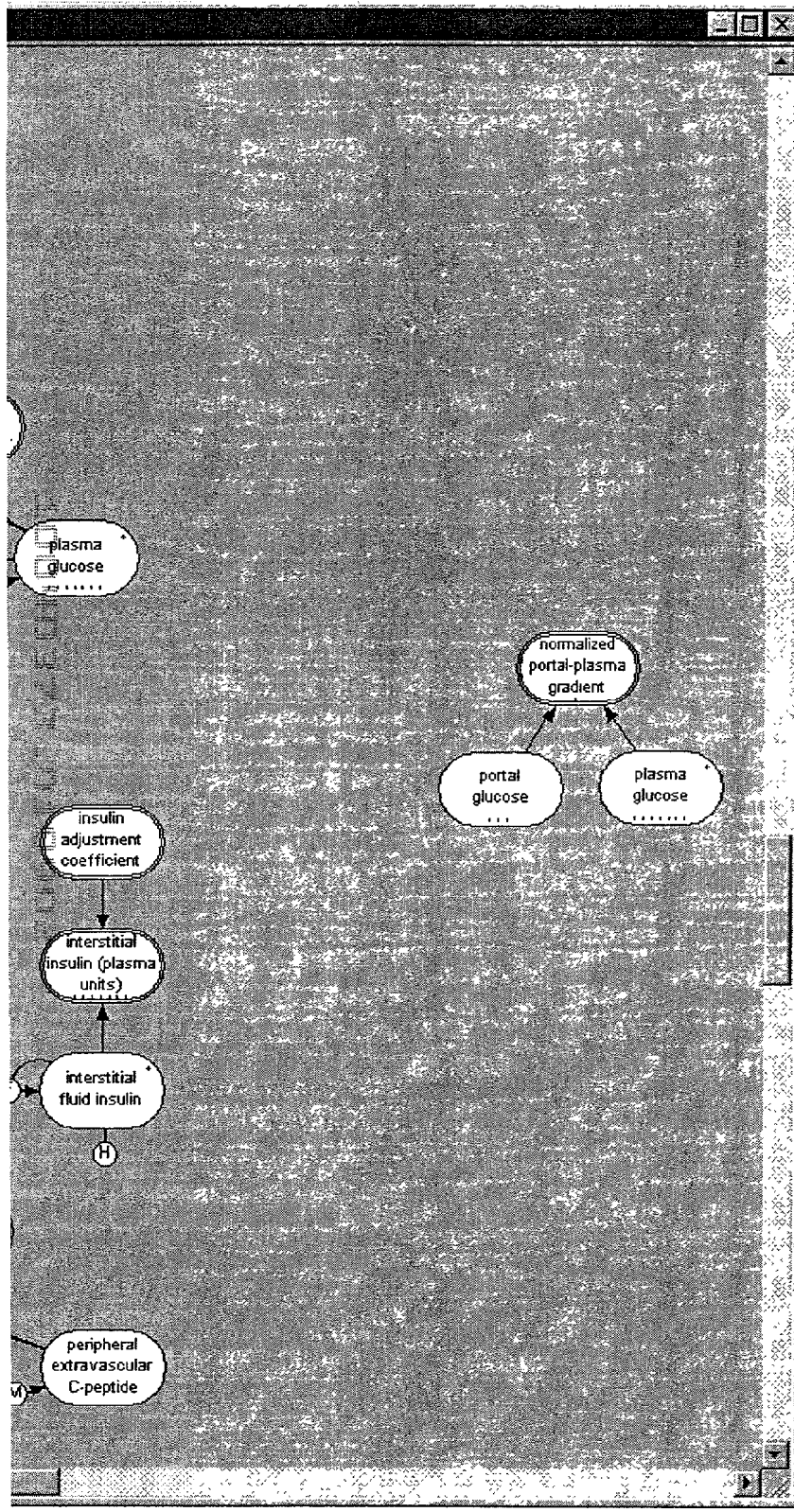

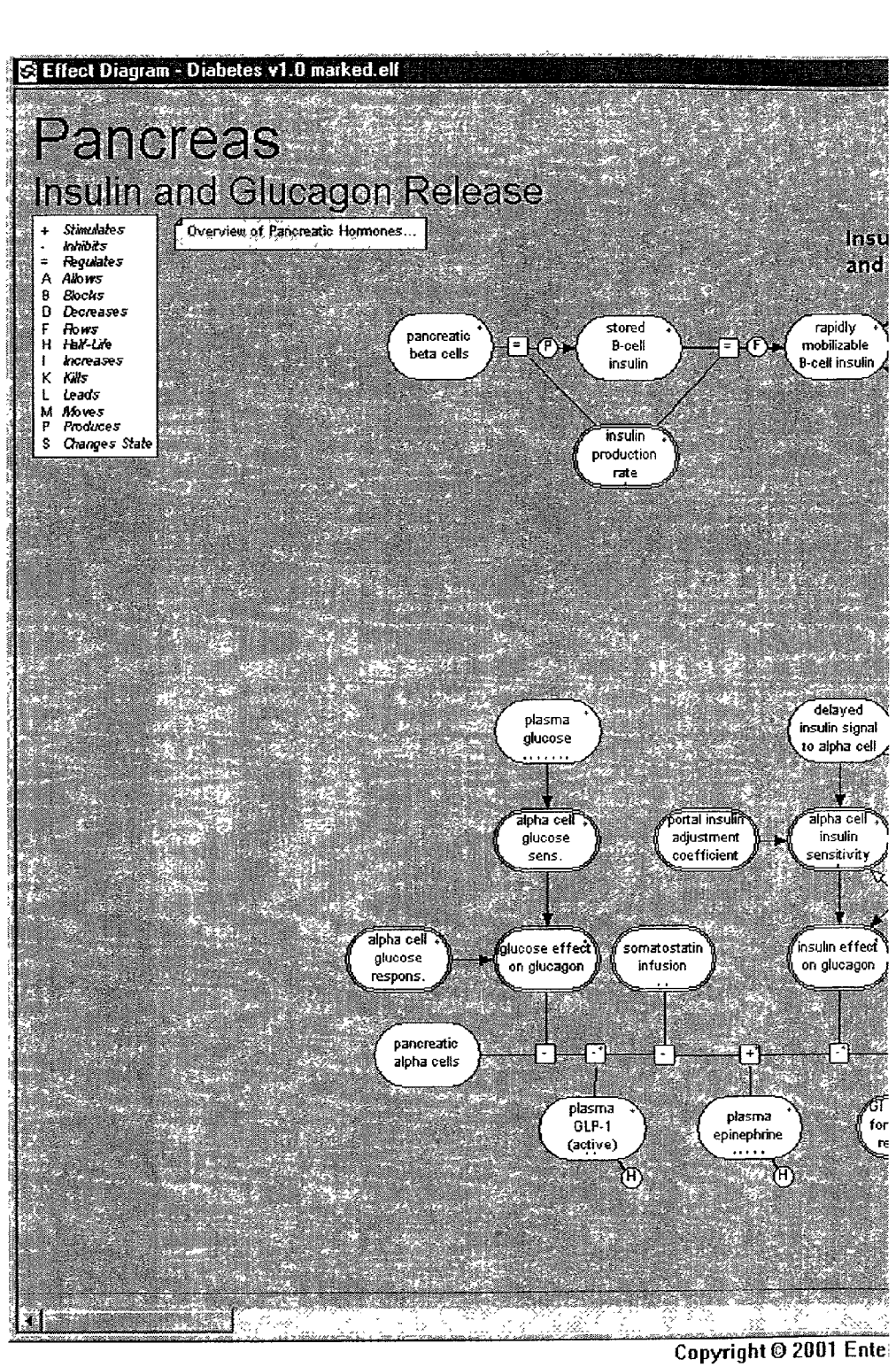

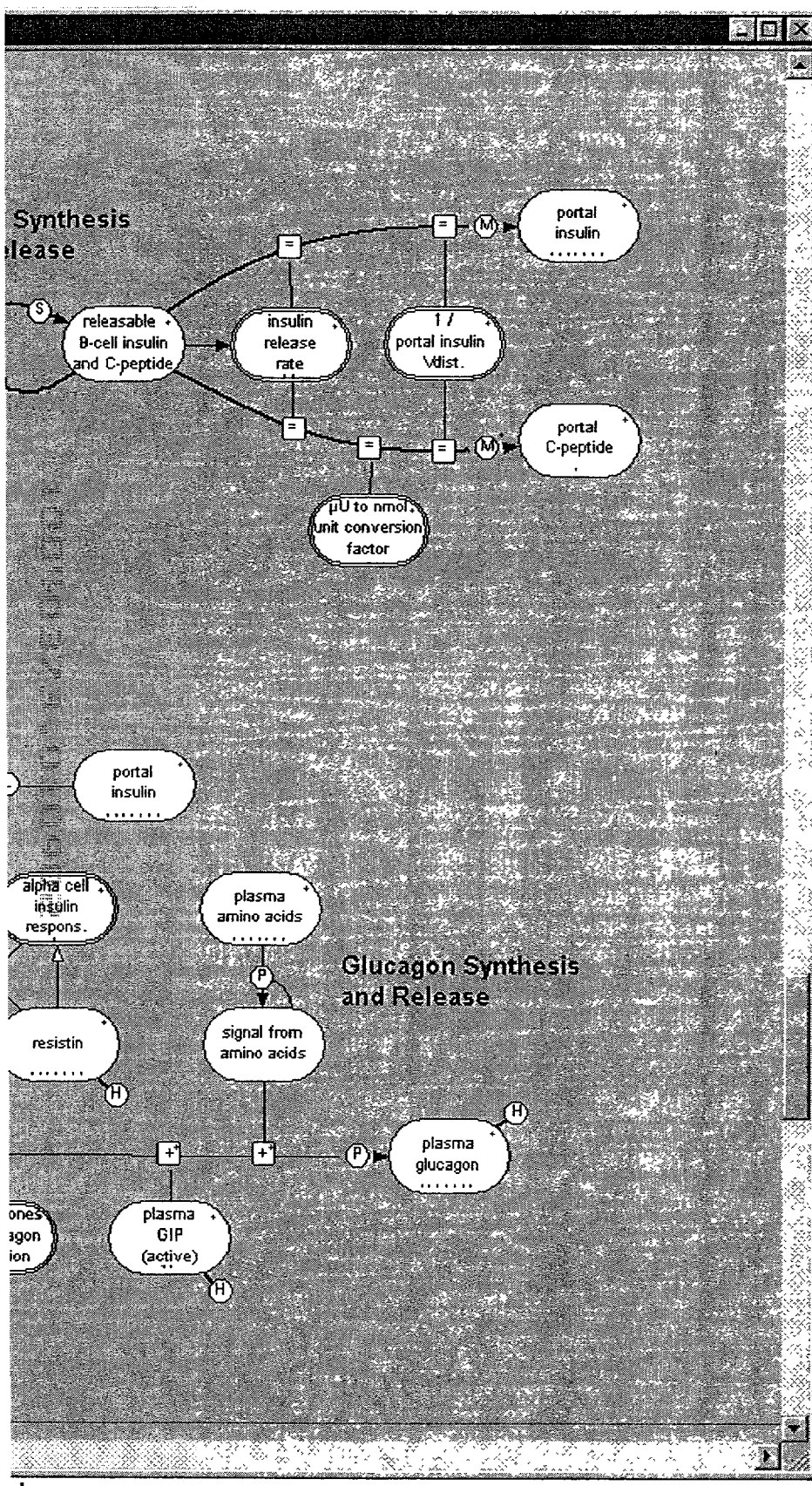

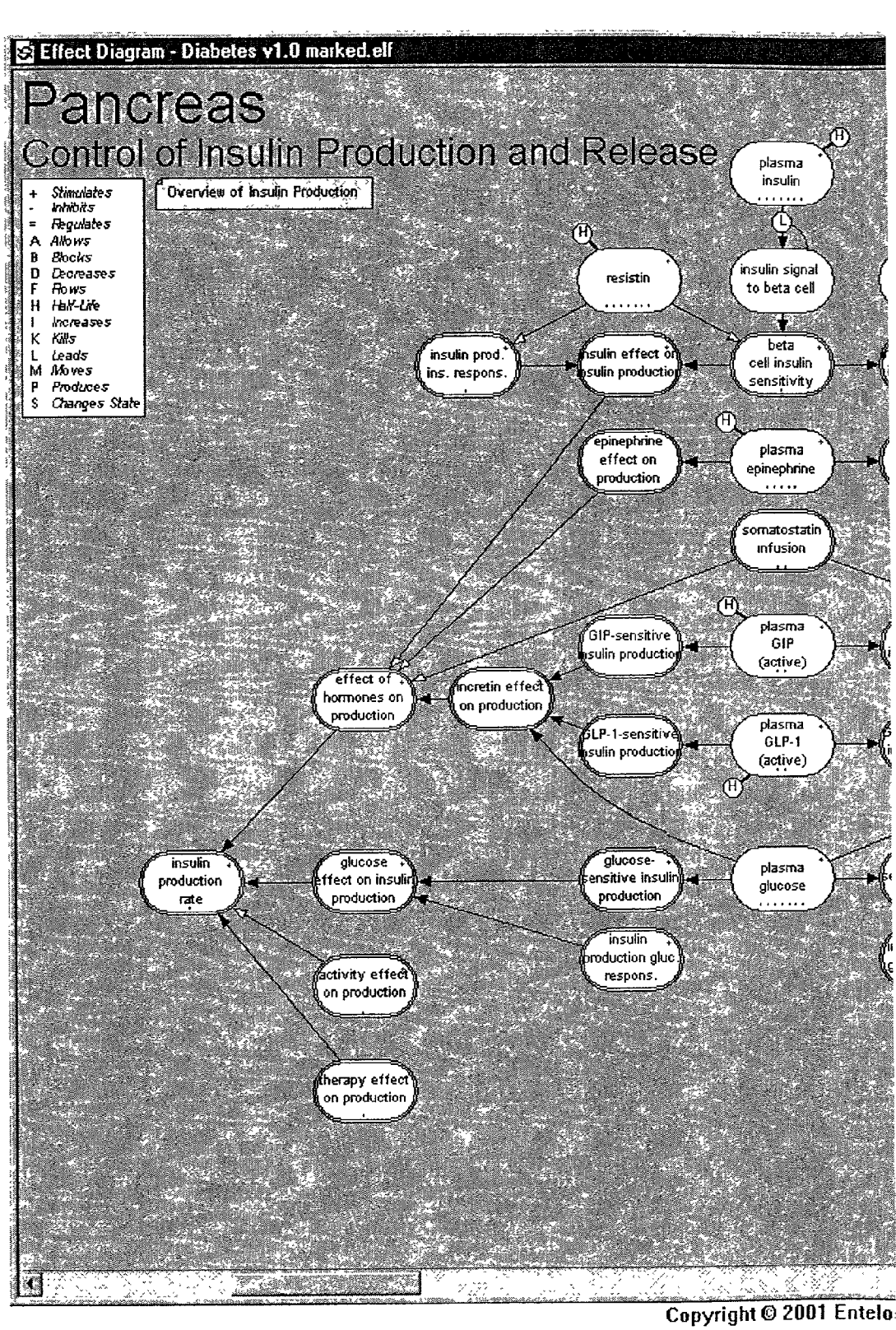

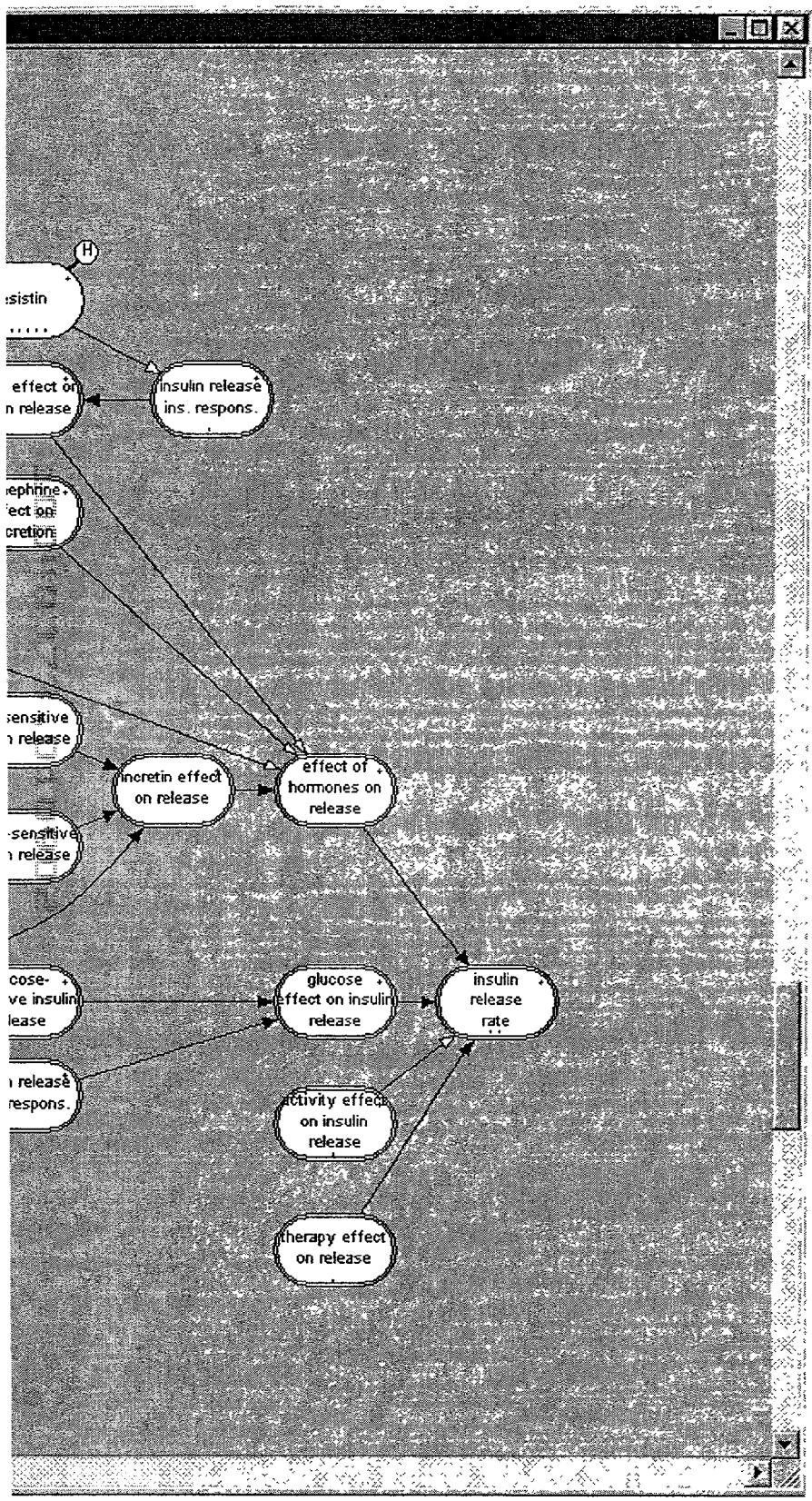

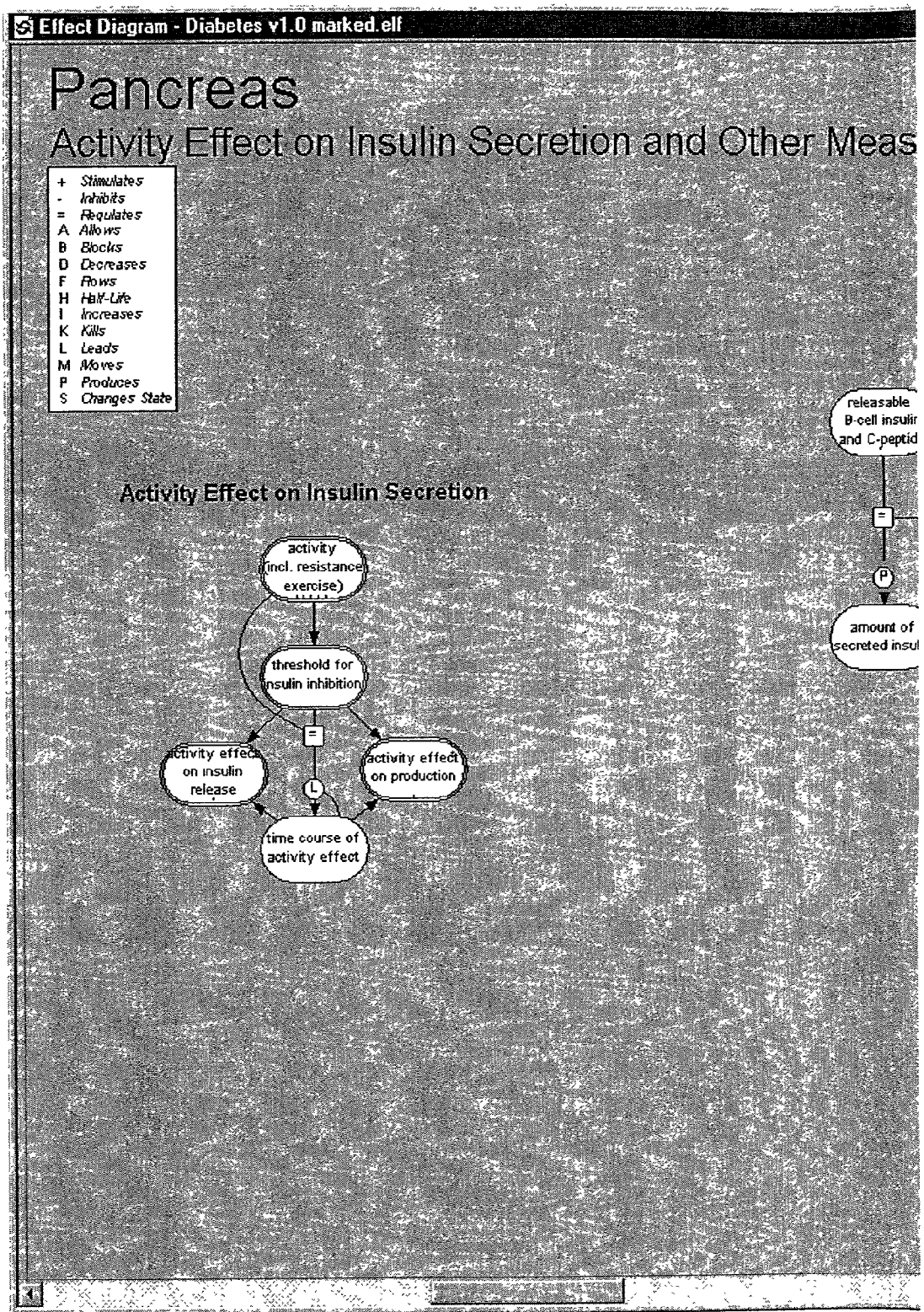

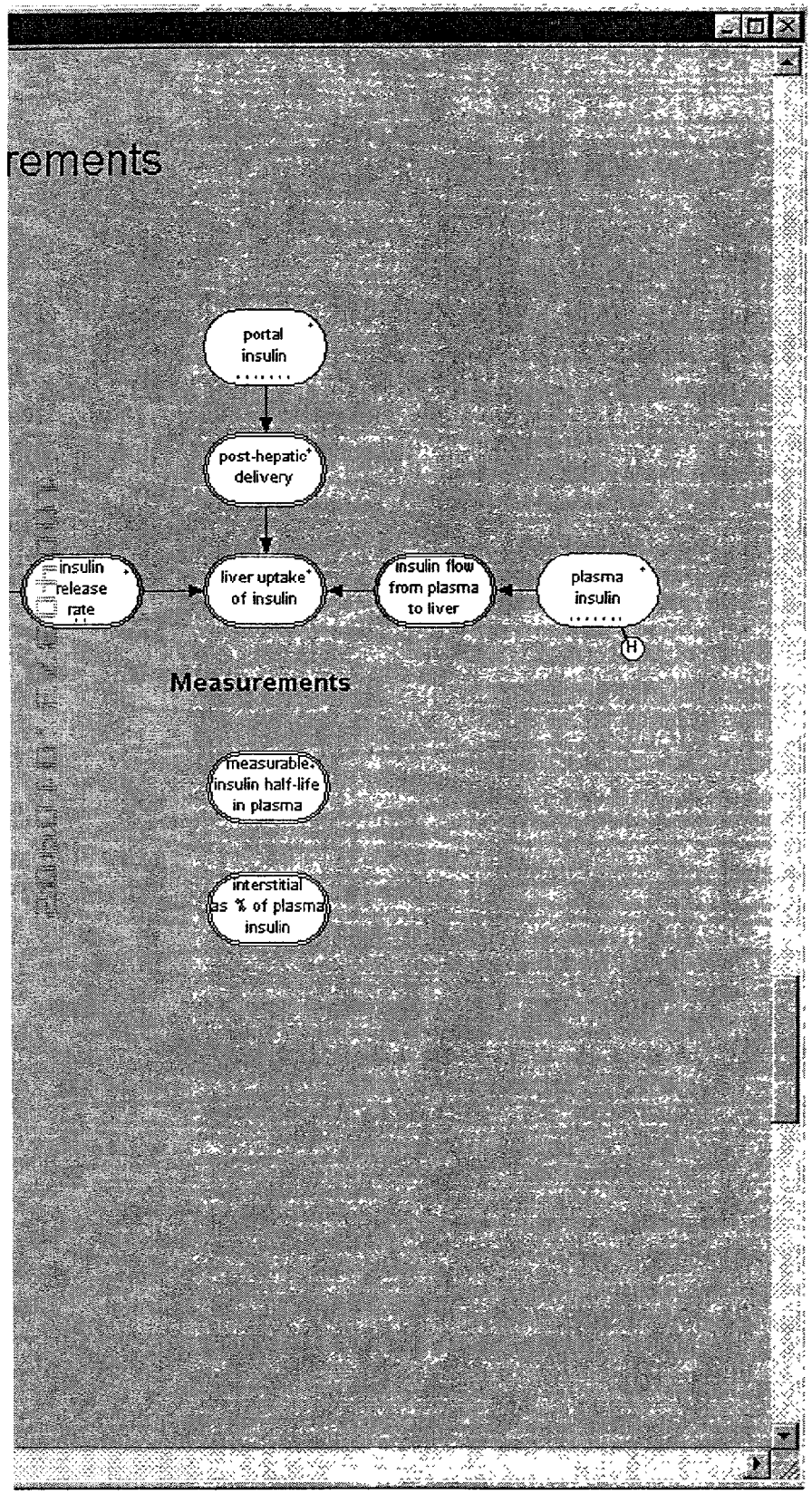

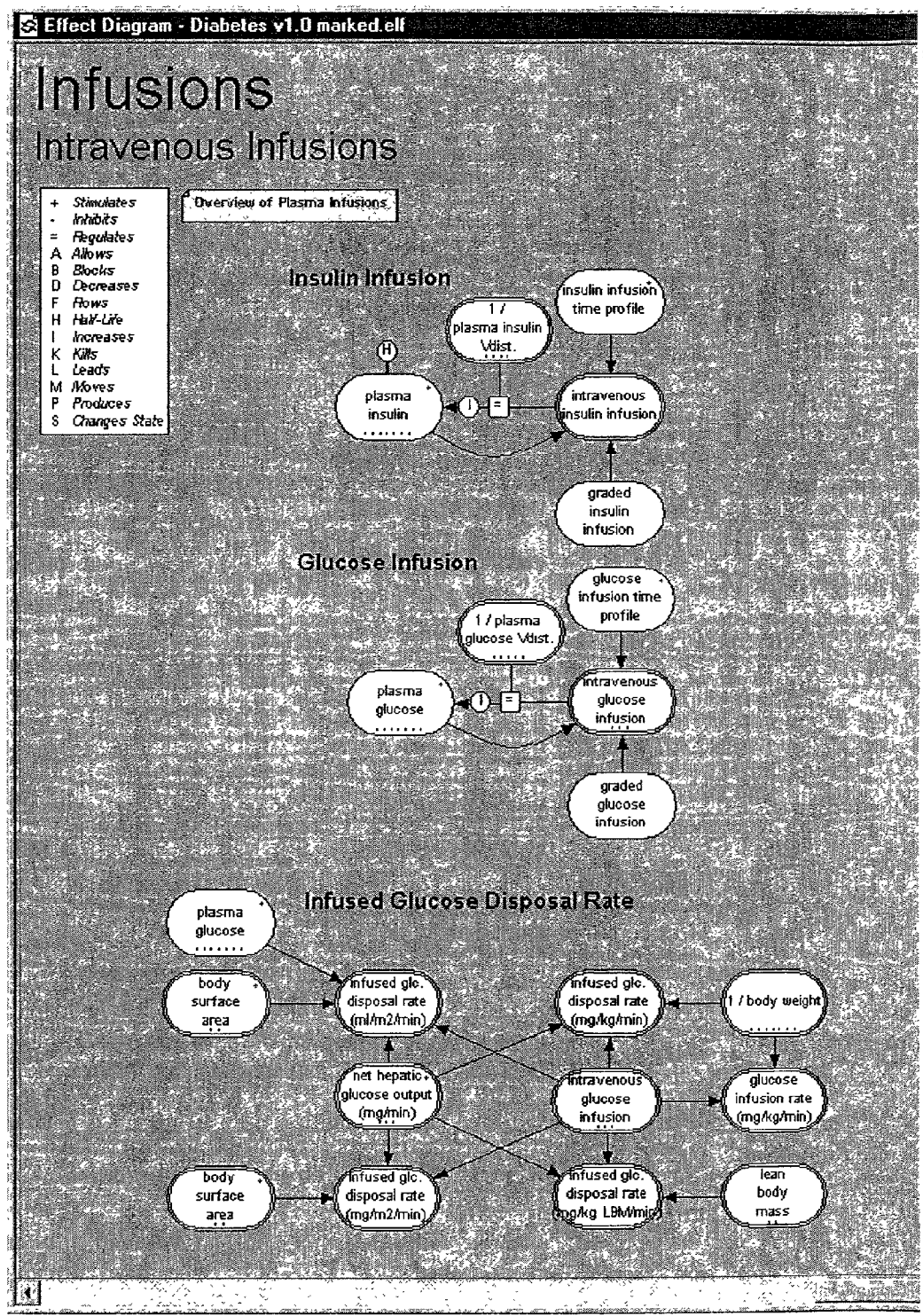

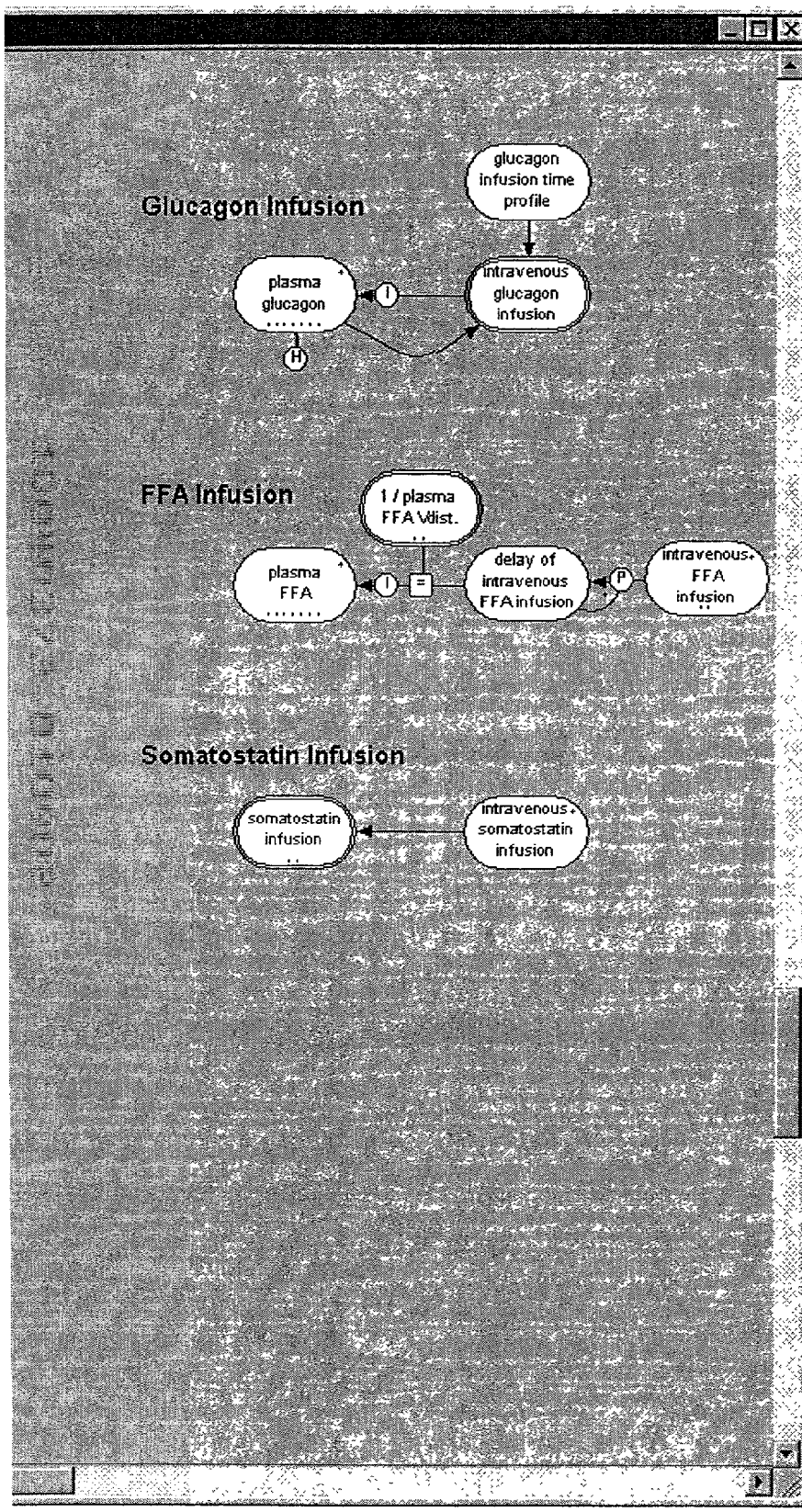

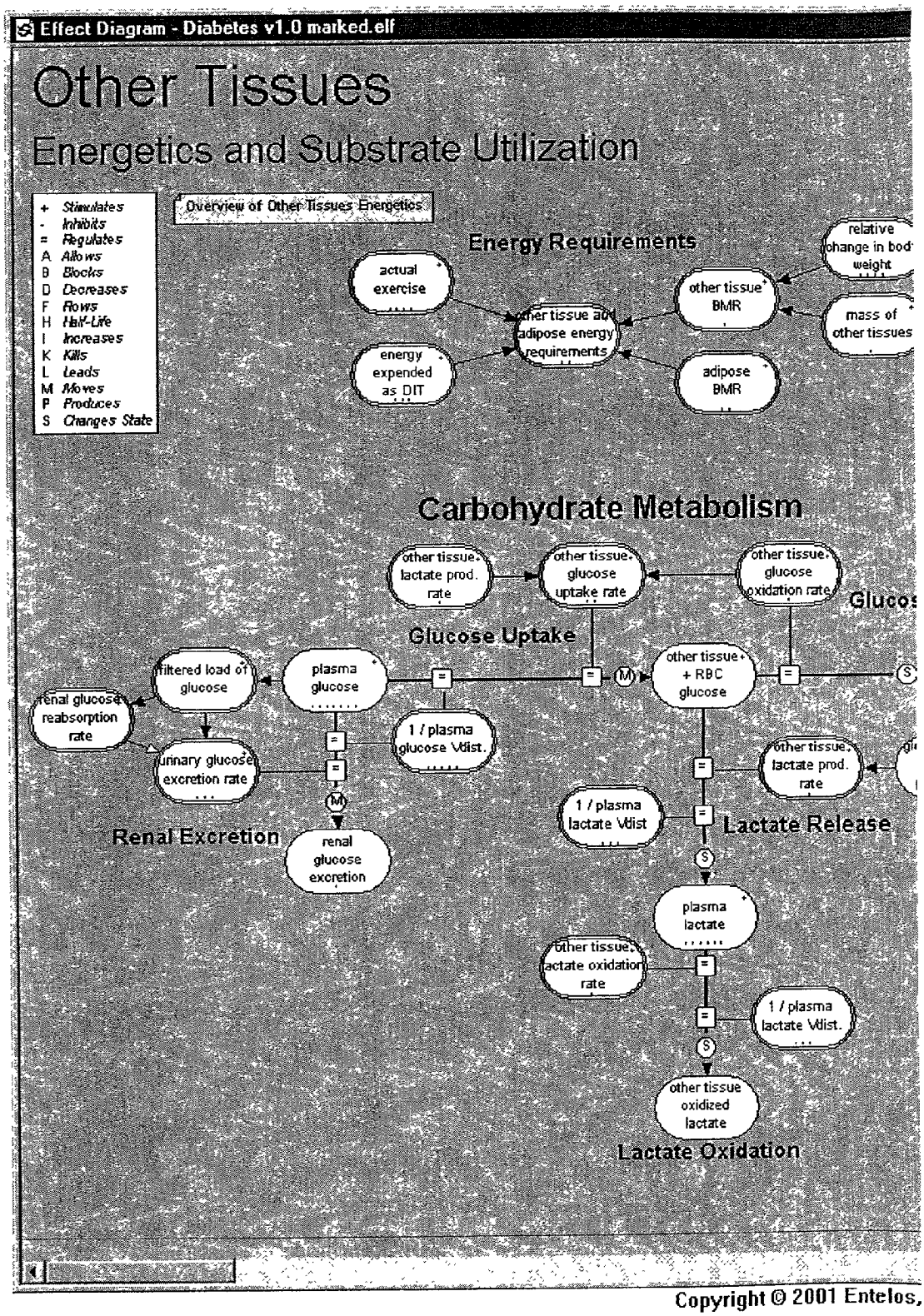

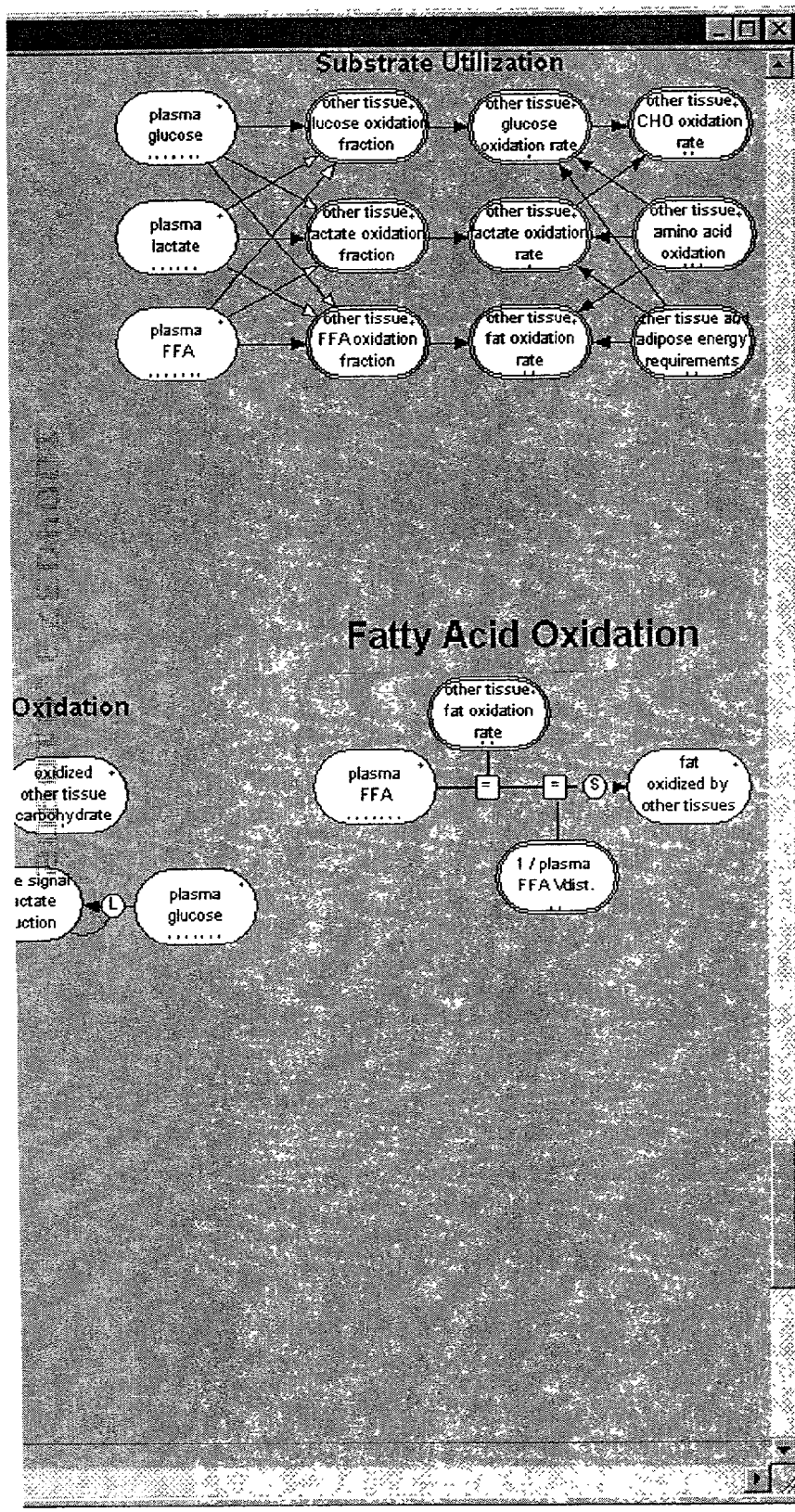

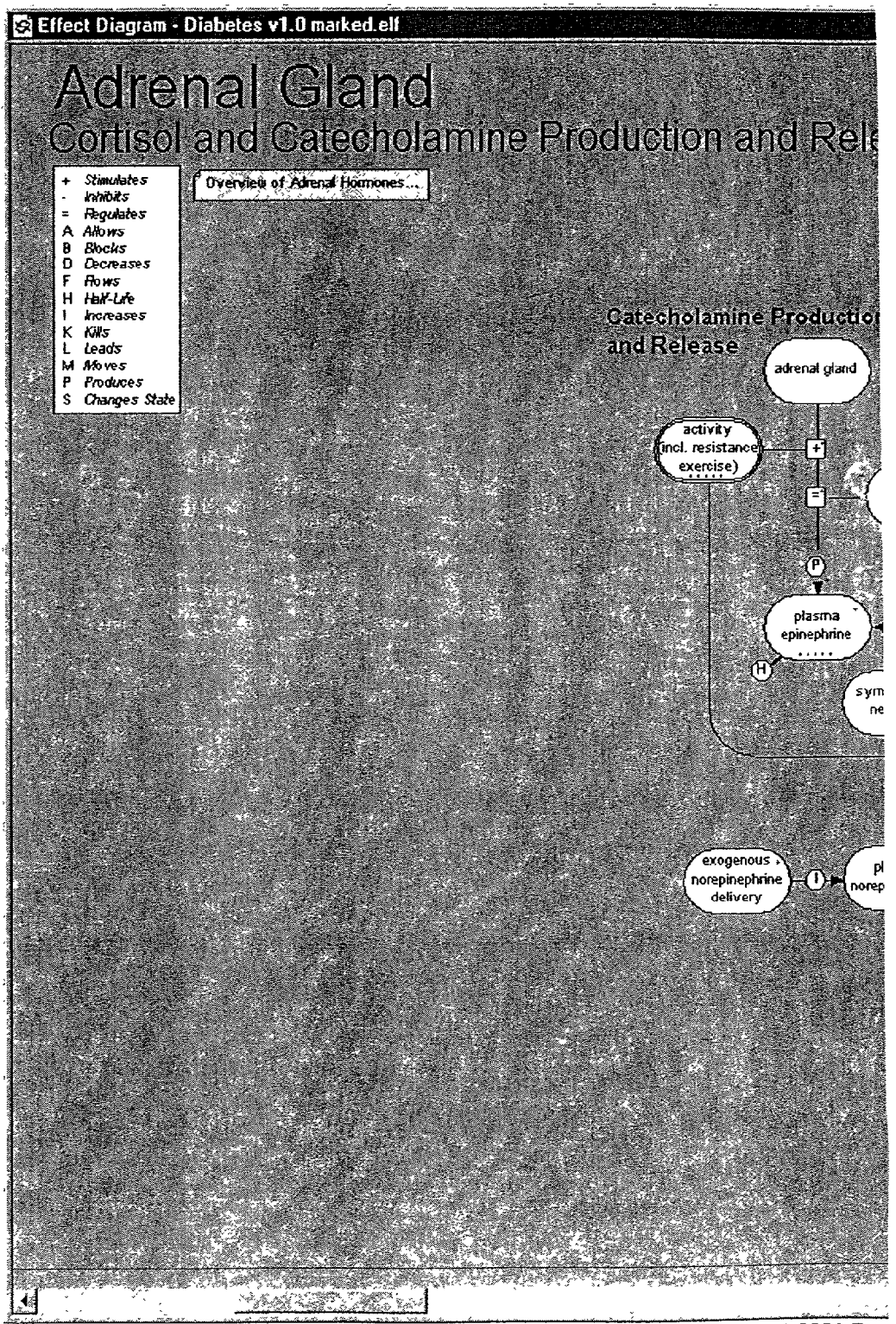

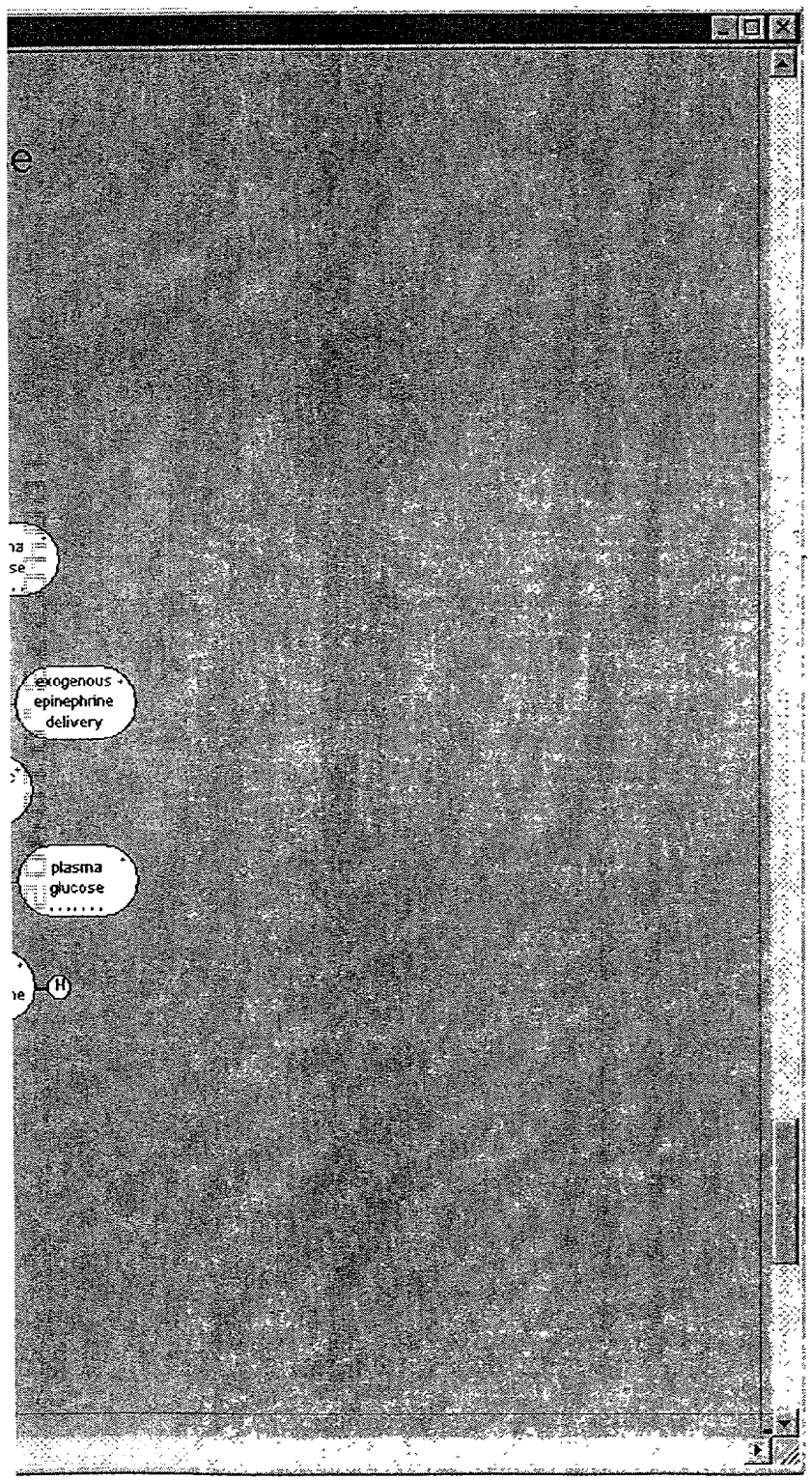

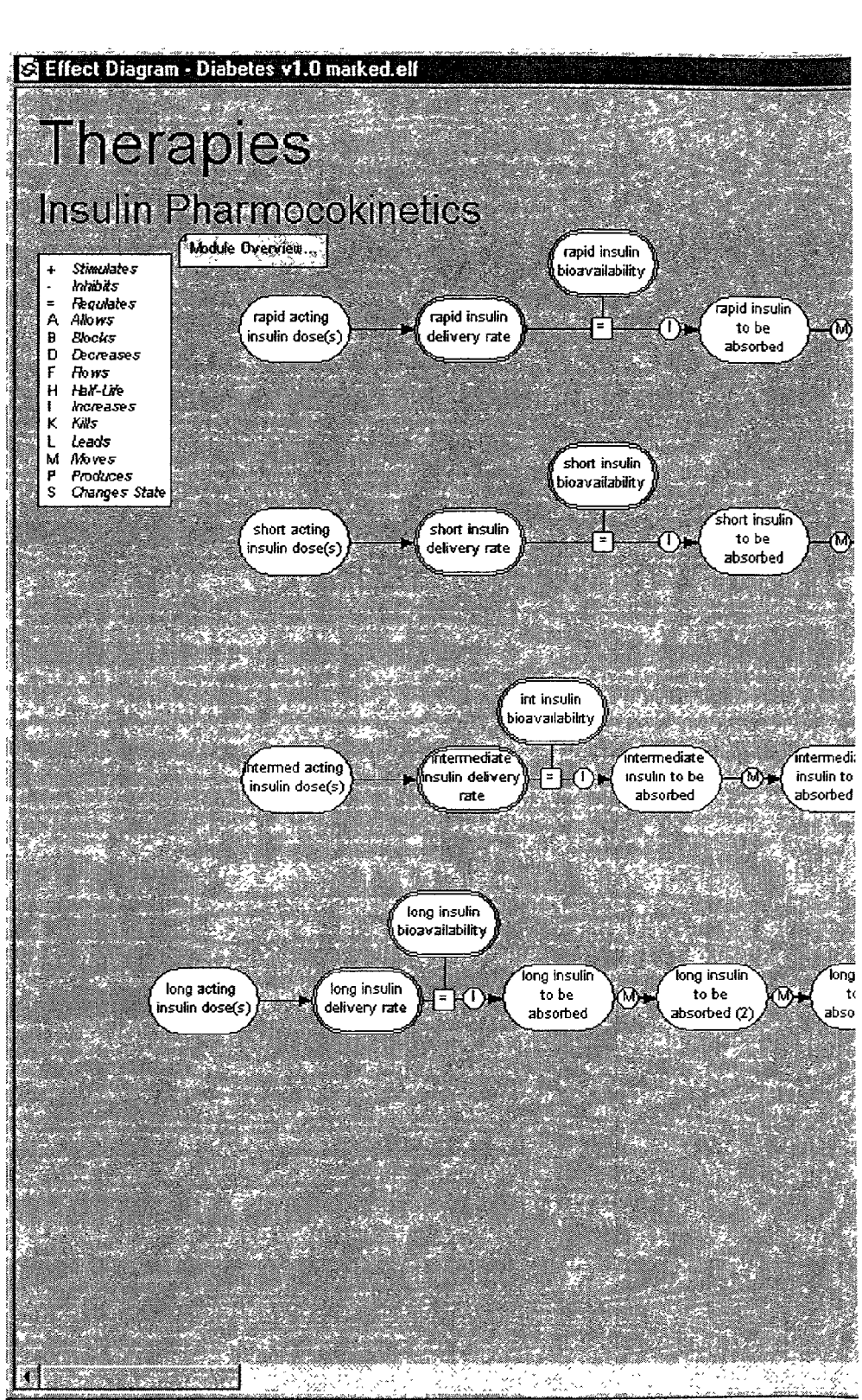

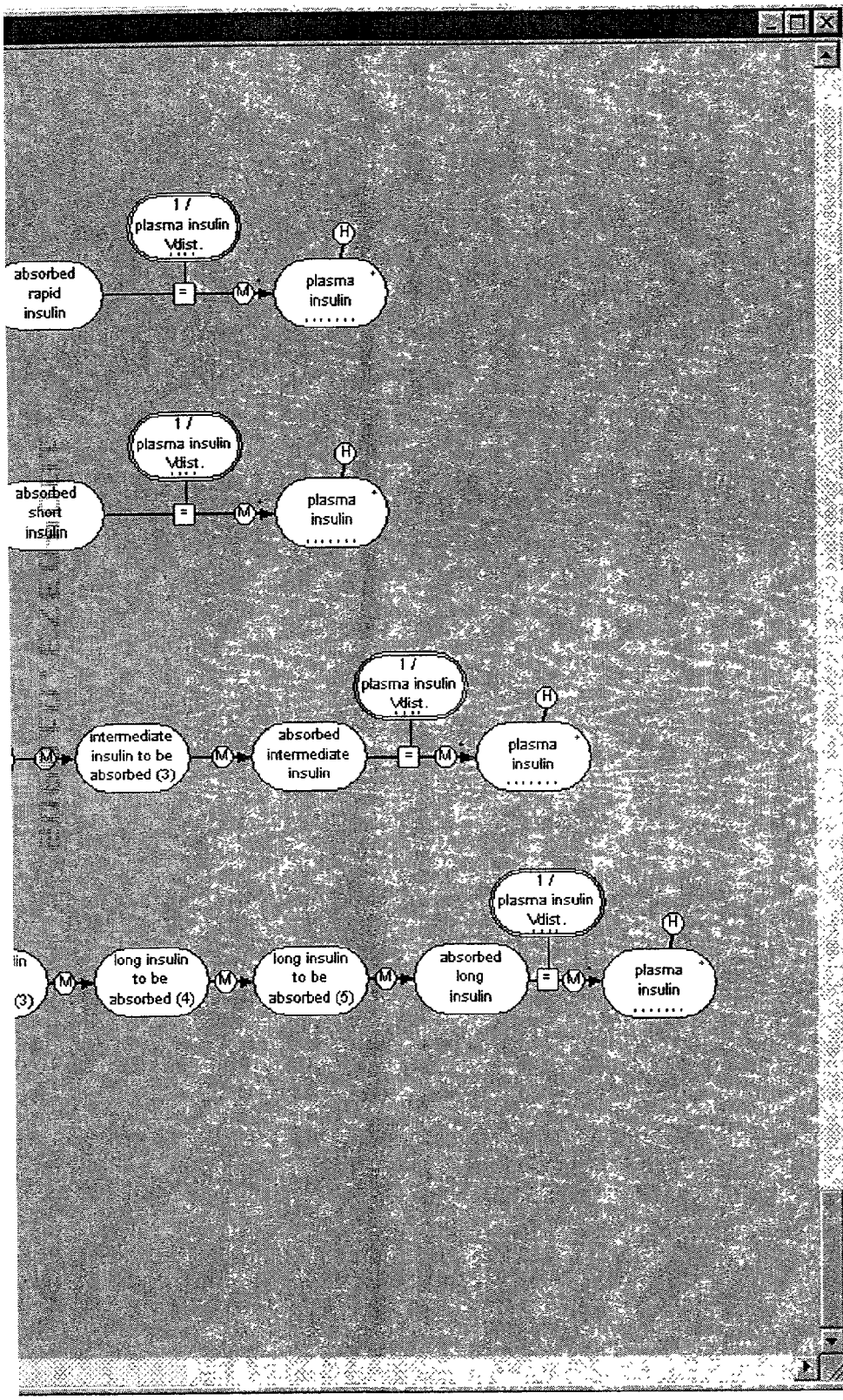

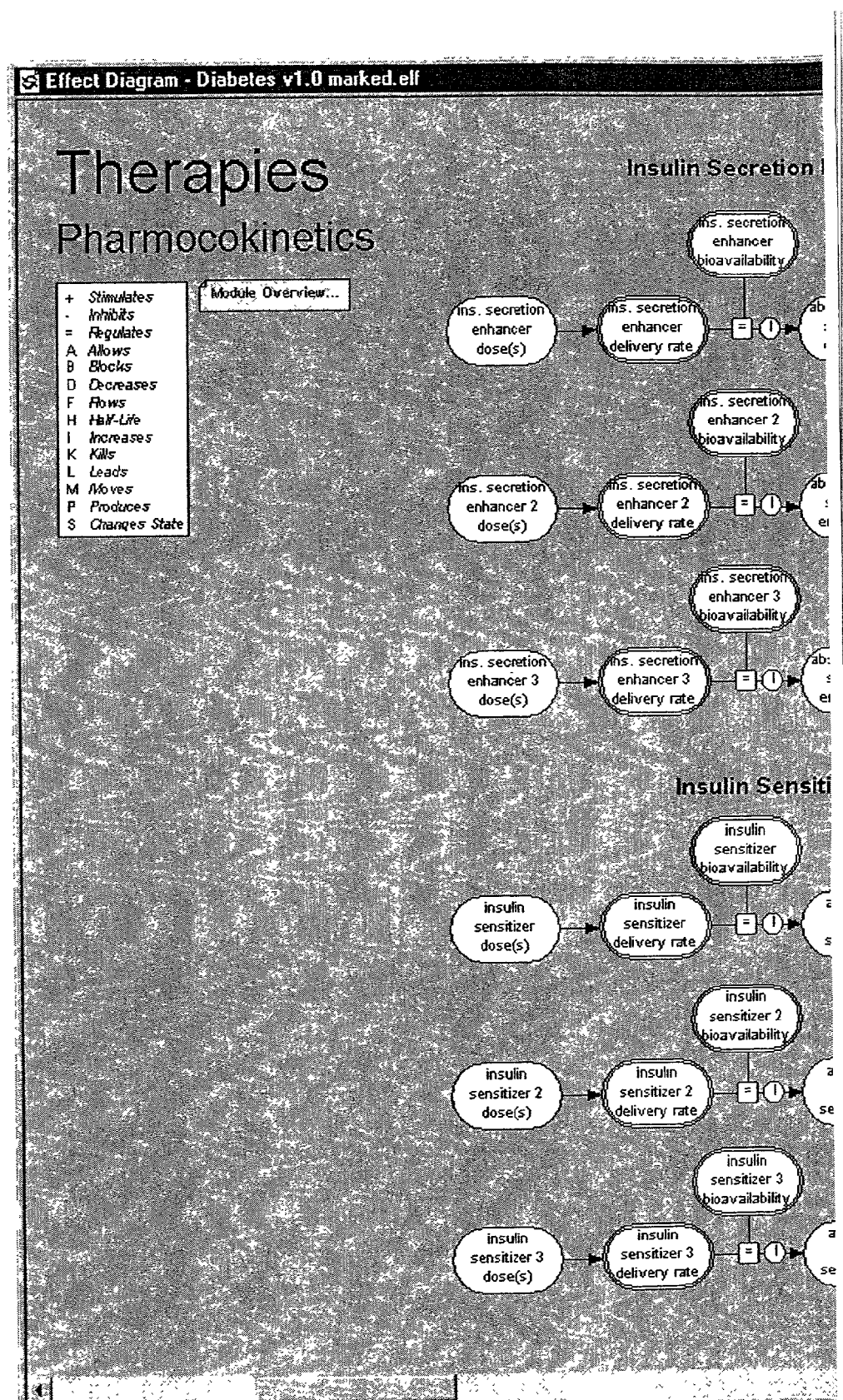

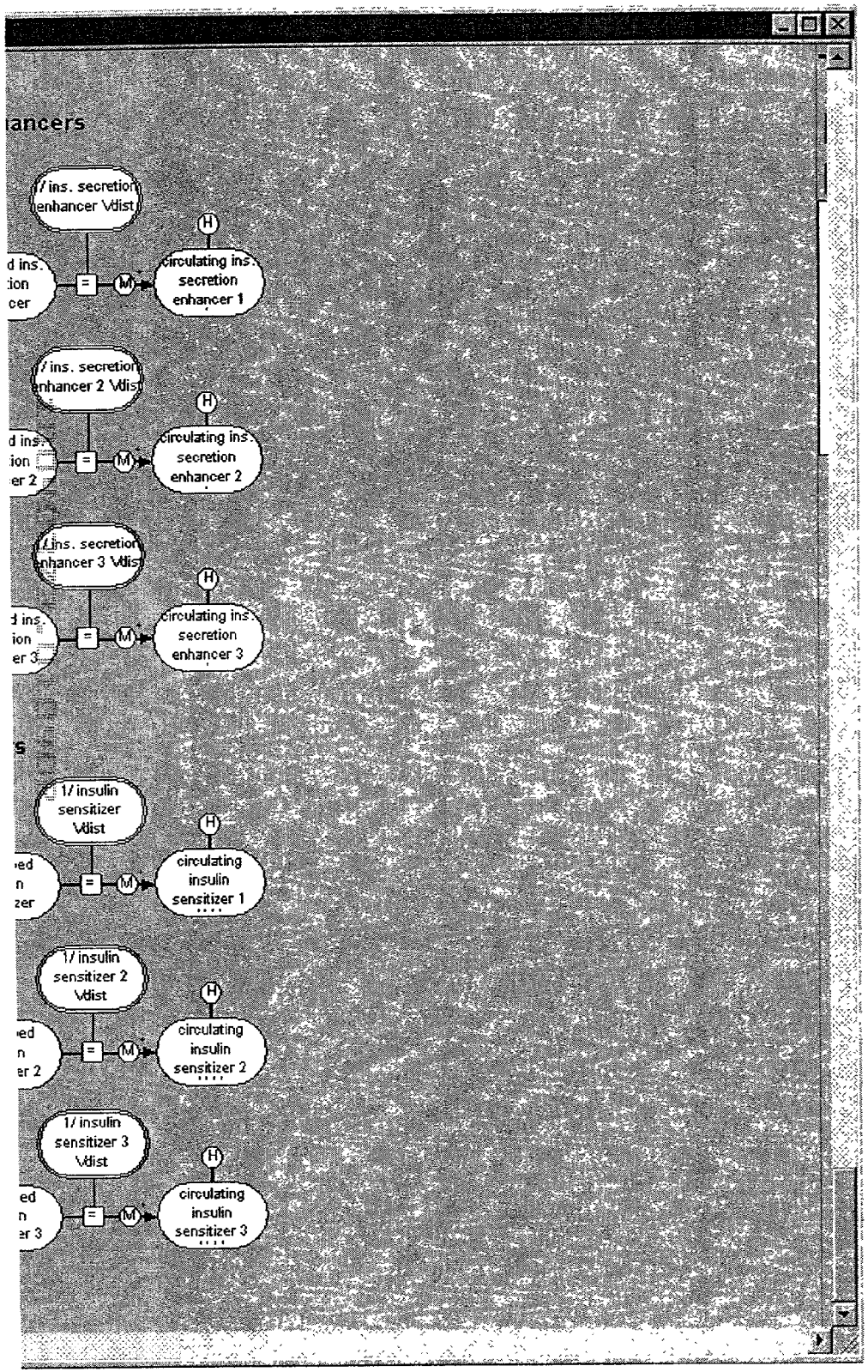

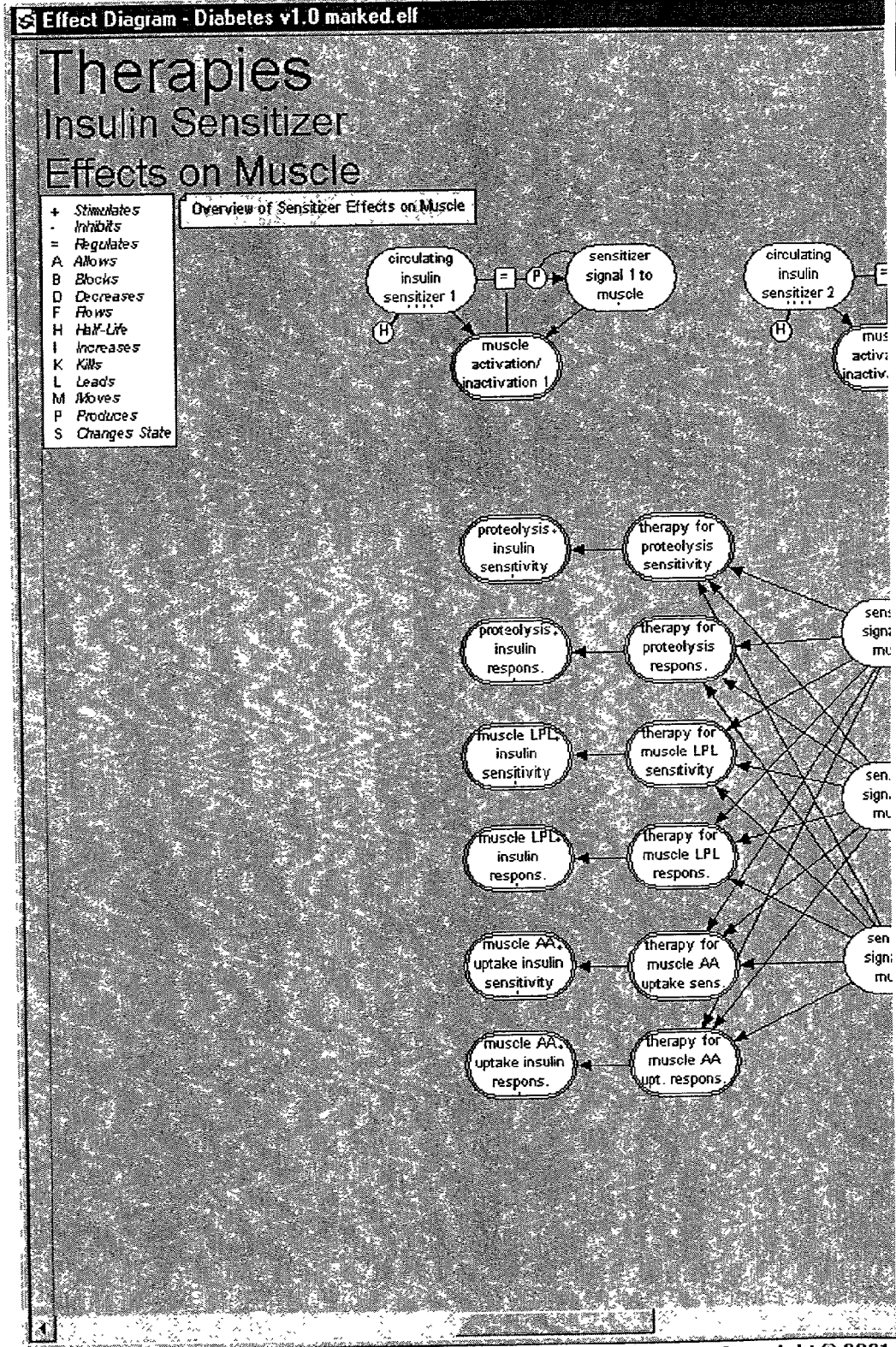

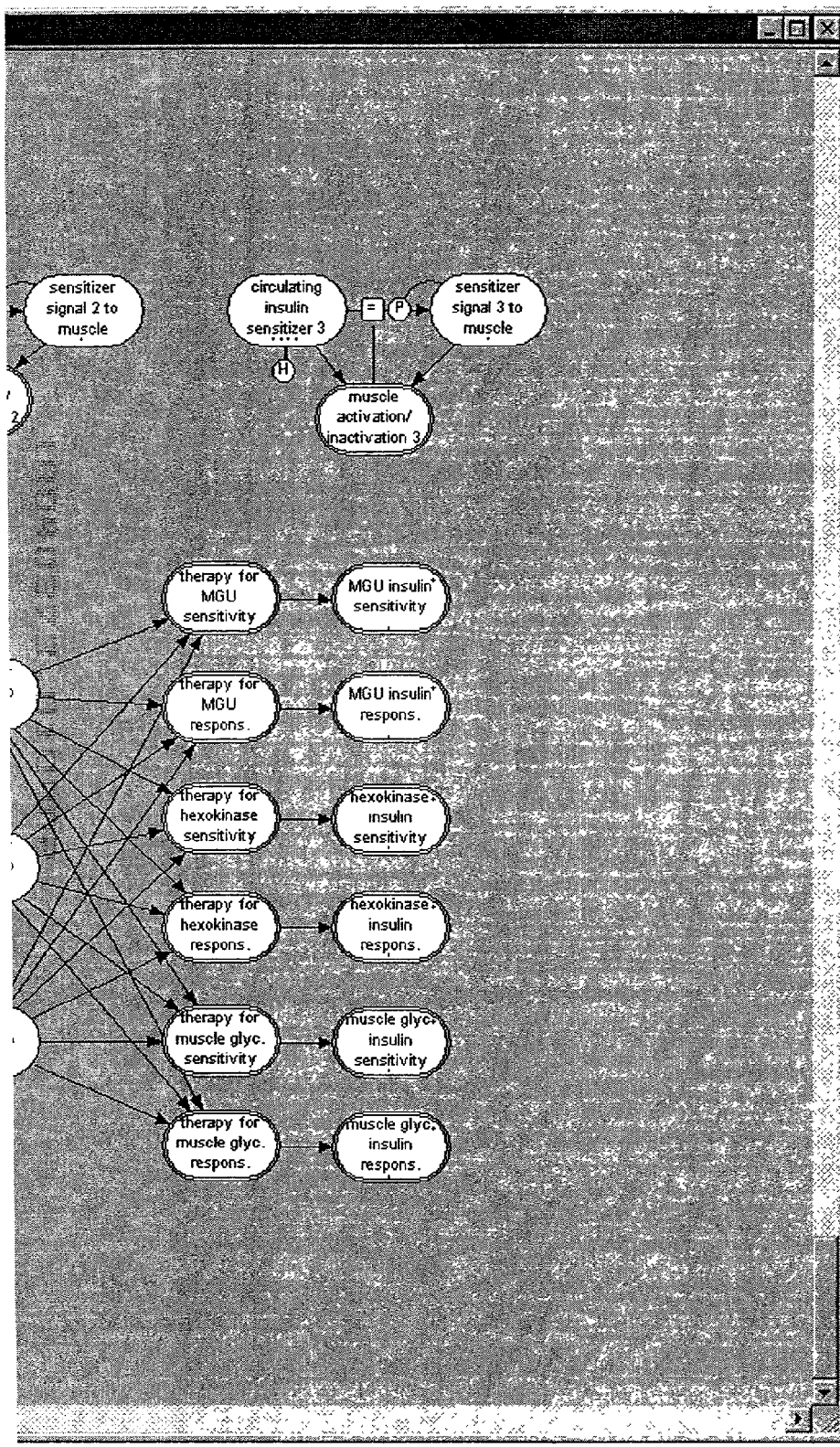

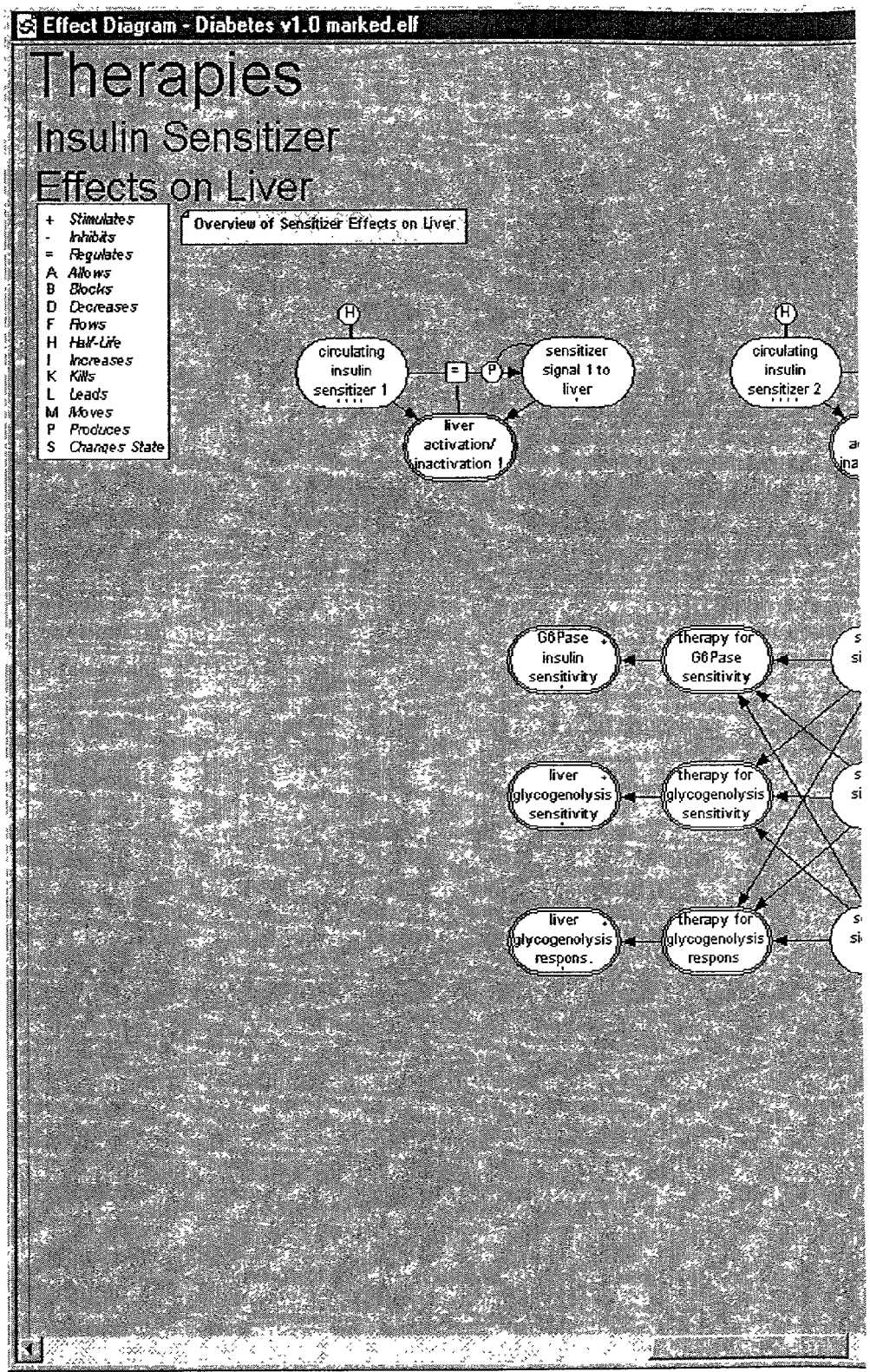

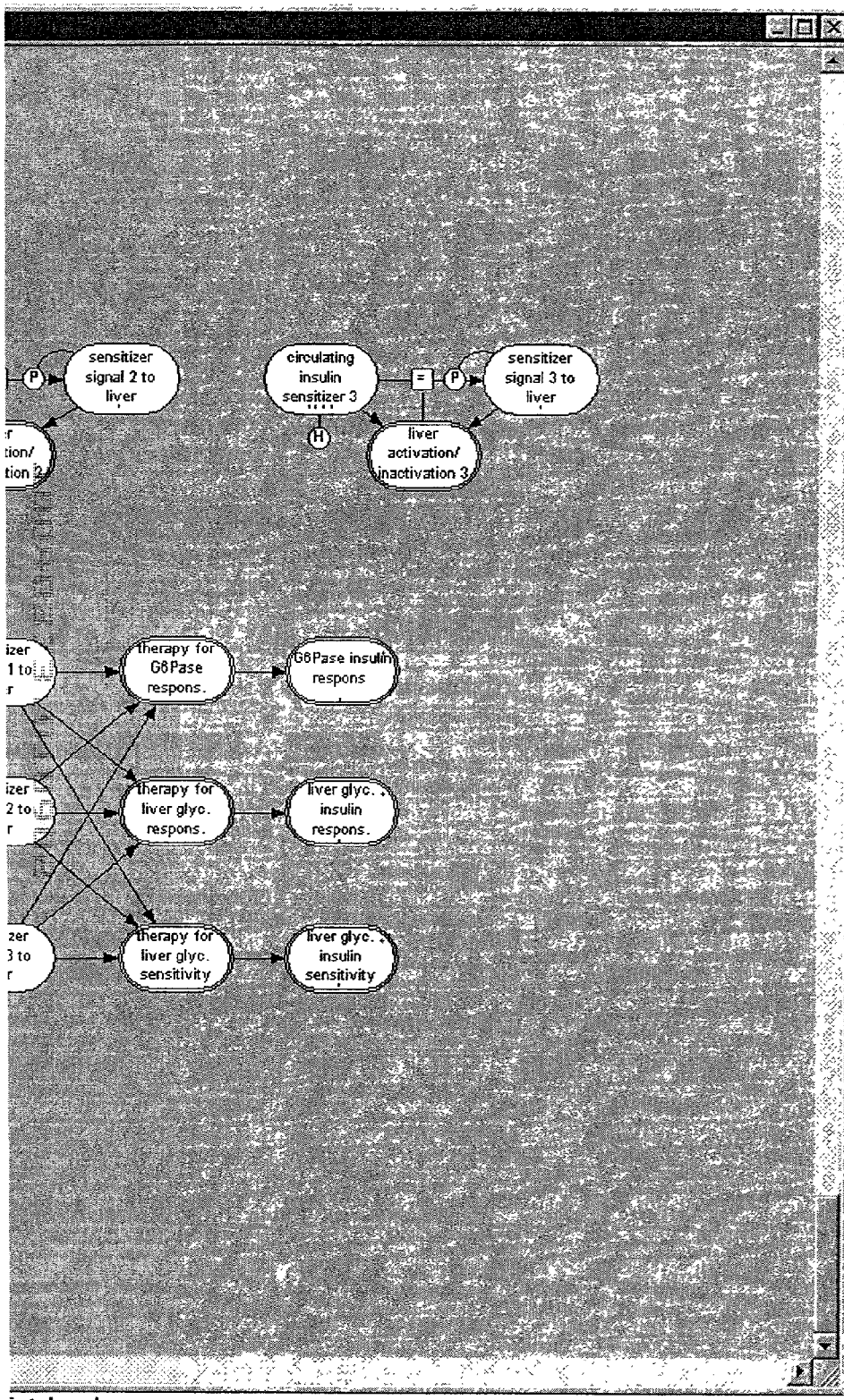

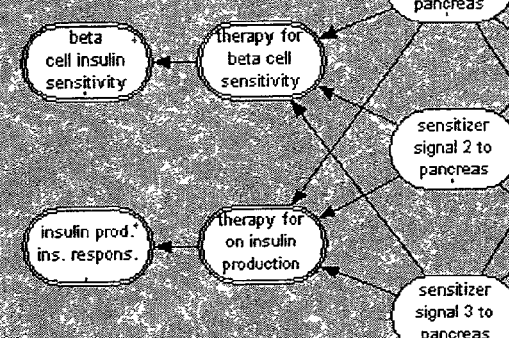

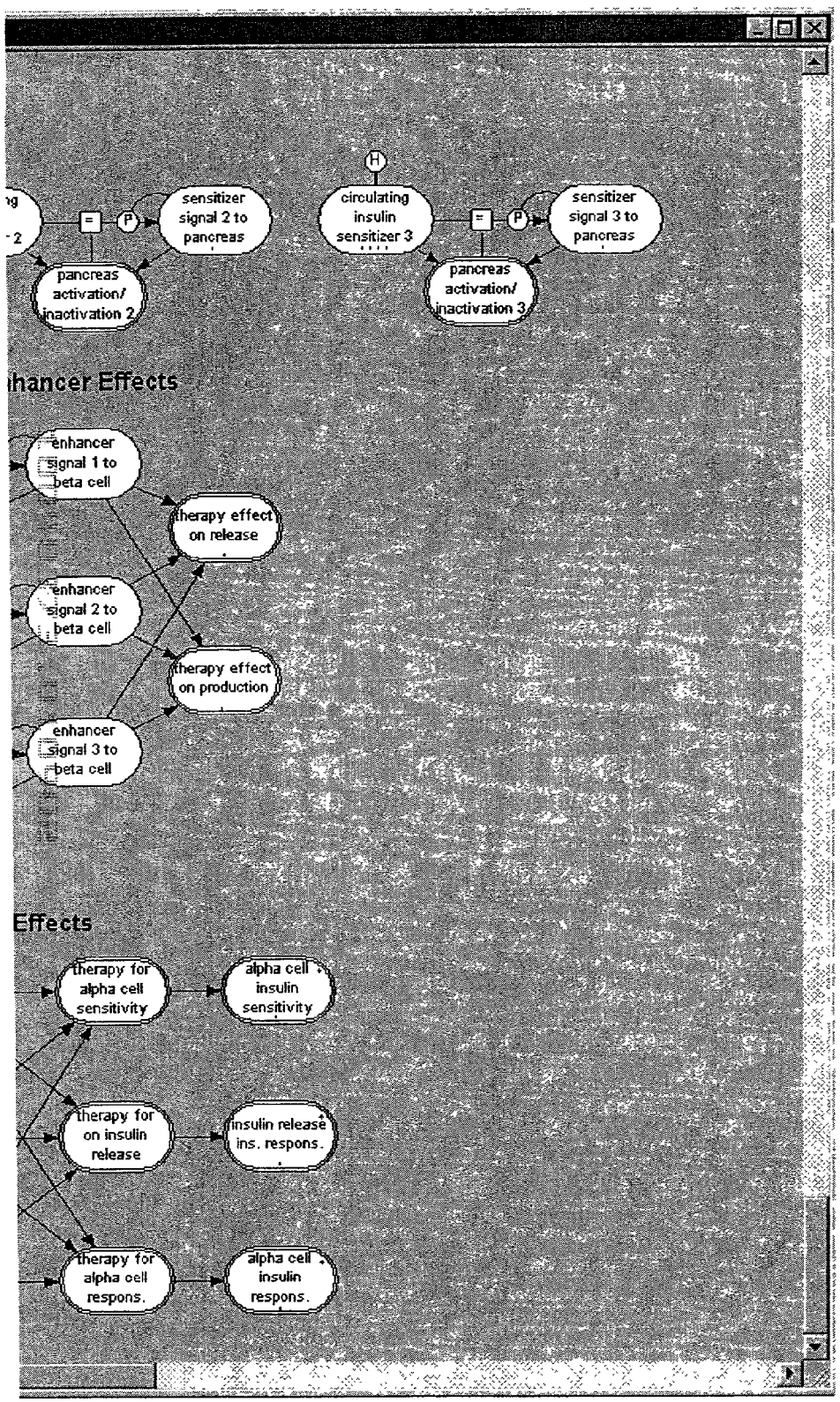

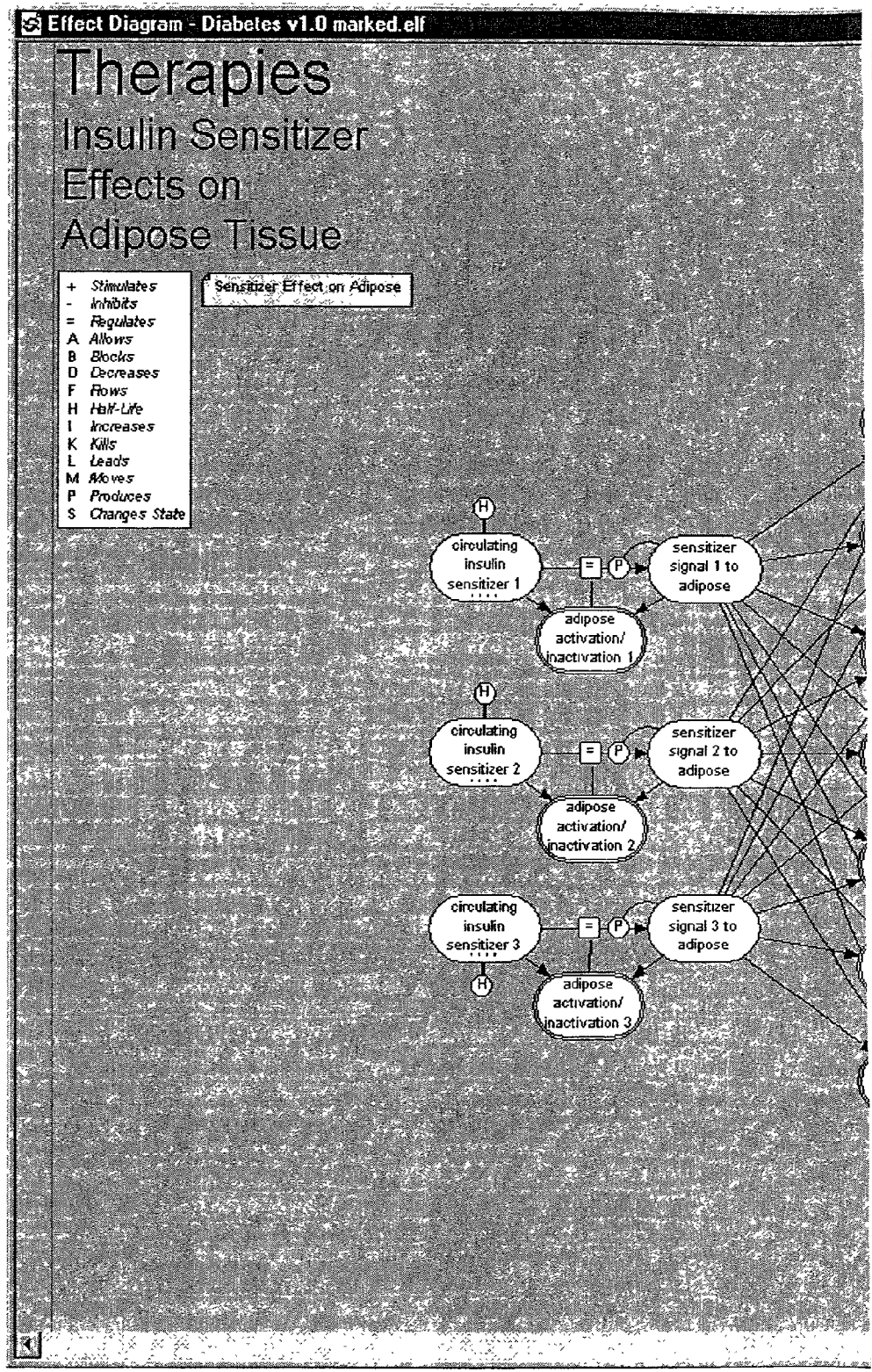

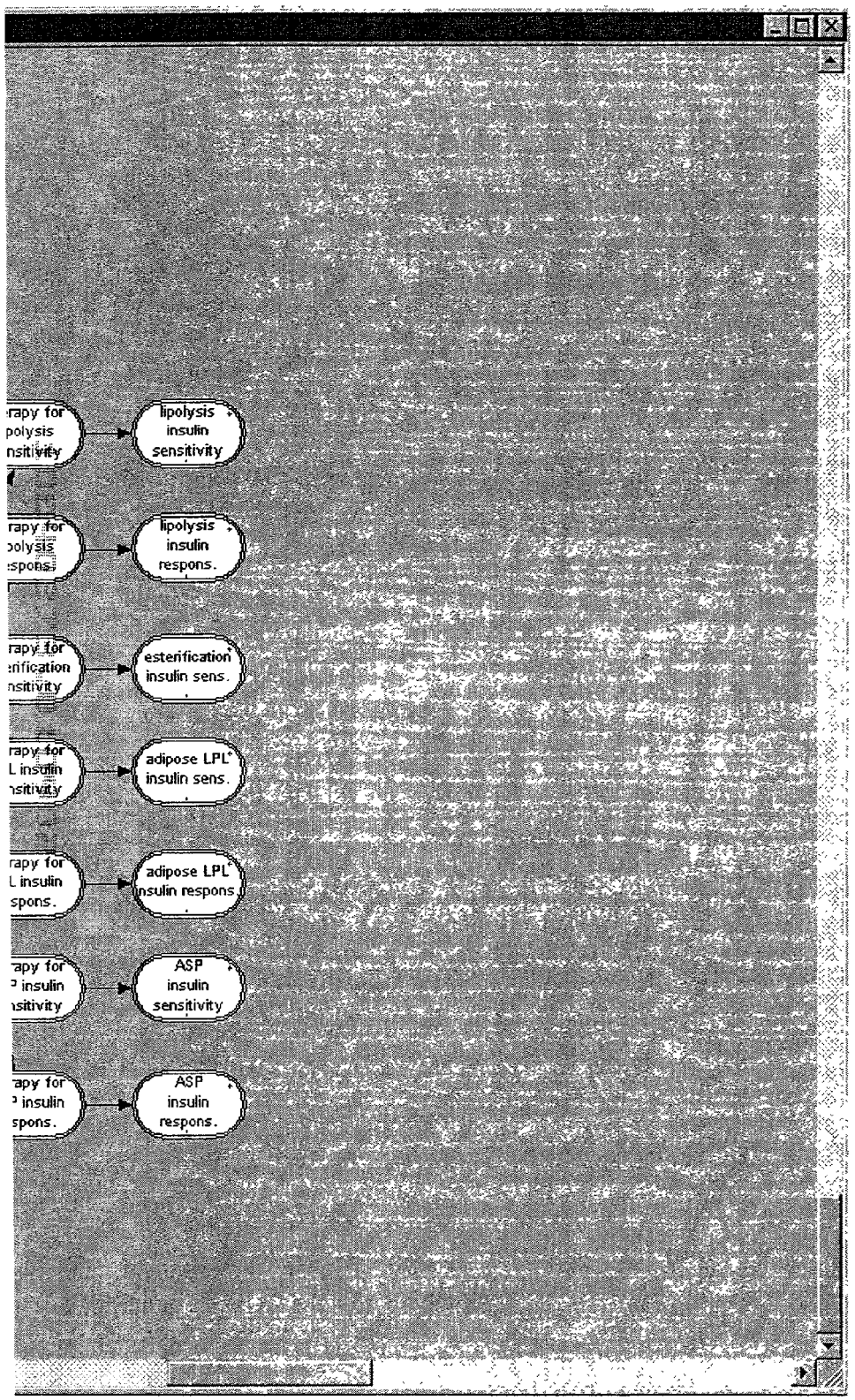

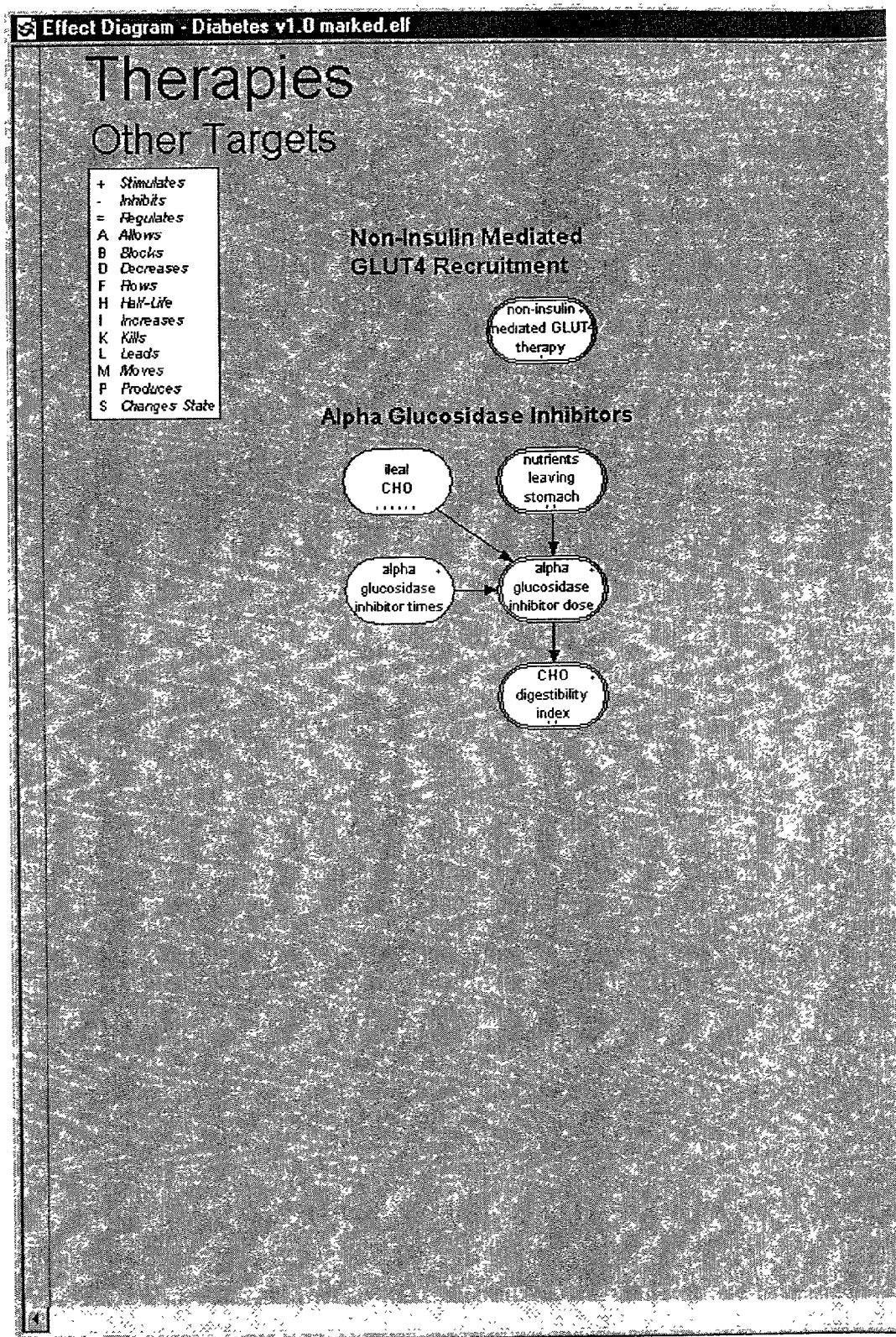

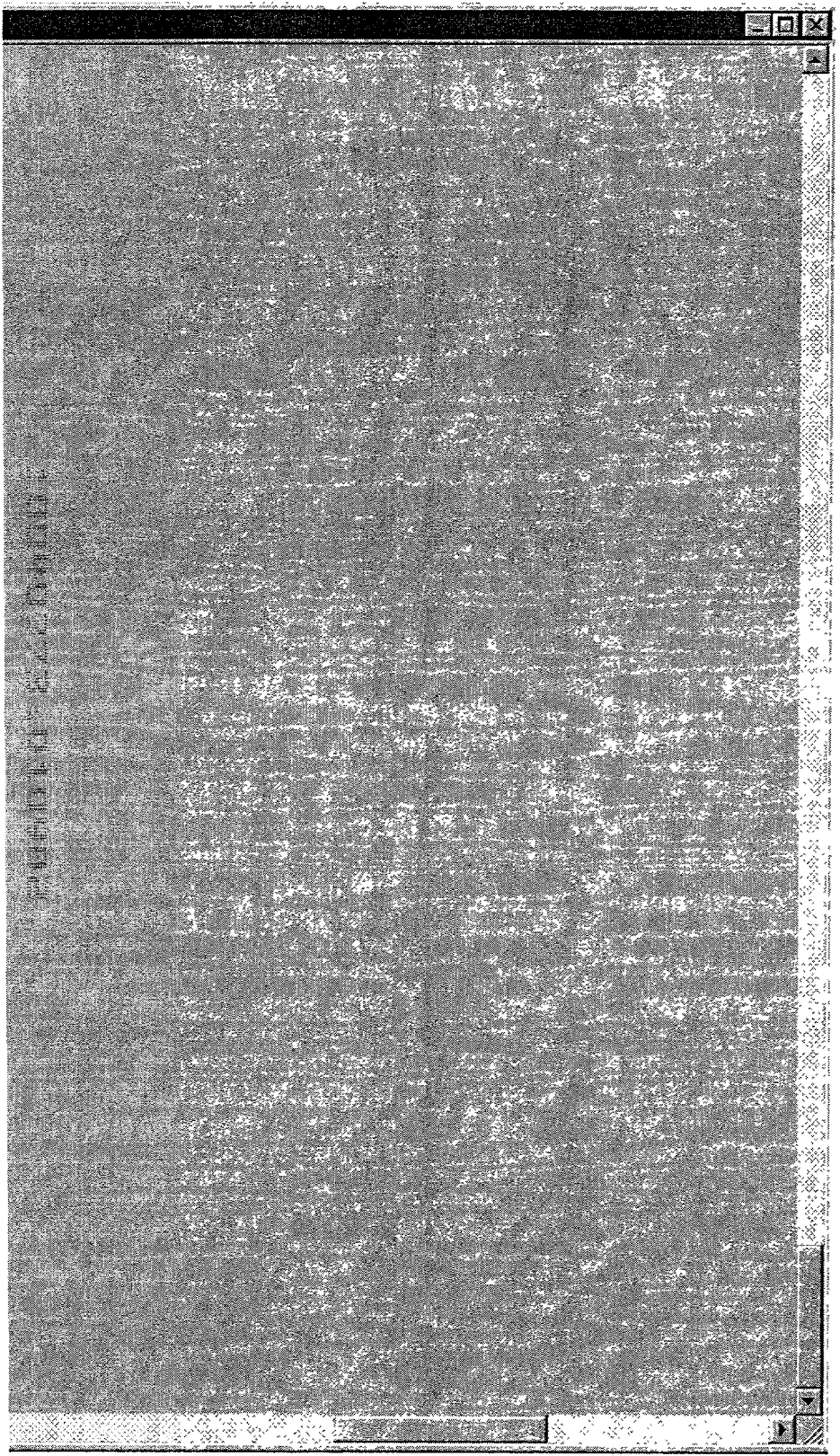

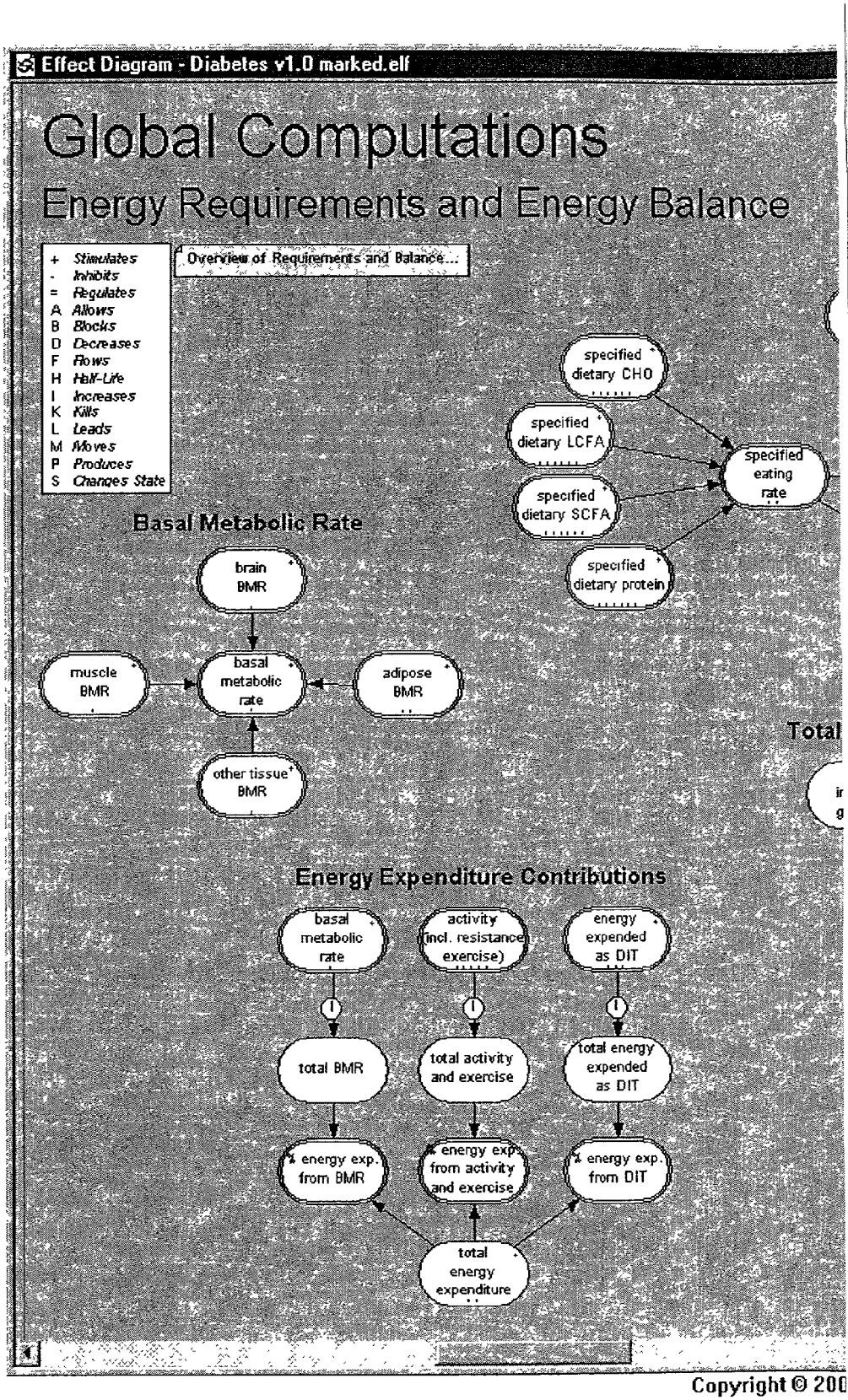

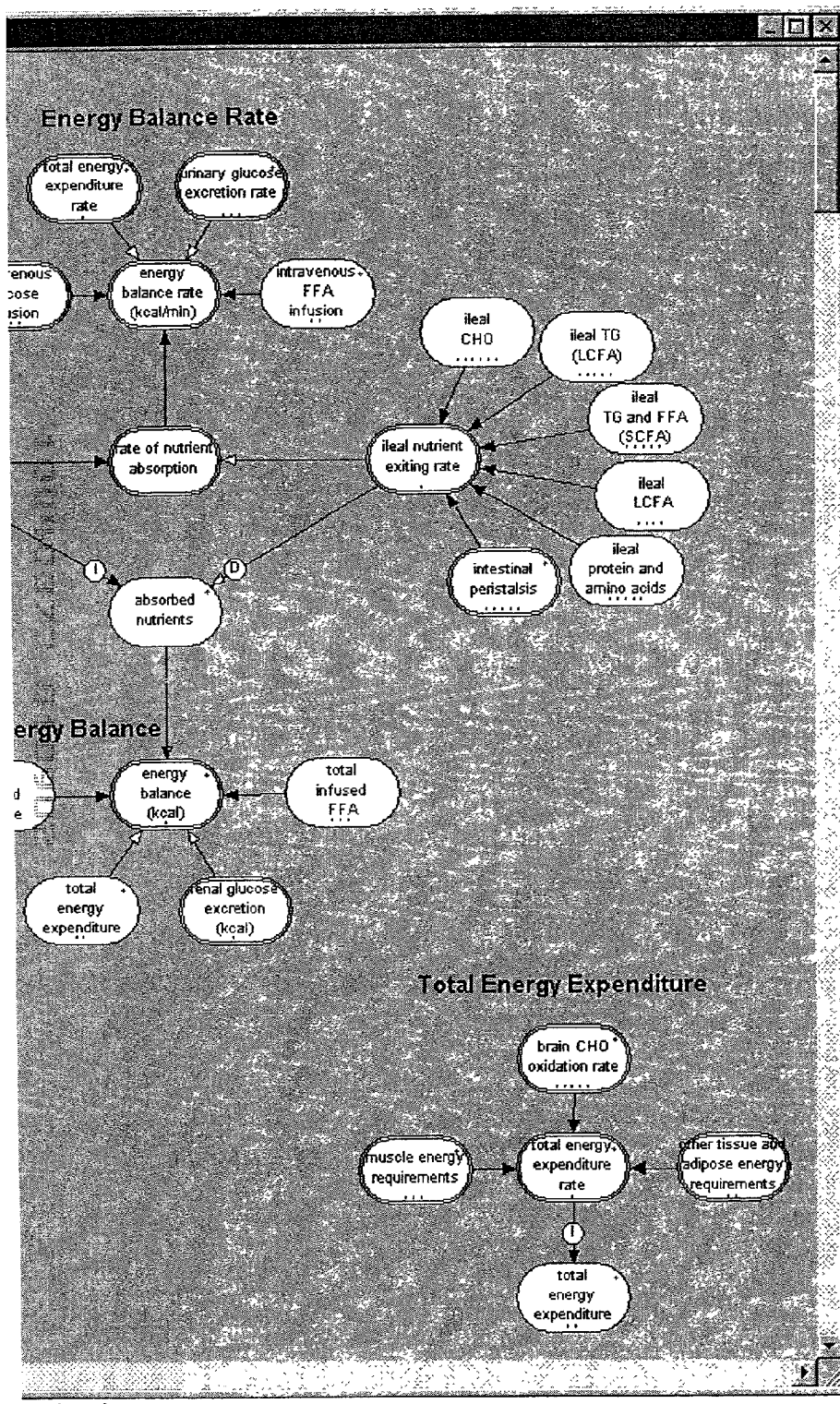

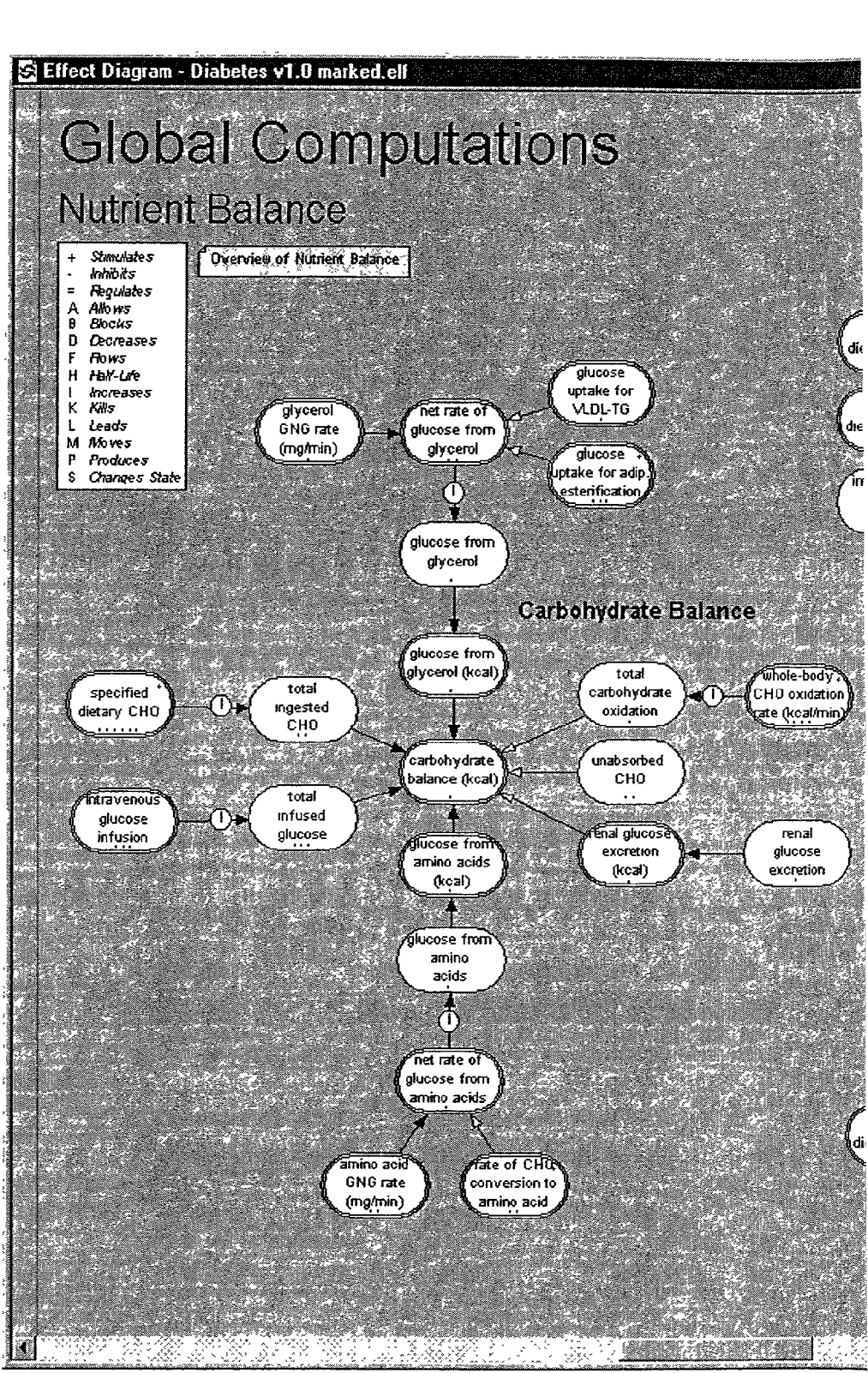

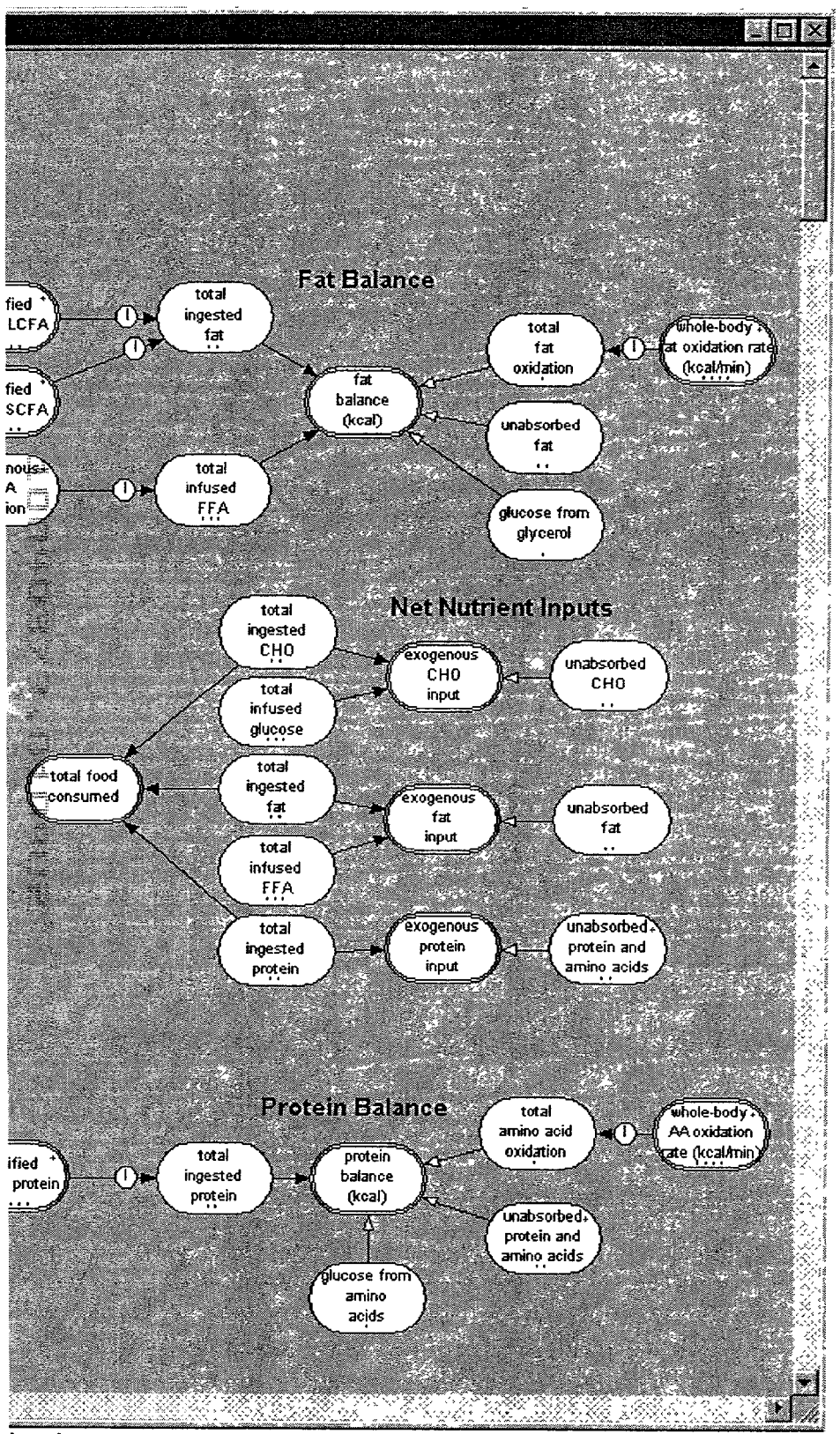

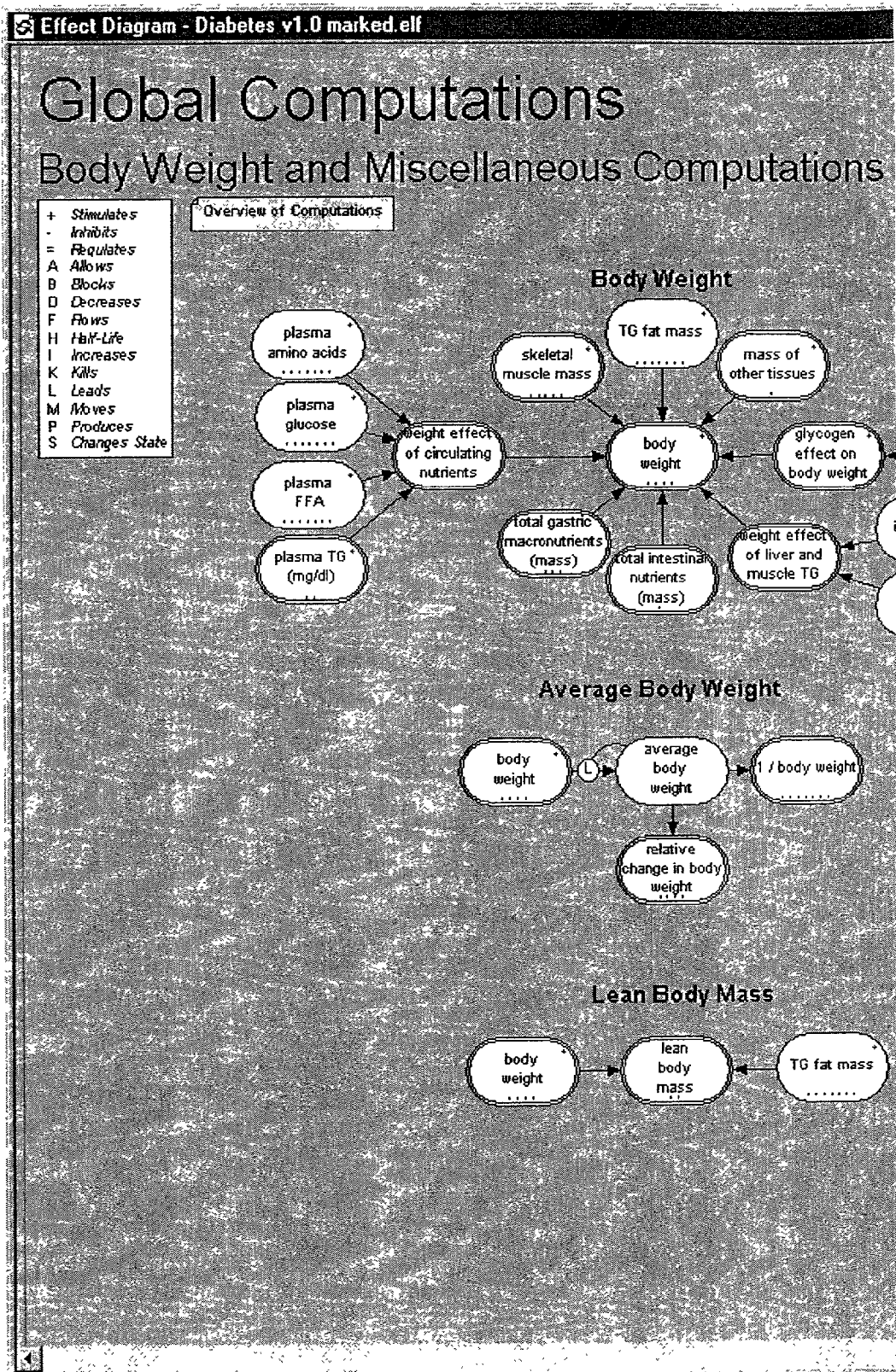

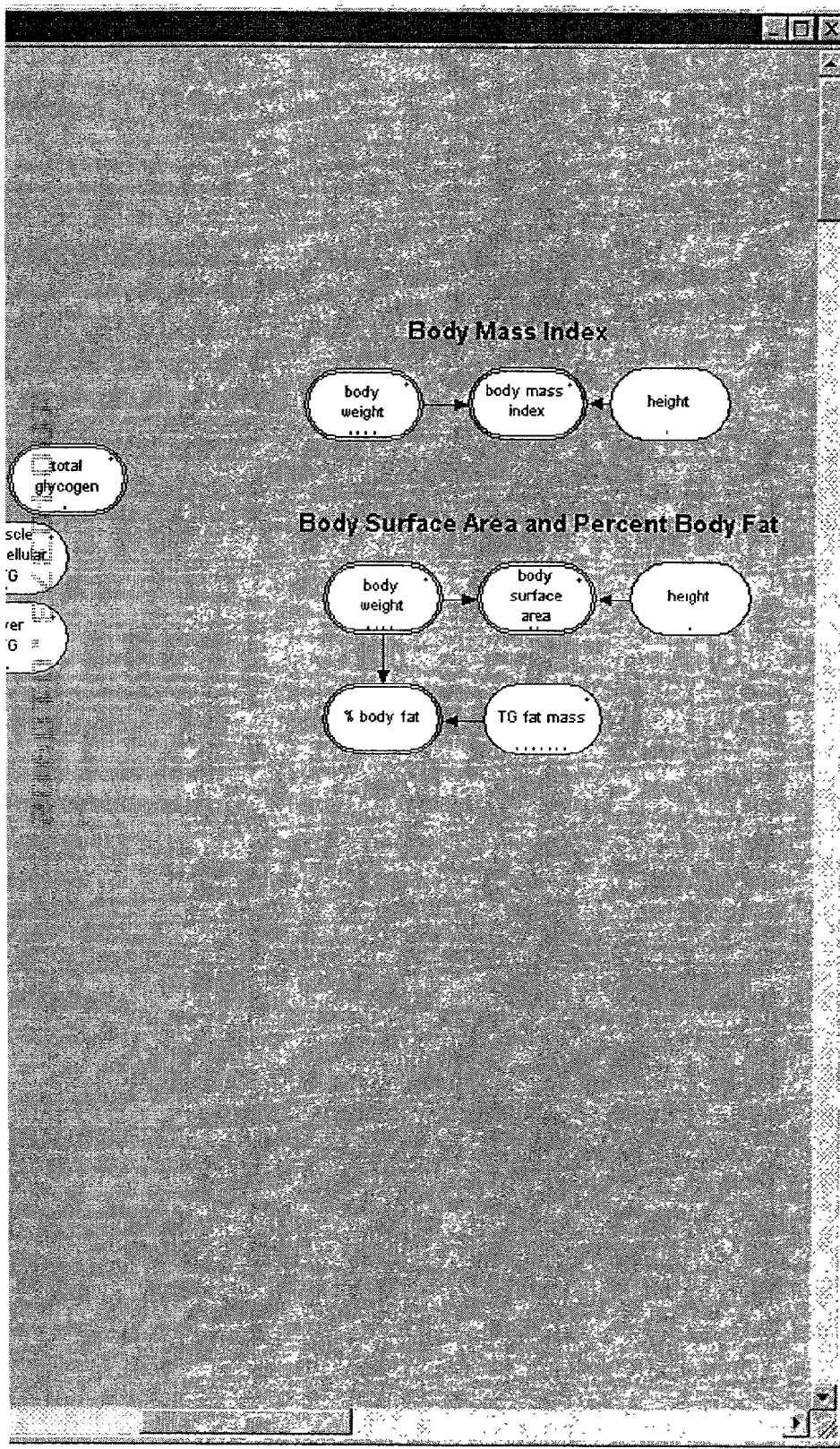

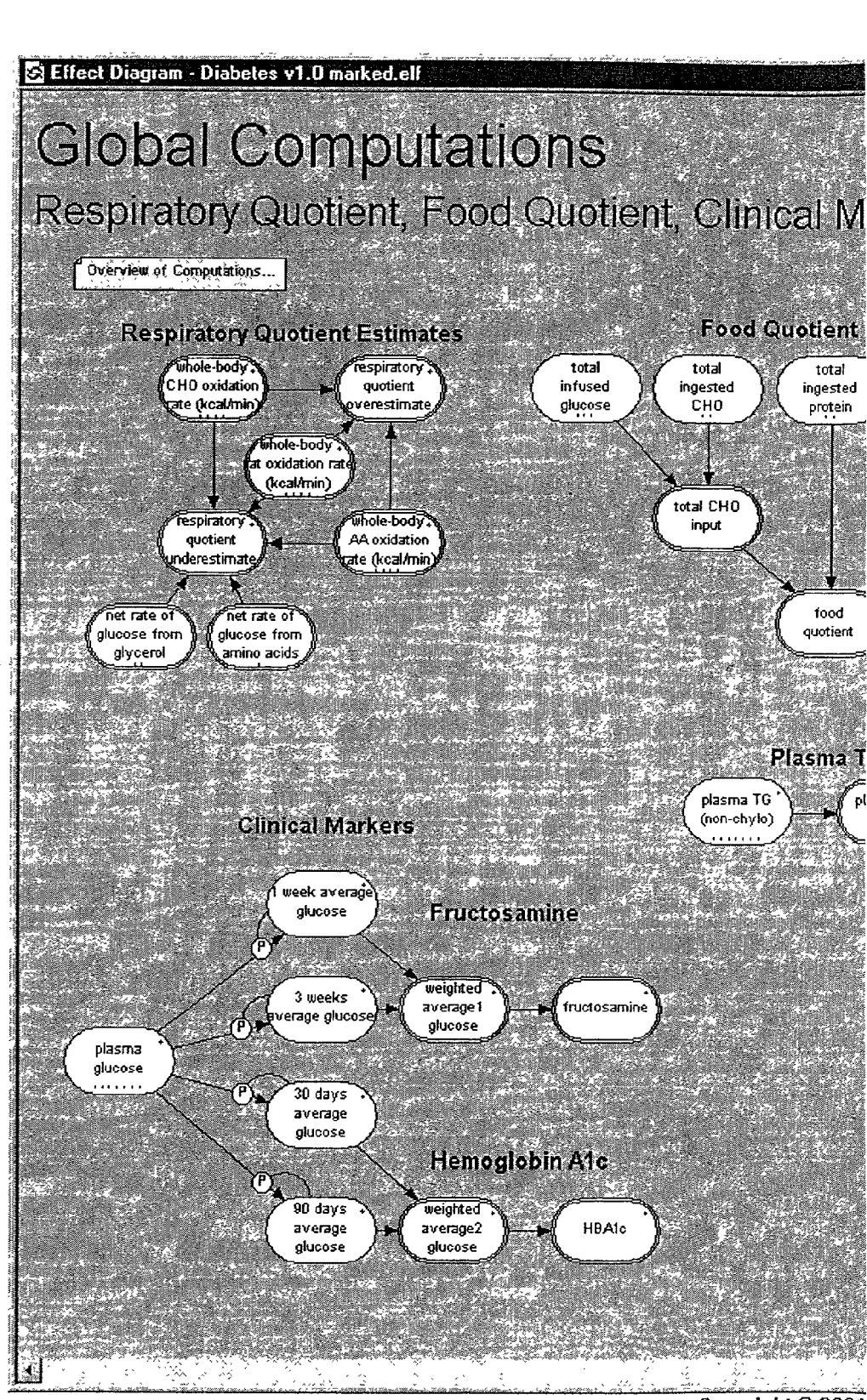

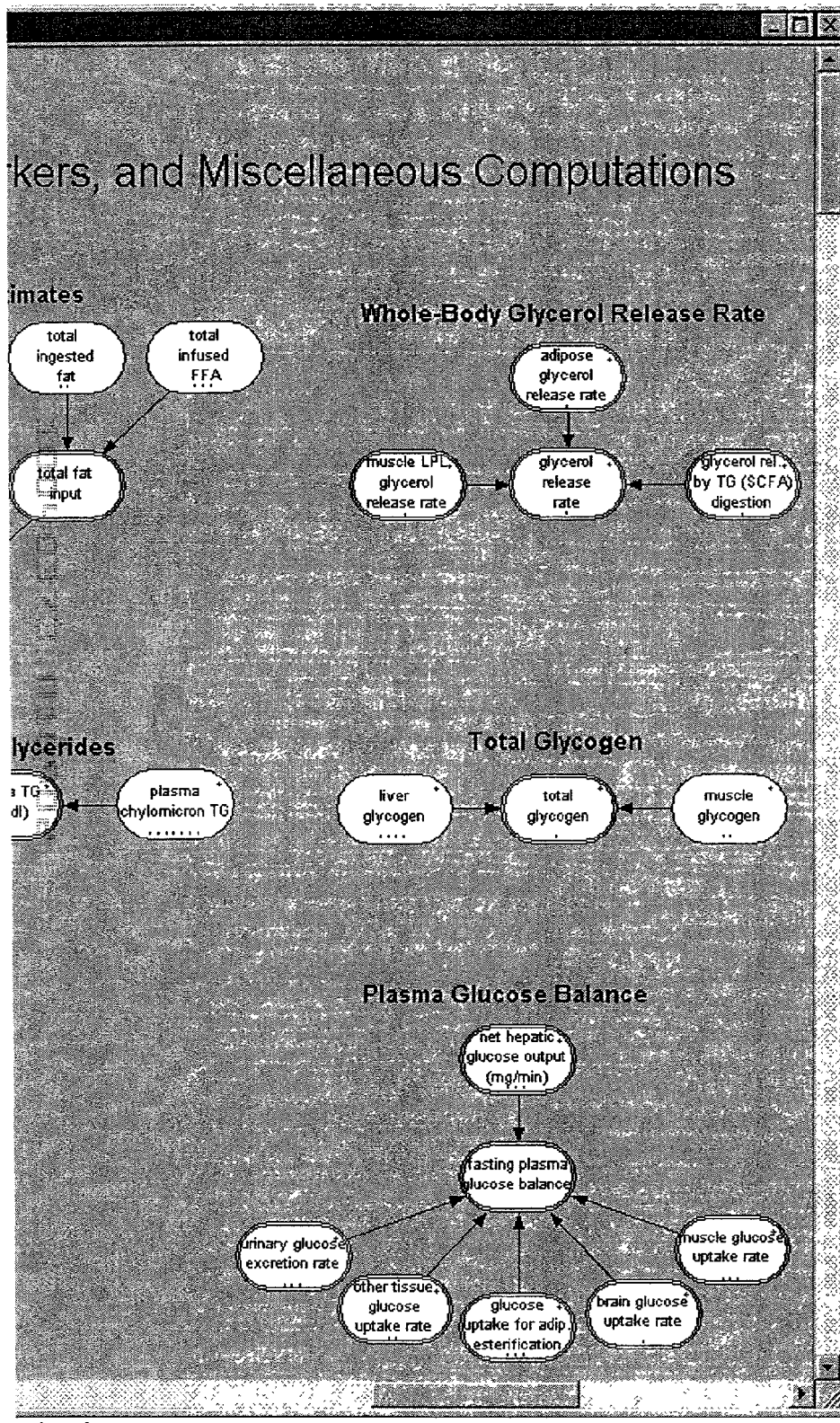

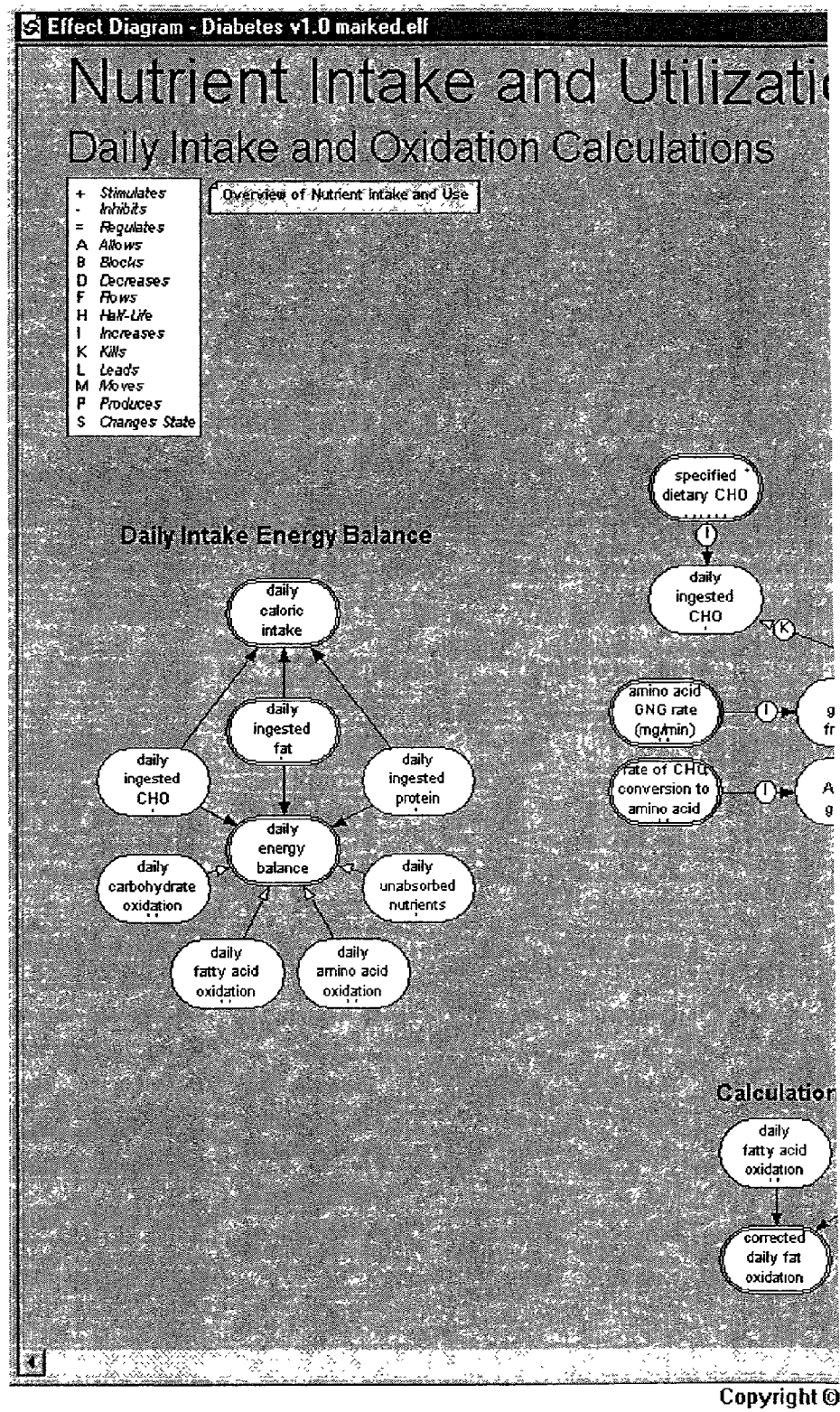

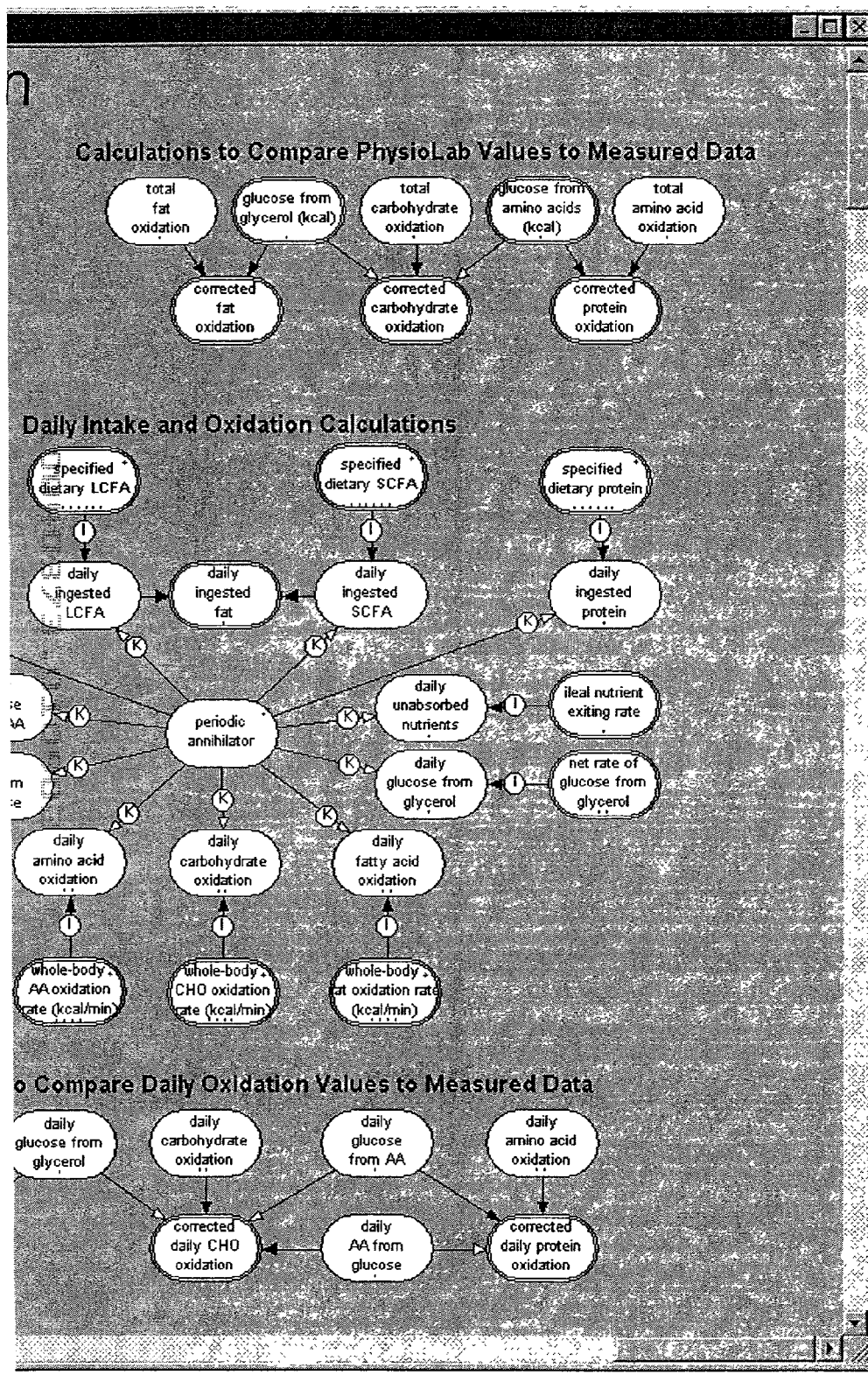

What is claimed is:

1. A method for creating a computer model of diabetes, comprising:
   identifying data relating to diabetes, the data relating changes in biological states to biological attributes of diabetes;
   identifying a plurality of biological processes related to the data, the plurality of biological processes defining at least one portion of the disease state of diabetes; and
   combining the plurality of biological processes to form a simulation of glucose metabolism, wherein the simulation comprises a representation of two macronutrient metabolisms selected from the group consisting of fat metabolism, protein metabolism and carbohydrate metabolism, wherein
      a representation of fat metabolism comprises a representation of at least one biological process selected from the group consisting of regulation of adipose tissue uptake of free fatty acid, regulation of adipose tissue lipolysis, regulation of adipose tissue triglyceride esterification, hepatic lipoprotein regulation, muscle free fatty acid uptake, and muscle free fatty acid utilization; and
      a representation of protein metabolism comprises a representation of at least one biological process selected from the group consisting of production of amino acids from carbohydrate in muscle, hepatic gluconeogenesis from amino acid substrate, oxidation of amino acids in muscle, oxidation of amino acids in liver, and regulation of skeletal muscle protein turnover in response to a stimulus selected from activity, exercise, fat mass, dietary composition, and insulin;
   producing a simulated biological attribute associated with at least one biological attribute of diabetes based on the combined plurality of biological processes; and
   storing the simulated biological attribute in a computer-readable medium.

2. The method of claim 1, further comprising:
   comparing the simulated biological attribute with a corresponding biological attribute associated with a reference pattern of diabetes; and
   identifying the computer model as a valid computer model of diabetes if the simulated biological attribute is substantially consistent with the biological attribute associated with a reference pattern of diabetes.

3. The method of claim 1, wherein combining the plurality of biological processes includes:
   forming a first mathematical relation among biological variables associated with a first biological process from the plurality of biological processes; and
   forming a second mathematical relation among biological variables associated with the first biological process and a second biological process from the plurality of biological variables associated with the plurality of biological processes.

4. The method of claim 3, further comprising:
   creating a set of parametric changes in the first mathematical relation and the second mathematical relation; and
   producing a simulated biological attribute based on at least one parametric change from the set of parametric changes, the simulated biological attribute being substantially consistent with at least one biological attribute associated with a reference pattern of diabetes.

5. The method of claim 3, further comprising:
   creating a set of parametric changes in the first mathematical relation and a set of parametric changes in the second mathematical relation, the set of parametric changes in the first mathematical relation being associated with a first diabetes defect having its own degree of severity, the set of parametric changes in the second mathematical relation being associated with a second diabetes defect having its own degree of seventy.

6. The method of claim 3, further comprising
   converting at least one biological variable from the group of the first mathematical relation or second mathematical relation into a biological variable that evolves over time; and
   producing a series of simulated biological attributes based on the converted biological variable, the series of simulated biological attributes being substantially consistent with a corresponding biological attribute associated with a reference pattern of diabetes, the series of simulated biological attributes representing the disease progression in the reference pattern of diabetes.

7. A computer model of a disease state of diabetes, comprising:
   a computer-readable memory storing:
      instructions defining a set of biological processes related to the disease state of diabetes, at least two biological processes from the set of biological processes being associated with a set of mathematical relationships related to interactions among biological variables associated with the biological processes, the instructions defining a simulation of glucose metabolism, wherein the simulation comprises a representation of two macronutrient metabolisms selected from the group consisting of fat metabolism, protein metabolism and carbohydrate metabolism, wherein
         a representation of fat metabolism comprises a representation of at least one biological process selected from the group consisting of regulation of adipose tissue uptake of free fatty acid, regulation of adipose tissue lipolysis, regulation of adipose tissue triglyceride esterification, hepatic lipoprotein regulation, muscle free fatty acid uptake, and muscle free fatty acid utilization; and
         a representation of protein metabolism comprises a representation of at least one biological process selected from the group consisting of production of amino acids from carbohydrate in muscle, hepatic gluconeogenesis from amino acid substrate, oxidation of amino acids in muscle, oxidation of amino acids in liver, and regulation of skeletal muscle protein turnover in response to a stimulus selected from activity, exercise, fat mass, dietary composition, and insulin; and
   a processor coupled to the computer-readable memory, the processor configured to execute the instructions producing a simulated biological attribute and to store the simulated biological attribute in a computer-readable medium.

8. The computer model of claim 7, wherein, upon execution of the instruction, the processor is configured to produce a simulated biological attribute for the disease state of diabetes, the simulated biological attribute is substantially consistent with at least one biological attribute associated with a reference pattern of diabetes.

9. The computer model of claim 7, wherein the instructions further define a set of defects associated with diabetes, the set of defects including a first defect and a second defect, the first defect is a modification of a first biological process from the set of biological processes, the first biological process is related to biological attributes of diabetes in a reference pattern of diabetes, the second defect is a modification of the first biological process or a second biological process from the set of biological processes, the second biological process is related to biological attributes of diabetes in the reference pattern of diabetes.

10. A computer-readable medium having computer-readable instructions stored thereon that, upon execution by a processor, cause the processor to model a disease state of diabetes, the instructions comprising:

defining a normal biological state though a set of biological processes, each biological process from the set of biological processes having its own associated parameter set, the set of biological processes being related to glucose metabolism, wherein the set of biological processes comprises a representation of two macronutrient metabolisms selected from the group consisting of fat metabolism, protein metabolism and carbohydrate metabolism, wherein a representation of fat metabolism comprises a representation of at least one biological process selected from the group consisting of regulation of adipose tissue uptake of free fatty acid, regulation of adipose tissue lipolysis, regulation of adipose tissue triglyceride esterification, hepatic lipoprotein regulation, muscle free fatty acid uptake, and muscle free fatty acid utilization;

a representation of protein metabolism comprises a representation of at least one biological process selected from the group consisting of production of amino acids from carbohydrate in muscle, hepatic gluconeogenesis from amino acid substrate, oxidation of amino acids in muscle, oxidation of amino acids in liver, and regulation of skeletal muscle protein turnover in response to a stimulus selected from activity, exercise, fat mass, dietary composition, and insulin;

providing a plurality of predefined defect indicators, each predefined defect indicator from the plurality of predefined defect indicators being uniquely associated with a defect from a plurality of defects associated with a disease state of diabetes, each defect from the plurality of defects being associated with at least one biological process from the set of biological processes;

receiving a user-specified identification of a first defect indicator from the plurality of predefined defect indicators, a first defect from the plurality of defects being associated with the first defect indicator, the parameter set associated with each biological processes that is associated with the first defect being changed based on the user-specified identification to generate a changed parameter set; and storing the changed parameter set in a computer-readable medium.

11. The computer-readable medium of claim 10, wherein the instructions further comprise:

determining at least one simulated biological attribute based on the modified biological process associated with the first defect, the simulated biological attribute being substantially consistent with at least one corresponding biological attribute associated with diabetes in a reference pattern of diabetes.

12. The computer-readable medium of claim 10, wherein the instructions further comprise:

receiving a user-specified identification of a second defect indicator from the plurality of predefined defect indicators, a second defect from the plurality of defects being associated with the second defect indicator, the parameter set associated with each biological processes that is associated with the second defect being changed based on the user-specified identification.

13. The computer-readable medium of claim 12, wherein:

the first defect has an associated severity based on the change to the at least one associated parameter set; and the second defect has an associated severity based on the change to the at least one associated parameter set, the severity associated with the first defect being different from the severity associated with the second defect.

14. The computer-readable medium of claim 12, wherein:

the first defect has an associated severity based on the change to the at least one associated parameter set; and the second defect has an associated severity based on the change to the at least one associated parameter set, the severity associated with the first defect being substantially similar to the severity associated with the second defect.

15. The computer-readable medium of claim 10, wherein the instructions further comprise:

producing a simulated biological attribute based on the parameter set associated with each biological processes that is associated with the first defect, the simulated biological attribute being substantially consistent with biological attributes of a reference pattern of diabetes.

16. A computer-readable medium having computer-readable instructions stored thereon that, upon execution by a processor, cause the processor to model a disease state of diabetes, the instructions comprising:

providing a plurality of predefined defect indicators, each predefined defect indicator from the plurality of predefined defect indicators being uniquely associated with a defect from a plurality of defects associated with a disease state, each defect from the plurality of defects being associated with at least one biological process from a set of biological processes, the set of biological processes being related to glucose metabolism, wherein the set of biological processes comprises a representation of two macronutrient metabolisms selected from the group consisting of fat metabolism, protein metabolism and carbohydrate metabolism, wherein a representation of fat metabolism comprises a representation of at least one biological process selected from the group consisting of regulation of adipose tissue uptake of free fatty acid, regulation of adipose tissue lipolysis, regulation of adipose tissue triglyceride esterification, hepatic lipoprotein regulation, muscle free fatty acid uptake, and muscle free fatty acid utilization; and a representation of protein metabolism comprises a representation of at least one biological process selected from the group consisting of production of amino acids from carbohydrate in muscle, hepatic gluconeogenesis from amino acid substrate, oxidation of amino acids in muscle, oxidation of amino acids in liver, and regulation of skeletal muscle protein turnover in response to a stimulus selected from activity, exercise, fat mass, dietary composition, and insulin;

receiving a user-specified identification of a first defect indicator from the plurality of predefined defect indicators, a first defect from the plurality of defects being associated with the first defect indicator, the first defect being associated with at least one biological process and its associated parameter set, the at least one parameter set associated with the first defect being changed based on the user-specified identification; and receiving a user-specified identification of a second defect indicator from the plurality of predefined defect indicators, a second defect from the plurality of defects being associated with the second defect indicator, the second defect being associated with at least one biological process and its associated parameter set, the at least one parameter set associated with the second defect being changed based on the user-specified identification to generate a changed parameter set; and storing the changed parameter set in a computer-readable medium.

17. The computer-readable medium of claim 16, wherein:
the first defect having an associated severity based on the change to the at least one associated parameter set, the second defect having an associated severity based on the change to the at least one associated parameter set, the severity associated with the first defect being different from the severity associated with the second defect.

18. The computer-readable medium of claim 16, wherein the instructions further comprise:
defining a normal biological state through the set of biological processes, each biological process from the set of biological processes being associated with its own parameter set.

19. The computer-readable medium of claim 16, wherein the plurality of defects are associated with type 2 diabetes.

20. A computer-readable medium having computer-readable instructions stored thereon that, upon execution by a processor, cause the processor to model a disease state of diabetes the instructions comprising:
defining a plurality of biological processes related to a disease state of diabetes, wherein the plurality of biological processes comprises a representation of two macronutrient metabolisms selected from the group consisting of fat metabolism, protein metabolism and carbohydrate metabolism, wherein
a representation of fat metabolism comprises a representation of at least one biological process selected from the group consisting of regulation of adipose tissue uptake of free fatty acid, regulation of adipose tissue lipolysis, regulation of adipose tissue triglyceride esterification, hepatic lipoprotein regulation, muscle free fatty acid uptake, and muscle free fatty acid utilization; and
a representation of protein metabolism comprises a representation of at least one biological process selected from the group consisting of production of amino acids from carbohydrate in muscle, hepatic gluconeogenesis from amino acid substrate, oxidation of amino acids in muscle, oxidation of amino acids in liver, and regulation of skeletal muscle protein turnover in response to a stimulus selected from activity, exercise, fat mass, dietary composition, and insulin;

producing a simulated biological attribute associated with at least one biological attribute of diabetes based on the plurality of biological processes; and storing the simulated attribute in the computer-readable medium wherein the step of defining includes:
defining a set of mathematical relations associated with a first biological process from the plurality of biological processes and associated with interactions among biological variables associated with the first biological process, and defining a set of mathematical relations associated with a second biological process from the plurality of biological processes and associated with interactions among biological variables associated with the second biological process, a first biological process from the plurality of biological processes being associated with metabolism of at least two from the group of carbohydrates, fats and proteins, a second biological process from the plurality of biological processes being associated with metabolism of glucose.

21. The computer-readable medium of claim 20, wherein the instructions further comprise:
defining a set of parametric changes for a first biological process; and receiving a user-specified identification of a first defect indicator from a plurality of predefined defect indicators, the first defect indicator from the plurality of defect indicators being uniquely associated with a first defect from a plurality of defects that is associated with a disease state of diabetes, the set of parametric changes being changed based on the user-specified identification.

22. The computer-readable medium of claim 21, wherein the instructions further comprise:
receiving a user-specified identification of a second defect indicator from the plurality of predefined defect indicators, the second defect indicator from the plurality of defect indicators being uniquely associated with a second defect from the plurality of defects that is associated with the disease state of diabetes, the second defect being associated with at least one biological process and its associated parameter set, the at least one parameter set associated with the second defect being changed based on the user-specified identification, the first defect having an associated severity based on the change to the at least one associated parameter set, the second defect having an associated severity based on the change to the at least one associated parameter set, the severity associated with the first defect being different from the severity associated with the second defect.

23. The computer-readable medium of claim 20, wherein the instructions further comprise:
receiving a user selection of a link representation from a set of predefined link representations, each predefined link representation in the set of predefined link representations being associated with a different mathematical relationship, the user-selected link representation being associated with the interrelationship between a first biological variable and a second biological variable, a first link representation from the set of predefined link representations being a representation of the first biological variable having an effect on the second biological variable, a second link representation from the set of predefined link representations being a representation of instances of the first biological variable being converted to instances of the second biological variable.

24. A method for creating a computer model of diabetes, comprising:
receiving a plurality of user-selected indications to define a plurality of biological processes, each biological process from the plurality of biological processes being based on data that relates to changes in biological states to biological attributes of diabetes, wherein the plurality of biological processes comprises a representation of two macronutrient metabolisms selected from the group consisting of fat metabolism, protein metabolism and carbohydrate metabolism, wherein a representation of fat metabolism comprises a representation of at least one biological process selected from the group consisting of regulation of adipose tissue uptake of free fatty acid, regulation of adipose tissue lipolysis, regulation of adipose tissue triglyceride esterification, hepatic lipoprotein regulation, muscle free fatty acid uptake, and muscle free fatty acid utilization; and a representation of protein metabolism comprises a representation of at least one biological process selected from the group consisting of production of amino acids from carbohydrate in muscle, hepatic gluconeogenesis from amino acid substrate, oxidation of amino acids in muscle, oxidation of amino acids in liver, and regulation of skeletal muscle protein turnover in response to a stimulus selected from activity, exercise, fat mass, dietary composition, and insulin;

producing a representation of the plurality of biological processes based on the user-selected indications, the plurality of biological processes defining at least one portion of the disease state of diabetes;

producing a simulated biological attribute associated with at least one biological attribute of diabetes based on the combined plurality of biology processes; and assessing a validity of the computer model based on a comparison between the simulated biological attribute and a corresponding biological attribute associated with a reference pattern of diabetes; and storing the simulated biological attribute in a computer-readable medium.

25. A method for creating a computer model of diabetes, comprising:

identifying data relating to diabetes, the data relating changes in biological states to biological attributes of diabetes;

identifying a plurality of biological processes related to the data, the plurality of biological processes defining at least one portion of the disease state of diabetes;

combining the plurality of biological processes to form a simulation of at least one biological attribute of diabetes, wherein the simulation comprises a representation of fat metabolism, wherein the representation of fat metabolism comprises a representation of at least one biological process selected from the group consisting of regulation of adipose tissue uptake of free fatty acid, regulation of adipose tissue lipolysis, regulation of adipose tissue triglyceride esterification, hepatic lipoprotein regulation, muscle free fatty acid uptake, and muscle free fatty acid utilization;

producing a simulated biological attribute associated with at least one biological attribute of diabetes based on the combined plurality of biological processes; and storing the simulated biological attribute in a computer-readable medium.

26. A method for creating a computer model of diabetes, comprising:

identifying data relating to diabetes, the data relating changes in biological states to biological attributes of diabetes;

identifying a plurality of biological processes related to the data, the plurality of biological processes defining at least one portion of the disease state of diabetes;

combining the plurality of biological processes to form a simulation of at least one biological attribute of diabetes, wherein the simulation comprises a representation of protein metabolism, wherein the representation of protein metabolism comprises a representation of at least one biological process selected from the group consisting of production of amino acids from carbohydrate in muscle, hepatic gluconeogenesis from amino acid substrate, oxidation of amino acids in muscle, oxidation of amino acids in liver, and regulation of skeletal muscle protein turnover in response to a stimulus selected from activity, exercise, fat mass, dietary composition, and insulin;

producing a simulated biological attribute associated with at least one biological attribute of diabetes based on the combined plurality of biological processes; and storing the simulated biological attribute in a computer-readable medium.

27. A computer model of a disease state of diabetes, comprising:

a computer-readable memory storing:

instructions defining a set of biological processes related to the disease state of diabetes, at least two biological processes from the set of biological processes being associated with a set of mathematical relationships related to interactions among biological variables associated with the biological processes, the instructions defining a simulation of at least one biological attribute of diabetes, wherein the simulation comprises a representation of fat metabolism, wherein the representation of fat metabolism comprises a representation of at least one biological process selected from the group consisting of regulation of adipose tissue uptake of free fatty acid, regulation of adipose tissue lipolysis, regulation of adipose tissue triglyceride esterification, hepatic lipoprotein regulation, muscle free fatty acid uptake, and muscle free fatty acid utilization; and a processor coupled to the computer-readable memory, the processor configured to execute the instructions producing a simulated biological attribute and to store the simulated biological attribute in a computer-readable medium.

28. A computer model of a disease state of diabetes, comprising:

a computer-readable memory storing:

instructions defining a set of biological processes related to the disease state of diabetes, at least two biological processes from the set of biological processes being associated with a set of mathematical relationships related to interactions among biological variables associated with the biological processes, the instructions defining a simulation of at least one biological attribute of diabetes, wherein the simulation comprises a representation of protein metabolism, wherein the representation of protein metabolism comprises a representation of at least one biological process selected from the group consisting of production of amino acids from carbohydrate in muscle, hepatic gluconeogenesis from amino acid substrate, oxidation of amino acids in muscle, oxidation of amino acids in liver, and regulation of skeletal muscle protein turnover in response to a stimulus selected from activity, exercise, fat mass, dietary composition, and insulin;

a processor coupled to the computer-readable memory, the processor configured to execute the instructions producing a simulated biological attribute and to store the simulated biological attribute in a computer-readable medium.

29. The method of claim 1, wherein the simulation comprises a representation of carbohydrate metabolism and a representation of fat metabolism or protein metabolism.

30. The method of claim 1, wherein the simulation comprises a representation of carbohydrate metabolism, fat metabolism and protein metabolism.

31. The computer model of claim 7, wherein the simulation comprises a representation of carbohydrate metabolism and a representation of fat metabolism or protein metabolism.

32. The computer model of claim 7, wherein the simulation comprises a representation of carbohydrate metabolism, fat metabolism and protein metabolism.

33. The computer-readable medium of claim 10, wherein the set of biological processes comprises a representation of carbohydrate metabolism, protein metabolism and fat metabolism.

34. The computer-readable medium of claim 16, wherein the set of biological processes comprises a representation of carbohydrate metabolism, protein metabolism and fat metabolism.

35. The method of claim 25, wherein the simulation further comprises a representation of carbohydrate metabolism or protein metabolism.

36. The method of claim 26, wherein the simulation further comprises a representation of carbohydrate metabolism or fat metabolism.

37. The computer model of claim 27, wherein the simulation further comprises a representation of carbohydrate metabolism or protein metabolism.

38. The computer model of claim 28, wherein the simulation further comprises a representation of carbohydrate metabolism or fat metabolism.

* * * * *